(12) United States Patent
Arora et al.

(10) Patent No.: US 10,646,381 B2
(45) Date of Patent: *May 12, 2020

(54) CRIMPED FIBER SPUNBOND NONWOVEN WEBS / LAMINATES

(71) Applicant: The Procter & Gamble Company, Cincinnati, OH (US)

(72) Inventors: Kelyn Anne Arora, Cincinnati, OH (US); Stephanie Niezgoda Moss, Cincinnati, OH (US); Shirdish Poondru, Cincinnati, OH (US); Timothy Ian Mullane, Union, KY (US); Nathan Ray Whitely, Liberty Township, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/426,095

(22) Filed: Feb. 7, 2017

(65) Prior Publication Data

US 2017/0143561 A1    May 25, 2017

Related U.S. Application Data

(63) Continuation of application No. 14/933,028, filed on Nov. 5, 2015.
(Continued)

(51) Int. Cl.
*B32B 3/24* (2006.01)
*A61F 13/511* (2006.01)
(Continued)

(52) U.S. Cl.
CPC .......... *A61F 13/5116* (2013.01); *A61F 13/45* (2013.01); *A61F 13/472* (2013.01);
(Continued)

(58) Field of Classification Search
CPC .................. A61F 13/5116; A61F 13/5146
See application file for complete search history.

(56) References Cited

U.S. PATENT DOCUMENTS

| | | | |
|---|---|---|---|
| 599,335 A | 2/1898 | Keifel, Jr. | |
| 3,559,648 A | 2/1971 | Mason, Jr. | |

(Continued)

FOREIGN PATENT DOCUMENTS

| | | |
|---|---|---|
| CA | 2182304 | 1/1997 |
| CA | 2183776 | 3/1997 |

(Continued)

OTHER PUBLICATIONS

International Search Report and Written Opinion (PCT/US2015/059234) dated Mar. 8, 2016.
(Continued)

*Primary Examiner* — William P Watkins, III
(74) *Attorney, Agent, or Firm* — Wednesday G. Shipp; George H. Leal

(57) ABSTRACT

Nonwoven webs/nonwoven laminates for use in absorbent articles are disclosed. The nonwoven laminate includes a first nonwoven web with continuous spunbond crimped fibers and a second web joined to the first nonwoven web. A plurality of apertures extend through at least one of the first nonwoven web or the second web. The nonwoven web includes a plurality of continuous spunbond crimped fibers wherein a plurality of apertures extend through the nonwoven web.

12 Claims, 72 Drawing Sheets

Related U.S. Application Data

(60) Provisional application No. 62/168,199, filed on May 29, 2015, provisional application No. 62/076,043, filed on Nov. 6, 2014, provisional application No. 62/177,405, filed on Mar. 13, 2015.

(51) Int. Cl.
| | | |
|---|---|---|
| *A61F 13/512* | (2006.01) | |
| *A61F 13/514* | (2006.01) | |
| *A61F 13/513* | (2006.01) | |
| *D04H 1/50* | (2012.01) | |
| *A61F 13/45* | (2006.01) | |
| *A61F 13/476* | (2006.01) | |
| *A61F 13/472* | (2006.01) | |
| *B32B 3/26* | (2006.01) | |
| *B32B 5/02* | (2006.01) | |
| *B32B 5/26* | (2006.01) | |
| *A61F 13/51* | (2006.01) | |

(52) U.S. Cl.
CPC .......... *A61F 13/476* (2013.01); *A61F 13/513* (2013.01); *A61F 13/5126* (2013.01); *A61F 13/5146* (2013.01); *A61F 13/51113* (2013.01); *A61F 13/51394* (2013.01); *A61F 13/51462* (2013.01); *A61F 13/51478* (2013.01); *B32B 3/266* (2013.01); *B32B 5/022* (2013.01); *B32B 5/26* (2013.01); *D04H 1/50* (2013.01); *A61F 2013/51009* (2013.01); *A61F 2013/51061* (2013.01); *A61F 2013/51117* (2013.01); *A61F 2013/51178* (2013.01); *B32B 2307/726* (2013.01); *B32B 2555/02* (2013.01)

(56) References Cited

U.S. PATENT DOCUMENTS

| | | | |
|---|---|---|---|
| 3,814,101 A | 6/1974 | Kozak |
| 3,849,845 A | 11/1974 | Obenaus |
| 3,860,003 A | 1/1975 | Buell |
| 3,886,941 A | 6/1975 | Duane et al. |
| 3,890,974 A | 6/1975 | Kozak |
| 3,911,173 A | 10/1975 | Sprague, Jr. |
| 4,323,069 A | 4/1982 | Ahr et al. |
| 4,324,246 A | 4/1982 | Mullane et al. |
| 4,327,730 A | 5/1982 | Sorensen |
| 4,573,986 A | 3/1986 | Minetola et al. |
| 4,610,678 A | 9/1986 | Weisman et al. |
| 4,629,643 A | 12/1986 | Curro et al. |
| 4,673,402 A | 6/1987 | Weisman et al. |
| 4,676,784 A | 6/1987 | Erdman et al. |
| 4,704,112 A | 11/1987 | Suzuki et al. |
| 4,741,941 A | 5/1988 | Englebert et al. |
| 4,780,352 A | 10/1988 | Palumbo |
| 4,785,996 A | 11/1988 | Ziecker et al. |
| 4,798,604 A | 1/1989 | Carter |
| 4,818,587 A | 4/1989 | Ejima et al. |
| 4,834,735 A | 5/1989 | Alemany et al. |
| 4,840,829 A | 6/1989 | Suzuki et al. |
| 4,842,666 A | 6/1989 | Werenicz |
| 4,888,231 A | 12/1989 | Angstadt |
| 5,151,092 A | 2/1992 | Buell et al. |
| 5,108,820 A | 4/1992 | Kaneko et al. |
| 5,122,407 A | 6/1992 | Yeo et al. |
| 5,147,345 A | 9/1992 | Young et al. |
| 5,234,423 A | 8/1993 | Alemany et al. |
| H1377 H | 11/1994 | Bruce |
| 5,369,858 A | 12/1994 | Gilmore et al. |
| 5,385,773 A | 1/1995 | Yau et al. |
| 5,418,045 A | 5/1995 | Pike et al. |
| 5,433,715 A | 7/1995 | Tanzer et al. |
| 5,437,653 A | 8/1995 | Gilman et al. |
| 5,456,982 A | 10/1995 | Hansen et al. |
| 5,485,662 A | 1/1996 | Hodges, Jr. et al. |
| 5,518,801 A | 5/1996 | Chappell et al. |
| 5,520,673 A | 5/1996 | Yarbrough et al. |
| 5,536,555 A | 7/1996 | Zelazoski et al. |
| 5,597,645 A | 1/1997 | Pike et al. |
| 5,605,749 A | 2/1997 | Pike et al. |
| 5,607,760 A | 3/1997 | Roe |
| 5,609,587 A | 3/1997 | Roe |
| 5,628,097 A | 5/1997 | Benson et al. |
| 5,635,191 A | 6/1997 | Roe et al. |
| 5,643,588 A | 7/1997 | Roe et al. |
| 5,660,788 A | 8/1997 | Gray et al. |
| 5,667,562 A | 9/1997 | Midkiff |
| 5,704,101 A | 1/1998 | Majors et al. |
| 5,709,735 A | 1/1998 | Midkiff et al. |
| 5,735,984 A | 4/1998 | Hoff et al. |
| H1732 H | 6/1998 | Johnson |
| 5,770,144 A | 6/1998 | James et al. |
| 5,780,155 A | 7/1998 | Ishizawa et al. |
| 5,797,894 A | 8/1998 | Cadieux et al. |
| 5,824,352 A | 10/1998 | Yang et al. |
| 5,873,968 A | 2/1999 | Pike et al. |
| 5,874,160 A | 2/1999 | Keck |
| 5,885,267 A | 3/1999 | Mishima et al. |
| 5,895,380 A | 4/1999 | Turi et al. |
| 5,897,543 A | 4/1999 | Francis |
| 5,916,661 A | 6/1999 | Benson et al. |
| 5,919,177 A | 7/1999 | Georger et al. |
| 5,941,864 A | 8/1999 | Roe |
| 5,965,468 A | 10/1999 | Marmon et al. |
| 5,968,025 A | 10/1999 | Roe et al. |
| 5,998,696 A | 12/1999 | Schone |
| 6,015,936 A | 1/2000 | Takai et al. |
| 6,030,372 A | 2/2000 | Buell et al. |
| 6,093,871 A | 7/2000 | Takai et al. |
| 6,114,595 A | 9/2000 | Moore et al. |
| 6,117,524 A | 9/2000 | Hisanaka et al. |
| 6,159,881 A | 12/2000 | Datta et al. |
| 6,168,849 B1 | 1/2001 | Braverman et al. |
| 6,203,905 B1 | 3/2001 | Pike |
| 6,206,865 B1 | 3/2001 | Chen et al. |
| 6,228,462 B1 | 5/2001 | Lee et al. |
| 6,270,623 B1 | 8/2001 | Goda et al. |
| 6,274,237 B1 | 8/2001 | Nakajima et al. |
| 6,303,208 B1 | 10/2001 | Pelkie |
| 6,410,823 B1 | 6/2002 | Daley et al. |
| 6,452,064 B1 | 9/2002 | Thoren et al. |
| 6,454,747 B1 | 9/2002 | Shimada et al. |
| 6,454,989 B1 | 9/2002 | Neely et al. |
| 6,468,626 B1 | 10/2002 | Takai et al. |
| 6,479,130 B1 | 11/2002 | Takai et al. |
| 6,498,284 B1 | 12/2002 | Roe |
| 6,506,473 B1 | 1/2003 | Hisanaka et al. |
| 6,528,439 B1 | 3/2003 | Stokes et al. |
| 6,534,149 B1 | 3/2003 | Daley et al. |
| 6,572,595 B1 * | 6/2003 | Klemp .............. A61F 13/49015 |
| | | 604/383 |
| 6,610,391 B2 | 8/2003 | Molee |
| 6,632,504 B1 | 10/2003 | Gillespie et al. |
| 6,649,547 B1 | 11/2003 | Arnold et al. |
| 6,676,646 B2 | 1/2004 | Bast et al. |
| 6,716,441 B1 | 4/2004 | Osborne et al. |
| 6,846,561 B1 | 1/2005 | Gownder et al. |
| 6,849,065 B2 | 2/2005 | Schmidt et al. |
| 6,849,319 B2 | 2/2005 | Cree et al. |
| 6,996,851 B2 | 2/2006 | Nordness et al. |
| 7,005,558 B1 | 2/2006 | Johansson et al. |
| 7,033,340 B1 | 4/2006 | Muscat et al. |
| 7,037,569 B2 | 5/2006 | Curro et al. |
| 7,118,639 B2 | 10/2006 | DeLucia et al. |
| 7,371,919 B1 | 5/2008 | Busam et al. |
| 7,964,801 B2 | 6/2011 | Shih |
| 8,022,267 B2 | 9/2011 | Hellstrom et al. |
| 8,186,296 B2 | 5/2012 | Brown et al. |
| 8,226,625 B2 | 7/2012 | Turner et al. |
| 8,226,626 B2 | 7/2012 | Turner et al. |
| 8,231,595 B2 | 7/2012 | Turner et al. |
| 8,388,594 B2 | 3/2013 | Turner et al. |
| 8,454,571 B2 * | 6/2013 | Rezai ................... A61F 13/581 |
| | | 604/387 |

(56) References Cited

U.S. PATENT DOCUMENTS

| | | |
|---|---|---|
| 2001/0005540 A1 | 6/2001 | Hisanaka et al. |
| 2001/0053901 A1 | 12/2001 | Mizutani et al. |
| 2002/0013563 A1 | 1/2002 | Lassen et al. |
| 2002/0022817 A1 | 2/2002 | Ishikawa |
| 2002/0028624 A1 | 3/2002 | Mizutani et al. |
| 2002/0062113 A1 | 5/2002 | Thomas et al. |
| 2002/0062115 A1 | 5/2002 | Wada et al. |
| 2002/0081927 A1 | 6/2002 | Maldonado et al. |
| 2002/0089079 A1 | 7/2002 | Shelley et al. |
| 2002/0098762 A1 | 7/2002 | Shelley et al. |
| 2002/0172371 A1 | 11/2002 | Baker et al. |
| 2002/0182396 A1 | 12/2002 | DeLucia et al. |
| 2003/0003269 A1 | 1/2003 | Lee et al. |
| 2003/0004481 A1 | 1/2003 | Matsuoka et al. |
| 2003/0011099 A1 | 1/2003 | Maldonado et al. |
| 2003/0021951 A1 | 1/2003 | Desai et al. |
| 2003/0077430 A1 | 4/2003 | Grimm et al. |
| 2003/0082377 A1 | 5/2003 | Hartzog et al. |
| 2003/0082979 A1 | 5/2003 | Bean et al. |
| 2003/0104748 A1 | 6/2003 | Brown et al. |
| 2003/0109839 A1 | 6/2003 | Costea et al. |
| 2003/0145517 A1 | 8/2003 | Miller |
| 2003/0149412 A1 | 8/2003 | Damaghi et al. |
| 2004/0005456 A1 | 1/2004 | Takeuchi |
| 2004/0043189 A1 | 3/2004 | Huang |
| 2004/0067709 A1 | 4/2004 | KIshine et al. |
| 2004/0092902 A1 | 5/2004 | Hoffman et al. |
| 2004/0116027 A1 | 6/2004 | Termonia et al. |
| 2004/0118811 A1 | 6/2004 | Stone et al. |
| 2004/0122396 A1 | 6/2004 | Maldonado et al. |
| 2004/0127128 A1 | 7/2004 | Thomas |
| 2004/0127875 A1 | 7/2004 | Hammons et al. |
| 2004/0161586 A1 | 8/2004 | Cree et al. |
| 2004/0162536 A1 | 8/2004 | Becker et al. |
| 2004/0181199 A1 | 9/2004 | Moberg-Alehammar et al. |
| 2004/0209042 A1 | 10/2004 | Peacock |
| 2005/0025964 A1 | 2/2005 | Fairbanks et al. |
| 2005/0026527 A1 | 2/2005 | Schmidt et al. |
| 2005/0027270 A1 | 2/2005 | Cree et al. |
| 2005/0096614 A1 | 5/2005 | Perez et al. |
| 2005/0148971 A1 | 7/2005 | Kuroda et al. |
| 2005/0175385 A1 | 8/2005 | Cho et al. |
| 2005/0202208 A1 | 9/2005 | Kelly |
| 2005/0233140 A1 | 10/2005 | Oh et al. |
| 2005/0244619 A1 | 11/2005 | Kauschke et al. |
| 2005/0256475 A1 | 11/2005 | Komatsu et al. |
| 2005/0288647 A1 | 12/2005 | Ellingson et al. |
| 2006/0019063 A1 | 1/2006 | Kelly |
| 2006/0068176 A1 | 3/2006 | Zafiroglu et al. |
| 2006/0069361 A1 | 3/2006 | Olson |
| 2006/0087053 A1 | 4/2006 | O'Donnell et al. |
| 2006/0135026 A1 | 6/2006 | Arendt et al. |
| 2006/0135923 A1 | 6/2006 | Boggs et al. |
| 2006/0141885 A1 | 6/2006 | Cobbs et al. |
| 2007/0015427 A1 | 1/2007 | Yanagawase et al. |
| 2007/0021022 A1 | 1/2007 | Kishine et al. |
| 2007/0036943 A1 | 2/2007 | Hirose et al. |
| 2007/0048498 A1 | 3/2007 | Cree |
| 2007/0073254 A1 | 3/2007 | Ponomarenko et al. |
| 2007/0088307 A1 | 4/2007 | Arizti et al. |
| 2007/0135787 A1 | 6/2007 | Raidel et al. |
| 2007/0256286 A1 | 11/2007 | Ngai |
| 2007/0275622 A1 | 11/2007 | Masuda et al. |
| 2008/0138574 A1 | 6/2008 | Maschino et al. |
| 2008/0143009 A1 | 6/2008 | Kurian et al. |
| 2008/0294135 A1 | 11/2008 | Hara et al. |
| 2008/0294138 A1 | 11/2008 | Andersson et al. |
| 2008/0312622 A1 | 12/2008 | Hundorf et al. |
| 2008/0317984 A1 | 12/2008 | Yamashita et al. |
| 2009/0030390 A1 | 1/2009 | Hammons et al. |
| 2009/0030391 A1 | 1/2009 | Hammons et al. |
| 2009/0082746 A1 | 3/2009 | Thomas et al. |
| 2009/0104831 A1 | 4/2009 | Bomemann et al. |
| 2009/0124155 A1 | 5/2009 | Tiemeier et al. |
| 2009/0131896 A1 | 5/2009 | Ebitsuka et al. |
| 2009/0233046 A1 | 9/2009 | Iulianetti |
| 2009/0247978 A1 | 10/2009 | Boissier |
| 2009/0299316 A1 | 12/2009 | Seyler |
| 2009/0318050 A1 | 12/2009 | Okaya |
| 2010/0004615 A1 | 1/2010 | Boissier |
| 2010/0019415 A1 | 1/2010 | Stone et al. |
| 2010/0035014 A1 | 2/2010 | Hammons et al. |
| 2010/0036338 A1 | 2/2010 | Hammons et al. |
| 2010/0036346 A1 | 2/2010 | Hammons et al. |
| 2010/0105273 A1 | 4/2010 | Motomura et al. |
| 2010/0130952 A1 | 5/2010 | Murai |
| 2010/0159770 A1 | 6/2010 | Walser et al. |
| 2010/0164733 A1 | 7/2010 | Ales et al. |
| 2010/0196653 A1 | 8/2010 | Curro et al. |
| 2010/0227130 A1 | 9/2010 | Takahashi |
| 2010/0233438 A1 | 9/2010 | Stone et al. |
| 2010/0252138 A1 | 10/2010 | Tseng |
| 2010/0261399 A1 | 10/2010 | Katsuya et al. |
| 2010/0280471 A1 | 11/2010 | Shah |
| 2010/0330326 A1 | 12/2010 | Turner et al. |
| 2011/0106036 A1 | 5/2011 | Stahl et al. |
| 2011/0184370 A1 | 7/2011 | Seyler et al. |
| 2011/0189915 A1 | 8/2011 | Morimoto et al. |
| 2011/0196330 A1 | 8/2011 | Hammons et al. |
| 2011/0236683 A1 | 9/2011 | Takebe et al. |
| 2011/0305870 A1 | 12/2011 | Curro et al. |
| 2011/0313385 A1 | 12/2011 | Hammons et al. |
| 2012/0003423 A1 | 1/2012 | Cree |
| 2012/0095426 A1 | 4/2012 | Visscher et al. |
| 2012/0121882 A1 | 5/2012 | Okaya |
| 2012/0171913 A1 | 7/2012 | Fox et al. |
| 2012/0296304 A1 | 11/2012 | Choo et al. |
| 2013/0012898 A1 | 1/2013 | Bergendahl et al. |
| 2013/0029555 A1 | 1/2013 | Morimoto |
| 2014/0066873 A1 | 3/2014 | Kawakami et al. |
| 2014/0087130 A1 | 3/2014 | Seyler et al. |
| 2014/0088535 A1 | 3/2014 | Xu et al. |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0324009 A1 | 10/2014 | Lee et al. |
| 2014/0336605 A1 | 11/2014 | Hardie et al. |
| 2016/0166443 A1 | 6/2016 | Arora et al. |
| 2016/0167334 A1 | 6/2016 | Arora et al. |

FOREIGN PATENT DOCUMENTS

| | | |
|---|---|---|
| CN | 2567250 | 8/2003 |
| CN | 1772984 | 5/2006 |
| CN | 2897211 | 5/2007 |
| CN | 201505226 | 6/2010 |
| CN | 201618014 | 11/2010 |
| CN | 201855363 | 6/2011 |
| CN | 101940514 | 12/2013 |
| DE | 2806401 | 8/1979 |
| DE | 19647459 | 5/1998 |
| DE | 19846857 | 10/1998 |
| EP | 0165807 | 12/1985 |
| EP | 0330212 | 8/1989 |
| EP | 0359501 | 3/1990 |
| EP | 0495212 | 7/1992 |
| EP | 0535579 | 4/1993 |
| EP | 0589224 | 3/1994 |
| EP | 0691427 A1 | 1/1996 |
| EP | 0696655 A1 | 2/1996 |
| EP | 0761846 A2 | 3/1997 |
| EP | 0545423 | 8/1997 |
| EP | 0749737 | 11/1999 |
| EP | 0749738 | 11/1999 |
| EP | 0749736 | 1/2000 |
| EP | 0983758 | 3/2000 |
| EP | 0749739 | 11/2000 |
| EP | 1086676 | 3/2001 |
| EP | 0749740 | 12/2001 |
| EP | 1022007 | 3/2006 |
| EP | 2110472 A1 | 10/2009 |
| EP | 1988793 | 7/2014 |

(56) References Cited

FOREIGN PATENT DOCUMENTS

| | | |
|---|---|---|
| EP | 2347872 | 1/2015 |
| GB | 2103933 | 9/1985 |
| GB | 2225724 | 7/1992 |
| GB | 2296464 | 7/1996 |
| GB | 2310606 | 9/1999 |
| JP | 04327256 A | 11/1992 |
| JP | H042327211 A | 11/1992 |
| JP | H05195406 A | 8/1993 |
| JP | 06038818 | 2/1994 |
| JP | H07216653 A | 8/1995 |
| JP | 2587116 | 3/1997 |
| JP | 09059823 | 3/1997 |
| JP | 09310226 A | 12/1997 |
| JP | H10272152 | 10/1998 |
| JP | 111 52624 A | 6/1999 |
| JP | 2002180331 | 6/2002 |
| JP | 2003003334 A | 1/2003 |
| JP | 2004041870 A | 2/2004 |
| JP | 2005200795 | 7/2005 |
| JP | 2008127705 | 6/2008 |
| JP | 2007174880 A | 7/2008 |
| JP | 2008179939 A | 8/2008 |
| JP | 2010269029 | 12/2010 |
| JP | 2011135979 | 7/2011 |
| JP | 2011239835 | 12/2011 |
| JP | 2012050548 | 3/2012 |
| JP | 2013011051 | 1/2013 |
| JP | 2014034741 A | 2/2014 |
| KR | 20010064584 | 7/2001 |
| KR | 20030089593 | 11/2003 |
| KR | 100648560 B1 | 11/2006 |
| WO | WO199110415 | 7/1991 |
| WO | WO199311726 | 6/1993 |
| WO | WO199315701 | 8/1993 |
| WO | WO199513773 | 5/1995 |
| WO | WO199517867 | 7/1995 |
| WO | WO199610481 | 4/1996 |
| WO | WO199611107 | 4/1996 |
| WO | WO199619313 | 6/1996 |
| WO | WO199621759 A1 | 7/1996 |
| WO | WO1199702133 | 1/1997 |
| WO | WO199703818 | 2/1997 |
| WO | WO1998053896 A1 | 12/1998 |
| WO | WO1999060975 | 12/1999 |
| WO | WO200001334 | 1/2000 |
| WO | WO200028929 | 5/2000 |
| WO | WO2000062826 | 10/2000 |
| WO | WO200172251 | 10/2001 |
| WO | WO2002100632 | 12/2002 |
| WO | WO2003008688 | 1/2003 |
| WO | WO2003015681 A1 | 2/2003 |
| WO | WO2003071019 | 8/2003 |
| WO | WO2004009009 | 1/2004 |
| WO | WO2004058497 | 7/2004 |
| WO | WO2004098474 | 11/2004 |
| WO | WO2010141309 | 12/2010 |
| WO | WO2011017285 A1 | 2/2011 |
| WO | WO2012052172 A1 | 4/2012 |
| WO | WO2013114231 | 8/2013 |
| WO | WO2014022652 | 2/2014 |
| WO | WO2014108106 A1 | 7/2014 |

OTHER PUBLICATIONS

International Search Report and Written Opinion for PCT/US2015/059249 dated Feb. 10, 2016.
All Office Actions, U.S. Appl. No. 14/933,015.
All Office Actions, U.S. Appl. No. 14/933,021.
All Office Actions, U.S. Appl. No. 14/933,024.
All Office Actions, U.S. Appl. No. 14/933,030.
All Office Actions, U.S. Appl. No. 14/933,034.
All Office Actions, U.S. Appl. No. 14/933,039.

* cited by examiner

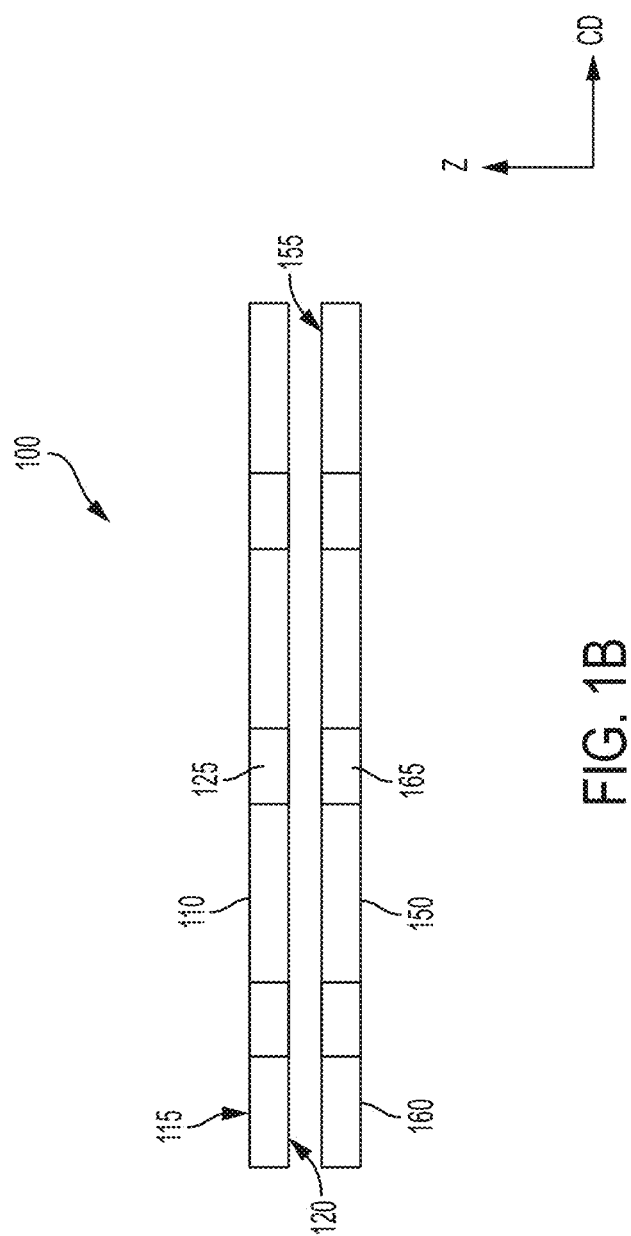

CRIMPED FIBER SPUNBOND NONWOVEN WEBS / LAMINATES

FIELD OF THE INVENTION

The disclosure herein relates generally to a crimped fiber spunbond nonwoven web and an article incorporating the nonwoven web.

BACKGROUND OF THE INVENTION

Topsheets of disposable absorbent articles perform a valuable function. Topsheets are typically the interface between the disposable absorbent article and the user. As such, topsheets should be tactilely appealing to the user. Additionally, particularly in the context of hygiene articles, topsheets can mask staining caused by menses and/or urine. If the topsheet does not successfully mask the staining caused by menses/urine, the user may be left with the impression that the disposable absorbent article did not perform well. Also, in some applications, topsheets with the ability to acquire liquid insults rapidly to reduce the likelihood of leakage can be desired.

There are a variety of topsheets known in the art. For example, in some conventional feminine hygiene articles, topsheets may comprise a film. Films are typically desirable because they provide good masking benefits regarding menses/urine staining. However, without substantial processing, films can provide the user with a displeasing tactile sensation. And, even with the substantial processing, some users describe a film topsheet as having a "plastic feel" which some users find displeasing. Additionally, films can sometimes leave residual liquid, e.g. menses and/or urine, in contact with the skin of the wearer which can exacerbate any unpleasant feelings as well as create a perception of "uncleanliness" in the mind of the user.

Other conventional feminine hygiene articles comprise nonwoven topsheets. Nonwoven topsheets can provide a soft feel to the user; however, nonwoven topsheets typically do not have good masking capability with regard to menses/urine stains. Unfortunately, nonwovens which do provide good masking properties often provide less than adequate liquid performance.

Based on the foregoing, there is a need for a topsheet which can provide a soft feel to the user while also providing good acquisition of liquids insults. Additionally, a topsheet which can mask menses/urine stains in conjunction with the foregoing or independently thereof, would be beneficial.

SUMMARY OF THE INVENTION

Disclosed herein are nonwoven webs and nonwoven laminates which can be used as a topsheet of a disposable absorbent article as well as other components of an absorbent article. The nonwoven webs/nonwoven laminate of the present invention, when utilized as a topsheet of a feminine hygiene article, can provide a soft feel to the user and can provide good acquisition of menses/urine insults.

In some forms, nonwoven laminates of the present invention comprise a first nonwoven web with continuous spunbond crimped fibers and a second web joined to the first nonwoven web. A plurality of apertures extend through at least one of the first nonwoven web or the second web. Additional forms include a nonwoven web comprising a plurality of continuous spunbond crimped fibers, wherein a plurality of apertures extend through the nonwoven web.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1B is a schematic representation of a nonwoven laminate of the present invention shown in an exploded cross sectional view of the nonwoven laminate;

FIG. 7A top view of a spunbond crimped fiber nonwoven web;

DETAILED DESCRIPTION OF THE INVENTION

Figure 1A:
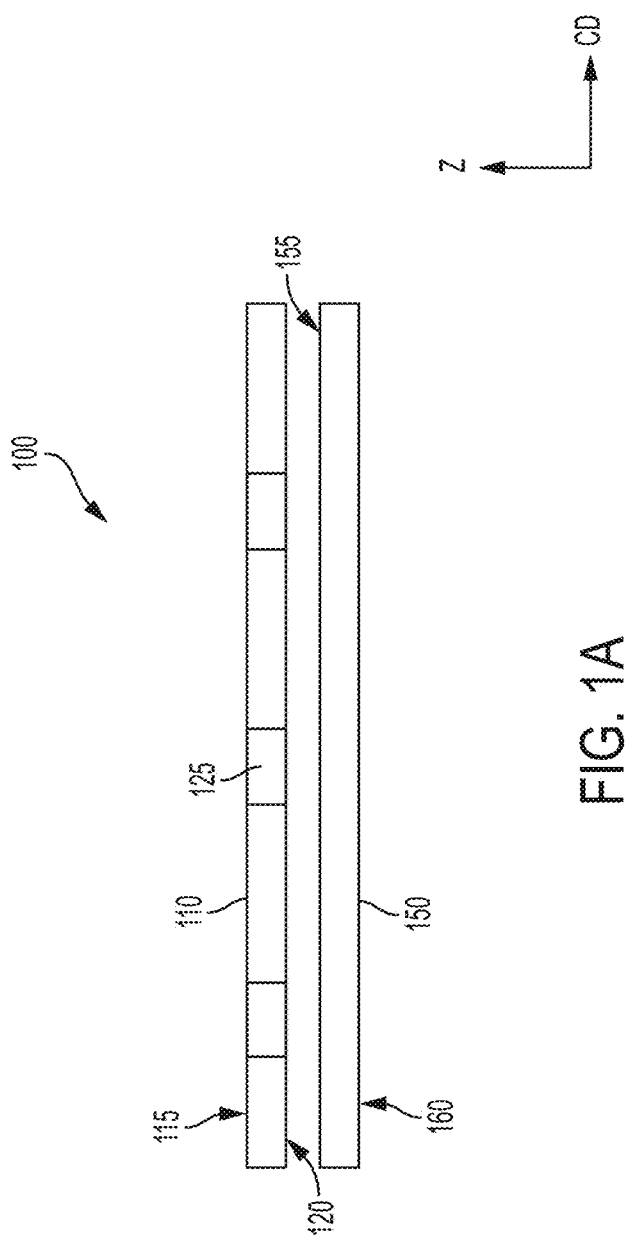
FIG. 1A is a schematic representation of a nonwoven laminate of the present invention shown in an exploded cross sectional view of the nonwoven laminate.

The term "fibrils" refers to projections, elongate projections, bumps that extend outwardly from a surface or generally radially outwardly from an outer surface of a fiber. In some instances, the projections, elongate projections, or bumps may extend radially outwardly relative to a longitudinal axis of the fiber. Radially outwardly means in the range of 1 to 89 degrees relative to the longitudinal axis. In still other instances, the projections, elongate projections, or bumps may extend radially outwardly from a surface of a fiber at least in a longitudinal central third of the fiber. The projections, elongate projections, or bumps comprise, consist of, or consist essentially of (e.g., 51% to 100% or 51% to 99%), melt additives. The projections, elongate projections, or bumps grow from the fibers post-nonwoven substrate formation only after a time period (e.g., 6-100 hours) under ambient conditions. Fibrils can be viewed using an SEM at, at least 1,000 times magnification.

As used herein, the term "nonwoven web" refers to a web having a structure of individual fibers or threads which are interlaid, but not in a repeating pattern as in a woven or knitted fabric, which do not typically have randomly oriented fibers. The basis weight of nonwoven fabrics is usually expressed in grams per square meter (gsm). The basis weight of a nonwoven web/laminate is the combined basis weight of the constituent layers and any other added components. Fiber diameters are usually expressed in microns; fiber size can also be expressed in denier, which is a unit of weight per length of fiber.

As used herein "philic" and "phobic" have meanings as well established in the art with respect to the contact angle of a referenced liquid on the surface of a material. Thus, a material having a liquid contact angle of greater than about 75 degrees is considered phobic, and a material having a liquid contact angle of less than about 75 degrees is considered philic.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 8 and 40 microns.

As used herein, "spunbond crimped fibers" refers to bi-component fibers which may be configured in a side-by-side, core-eccentric sheath or other suitable configuration. The selection of suitable resin combinations and bi-component fiber configuration can lead to a helical crimp or curl generated in the fibers. The crimp may occur spontaneously during the spinning or laydown process, on its own after web formation. In some instances, the webs may require an additional step (e.g. heating or mechanical deformation) to induce the fibers to crimp.

By "substantially randomly oriented" it is meant that, due to processing conditions of a nonwoven layer, there may be a higher amount of fibers oriented in the machine direction (MD) than the cross direction (CD), or vice-versa.

As used herein, the term "absorbent article", refers to devices which absorb and contain body exudates, and, more specifically, refers to devices which are placed against or in proximity to the body of the wearer to absorb and contain the various bodily exudates discharged from the body. The term absorbent article includes, but is not limited to, diapers, pants, training pants, adult incontinence products, sanitary napkins, tampons, wipes, and liners. The term "absorbent article" also encompasses cleaning or dusting pads or substrates that have some absorbency.

The present invention pertains to crimped fiber spunbond nonwoven webs that are suitable for use in a disposable absorbent article. The present invention also pertains to nonwoven laminates which comprise at least one layer which is a crimped fiber spunbond nonwoven web. As discussed hereafter, the crimped fiber spunbond nonwoven webs/nonwoven laminates of the present invention may comprise caps and/or tufts or other out-of-plane deformations which provide a softness benefit, a masking benefit and/or a fluid handling benefit. Optionally, the crimped fiber spunbond nonwoven webs or other webs of a nonwoven laminate of the present invention may comprise an additive either applied post formation and/or blended into the fiber (discussed hereafter) so that the additive is present during the formation of the constituent fibers. The inventors have found that these additives can provide masking benefits such that menses/urine stains are less visible to a user of the disposable absorbent article. Additionally, the inventors have found that the additives can provide the treated web with better draining capability such that less fluid sticks to the fibers and/or interstices between intersecting fibers. This draining capability can also result in better masking of urine/menses stains. Also, the inventors have found that the additives can provide the crimped fiber spunbond nonwoven web or other webs of a nonwoven laminate of the present invention with improved acquisition time for liquid insults which reduces the likelihood of leaking. Some suitable additives contemplated are with regard to hydrophobicity, hydrophilicity, softness, reduction of coefficient of friction, or the like. Some suitable additives are discussed herein.

Nonwoven Webs/Laminates

A nonwoven web constructed in accordance with the present invention comprises spunbond crimped fibers. In other forms of the present invention, crimped fiber spunbond webs of the present invention may comprise multiple substrates. For example, a crimped fiber spunbond web of the present invention may be made via a spunbond process comprising multiple spinbeams. In such forms, a first substrate created from a first spinbeam may comprise continuous spunbond fibers while a second substrate created from a second spinbeam may comprise continuous crimped spunbond fibers. The method of making the crimped fiber spunbond webs and laminates of the present invention is discussed in additional detail hereafter.

Laminates constructed in accordance with the present invention may comprise at least two webs (layers) at least one of which is a crimped fiber spunbond nonwoven web. In other forms, the laminate may comprise a film web and a crimped fiber spunbond nonwoven web. In other forms, the laminate may comprise a crimped fiber spunbond nonwoven web and another nonwoven web.

The crimped fiber spunbond nonwoven webs and nonwoven laminates of the present invention have a machine direction (MD) (perpendicular to the plane of the sheets showing FIGS. 1A, 1B, and 2A-2C), a cross machine direction (CD), and a Z direction, as is commonly known in the art of web manufacture. Each of the nonwoven laminates of the present invention comprises at least two nonwoven webs which are referred to herein as generally planar, two-dimensional webs. Crimped fiber spunbond nonwoven webs are also referred to herein as generally planar, two-dimensional webs.

FIG. 1A shows an exploded cross sectional view of a nonwoven laminate 100 of the present invention. The nonwoven laminate 100 comprises a first layer 110 having a first surface 115 and a second surface 120, each of which are generally planar. The nonwoven laminate 100 further comprises a second layer 150A having a first surface 155 and a second surface 160 each of which are generally planar. The first surfaces 115 and 155 of the first layer 110 and the second layer 150, respectively, can be body-facing surfaces and the second surfaces 120 and 160 of the first layer 110 and the second layer 150A, respectively, can be garment-facing surfaces.

At least one of the first layer or second layer comprises a crimped fiber spunbond nonwoven web. For example, the first layer may comprise spunbond crimped fibers while the second layer does not comprise spunbond crimped fibers. In another example, the first layer may not comprise spunbond crimped fibers while the second layer comprises spunbond crimped fibers. In yet another example, both the first layer and the second layer may comprise spunbond crimped fibers.

The first layer 110 may comprise a first plurality of apertures 125 that extend through the first layer 110 from the first surface 115 to the second surface 120. As shown, the second layer 150, in some forms, may not include apertures. However, as shown in FIG. 1B, the second layer 150 may comprise a second plurality of apertures 165. As shown, the first plurality of apertures 125 and the second plurality of apertures 165 may be substantially aligned.

Substantially aligned, in the context of the apertures herein, means that the majority of the first plurality of apertures, i.e. at least 51%, comprise a reciprocal aperture in the second layer 150, and of those apertures in the first layer 110 comprising a reciprocal aperture in the second layer 150, at least 51% of the open area of each of those apertures in the first layer 110 corresponds to open area of an aperture in the second layer 150. In some forms, the first plurality of apertures 125 and the second plurality of apertures 165 are created contemporaneously and may be coterminous. Still in other forms, the first plurality of apertures 165 and the second plurality of apertures 165 may be produced separately such that a portion of the second layer 150 may be exposed through at least one of the first plurality of apertures 150 and vice versa. Some suitable aperturing processes are discussed hereafter.

The first layer 110 and the second layers 150, may be joined about the periphery of each of the first plurality of apertures 125. For example, for those processes where apertures are created by melting fibers of the first layer 110 typically an aperture periphery is formed. Additionally during the melting, the melted fiber material can form bonds with surrounding fibers including the fibers of the second layer 150. The same can occur where both the first layer 110 and the second layer 150 comprise apertures. In such forms, the first layer 110 and the second layer 150 are attached to one another about at least a portion of the periphery of each of the second plurality of apertures 165. In some forms, the first layer 110 and the second layer 150 are attached to one another about at least a portion of the periphery of each of the first plurality of apertures 125. One of the benefits of utilizing a crimped fiber spunbond nonwoven web is that the melted fibers are less noticeable with the higher caliper of the crimped fiber spunbond nonwoven web.

The nonwoven laminate 100 of FIGS. 1A and 1B can provide a soft feel to a user of an absorbent article incorporating the nonwoven laminate 100 as the topsheet of the absorbent article. An additional softness benefit, masking benefit and/or fluid handling benefit can be gained by the out-of-plane deformations described with regard to FIGS. 2A-2C.

Figure 2A:
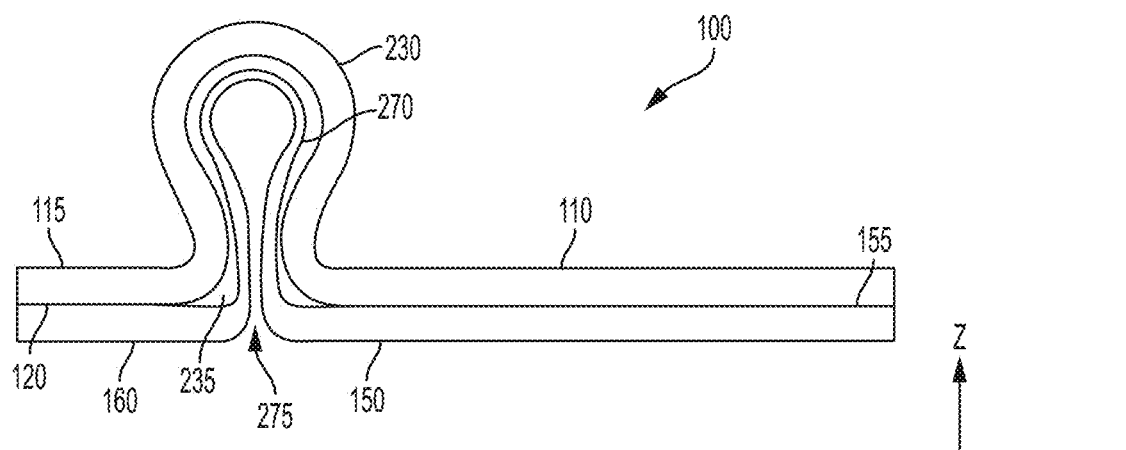
FIG. 2A is a schematic representation of a nonwoven laminate of the present invention shown in cross section.

With regard to FIG. 2A, a schematic representation of the nonwoven laminate 100 constructed in accordance with the present invention is shown. In some forms of the present invention, the first layer 110 may additionally comprise a first plurality of discontinuities 235 in the second surface 120 of the first layer 110. The first plurality of discontinuities 235 are formed when localized areas of constituent material of the first layer 110 are urged in the Z-direction such that the constituent material of the first layer 110 is disposed superjacent to the first surface 115 of the first layer 110. The disposition of the constituent material, may, in some forms, create an out-of-plane deformation, e.g. a cap 230. The first layer 110 may comprise a plurality of caps 230 positioned above the first surface 115. Each of the plurality of caps 230 can partially overlie at least one of the first plurality of discontinuities 235. For example, a first cap may at least partially overlay a first discontinuity, and a second cap may at least partially overlay a second discontinuity and so on. Caps 230 are discussed in additional detail hereafter.

Similarly, the second surface 160 of the second layer 150 may comprise a second plurality of discontinuities 275. The second plurality of discontinuities 275 can be formed as provided above with regard to the first plurality of discontinuities 235 in the first layer 110. Namely, localized areas of constituent material of the second layer 150 are urged in the Z-direction such that these localized areas of constituent material are disposed superjacent to the first surface 155 of the second layer 150. In some forms, this Z-direction urging also forces the constituent material of the second layer 150 to extend through the first plurality of discontinuities 235 in the second surface 120 of the first layer 110. The urging of the constituent material of the second layer 150 can also form an out-of-plane deformation, e.g. a tuft 270. Each tuft 270 may extend through a corresponding discontinuity 235 in the first layer 110.

Figure 2B:
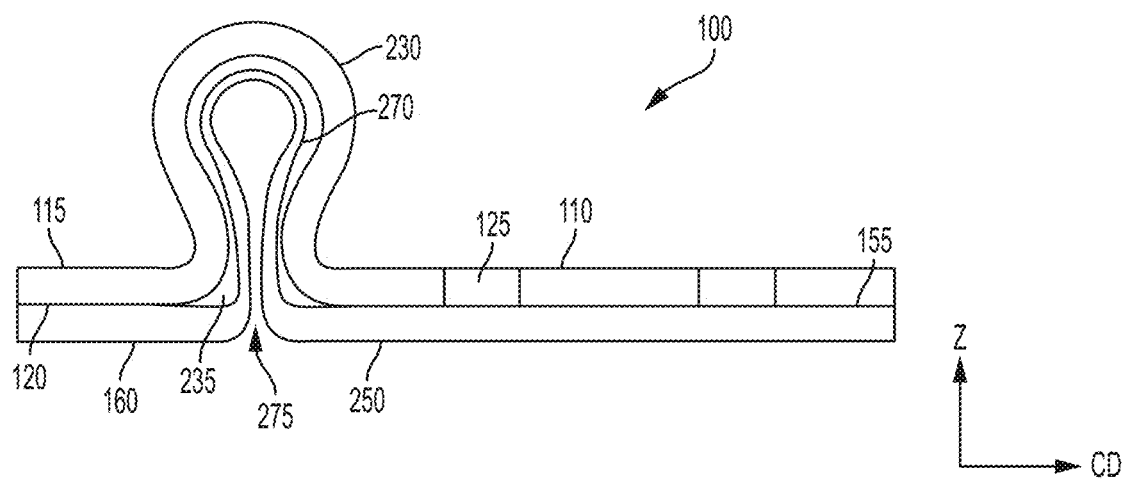
FIG. 2B is a schematic representation of a nonwoven laminate of the present invention shown in cross section.
Figure 2C:
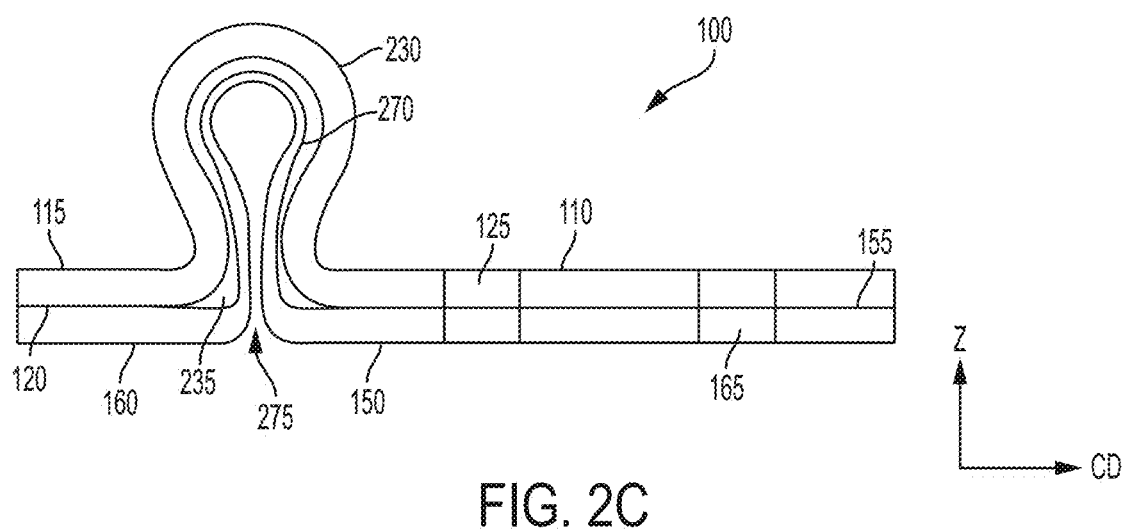
FIG. 2C is a schematic representation of a nonwoven laminate of the present invention shown in cross section.

As shown in FIG. 2B, the first layer 110 may in some forms comprise the first plurality of apertures 125 in the first layer 110. Similarly, with regard to FIG. 2C, the nonwoven laminate 100 may comprise the second layer 150 which comprises the second plurality of apertures 165. Additional forms are contemplated where the second layer 150 comprises apertures in the absence of apertures in the first layer 110.

Figure 3:
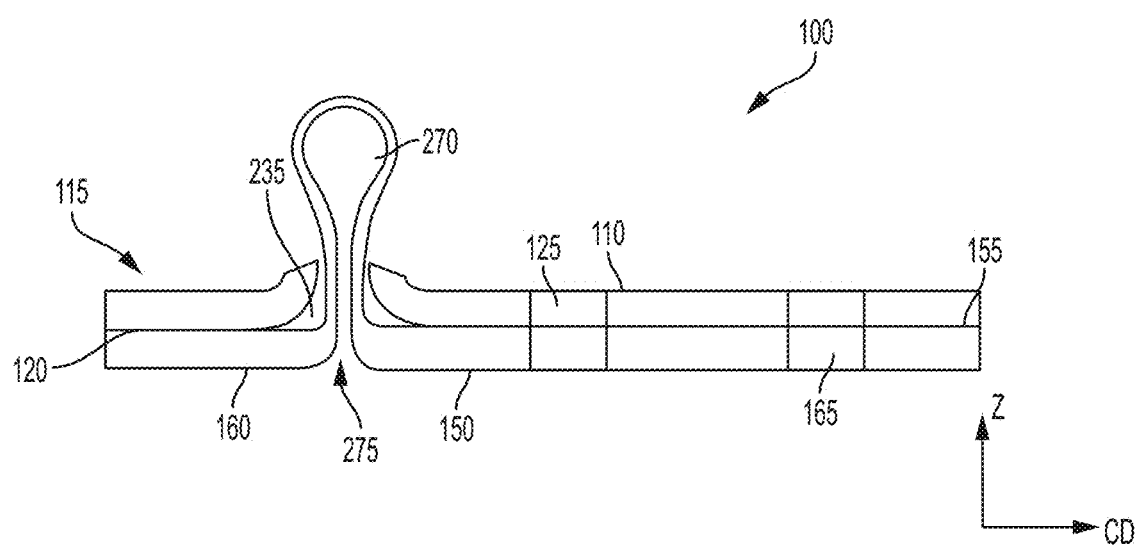
FIG. 3 is a schematic representation of a nonwoven laminate of the present invention shown in cross section.
Figure 4:
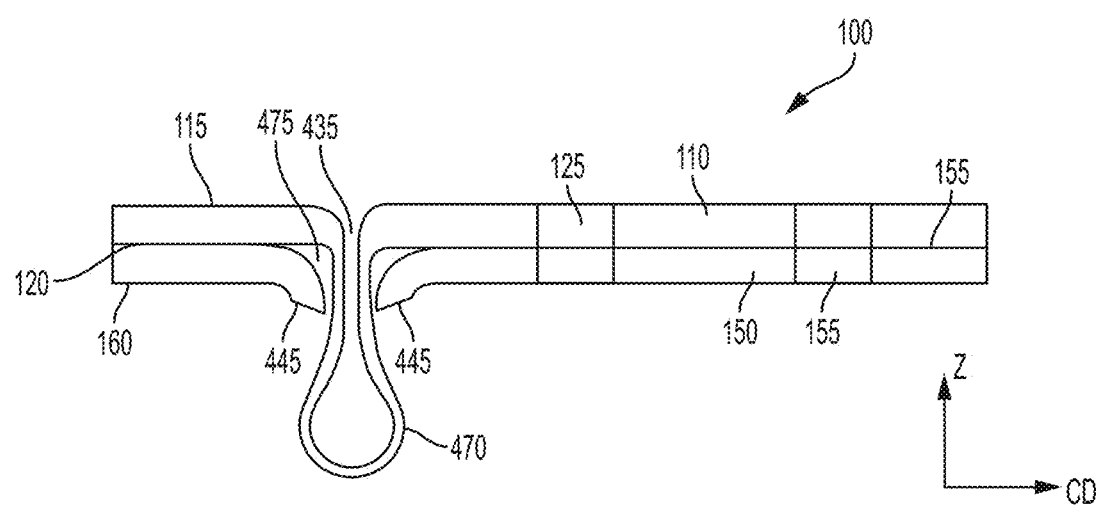
FIG. 4 is a schematic representation of a nonwoven laminate of the present invention shown in cross section.
Figure 5:
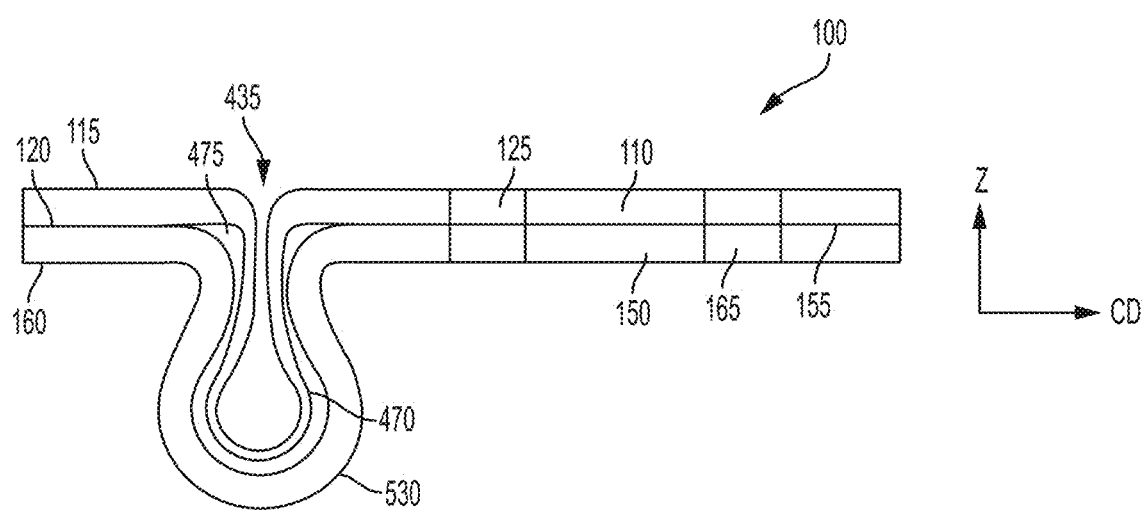
FIG. 5 is a schematic representation of a nonwoven laminate of the present invention shown in cross section.

Additional arrangements of caps and/or tufts are provided with respect to FIGS. 3-5. With regard to FIG. 3, the first layer 110, in some forms may not form a cap with the Z-direction urging described heretofore. In such forms, the constituent material, e.g. fibers, of the first layer 110 may break during the urging which allows the tuft 270 to be exposed through the first layer 110. In other forms, regarding FIG. 4, the nonwoven laminate 100 may comprise a first plurality of discontinuities 435. The first plurality of discontinuities 435 are formed when localized areas of constituent fibers of the first layer 110 are urged in the negative Z-direction such that the constituent material are disposed subjacent to the first surface 115 of the first layer 110 thereby forming out-of-plane deformations, e.g. tufts 470. In some forms, the tufts 470 may extend beyond the second surface 160 of the second layer 150 such that at least a portion of the tuft 470 is subjacent to the second surface 160.

The second layer 150 may comprise a second plurality of discontinuities 475. As shown, each of the plurality of tufts 470 may extend through each of the second plurality of discontinuities 475. The second plurality of discontinuities 475 may be created when localized areas of constituent material, e.g. fibers, of the second layer 150 are urged in the negative Z-direction such that the constituent material in the localized areas are disposed subjacent to the first surface 155 of the second layer 150. However, instead of forming a cap 230 (shown in FIGS. 2A-2C), the urging in the negative Z-direction of the constituent material of the second layer 150 may be such that a plurality of fibers/material break thereby forming the second plurality of discontinuities 475. Each tuft 470 extends through a corresponding discontinuity in the second layer 450. As shown, tufts 470 may be uncovered by a corresponding cap formed by the constituent fibers of the second layer 450.

With regard to FIG. 5, the disposition of the constituent fibers/material of the second layer 150 may form an out-of-plane deformation, e.g. a cap 530. The caps 530 may extend below the second surface 160. Each of the plurality of caps 530 can partially underlie at least one of the second plurality of discontinuities 475. For example, a first cap at least partially underlies a first discontinuity, and a second cap at least partially underlies a second discontinuity and so on.

Each of the first layers and second layers described herein may comprise substantially randomly oriented fibers. For those nonwoven laminates 100 described heretofore which comprise both tufts and caps, tufts need not necessarily be covered by a corresponding cap. For example, in some nonwoven laminates 100, at least 50% of tufts comprise a corresponding cap which substantially covers their respective tuft. In other examples, more than 75% of tufts of a nonwoven laminate 100 may comprise a corresponding cap. By "substantially covers" it is meant that more than 51% of the exterior surface of the tuft is covered by a corresponding cap.

Other exemplary laminates in accordance with the present invention include a first layer comprising a film and a second layer which comprises a crimped fiber spunbond web. In another example, the first layer may comprise a crimped fiber spunbond nonwoven web while the second layer comprises a film. In yet another example the first layer may comprise a crimped fiber spunbond nonwoven web and the second layer may comprise a nonwoven web. In such forms, the second layer may comprise a crimped fiber spunbond nonwoven web. Or, the second layer may comprise a nonwoven web which is spunbond sans spunbond crimped fibers. Or, the second layer may comprise a nonwoven web which is carded, meltblown, etc. The out-of-plane deformations described herein may be provided on any of the laminates of the present invention described herein.

Additionally, the inventors have found that when spunbond crimped fibers are utilized, the out-of-plane deformations described herein take on very different configurations. The configuration differences are highlighted with regard to FIGS. 6A-6C through FIG. 9B.

Figure 6A:
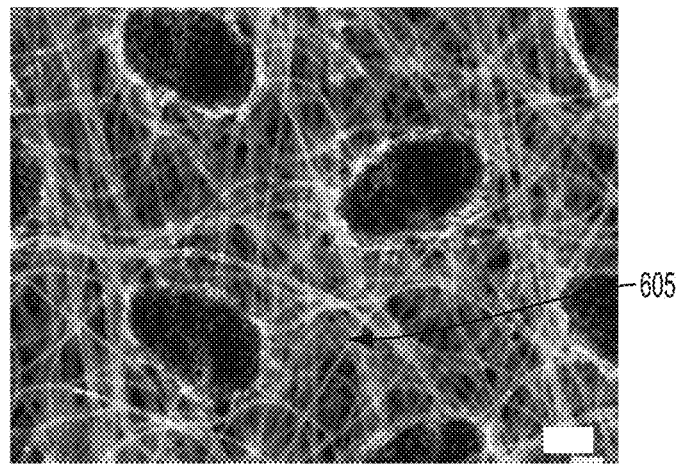
FIG. 6A is a photomicrograph of a portion of a spunbond nonwoven web showing a top view of the spunbond nonwoven web.
Figure 6B:
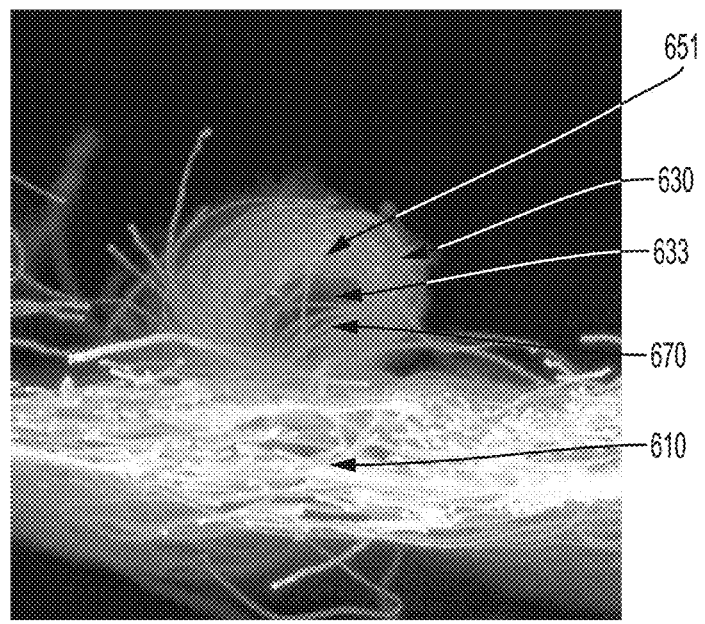
FIG. 6B is a photomicrograph of a laminate comprising two layers of the nonwoven of FIG. 6A showing a side view of a cap and tuft formed therefrom.
Figure 6C:
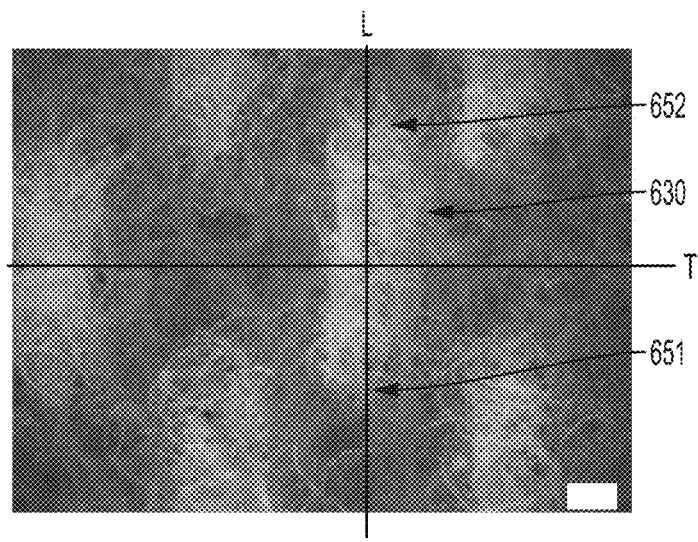
FIG. 6C is a photomicrograph showing a top view of the laminate of FIG. 6B.

FIGS. 6A-6C illustrate tufts which may be formed with nonwoven layers comprising extensible fibers. Shown in FIG. 6A is a spunbond nonwoven web 605—no spunbond crimped fibers. FIG. 6B shows a nonwoven laminate 610 comprising two layers of the spunbond nonwoven web shown in FIG. 6A—again, no spunbond crimped fibers. Each of the layers comprises bi-component, extensible fibers but neither comprises crimped fiber spunbond nonwoven webs. As shown, the laminate 610 comprises a plurality of caps 630 and tufts 670.

Regarding FIG. 6C, caps and tufts alike can comprise a plurality of looped fibers that are substantially aligned such that each of the caps and tufts have a distinct linear orientation and a longitudinal axis L. By "looped" fibers it is meant to refer to fibers of the tufts and/or caps that are integral with and begin and end in the nonwoven layer in which they begin but extend generally outwardly in the Z-direction (or negative Z-direction) from the first surface or second surface of the respective layer. By "aligned", it is meant that looped fibers are all generally oriented such that, if viewed in plan view, each of the looped fibers has a significant vector component parallel to a transverse axis and can have a major vector component parallel to the transverse axis. The transverse axis T is generally orthogonal to longitudinal axis in the MD-CD plane and the longitudinal axis is generally parallel to the MD.

As described below, another characteristic of tufts/caps shown in FIGS. 6A-6C—formed with extensible non-crimped fibers—can be their generally open structure characterized by open void area 633 defined interiorly of the cap 630 and/or tuft 670 cap 630 and/or tuft 670. The term "void area" is not meant to refer to an area completely free of any fibers. The void area 633 of caps 630 may comprise a first void space opening and a second void space opening. Rather, the term is meant as a general description of the general appearance of caps 630. Therefore, it may be that in some caps 630 a non-looped fiber or a plurality of loose non-looped fibers may be present in the void area 633. By "open" void area is meant that the two longitudinal ends of cap 630 are generally open and free of fibers, such that cap 630 can form something like a "tunnel" structure in an uncompressed state, as shown in FIGS. 6A-6C. The general shape of the tufts may be similar to that of the cap 630; and in some forms, the nonwoven may not comprise a corresponding cap for the tuft.

Looped fibers and/or non-looped fibers of cap 630 can originate and extend from either the first surface or the second surface of the first layer. Of course the looped fibers or non-looped fibers of cap 630 can also extend from an interior of first layer. In general, with regard to caps 630, the looped fibers and non-looped fibers comprise fibers that are integral with and extend from the fibers of the first layer.

The extension and/or urging of looped fibers and non-looped fibers as shown in FIGS. 6A-6C, can be accompanied by a general reduction in fiber cross sectional dimension (e.g., diameter for round fibers) due to plastic deformation of the fibers and Poisson's ratio effects. Therefore, the aligned looped fibers of caps and/or tufts 670 can have an average fiber diameter less than the average fiber diameter of the fibers of the layer from which the tuft and/or cap emanates.

In contrast to the caps 630 and tufts 670 shown in FIGS. 6A-6C, nonwoven laminates of the present invention comprising crimped fiber spunbond nonwoven webs form very different out-of-plane deformations than those shown in FIGS. 6A-6C. Shown in FIGS. 7B-9B are nonwoven laminates constructed utilizing crimped fiber spunbond nonwoven webs. The nonwoven laminates shown in FIGS. 7B-9B comprise at least one crimped fiber spunbond nonwoven web.

Figure 7A:
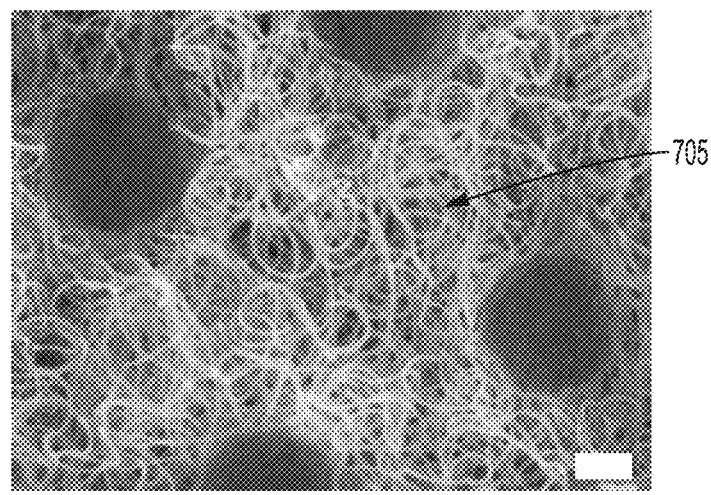
Figure 7B:
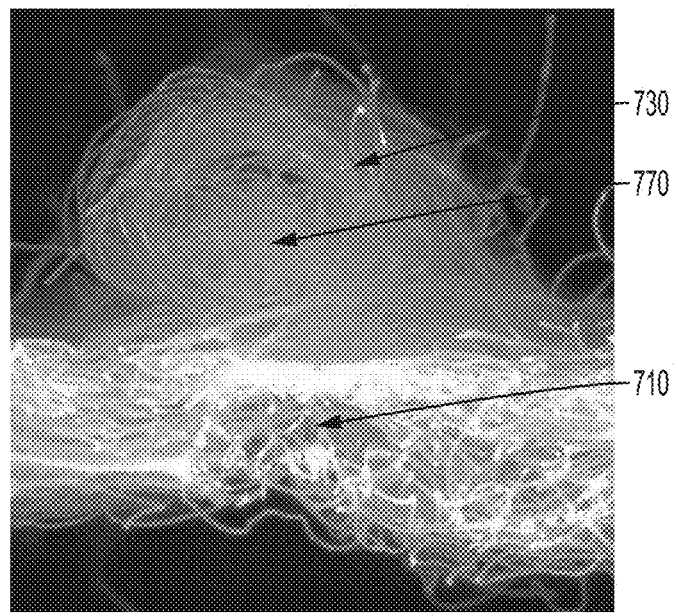
FIG. 7B is a photomicrograph showing a side view of a nonwoven laminate comprising the spunbond nonwoven of FIG. 6A as an upper layer and the spunbond crimped nonwoven of FIG. 7A as a lower layer, wherein the laminate comprises a cap and tuft formed therefrom.
Figure 7C:
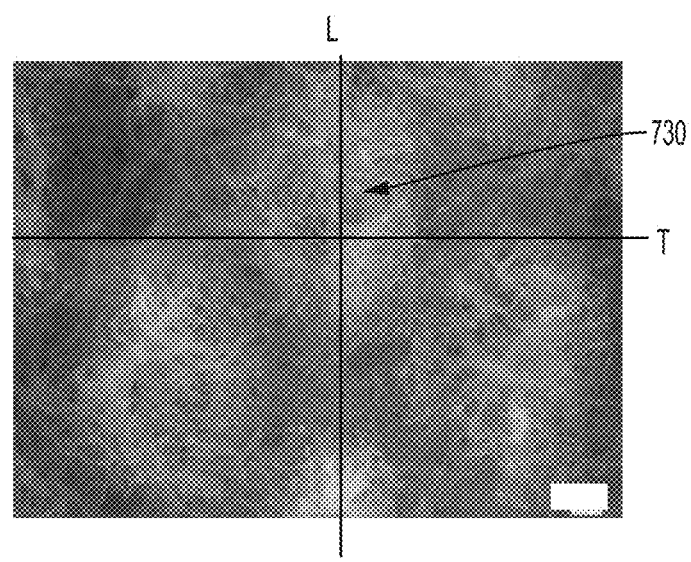
FIG. 7C is a photomicrograph showing a top view of the nonwoven laminate of FIG. 7B.

A nonwoven laminate 710 is shown in FIGS. 7B-7C. The nonwoven laminate 710 comprises a spunbond nonwoven web, e.g. 605 (shown in FIG. 6A) as an upper layer of the nonwoven laminate 710 and a crimped fiber spunbond nonwoven web 705 (shown in FIG. 7A) as a lower layer of the nonwoven laminate 710. The nonwoven laminate 710 comprises a tuft 770 formed from the constituent fibers of the crimped fiber spunbond nonwoven web 705 and a corresponding cap 730 formed from the constituent fibers of the spunbond nonwoven web 605. As shown, caps 730 and/or tufts 770 may have a similar shape to caps 630 and/or tufts 670. However, as shown, tufts 770, are substantially filled with looped fibers and/or non-looped fibers. Additionally notwithstanding the fact that the conventional spunbond nonwoven layer is the upper layer in the laminate 710, the looped fibers of the resultant out-of-plane deformation of FIG. 7C appear more random as opposed to being aligned with regard to the transverse axis T. The caps 730 can be configured similarly to caps 630 except as otherwise noted above. And, in contrast to the tufts 670, shown in FIGS. 6A-6C, it has been found that for the tufts 770, the constituent fiber is quite often uncoiled from its curly state rather than stretched and thinned.

Figure 8A:
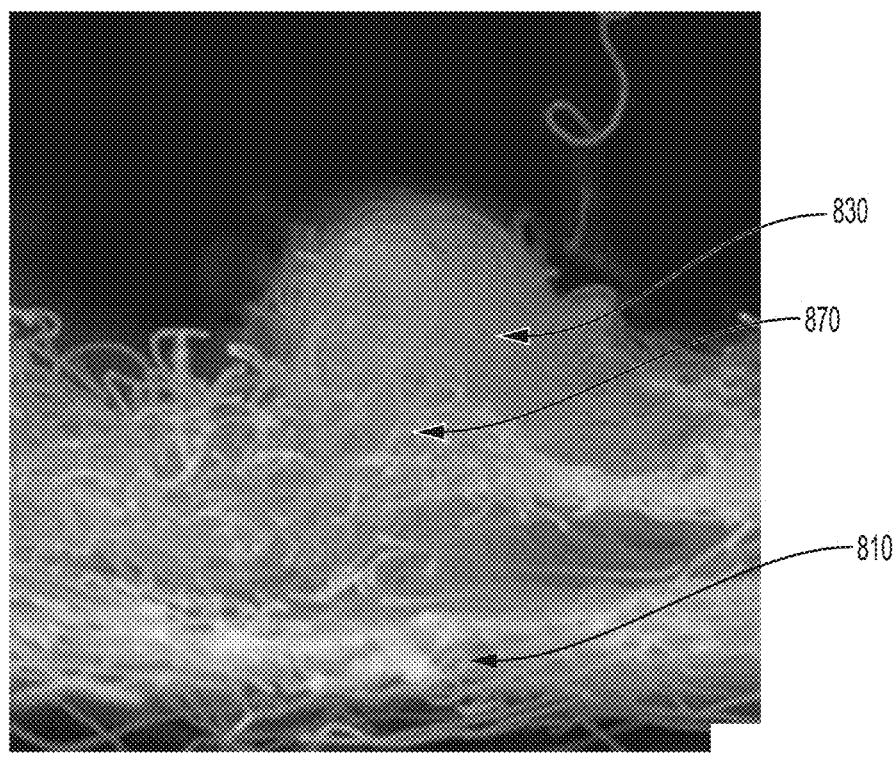
FIG. 8A is a photomicrograph showing a side view of a nonwoven laminate comprising the spunbond crimped nonwoven of FIG. 7A as an upper layer, and the spunbond nonwoven of FIG. 6A as a lower layer, wherein the laminate comprises a cap and tuft formed therefrom.
Figure 8B:
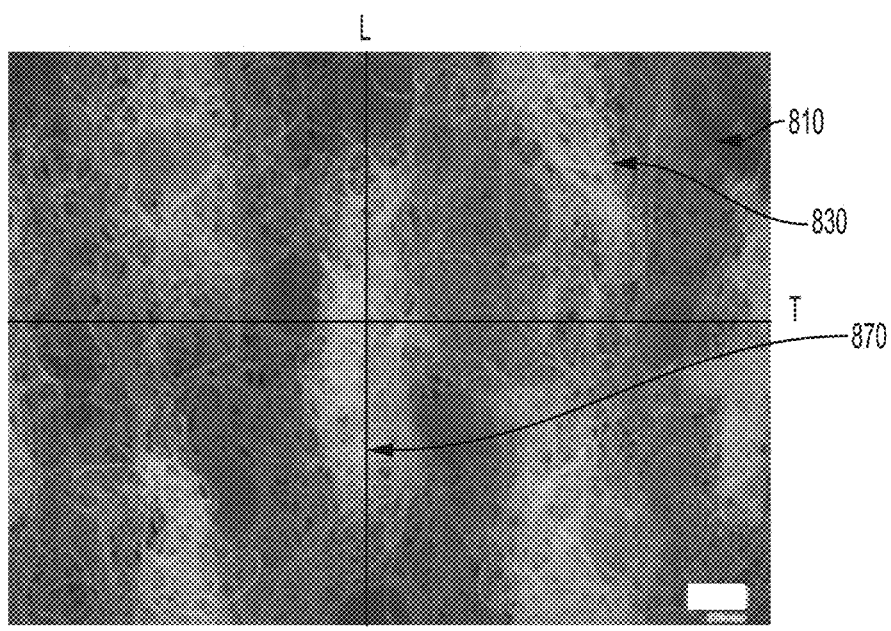
FIG. 8B is a photomicrograph showing a top view of the nonwoven laminate of FIG. 8A.

With regard to FIGS. 8A and 8B, nonwoven laminate 810 is the nonwoven laminate of FIGS. 7B-7C inverted. The crimped fiber spunbond nonwoven web 705 (shown in FIG. 7A) is utilized as an upper layer of the nonwoven laminate 810. The spunbond nonwoven web 605 (shown in FIG. 6A) is utilized as a lower layer of the nonwoven laminate 810. Much like the side view of nonwoven laminate 710 (shown in FIG. 7B) the side view of nonwoven laminate 810 reveals a cap 830 which is filled. And much like the nonwoven laminate 710 (shown in FIG. 7B), the structures formed on the nonwoven laminate 810 comprise fibers which are more random and curly as opposed to being aligned with regard to the transverse axis T.

Figure 9A:
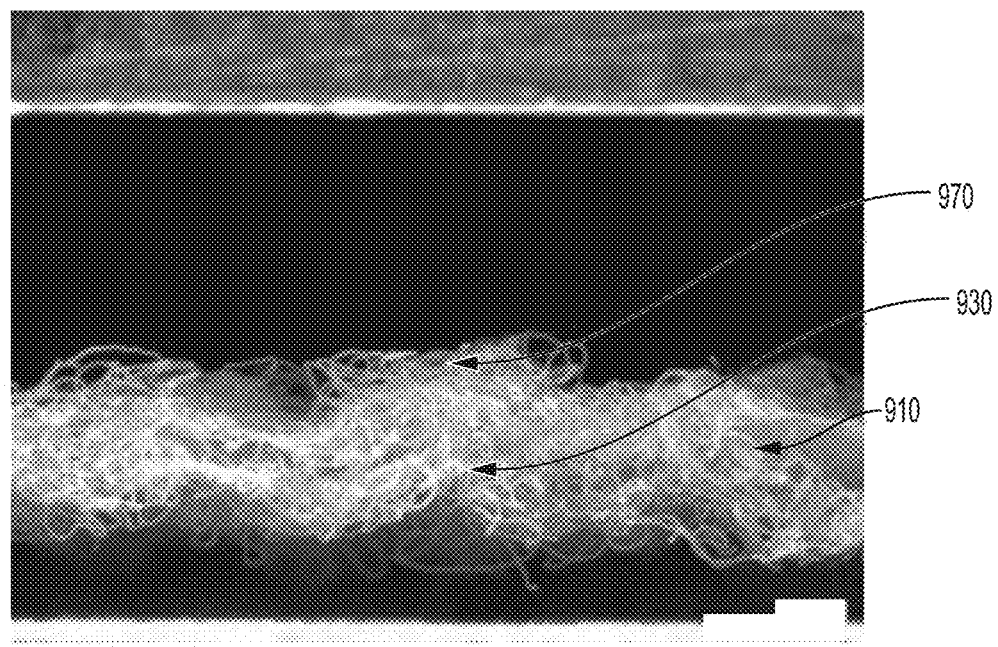
FIG. 9A is a photomicrograph showing a side view of a nonwoven laminate comprising two layers of the crimped fiber spunbond of FIG. 7A.
Figure 9B:
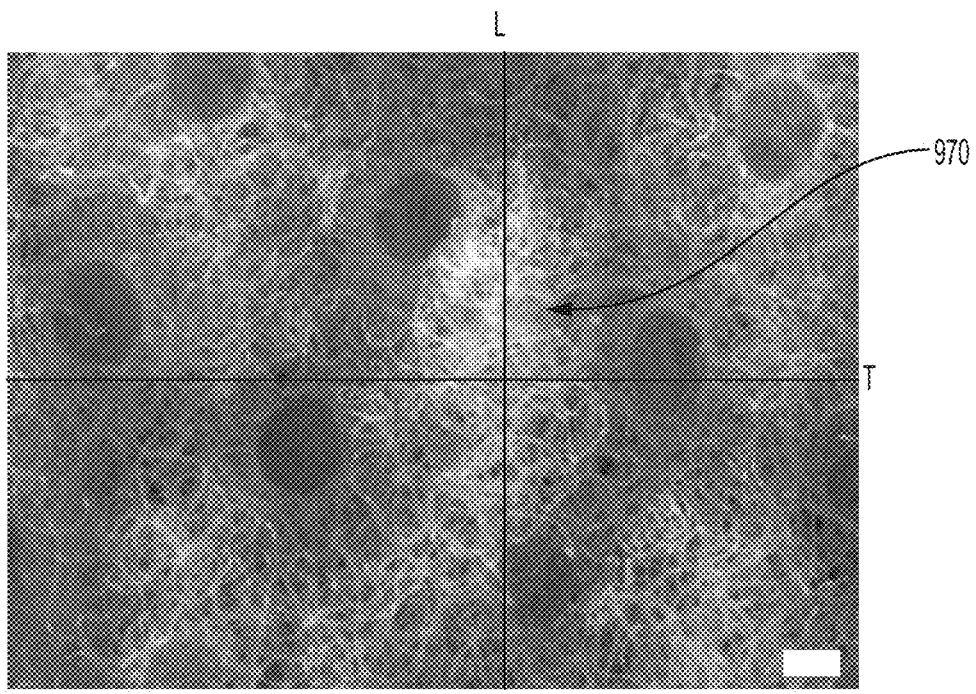
FIG. 9B is a photomicrograph showing a top view of the nonwoven laminate of FIG. 9A.

With regard to FIGS. 9A and 9B, a nonwoven laminate 910 shown comprises crimped fiber spunbond nonwoven webs, e.g. 705 (shown in FIG. 7A) as both upper and lower layers of the nonwoven laminate 910. In the side view shown in FIG. 9A, a tuft 970 and corresponding cap 930 are shown. Each is filled with the constituent fibers of their respective spunbond crimped nonwoven layers. And similar to the top views shown in FIGS. 7C and 8, the top view of the nonwoven laminate 910 shown in FIG. 9B depicts the constituent fibers which are more randomly oriented and curly compared to those shown in FIG. 6C.

The filled tufts 770 and 970 can be beneficial for those forms where the second layer comprises tufts 770, 970 which extend through the first layer. For example, if the first nonwoven does not include a corresponding cap over the tuft 770 or 970 liquid insults can have easy access to the material of the tuft 770, 970. And, if the material of the tufts 770 or 970 is hydrophilic either from a fiber standpoint and/or additive standpoint, the filled tuft 770, 970 will provide additional surface area for the liquid to contact. Similarly, even in those forms where a corresponding cap exists emanating from the first layer, the tuft 770, 970 may still provide great liquid handling properties. For example, as described with regard to FIG. 6B, the tuft 670 may comprise a first void opening 651 and a second void opening 652 exposing the void area 633. Caps constructed with non-crimped fibers may be similarly configured such that there are corresponding openings allowing fluid access to the underlying tufts 770, 970. Accordingly, the tuft 770, 970 may still have very good access to the liquid insults via the void openings in the cap. Similarly, caps 830 can provide these fluid handling benefits as well.

Caps of nonwoven laminates of the present invention are thought to mask or partially mask fluid that is collected by the nonwoven laminate remaining in the capillaries between fibers of the tufts. Such nonwoven laminates employed in an absorbent article such as a wipe, a sanitary napkin, a tampon, or a diaper can be appealing to the user (or caregiver) in that potentially unsightly fluids retained in the capillaries between fibers of the tufts will be obscured or partially obscured from the viewer. The tufts/caps may cover or partially cover interstices in which fluids can be held. Such a feature can make the nonwoven laminate appear less soiled. Additionally, because the nonwoven laminates of the present invention comprises at least one crimped fiber spunbond nonwoven web, the resultant nonwoven laminate has a higher caliper for a given basis weight. This higher caliper in turn delivers consumer benefits of comfort due to cushiony softness, faster absorbency due to higher permeability, and improved masking. Additional benefits may include less redmarking, higher breathability and resiliency.

A crimped fiber spunbond nonwoven web may provide similar benefits. For example, tufts created in the crimped fiber spunbond nonwoven web could provide a masking benefit even if utilized independently with no additional layers.

Additionally, the incorporation of a crimped fiber spunbond nonwoven web into a laminate or an absorbent article provides many additional advantages. For example, for the creations of many out-of-plane deformations, constituent materials that are not extensible generally break or tear when subjected to such processes. However, constituent materials for crimped fiber spunbond nonwoven webs do not require such extensibility. Specifically, during processing for out-of-plane deformations, rather than stretching and thinning fibers, fibers of the crimped fiber spunbond nonwovens tend to uncurl. As such, materials which would ordinarily not be suited for out-of-plane deformation processing, may be suitable for such processing if configured in a crimped fiber spunbond nonwoven web. Suitable materials for the crimped fiber spunbond nonwoven webs of the present invention are discussed hereafter. Additionally, crimped fiber spunbond nonwoven webs generally exhibit better elastic recovery from out-of-plane deformation processing than conventional bi-component fibers in spunbond webs.

Figure 64:
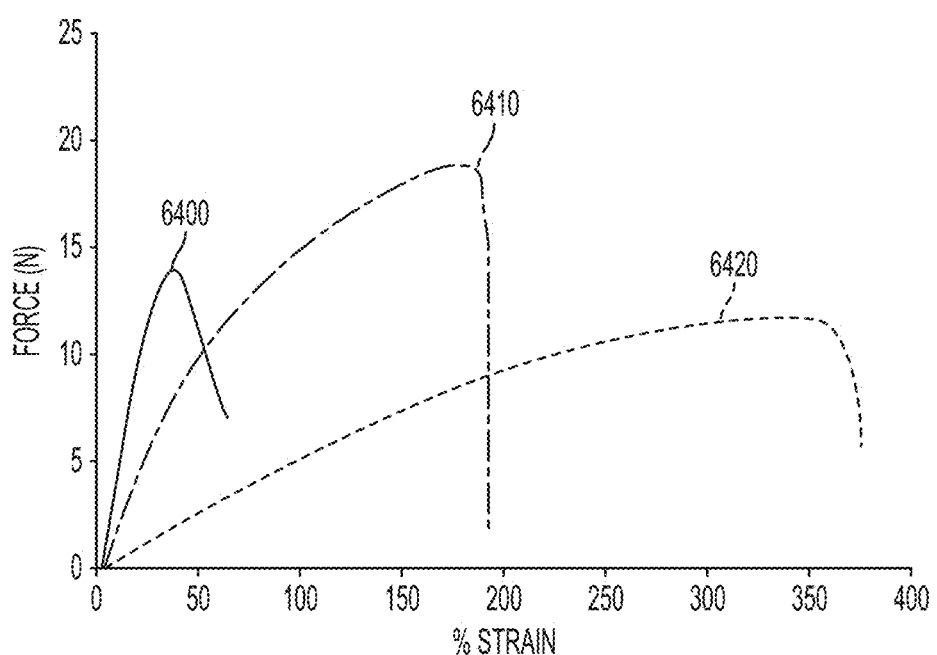
FIG. 64 is a graph depicting stress stain curves for a spunbond nonwoven web and two crimped fiber spunbond nonwoven webs.
Figure 65:
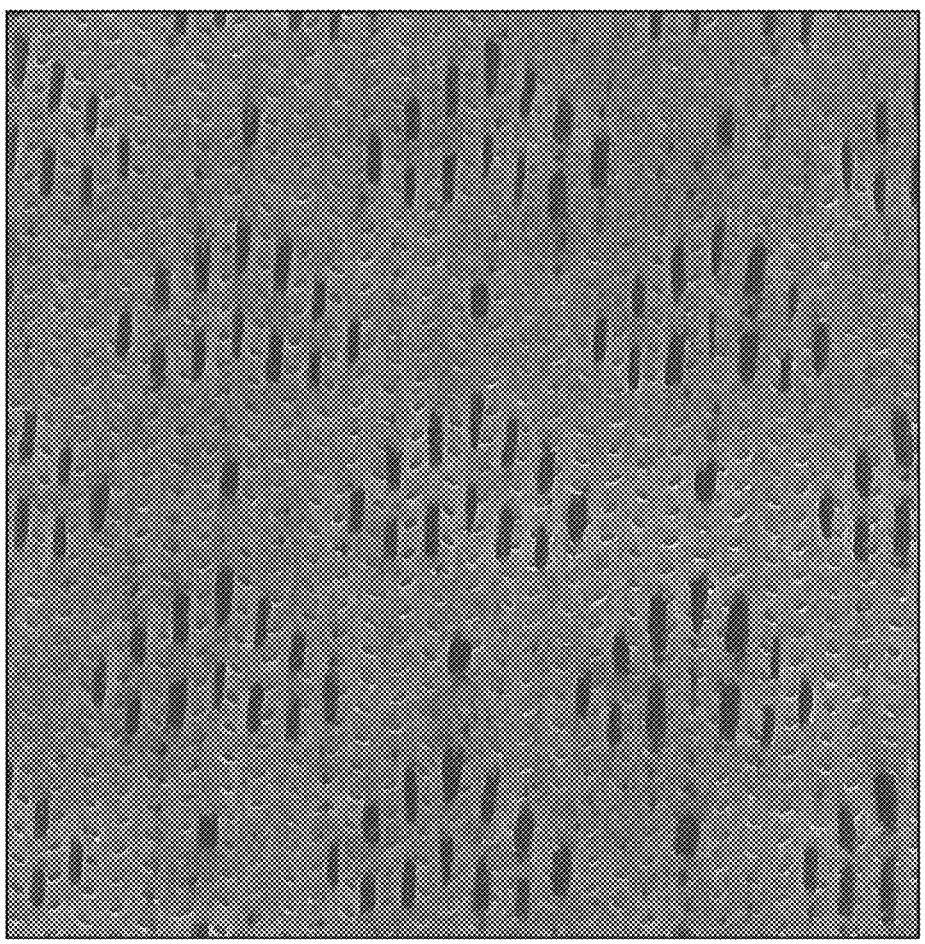
FIGS. 65-74 are photographs of patterned apertured webs in accordance with the present disclosure.
Figure 66:
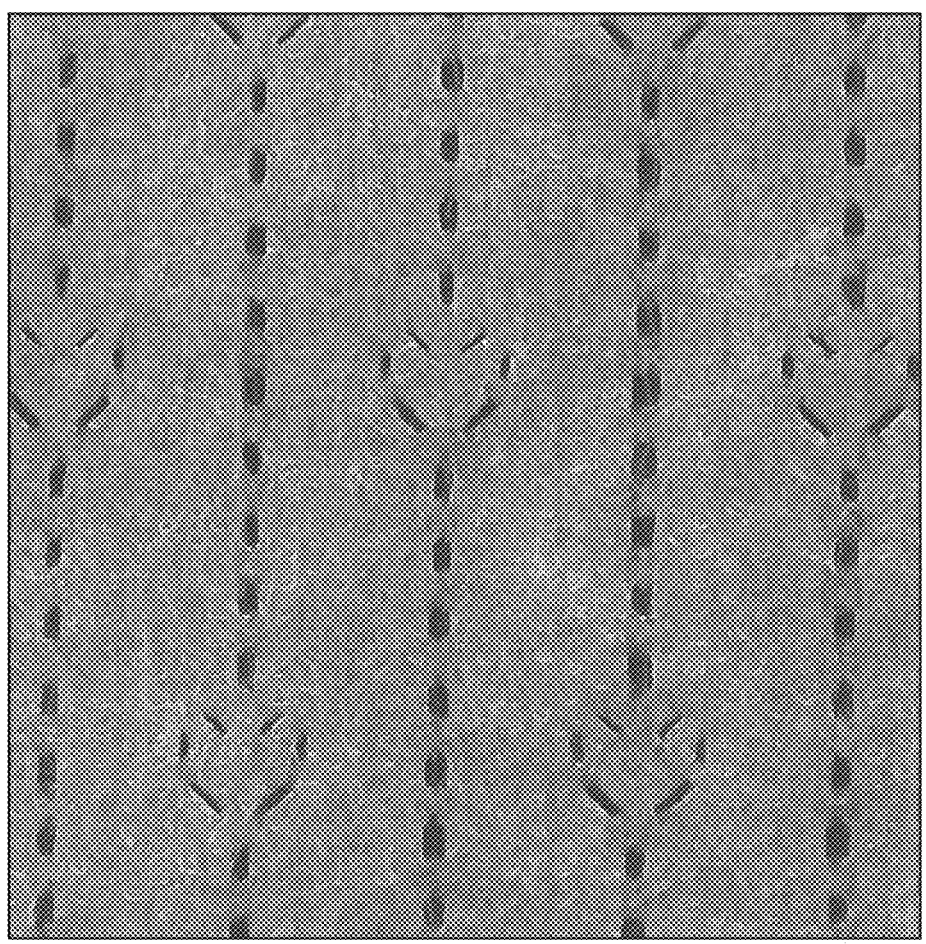
Figure 67:
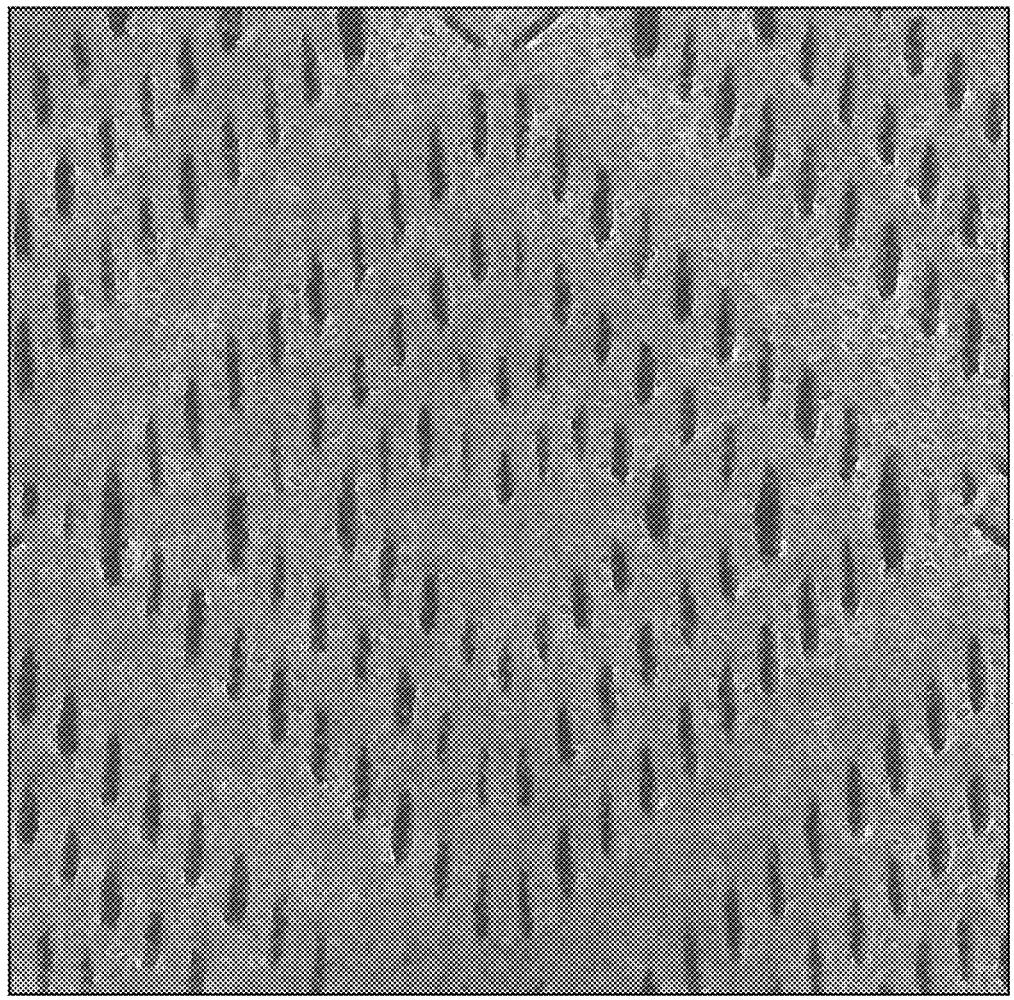
Figure 68:
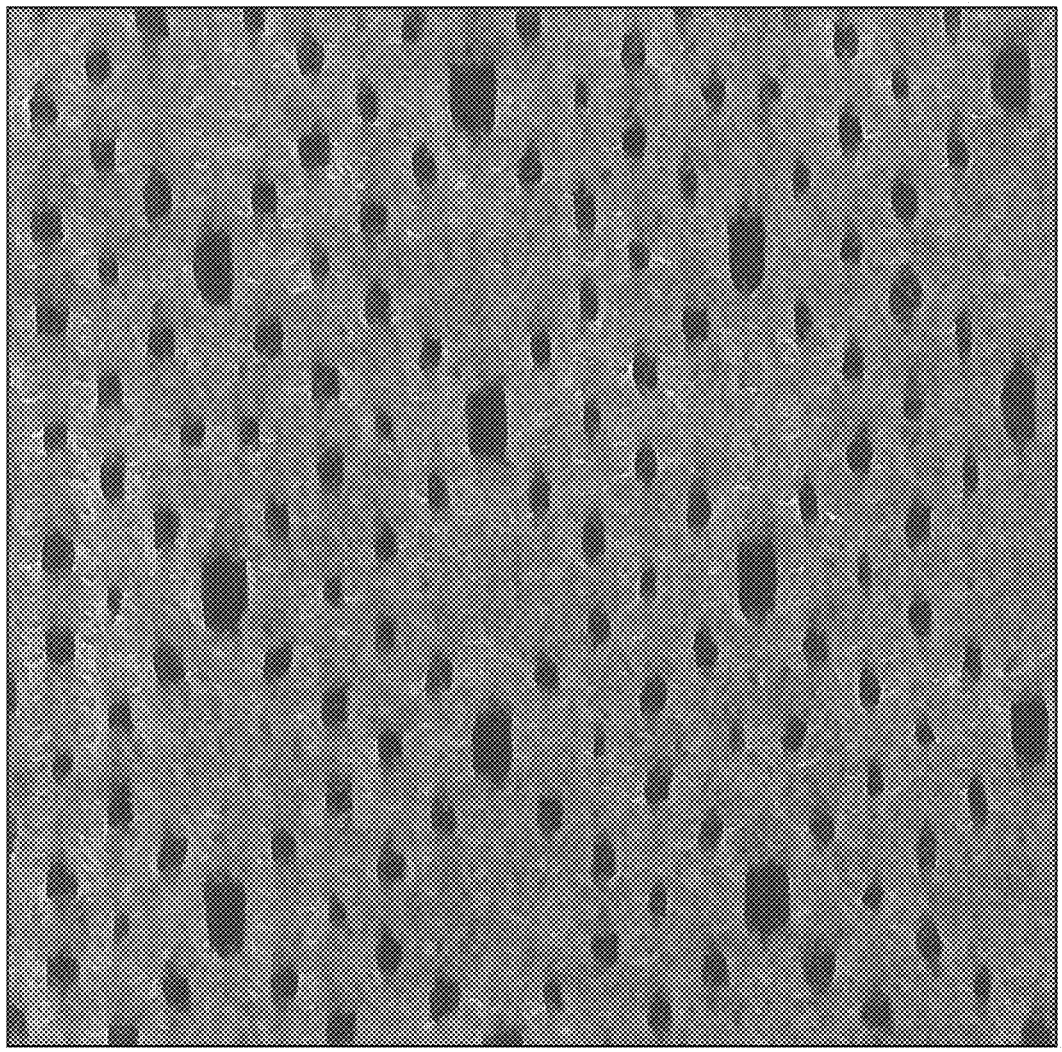
Figure 69:
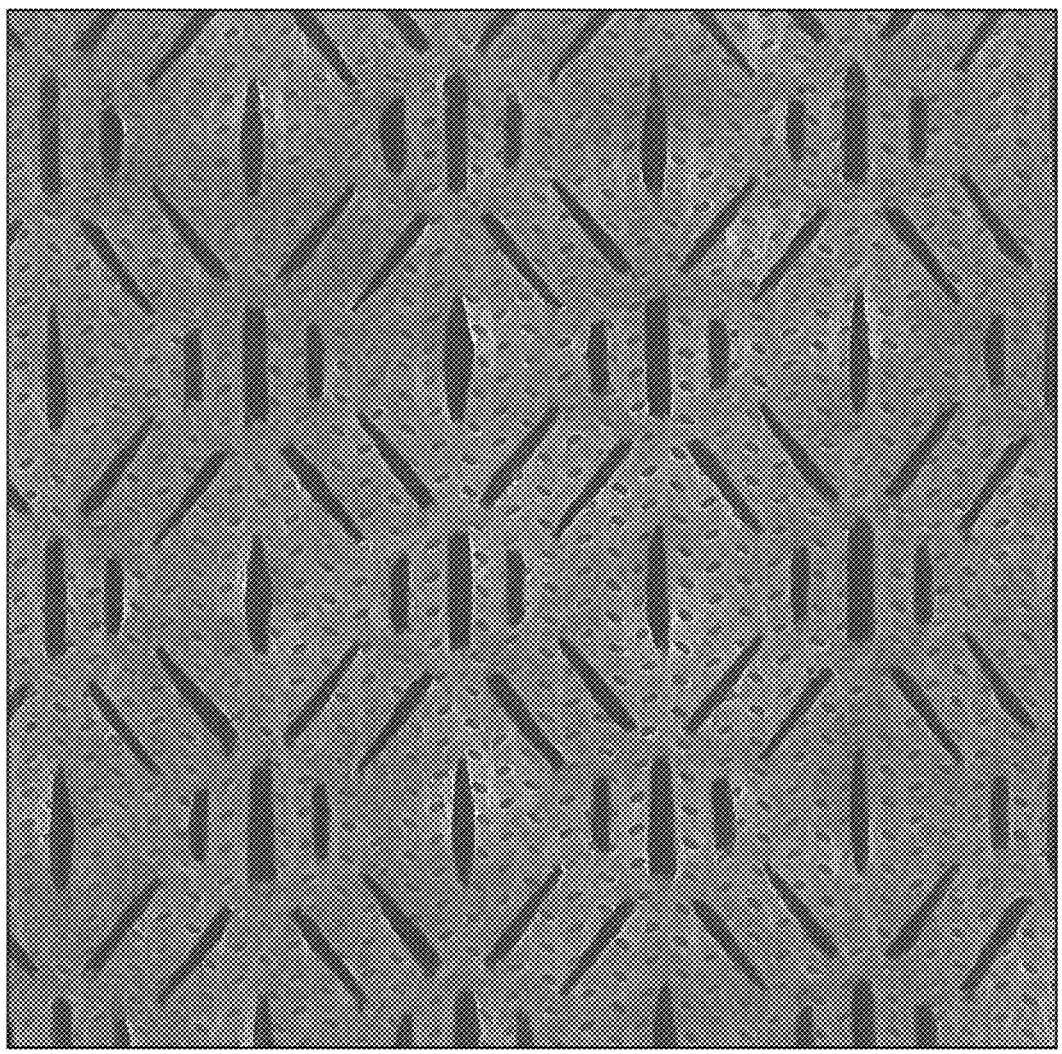
Figure 70:
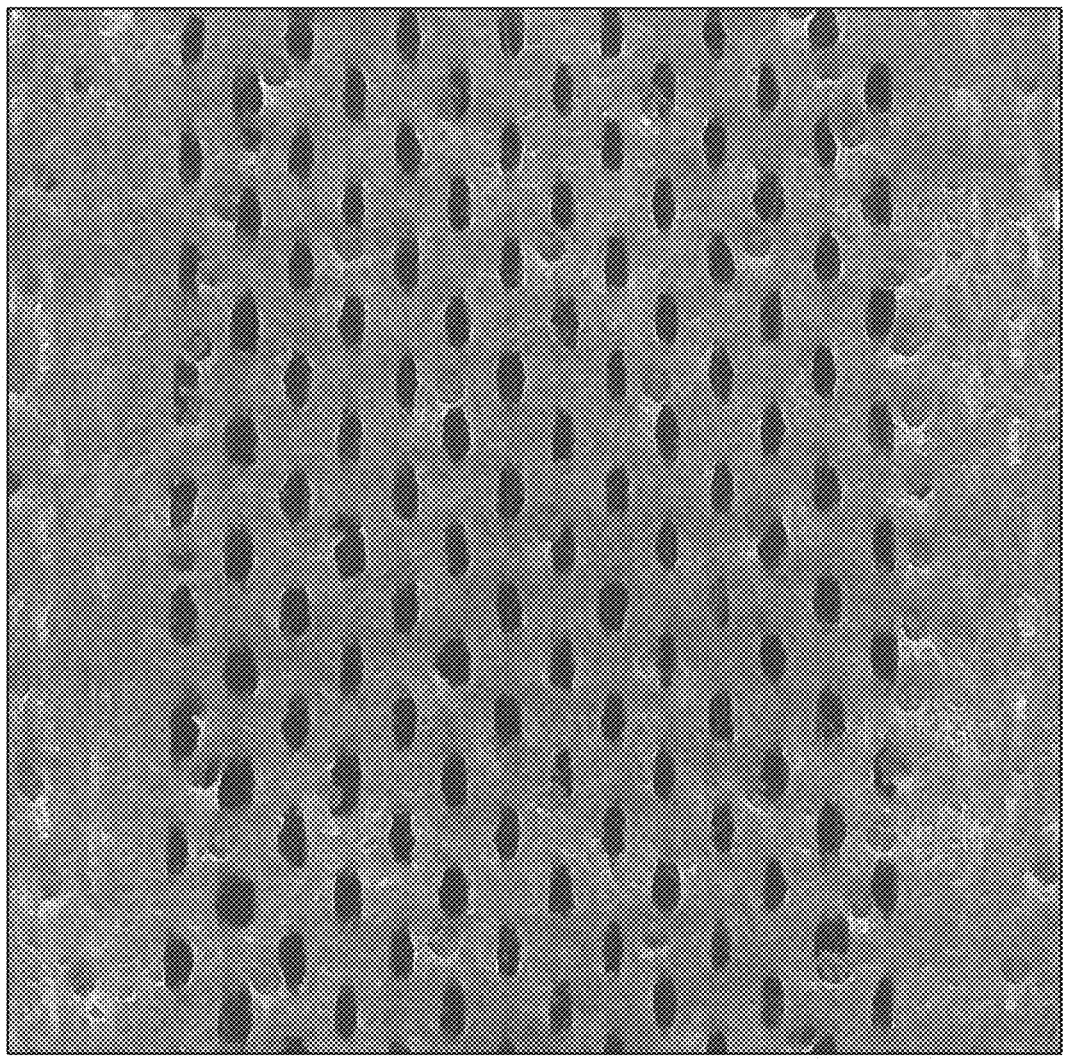
Figure 71:
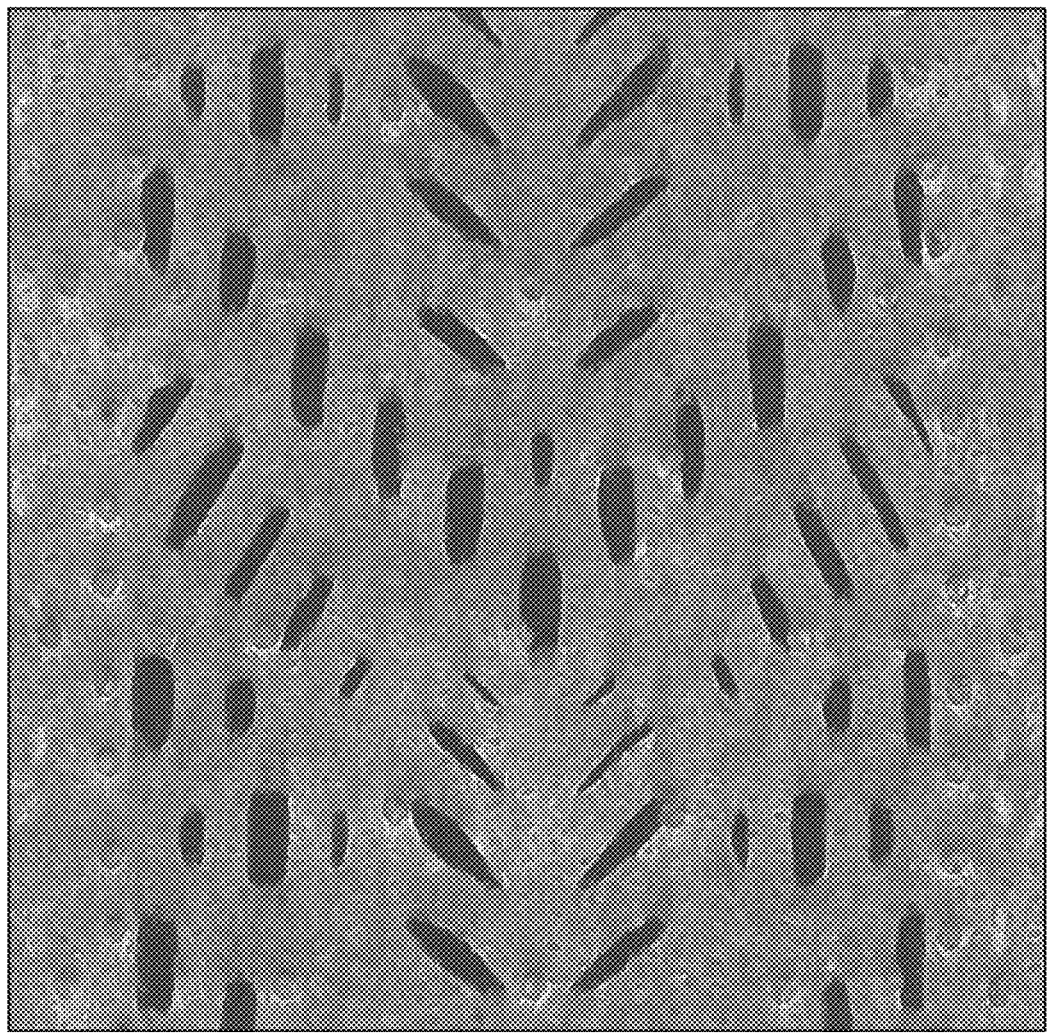
Figure 72:
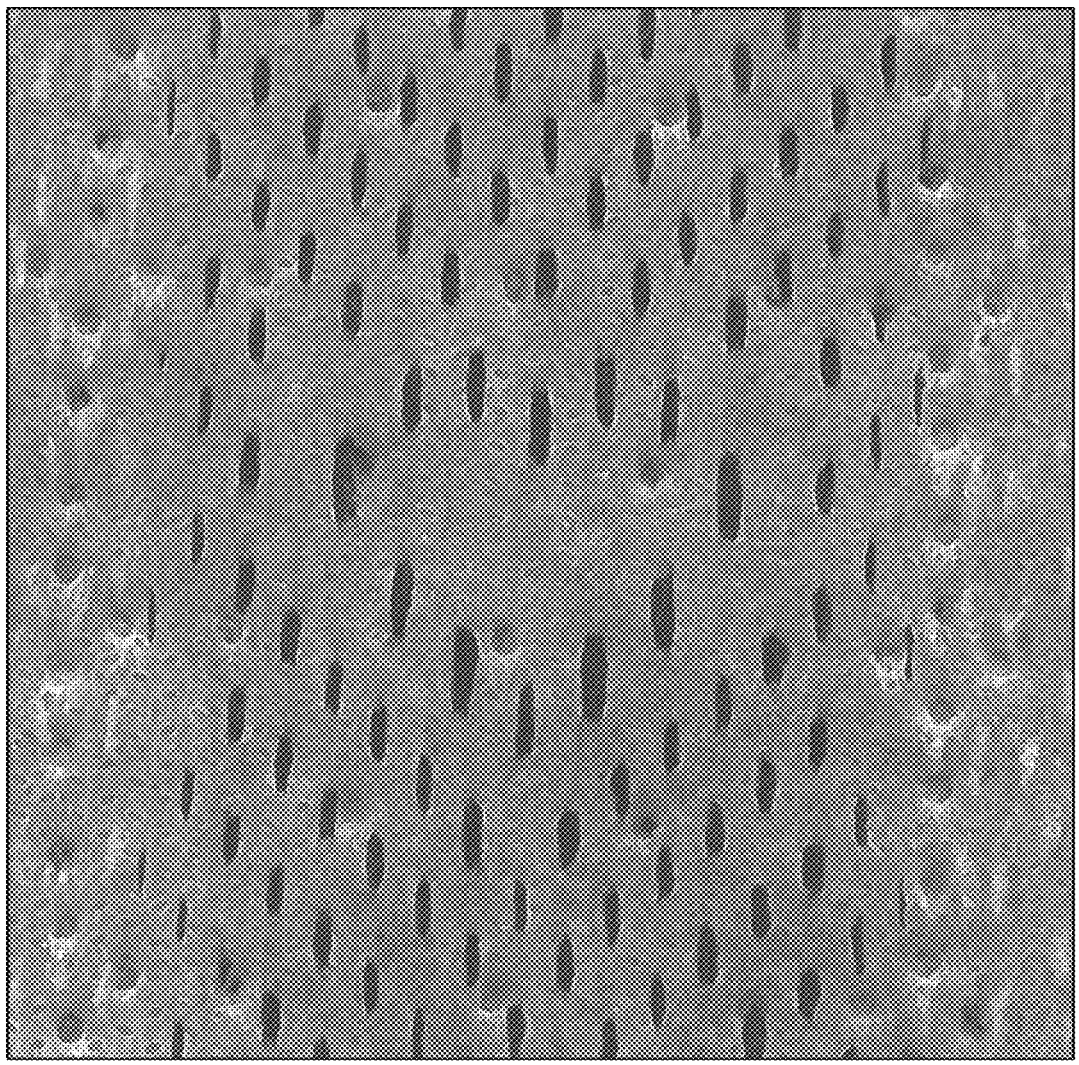
Figure 73:
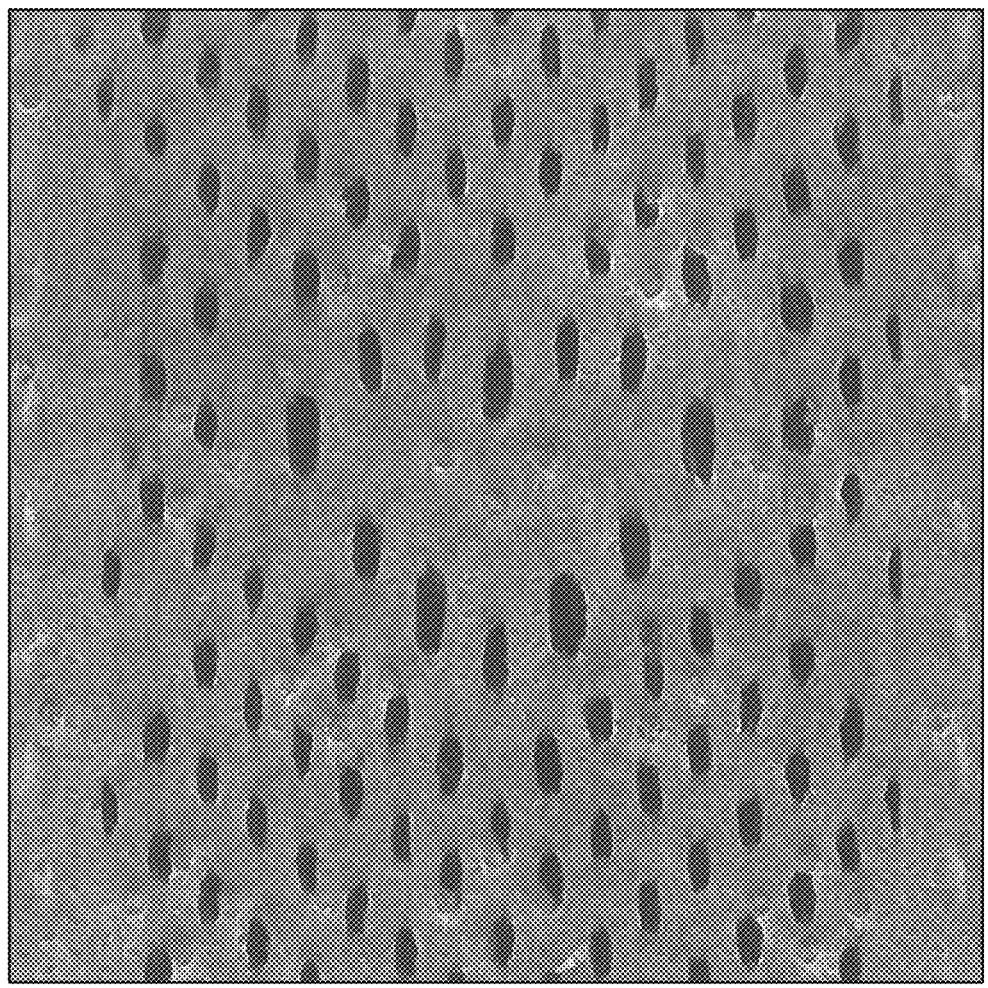
Figure 74:
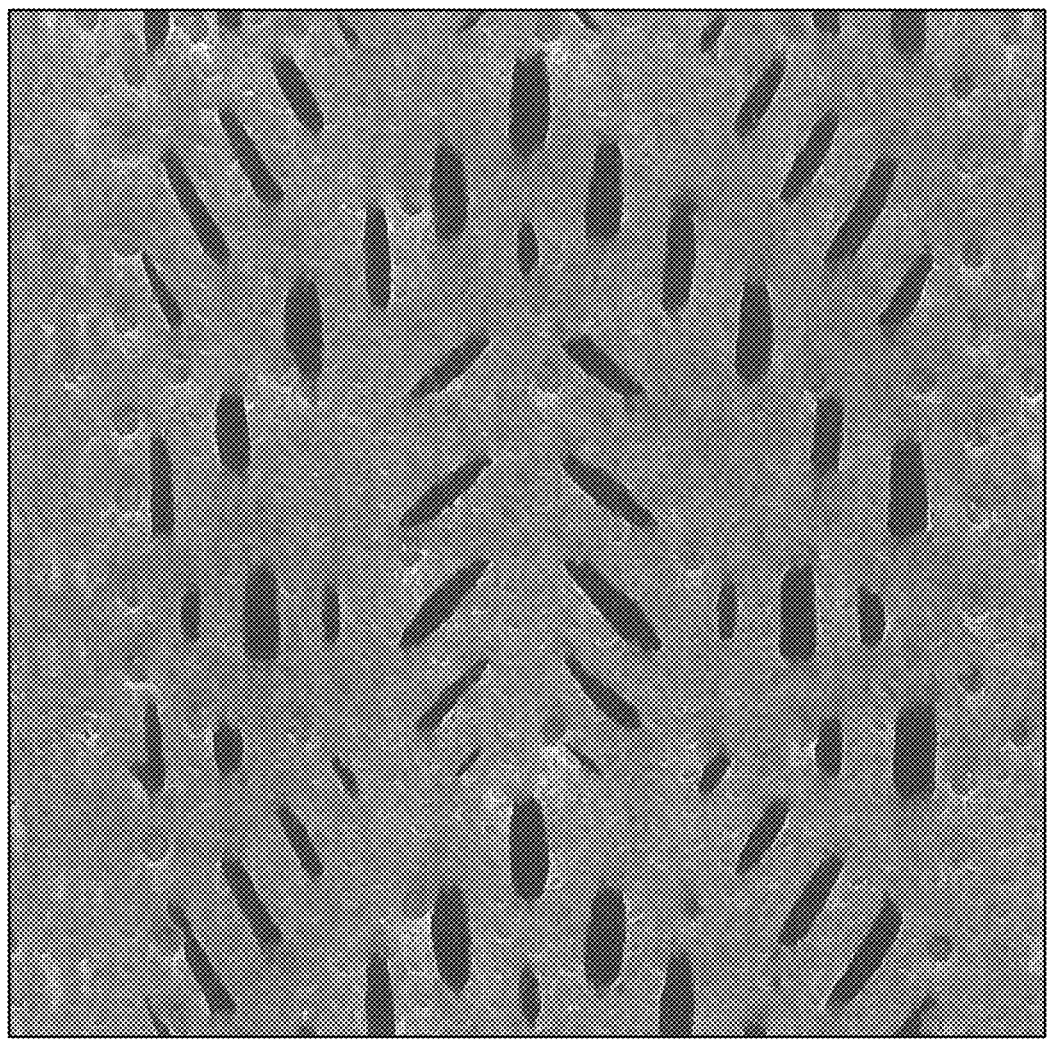

Additionally, some crimped fiber spunbond nonwoven webs may comprise better tensile elongation than spunbond nonwoven webs. In one specific example, crimped fiber spunbond nonwoven webs comprising polypropylene/polypropylene bi-component fibers may exhibit a higher tensile elongation than a spunbond nonwoven comprising polypropylene monocomponent fibers. A graph depicted in FIG. 64 shows the difference in tensile elongation between an exemplary crimped fiber spunbond nonwoven web and spunbond nonwoven webs.

As shown, spunbond nonwoven web 6400 exhibited lower tensile elongation than did the crimped fiber spunbond nonwoven webs 6410 and 6420. The spunbond nonwoven web 6400 was a 30 gsm spunbond nonwoven comprising 2.5 denier per filament monocomponent fibers comprising 100% Lyondell Basell HP561R. This spunbonded nonwoven web 6400 was calendar bonded to an 18 percent bond area.

The crimped fiber spunbond nonwoven web 6410 was a 26 gsm nonwoven web comprising 2.6 denier per filament bi-component fibers which were a 60/40 side-by-side configured polypropylene. Where the first component of the bi-component fiber was a polypropylene from Lyondell Basell HP561R and the second component was also a polypropylene from Lyondell Basell HP552 R. The first component further comprised 17% Techmer PPM17000 High Load hydrophobic masterbatch and 1% $TiO_2$ masterbatch. The second component comprised 14% Techmer PPM17000 High Load hydrophobic masterbatch. The crimped fiber spunbonded nonwoven web 6410 was calendar bonded to an 18 percent bond area.

The crimped fiber spunbonded nonwoven web 6420 was a 30 gsm nonwoven web which comprised fibers having 2.6 denier per filament bi-component fibers. The bi-component fibers were configured in a 60/40 side-by-side arrangement. A first component comprised Lyondell Basell HP561R polypropylene and a second component comprised Lyondell Basell HP552 R polypropylene. The first and second components both additionally comprised 16% Techmer PPM17000 High Load Hydrophobic masterbatch. The second component additionally comprised 1.5% $TiO_2$. The crimped fiber spunbonded nonwoven web 6420 was calendar bonded to a 12 percent bond area.

Additionally, tensile strength for spunbond crimped fiber nonwoven webs may be greater than the tensile strength exhibited by carded crimped fiber nonwoven webs. In general, the spunbond process, including the spunbond crimped fiber process, utilizes continuous fibers while the carded spunbond fiber process utilizes staple fibers—fixed length not continuous. Still another distinction between crimped fiber spunbond nonwoven webs and crimped fiber carded nonwoven webs is that a tensile strength ratio between the MD and CD is generally more balanced for crimped fiber spunbond nonwoven webs. In general, crimped fiber carded nonwoven webs have a much higher tensile strength in the MD as the fibers are typically combed to be aligned in the MD direction.

Additional benefits of utilizing crimped fiber spunbond nonwoven webs is that in some forms, particularly where the fibers comprise bi-component polypropylene/polypropylene, better bond strength can be achieved which makes this crimped fiber spunbond nonwoven web more abrasion resistant.

Even still more additional benefits of crimped fiber spunbond nonwoven webs include compatibility with like chemistries. For example, crimped fiber spunbond nonwoven webs comprising polypropylene/polypropylene bi-component fibers may be thermally joined (bonded) to subjacent materials in a disposable absorbent article which are polypropylene based. Also, the cost associated with polypropylene/polypropylene fibers can be less than the cost associated with other bi-component fibers. And, polypropylene/polypropylene fibers or fibers comprising two different polyesters may be recyclable versus bi-component fibers comprising polyethylene/polypropylene.

Regarding permeability, nonwoven laminates of the present invention, which include a crimped fiber spunbond nonwoven layer, have a higher permeability than nonwoven laminates which do not comprise a crimped fiber spunbond nonwoven layer. This is illustrated in Table 2. Table 2 also includes data regarding individual nonwoven webs.

EXAMPLES

All Crimped Fiber Spunbond ("CFSB") nonwoven web samples below are 25 gsm webs comprised of fibers 2.6 denier per filament, side-by-side polypropylene/polypropylene, using Lyondell Basell HP561R in the first component and Lyondell Basell HP552R in the second component. Both components additionally comprise 1% of $TiO_2$ masterbatch (MBWhite009). The CFSB nonwoven web samples were produced by Reifenhauser GmbH located in Troisdorf, Germany.

CFSB1: In addition to above description, CFSB1 had a 60/40 ratio of polypropylene components. Both components additionally comprised 16% Techmer PPM17000 High Load Hydrophobic masterbatch. The nonwoven layer was calendar bonded with a dot bond pattern having 12% bond area.

CFSB2: In addition to the above description, CFSB2 has a 70/30 ratio of polypropylene components. The nonwoven layer was calendar bonded with a dot bond pattern having 12% bond area and coated with 0.4% by weight Silastol PHP26 surfactant made by Schill & Seilacher, Germany.

CFSB3: In addition to the above description, CFSB3 has a 70/30 ratio of polypropylene components. The nonwoven layer is calendar bonded with a diamond bond pattern having 14.6% bond area.

All Spunbond ("SB") samples below are spunbond nonwoven webs comprised of polyethylene/polypropylene sheath/core bi-component fibers.

SB1: In addition to the above description, SB1 is a 25 gsm nonwoven web comprising fibers which are 2.5 denier per filament with 30/70 polyethylene/polypropylene ratio from Fibertex Personal Care in Nilai, Malaysia. The fibers additionally comprise 17% of Techmer PPM 17000 High Load Hydrophobic masterbatch in the sheath.

SB2: In addition to the above description, SB2 is a 28 gsm nonwoven web comprising fibers which are 2.8 denier per filament with 50/50 polyethylene/polypropylene ratio purchased from Fitesa in Washougal, Wash. The web has been coated with 0.45% by weight of Silastol PST-N surfactant available from Schill & Seilacher, Germany.

SB3: In addition to the above description, SB3 is a 25 gsm nonwoven web comprising fibers which are 2.5 denier per filament with 30/70 polyethylene/polypropylene ratio from Pegas Nonwovens s.r.o., in Znojmo, Czech Republic.

All laminates below are comprised of two layers of nonwoven webs listed above.

TABLE 1

| | Upper Layer | Lower layer | Formation |
|---|---|---|---|
| Laminate 1 | CFSB1 | CFSB2 | Tufts/Caps |
| Laminate 2 | SB1 | SB2 | Tufts/Caps |
| Laminate 3 | SB1 | CFSB2 | Tufts/Caps |
| Laminate 4 | CFSB3 | CFSB2 | Apertures (both layers bonded around perimeter) |
| Laminate 5 | SB3 | SB2 | Apertures (both layers bonded around perimeter) |

For those nonwoven webs comprising Techmer PPM 17000 High Load Hydrophobic masterbatch, a fibril structure on the fiber surface was formed (discussed hereafter). The masterbatch comprised about 60 percent by weight polyethylene and about 40 percent by weight glycerol tristearate.

TABLE 2

| Material | Through-plane permeability CHH (Darcy) |
|---|---|
| CFSB1 | 39 |
| CFSB2 | 78 |
| SB1 | 19 |
| SB2 | 52 |
| Laminate 1: CFSB1/CFSB2 | 196 |
| Laminate 2: SB1/SB2 | 65 |
| Laminate 3: SB1/CFSB2 | 104 |

As shown in Table 2, CFSB1 had a higher permeability than SB1, and CFSB2 had a higher permeability than the SB2—comparing philic to philic additive and phobic to phobic additive.

Without wishing to be bound by theory, it is believed that crimped fiber spunbond nonwoven webs comprise an open structure in general. It is further believed that due to this open structure, the crimped fiber spunbond nonwoven webs and/or nonwoven laminates formed therefrom have a higher permeability. Higher permeability is believed to aid in transporting fluid faster through the nonwoven laminate. So, for those executions where Laminate 1 or Laminate 3 is utilized as a topsheet, the higher permeability would be believed to provide fluid handling benefits for the articles into which such topsheets were incorporated.

Additional fluid handling benefits are demonstrated in Table 3. As shown in Table 3, two nonwoven webs were compared with regard to their respective desorption potential.

TABLE 3

| Material Sample No. | eCWP Drainage Potential (micro J/g fluid) | Median desorption pressure (cm $H_2O$) |
|---|---|---|
| CFSB2 | 1793 | 13.3 |
| SB2 | 2251 | 17.8 |

As shown in Table 3, CFSB2 required less energy to drain than SB2. It is believed that for those configurations where a crimped fiber spunbond nonwoven web is disposed adjacent an absorbent core, the absorbent core may more easily drain the crimped fiber spunbond nonwoven web than the spunbond nonwoven web.

Figure 10:
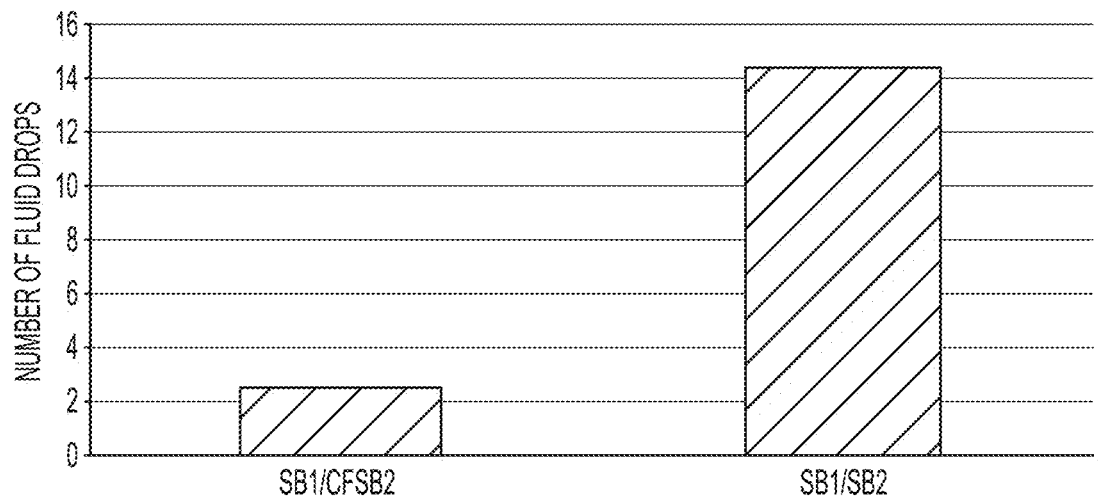
FIG. 10 depicts a graph showing results of a drip test comparing nonwoven laminates with crimped fiber spunbond nonwoven layers versus laminates with no crimped fiber spunbond nonwoven layers.

Additional benefits of crimped fiber spunbonds include fluid acquisition. FIG. 10 shows a comparison between various laminates. Laminate 3 versus Laminate 2 is shown. Recall that Laminate 3 comprises a crimped fiber spunbond nonwoven web as a lower layer and a spunbond nonwoven web as an upper layer while Laminate 2 comprises a spunbond nonwoven web as an upper and lower layer. The graph shown in FIG. 10 demonstrates that Laminate 3 (spunbond nonwoven web upper layer and crimped fiber spunbond nonwoven web lower layer) acquires liquid insults better than Laminate 2 (spunbond nonwoven web upper and lower layers).

Recall that as shown in FIGS. 7A-7C, the tufts formed by crimped fiber spunbond nonwoven webs are filled to a much larger extent than tufts formed by conventional spunbond nonwoven webs. It is believed that the filled tufts and lower web density created by the crimped fiber spunbond nonwoven webs can provide fluid insults better access to the fibers of the crimped fiber spunbond nonwoven web which in turn can lead to better fluid acquisition.

Figure 11:
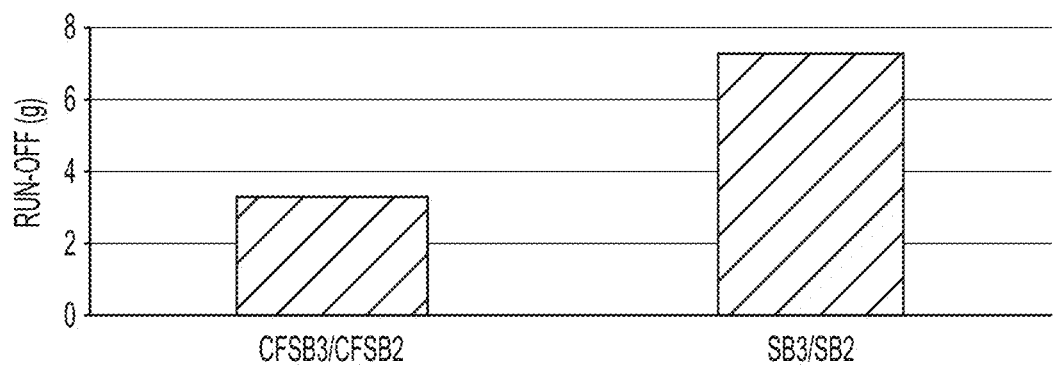
FIG. 11 depicts a graph showing results of a machine direction run-off test comparing nonwoven laminates with crimped fiber spunbond nonwoven layer versus laminates with no crimped fiber spunbond nonwoven layers.

Regarding FIG. 11, crimped fiber spunbond nonwoven webs can similarly provide better resistance to fluid runoff. The graph of FIG. 11 shows a comparison of fluid runoff for a pair of apertured nonwoven laminates. As described in Table 1, Laminate 4 comprises CFSB3 as an upper layer and CFSB 2 as a lower layer. Laminate 5 comprises SB3 as an upper layer and SB2 as a lower layer. While each of the laminates comprised tufts and/or caps, the fluid runoff test was performed in an area of the laminates which was apertured and absent out-of-plane deformations.

As shown in the graph of FIG. 11, Laminate 4 has less runoff than Laminate 5. Without wishing to be bound by theory, it is believed that crimped fiber spunbond nonwoven webs offer more resistance to fluid flow due to their lofty nature. This increased resistance helps to reduce fluid runoff which should result in less soiling of the skin of a wearer during use.

Regarding the tufts discussed heretofore, tufts may be spaced apart from adjacent tufts, and similarly caps may be spaced apart from adjacent caps. Each of the spaced apart tufts and/or spaced apart caps have generally parallel longitudinal axes L. The number of tufts and/or caps per unit area of a nonwoven laminate of the present invention, i.e., the area density of tufts and/or caps, can be varied from one tuft per unit area, e.g., square centimeter to as high as 100 tufts per square centimeter or similarly with regard to caps. There can be at least 10, or at least 20 tufts and/or caps per square centimeter, depending on the end use. In general, the area density need not be uniform across the entire area of nonwoven laminates of the present invention, and, in some embodiments, tufts and/or caps can be only in certain regions of nonwoven laminates of the present invention, such as in regions having predetermined shapes, such as lines, stripes, bands, circles, and the like.

As noted previously, the first layer and/or second layer may comprise apertures as disclosed herein and/or out-of-plane deformations, e.g. tufts, as disclosed herein. Some suitable examples of additional out-of-plane deformations for use in conjunction with the crimped fiber spunbond nonwoven webs/laminates of the present invention, include ridges, grooves, and/or valleys. Methods of forming ridges and/or grooves are discussed further in U.S. Pat. No. 7,954,213; U.S. Patent Application Publication Nos. US2012/0045620; US2012/0196091; US2012/0321839; US2013/0022784; and US2013/0017370; and PCT Patent Application Publication Nos. WO2011/125893; and WO2012/137553. Other suitable processes for producing ridges and/or recesses and the resulting structures are disclosed in U.S. Pat. Nos. 6,458,447; 7,270,861; 8,502,013; 7,625,363; 8,450,557; and 7,741,235. Additional suitable processes and structures are described in US Patent Application Publication Nos. US2003/018741; US2009/0240222; US20120141742; US2013/013732; US2013/0165883; US2013/0158497; US2013/0280481; US2013/0184665; US2013/0178815; and US2013/0230236700. Still additional suitable processes and structures are described with regard to PCT Patent Application Publication Nos. WO2008/156075; WO2010/055699; WO2013/018846; WO2013/047890; and WO2013/157365.

Additional out-of-plane deformations include embossing. Embossing of absorbent articles generally results in thinned out areas in the absorbent article. Embossing, similar to fusion bonding, involves the manipulation of material in a first layer and a second layer in the positive and/or negative Z-direction. Generally, embossing does not result in the fusion of layers. Unlike fusion bonds, embossing typically results in macro depressions in an absorbent article. Embossing is further discussed in U.S. Pat. Nos. 8,496,775 and 8,491,742.

Precursor Materials

The crimped fiber spunbond nonwoven webs/laminates of the present invention begin with constituent fibers. As noted previously, for nonwoven laminates of the present invention, at least one web is a crimped fiber spunbond nonwoven web. The plurality of randomly oriented fibers of the crimped fiber spunbond nonwoven webs/laminates may comprise any suitable thermoplastic polymer. Some suitable thermoplastic polymers, as used in the disclosed compositions, are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C. And, the molecular weight of the thermoplastic polymer should be sufficiently high to enable entanglement between polymer molecules and yet low enough to be melt spinnable.

The thermoplastic polymers can be derived any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof. Some exemplary polyolefins include polyethylene or copolymers thereof, including low density, high density, linear low density, or ultra-low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; poly-lactic acid; polyacrylates, polymethacrylates, and their copolymers such as poly(methyl methacrylates).

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler- Natta isotactic polypropylene from Unipetrol), Danimer 27510 (a polyhydroxyalkanoate polypropylene from Danimer Scientific LLC), Dow Aspun 6811A (a 27 melt index polyethylene polypropylene copolymer from Dow Chemical), Eastman 9921 (a polyester terephthalic homopolymer with a nominally 0.81 intrinsic viscosity from Eastman Chemical), Achieve 3155 (a 35 melt flow rate zinc isotactic polypropylene from Exxon Mobil), Moplen HP561R and Moplen HP552R, both of which are 25 melt flow rate Ziegler-Natta isotactic polypropylene from Lyondell-Basell).

The thermoplastic polymer component can be a single polymer species as described above or a blend of two or more thermoplastic polymers as described above, e.g. two different polypropylene resins. As an example, the constituent fibers of the first layer can be comprised of polymers such as polypropylene and blends of polypropylene and polyethylene. The nonwoven webs/laminates may comprise fibers selected from polypropylene, polypropylene/polyethylene blends, and polyethylene/polyethylene terephthalate blends. In some forms, the nonwoven webs/laminates may comprise fibers selected from cellulose rayon, cotton, other hydrophilic fiber materials, or combinations thereof. The fibers can also comprise a super absorbent material such as polyacrylate or any combination of suitable materials.

The fibers of the crimped fiber spunbond nonwoven webs/laminates of the present invention may comprise fibers which are bi-component, multi-component, and/or bi-constituent, round or non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >2 denier), shape (i.e. capillary and round) and the like. The constituent fibers can range from about 0.1 denier to about 100 denier.

For the nonwoven laminates of the present invention, layers of the laminate which are not the crimped fiber spunbond nonwoven web may comprise any of the above fibers. Additionally, such layers may comprise monocomponent fibers as well.

Forms of the present invention are contemplated where the first layer and/or second layer comprise additives in addition to their constituent chemistry. For example, suitable additives include additives for coloration, antistatic properties, lubrication, softness, hydrophilicity, hydrophobicity and the like and combinations thereof. These additives, for example titanium dioxide for coloration, are generally present in an amount less than about 5 weight percent and more typically about 2 weight percent or less.

As used herein, the term "monocomponent" fiber refers to a fiber formed from one extruder using one or more polymers. This is not meant to exclude fibers formed from one polymer to which small amounts of additives have been added for coloration, antistatic properties, opacity, lubrication, hydrophilicity, etc.

Figure 63:
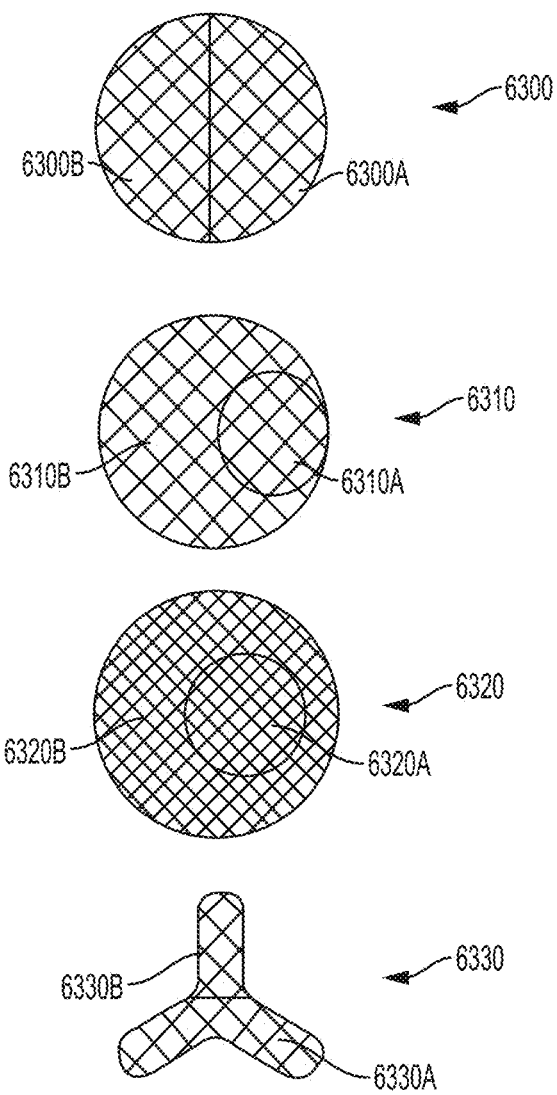
FIG. 63 is a schematic illustration of multiple cross sections of bi-component fibers for use with the present invention.

As used herein, the term "bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some suitable examples of bi-component fiber configurations are shown in FIG. 63. For example, fibers of the crimped fiber spunbond nonwoven webs of the present invention may comprise fibers having a cross section 6300 which comprises a first component 6300A and a second component 6300B arranged in a side by side configuration. As another example, crimped fiber spunbond nonwoven webs of the present invention may comprise fibers having a cross-section 6310 which comprises a first component 6310A and a second component 6310B in an eccentric sheath-core configuration. Another eccentric sheath-core configuration which may be utilized is shown with regard to cross-section 6320 which comprises a first component 6320A and a second component 6320B. Also, non-round fiber cross-sections are contemplated. For example, the crimped fiber spunbond nonwoven webs of the present invention may comprise fibers having a cross-section 6330 which is tri-lobal. The tri-lobal cross section 6330 comprises a first component 6330A and a second component 6330B, where the second component 6330B is one of the lobes of the tri-lobal cross section.

Some specific examples of fibers which can be used in the crimped fiber spunbond nonwoven webs of the present invention include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration. Still another example, is polypropylene/poly-lactic acid bi-component fiber. Still another example is polyethylene/poly-lactic acid bi-component fiber. For the bi-component fibers of polyethylene/poly-lactic acid, such fibers may be produced from renewable resources. For example, both the polyethylene and polylactic acid may be bio sourced. Additionally, polypropylene and poly-lactic acid based fibers would typically not withstand the out-of-plane deformation processing described herein; however, when configured as a crimped fiber, such fibers may withstand said processing.

Bi-component fibers may comprise two different resins, e.g. a first resin and a second resin. The resins may have different melt flow rates, molecular weights, branching, viscosity, crystallinity, rate of crystallization, and/or molecular weight distributions. Ratios of the 2 different polymers may be about 50/50, 60/40, 70/30, 80/20, 90/10 or any ratio within these ratios. The ratio may be selected to control the amount of crimp, strength of the nonwoven layer, softness, bonding or the like.

As used herein, the term "bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multiconstituent components.

As used herein, the term "non-round fibers" describes fibers having a non-round cross-section, and includes "shaped fibers" and "capillary channel fibers." Such fibers can be solid or hollow, and they can be tri-lobal, delta-shaped, and can be fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

The basis weight of nonwoven materials is usually expressed in grams per square meter (gsm). The basis weight of a single layer nonwoven material can range from about 8 gsm to about 100 gsm, depending on the ultimate use of the material. For example, each layer of a nonwoven laminate of the present invention may have a basis weight from about 8 to about 40 gsm or from about 8 to about 30 gsm. The basis weight of a multi-layer material is the combined basis weight of the constituent layers and any other added components. The basis weight of multi-layer materials of interest herein can range from about 20 gsm to about 150 gsm, depending on the ultimate use of the material.

As noted previously, at least one of the webs of the laminates of the present invention comprises spunbond crimped fibers. The other web(s) may be selected from any suitable type of material. Some suitable examples include spunbond nonwoven webs, thermally point bonded spunbond, carded nonwoven webs, through air bonded or hydroentangled nonwoven webs. Any suitable film may also be utilized.

Regarding the crimped fiber spunbond nonwoven webs/laminates of the present invention, the precursor materials may have certain desired characteristics. For example, the precursor materials each have a first surface, a second surface, and a thickness. The first and second surfaces of the precursor materials may be generally planar. And for those layers of the laminates of the present invention which are not crimped fiber spunbond nonwoven webs, it may be desirable for the precursor materials to have extensibility to enable the fibers to stretch and/or rearrange into the form of the apertures, tufts and/or caps. Extensibility is desirable in order to maintain at least some non-broken fibers in the sidewalls around the perimeter of the tufts and/or caps and to aperture without causing significant fiber breaking or web tearing. It may be desirable for individual precursor materials, or at least one of the webs within the laminates, to be capable of undergoing an elongation of greater than or equal to about one of the following amounts: 100% (that is double its unstretched length), 110%, 120%, or 130% up to about 200%, up to about 250% or more, at or before reaching the peak tensile force. It may also desirable for the precursor materials to be capable of undergoing plastic deformation to ensure that the structure of the out-of-plane deformations is "set" in place so that the nonwoven laminate will not tend to recover or return to its prior configuration. However, in the case crimped fiber spunbond webs, it may be desirable for the precursor material for these specific web(s) to be capable of experiencing no or minimal plastic deformation during processing.

As stated previously, in contrast to spunbond nonwoven webs, the constituent fibers of the crimped fiber spunbond nonwoven webs typically are uncoiled and/or displaced when processed as described herein. Because the crimped fibers tend to coil to some extent, the out-of-plane processing described herein typically displaces/uncoils the crimped fibers as opposed to plastically deforming the crimped fibers. As such, the crimped fibers have a different stress-strain profile versus conventional spunbond fibers.

Extensibility of a nonwoven web can be impacted by calendar bonding between constituent fibers. This is true for both spunbond nonwoven layers and crimped fiber spunbond nonwoven layers. For example, to increase extensibility in a nonwoven web, it may be desirable for the nonwoven web to be underbonded as opposed to optimally bonded prior to processing. A thermally bonded nonwoven web's tensile properties can be modified by changing the bonding temperature. A web can be optimally or ideally bonded, underbonded or overbonded. Optimally or ideally bonded webs are characterized by the highest peak tensile strength and elongation at tensile peak with a rapid decay in strength after tensile peak. Under strain, bond sites fail and a small amount of fibers pull out of the bond site. Thus, in an optimally bonded nonwoven, the fibers will stretch and break around the bond sites when the nonwoven web is strained beyond a certain point. Often there is a small reduction in fiber diameter in the area surrounding the thermal point bond sites. Underbonded webs have a lower peak tensile strength and elongation at tensile peak when compared to optimally bonded webs, with a slow decay in strength after tensile peak. Under strain, some fibers will pull out from the thermal point bond sites. Thus, in an underbonded nonwoven, at least some of the fibers can be separated easily from the bond sites to allow the fibers to pull out of the bond sites and rearrange when the material is strained. Overbonded webs also have a lowered peak tensile strength and elongation at tensile peak when compared to optimally bonded webs, with a rapid decay in strength after tensile peak. The above calendar bond sites look like films and result in complete bond site failure under strain.

Similarly, extensibility of crimped fiber spunbond nonwoven webs can be impacted by the degree of crimp in the constituent fibers. The more curl that the fibers comprise, the higher the tensile elongation of the crimped fiber spunbond nonwoven web. The level of curl of a crimped fiber spunbond nonwoven web can be tailored based upon material selection, ratio of the two polymers of the bi-component fiber, fiber cross section, amount of draw in the spunbond process, heat treatments, and melt additives. Additionally, the inventors have found that with a narrower molecular weight distribution in the material selection, more crimp can be achieved.

In some forms nonwoven laminates of the present invention may be configured with constituent nonwoven webs which have differing levels of extensibility. For example, a lower web may comprise a nonwoven having greater extensibility than an upper layer. In such configurations, after processing to create tufts/caps, there is a greater likelihood of creating tufts with no corresponding caps.

For crimped fiber spunbond nonwoven webs, calendar bonding of the web is also important. As shown in FIGS. 12A-15B, too low of a calendar bond area does not allow for good formation of tufts/caps. And too low of a calendar bond area yields a web with low strength and poor abrasion resistance. However, too high of a calendar bond area reduces the length of fibers between bonds which inhibits the amount of uncoiling and/or displacement possible. Specifically, too high of a calendar bond area inhibits the movement of the fibers such that when subjected to the processing described herein for the formation of tufts/caps, the crimped fibers have very limited ability to uncoil. In such configurations, the crimped fibers must undergo plastic deformation or break once the amount of uncoiling surpasses the amount of applied process strain. The inventors have found that calendar bond area above about 10 percent and less than about 18 percent allows for a good balance of fiber mobility and free fiber length available for uncoiling but still provides sufficient strength in the crimped fiber spunbond nonwoven web for manipulations of the crimped fiber spunbond nonwoven web as well as abrasion and tearing resistance in use.

Figure 12A:
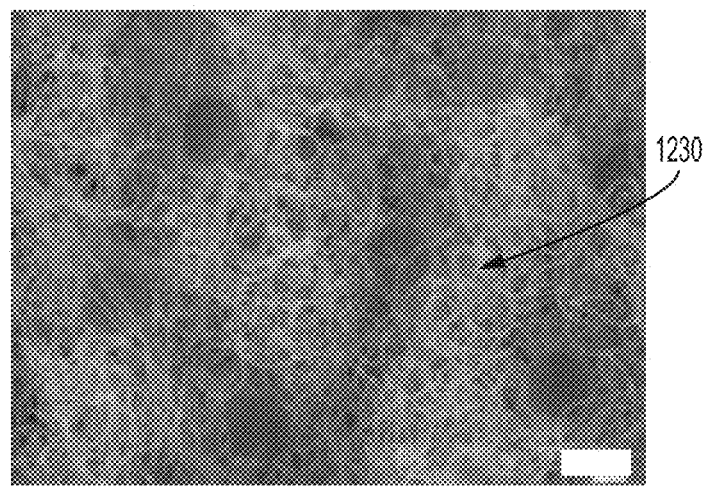
FIGS. 12A and 12B depict a top view and side view, respectively, of a nonwoven laminate of the present invention comprising tufts/caps.
Figure 12B:
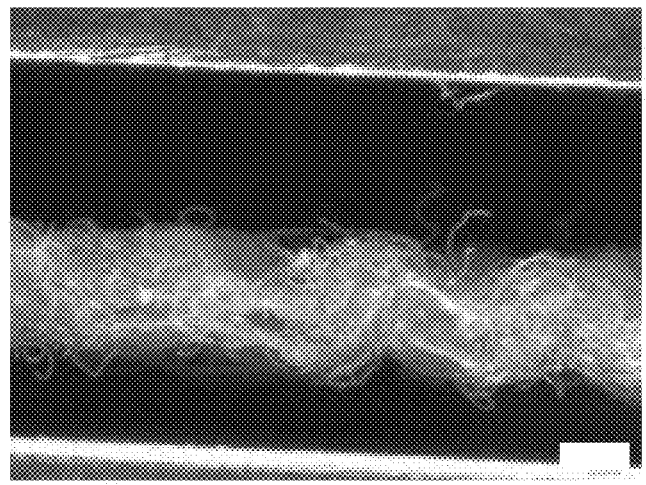

FIGS. 12A and 12B depict nonwoven laminates of the present invention comprising a crimped fiber spunbond nonwoven webs as the upper and lower layers. With regard to FIGS. 12A and 12B, the upper layer has a calendar bond area of about 10 percent while the lower layer has a bond area of about 12 percent. As shown, the tufts/caps 1230 are not very well defined. It is believed that with a bond area of below about 10 percent that there is too much fiber mobility and the fibers are not able to retain a tuft/cap form.

Figure 13A:
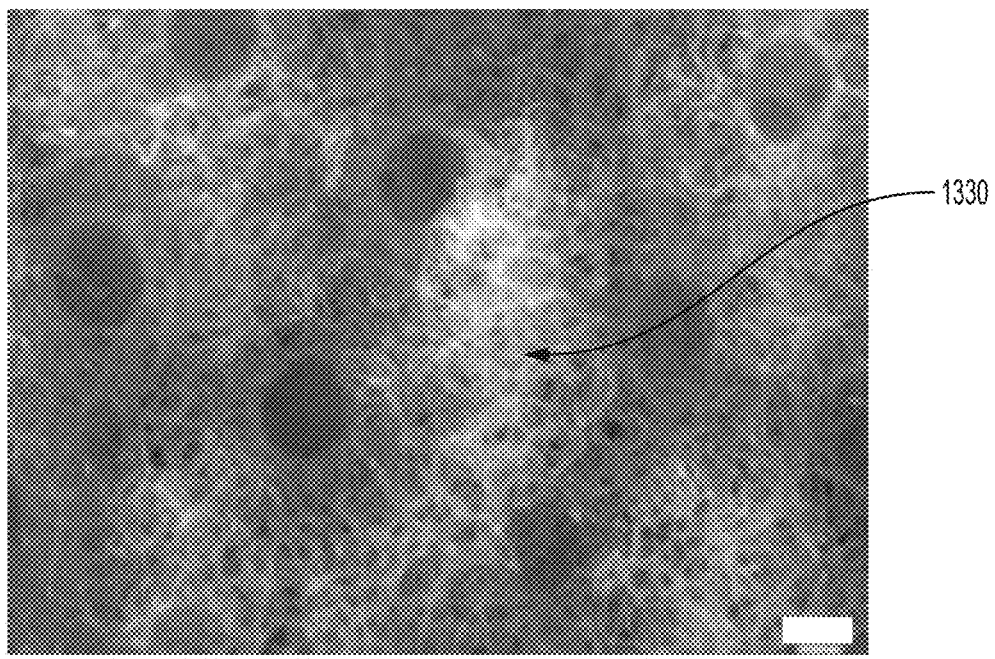
FIGS. 13A and 13B depict a top view and side view, respectively, of another nonwoven laminate of the present invention comprising tufts/caps.
Figure 13B:
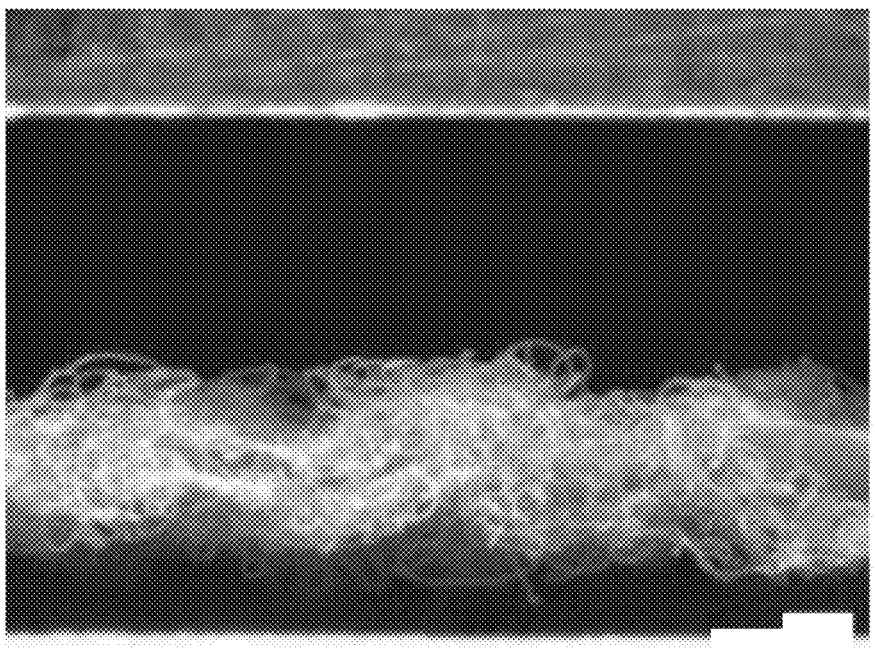

With regard to FIGS. 13A and 13B, both the upper and lower layers have a calendar bond area of about 12 percent. In contrast with the tufts/caps of FIGS. 12A and 12B, the tufts/caps 1330 of FIGS. 13A and 13B are more clearly defined. Namely, the tufts/caps 1330 have some recognizable shape in comparison to the surrounding crimped fibers.

Figure 14A:
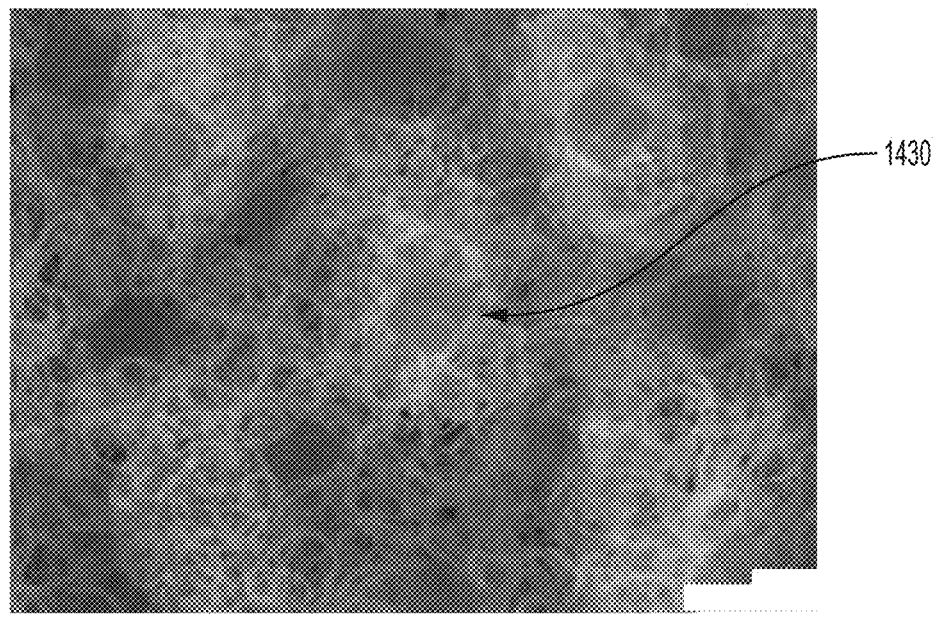
FIGS. 14A and 14B depict a top view and side view, respectively, of another nonwoven laminate of the present invention comprising tufts/caps.
Figure 14B:
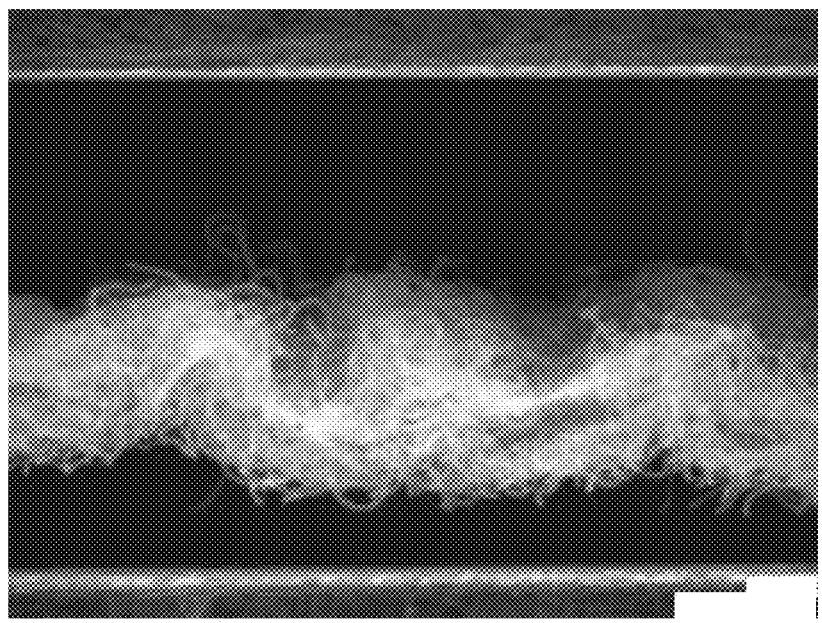

With regard to FIGS. 14A and 14B, both the upper and lower layers have a calendar bond area of about 14.6 percent. Much like the tufts/caps 1330 of FIGS. 13A and 13B, the tufts/caps 1430 are more clearly defined over the tufts/caps 1230 of FIGS. 12A and 12B.

Figure 15A:
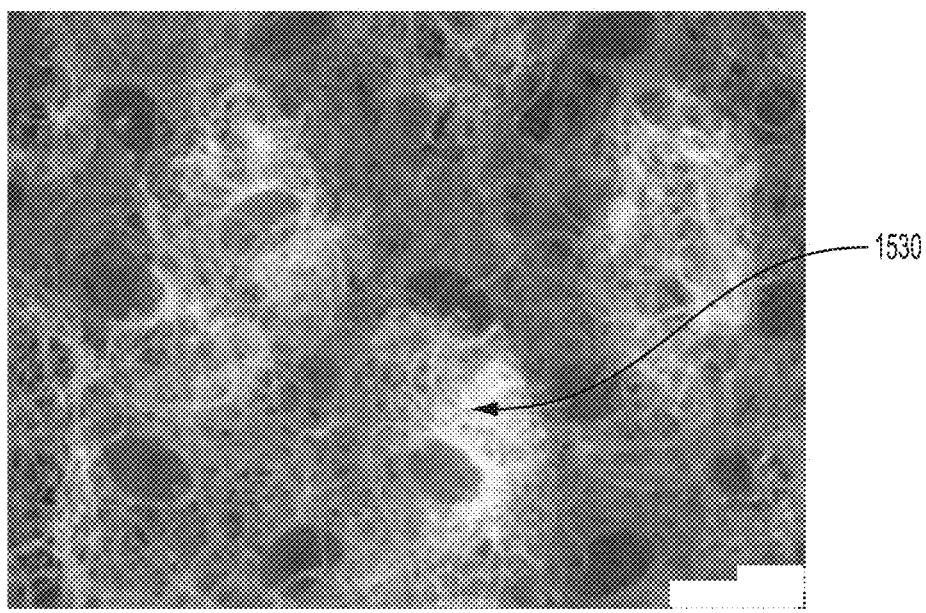
FIGS. 15A and 15B depict a top view and side view, respectively, of another nonwoven laminate of the present invention comprising tufts/caps.
Figure 15B:
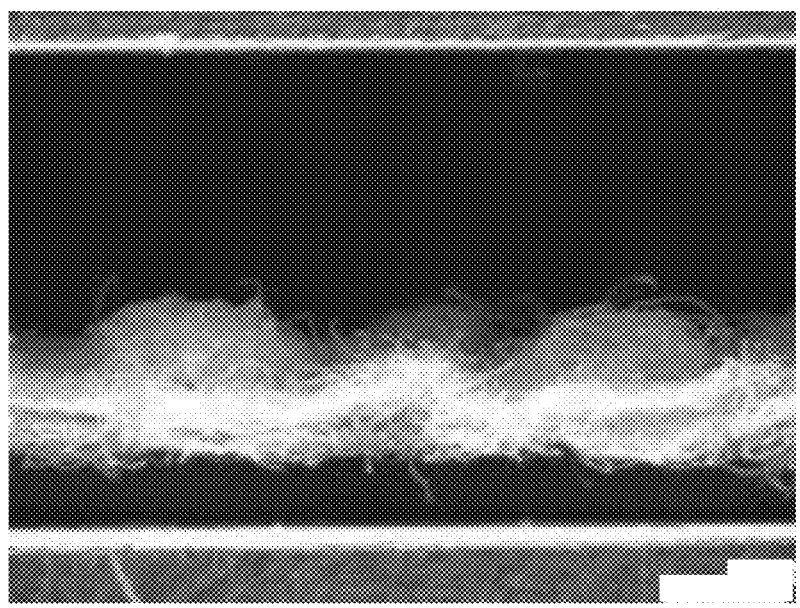

With regard to FIGS. 15A and 15B, both the upper and lower layers have a calendar bond area of about 18 percent. While the tufts/caps 1530 are well defined, the tufts/caps 1530 are not as fluffy as those depicted with the about 12 percent or about 14.6 percent bond area. As stated previously, it is believed that higher calendar bond areas inhibit the fiber movement and create lower path length for uncoiling of the crimped fibers. Namely, with a higher calendar bond area percentage, the crimped fibers have a shorter path length to uncoil and so will be forced to thin or break at a lower process strain. It is further believed that with calendar bond areas greater than about 18 percent, the softness, loft and permeability would also be negatively impacted as well as lower resultant strength due to increased fiber breakage.

In some forms of the present invention, the crimped fiber spunbond nonwoven webs may comprise a calendar bond area of between about 10 percent to about 18 percent or between about 12 percent and 16 percent or any value within these ranges. Spunbond nonwoven layers (not crimped) may comprise a calendar bond area of between about 5 percent to about 30 percent, between about 10 percent to about 20 percent, or any value within these ranges. The nonwoven webs may be bonded or underbonded as described above. The bonds can be shaped like dots, diamonds, ovals or any other suitable shape and may be arranged in any suitable pattern to provide the desired mechanical properties.

The webs of a nonwoven laminate of the present invention can be combined together in any suitable manner. In some cases, the layers can be unbonded to each other and held together autogenously (that is, by virtue of the formation of out-of-plane deformations therein). For example, both layers of the precursor materials may contribute fibers to out-of-plane deformations in a "nested" relationship that "locks" the precursor materials together, forming a multi-layer laminate without the use or need for adhesives or thermal bonding between the webs. In other forms, the webs can be joined together by other mechanisms. If desired an adhesive between the webs, ultrasonic bonding, chemical bonding, resin or powder bonding, thermal bonding, or bonding at discrete sites using a combination of heat and pressure can be selectively utilized to bond certain regions or all of the precursor webs. If adhesives are used, they can be applied in any suitable manner or pattern including, but not limited to: slots, spirals, spray, and curtain coating. Adhesives can be applied in any suitable amount or basis weight including, but not limited to between about 0.5 and about 30 gsm, alternatively between about 2 and about 5 gsm. Still in other configurations, the nonwoven layers may be combined together via an aperturing process. For example, two nonwoven webs may be fused together at a plurality of discrete locations—overbonds. The discrete locations may be subjected to incremental stretching which causes the discrete locations to fracture thereby forming an aperture. In general, at the perimeter of the aperture, the nonwoven webs are joined together via a melt/fused lip. The melt/fused lip can define at least a portion of an aperture perimeter when created via overbonding.

In other forms, the constituent nonwoven webs may comprise minimal fiber-to-fiber bonds. For example, the first layer and/or second layer can have a pattern of discrete thermal point bonds, as is commonly known in the art for nonwoven webs. However, as discussed previously, bonded area can impact the resultant structures of the nonwoven layers. In general, using fibers having relatively high diameters, and/or relatively high extension to break, and/or relatively high fiber mobility, might result in better and more distinctly formed tufts and/or caps. In another embodiment, the nonwoven webs can be through air bonded nonwoven material.

The constituent nonwoven webs of the nonwoven laminates of the present invention may be provided with structural integrity via a variety of different processes. Some examples include thermal point bonding, air through bonding, hydroentangling, and needlepunching each of which is well known in the art.

In some forms, the constituent fibers of the first nonwoven web are selected such that the first nonwoven web is hydrophobic, and the constituent fibers of the second nonwoven web are selected such that the second nonwoven web is hydrophilic.

As noted previously, some laminates of the present invention may additionally comprise film. Any suitable film may be utilized. Some suitable examples include those described in U.S. Pat. Nos. 3,929,135; 4,324,426; 4,324,314; 4,629,643; 4,463,045; and 5,006,394. Where laminates comprising film are utilized, the film may be extruded directly onto the crimped fiber spunbond nonwoven web during the making of the laminate.

Nonwoven Web/Laminate Processing

The manufacture of the crimped fiber spunbond nonwoven webs/laminates of the present invention may be via any suitable method. The first layer and/or second layer can be produced via the spunbonding nonwoven process which is well known in the art.

Figure 16A:
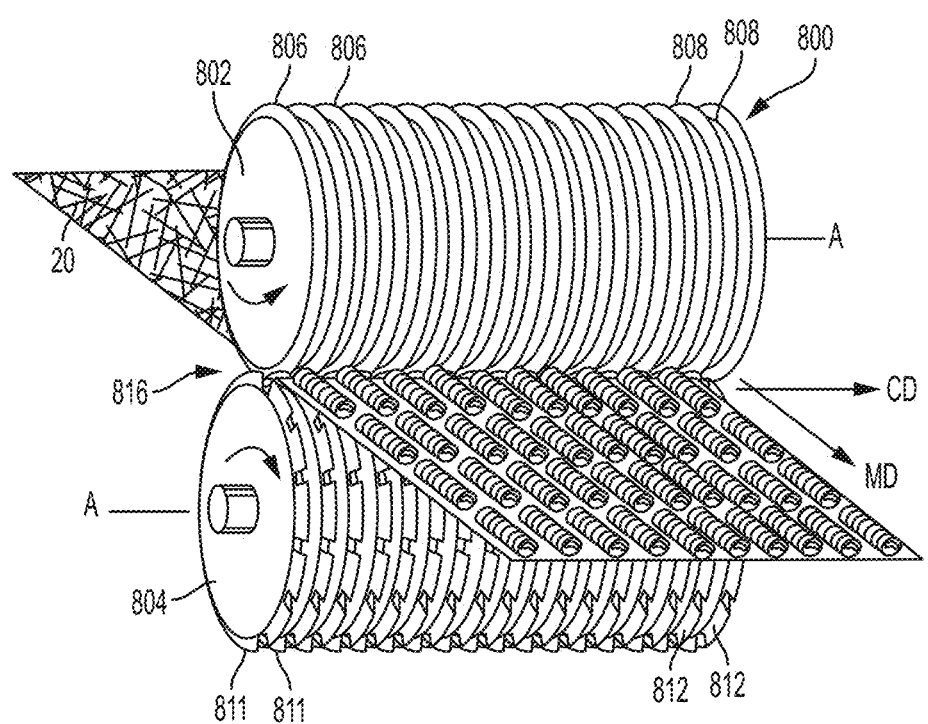
FIG. 16A is a perspective view of an apparatus for forming the nonwoven laminate of the present invention.

Depending on the orientations of caps and tufts described heretofore, processing of crimped fiber spunbond nonwoven laminates of the present invention can vary. Referring to FIG. 16A, there is shown an apparatus 800 and method for producing the crimped fiber spunbond nonwoven webs/laminates of the present invention. The apparatus 800 comprises a pair of intermeshing rolls 802 and 804, each rotating about an axis A—the axes A being parallel and in the same plane. Roll 802 comprises a plurality of ridges 806 and corresponding grooves 808 which can extend unbroken about the entire circumference of roll 802.

Roll 804 is similar to roll 802, but rather than having ridges that extend unbroken about the entire circumference, roll 804 comprises a plurality of rows of circumferentially-extending ridges that have been modified to be rows of circumferentially-spaced teeth 811 that extend in spaced relationship about at least a portion of roll 804. The individual rows of teeth 811 of roll 804 are separated by corresponding grooves 812. In operation, rolls 802 and 804 intermesh such that the ridges 806 of roll 802 extend into the grooves 812 of roll 804 and the teeth 811 of roll 804 extend into the grooves 808 of roll 802. A nip 816 is formed between the counter-rotating intermeshing rolls 802 and 804. Both or either of rolls 802 and 804 can be heated by means known in the art such as by using hot oil filled rollers or electrically-heated rollers.

The apparatus 800 is shown in a configuration having one patterned roll, e.g., roll 804, and one non-patterned grooved roll 802. However, in certain embodiments it may be preferable to use two patterned rolls similar to roll 804 having either the same or differing patterns, in the same or different corresponding regions of the respective rolls. Such an apparatus can produce laminates with tufts protruding from both sides of the nonwoven laminate of the present invention.

Nonwoven laminates of the present invention can be made by mechanically deforming the first layer and the second layer that can each be described as generally planar and two dimensional prior to processing by the apparatus shown in FIG. 16A. By "planar" and "two dimensional" is meant simply that the laminates start the process in a generally flat condition relative to the finished nonwoven laminate that has distinct, out-of-plane, Z-direction three-dimensionality due to the formation of tufts and/or caps. "Planar" and "two-dimensional" are not meant to imply any particular flatness, smoothness or dimensionality.

Some nonwoven laminates of the present invention described herein can be processed as described above with some variation. For example, in order to accomplish the negative Z-direction urging as described herein, the nonwoven webs may be provided to the apparatus 800 such that the second layer is disposed superjacent to the first layer. However, flipping the resultant nonwoven laminate at rapid production speeds for processing could prove difficult to manage and may introduce much complexity into the production of such nonwoven laminates. Alternatively, for the creation of tufts and/or caps protruding in the negative Z-direction, the rolls 802 and 804 of apparatus 800 can be inverted. For example, the patterned roll 804 may be positioned superjacent to the non-patterned grooved roll 802.

The number, spacing, and dimensions of tufts and/or caps can be varied to give varying texture to crimped fiber spunbond nonwoven webs/laminates of the present invention. For example, if tufts and/or caps are sufficiently closely spaced the resultant nonwoven laminate can have a terry cloth-like feel. Alternatively, tufts and/or caps can be arranged in patterns such as lines or filled shapes to create portions of a laminate having greater texture, softness, bulk, absorbency or visual design appeal. For example, when tufts and/or caps are arranged in a pattern of a line or lines, the tufts and/or caps can have the appearance of stitching. Likewise, the size dimensions, such as the height, length and width of individual tufts can be varied.

Single tufts and/or caps can be as long as about 3 cm in length and can be made alone or dispersed among tufts and/or caps of various sizes. In some embodiments, the tufts and/or caps may have a length ranging from about 1 mm to about 10 mm. In some embodiments, the tufts and/or caps may have a length ranging from about 2 mm to about 8 mm; from about 3 mm to about 7 mm, or any ranges within the values recited or any numbers within the values recited.

Additionally, forms of crimped fiber spunbond nonwoven webs/laminates are contemplated which comprise a plurality of tufts and/or caps which are configured differently. For example, a nonwoven laminate of the present invention may comprise a tuft 270 (shown in FIGS. 2A-2C) and a cap 230 (shown in FIGS. 2A-2C) in a first area of the nonwoven laminate and may comprise a tuft 370 (shown in FIG. 3) in a second area of the nonwoven laminate without a corresponding cap. In another example, nonwoven laminate of the present invention may comprise a tuft 470 (shown in FIG. 4) in a first area of a nonwoven laminate and may comprise a tuft 270 and a cap 230 (shown in FIGS. 2A-2C) in a second area of the nonwoven laminate. In yet another example, a nonwoven laminate of the present invention may comprise a tuft 370 (shown in FIG. 3) in a first area of the nonwoven laminate and a tuft 470 (shown in FIG. 4) in a second area of the nonwoven laminate. In yet another example, a nonwoven laminate of the present invention may comprise a tuft 270 and a cap 230 (shown in FIGS. 2A-2C) in a first area of the nonwoven laminate and a tuft 570 and a cap 530 (shown in FIG. 5) in a second area of the nonwoven laminate. In yet another example, a nonwoven laminate of the present invention may comprise a tuft 570 and a cap 530 (shown in FIG. 5) in a first area of the nonwoven laminate and a tuft 370 (shown in FIG. 3) in a second area of the nonwoven laminate. In yet another example, a nonwoven laminate of the present invention may comprise a tuft 570 and a cap 530 (shown in FIG. 5) in a first area of the nonwoven laminate and may comprise a tuft 470 (shown in FIG. 4) in a second area of the nonwoven laminate. Crimped fiber spunbond nonwoven webs/laminates of the present invention may utilize any and all combinations of the tufts and/or caps described with regard to FIGS. 2A-2C and 3-5), e.g. first area with first set of tufts and/or caps, second area with second set of tufts and/or caps, third area with third set of tufts and/or caps, and so on, wherein each of the first, second and third sets of tufts and/or caps are different. Additional examples include variation in spacing between tufts/caps in addition to or independent of variations in the tufts/caps themselves.

Referring back to FIG. 16A, the first layer and the second layer can be moved in the machine direction to the nip 816 of counter-rotating intermeshing rolls 802 and 804. The first layer and the second layer are preferably held in a sufficient web tension so as to enter the nip 816 in a generally flattened condition by means well known in the art of web handling. As each of the first layer and the second layer goes through the nip 816, the teeth 810 of roll 804—which are intermeshed with grooves 808 of roll 802—simultaneously urge fibers of the first layer out of the plane of the first layer thereby forming caps and urge fibers of the second layer out of the plane of the second layer and through the plane of the first layer to form tufts.

The number, spacing, and size of tufts and/or caps can be varied by changing the number, spacing, and size of teeth 811 and making corresponding dimensional changes as necessary to roll 804 and/or roll 802. This variation, together with the variation possible in first layer and the second layer permits many varied crimped fiber spunbond nonwoven laminates to be made for many purposes. The size of teeth as well as additional details regarding processing of nonwovens and laminates comprising nonwovens can be found in U.S. Pat. Nos. 7,410,683; 7,789,994; 7,838,099; 8,440,286; and 8,697,218.

The out-of-plane deformations disclosed herein with regard to FIGS. 2A-9B, may be provided in arrays or a plurality thereof. Such arrays of out-of-plane deformations or plurality of arrays of structures may comprise a pattern or a plurality of patterns which form graphics and/or other depictions, hereafter, "structural indicia." Additional forms are contemplated where the out-of-plane deformations described herein may be utilized in any combination.

As stated previously, the first layer and the second layer, as described herein, may be provided as discrete layers. For example, forms are contemplated where the first layer is derived from a first supply roll having a first specific fiber makeup while the second layer is derived from a second supply roll having a second specific fiber makeup. In some embodiments, the fiber makeup between the first supply roll and the second supply roll can be different as described herein.

The crimped fiber spunbond nonwoven webs of the present invention may be processed similar to the laminates described herein. For those forms including a crimped fiber spunbond nonwoven web and a film layer, processing may be as described above. However, the film layer may be subjected to additional processing in an effort to enhance the softness/feel of the film. Such processing of film layers is disclosed in U.S. Patent Application Publication No. 2005/0214506; U.S. Pat. Nos. 4,609,518; 4,629,643; 4,637,819; 4,681,793; 4,695,422; 4,778,644; 4,839,216; and 4,846,821.

Figure 16B:
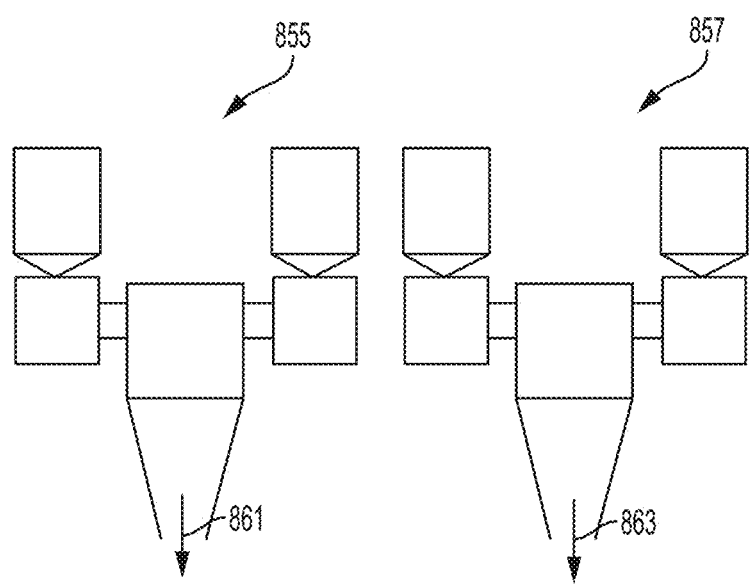
FIG. 16B is a schematic illustration of an apparatus for forming crimped fiber spunbond nonwoven webs.
Figure 16C:
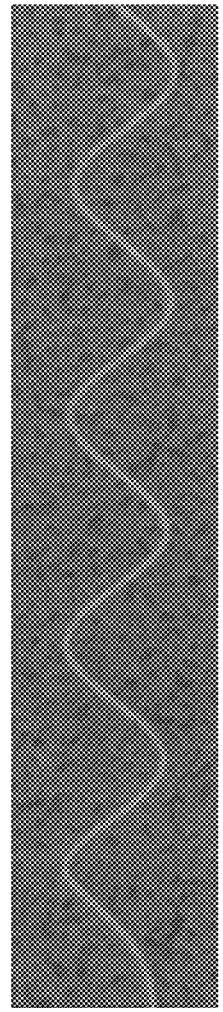
FIG. 16C is a photograph showing a crimped fiber.
Figure 16D:
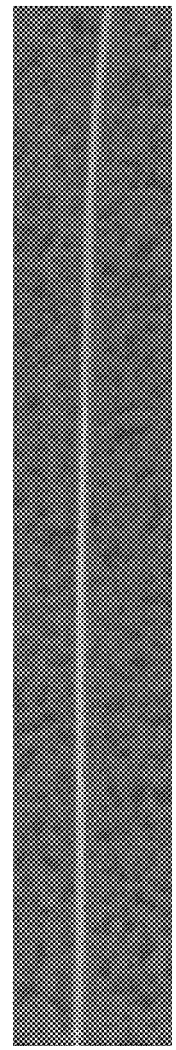
FIG. 16D is a photograph showing a straight fiber.

Additional forms are contemplated where crimped fiber spunbond nonwoven webs are utilized which comprise a heterogeneous structure. For example, as shown in FIG. 16B, a crimped fiber spunbond nonwoven web of the present invention may be produced via a spunbond process comprising multiple spinbeams 855, 857. In some forms, the first spinbeam 855 may deposit a first plurality of continuous fibers 861 onto a belt. The first plurality of continuous fibers 861 may comprise crimped fibers, e.g. side by side configurations. The second spinbeam 857 may deposit a second plurality of continuous fibers 863 onto the belts over the top of the first plurality of continuous fibers 861. The second plurality of continuous fibers may be configured differently than the first plurality of continuous fibers. For example, in some forms, the second plurality of continuous fibers may comprise non crimped fibers—straight fibers. An example of crimped fiber versus straight fiber is shown in FIGS. 16C and 16D, respectively. Additional forms are contemplated where the first plurality of continuous fibers 861 comprises a first melt additive, and the second plurality of continuous fibers 863 comprises a second melt additive. In some forms of the present invention, the melt additives can be different. For example, the first melt additive may be hydrophilic where the second melt additive is hydrophobic. In other forms, the first plurality of continuous fibers 861 may be chosen such that the fibers are hydrophilic and the second plurality of continuous fibers 863 comprises crimped fibers which comprise a hydrophobic melt additive.

In some forms, the first plurality of continuous fibers 861 and the second plurality of continuous fibers 863 may be the same such that the resultant crimped fiber spunbond nonwoven web is homogeneous with regard to the fibers. Additional beams may be provided to provide additional continuous fibers or melt-blown fibers. In some forms, a single beam may be utilized to produce a crimped fiber spunbond nonwoven web.

Additives

And as noted previously, the first layer may include a hydrophobic melt additive and/or the second layer may include a hydrophilic melt additive or topical hydrophilic. Still in other forms, the nonwoven laminates of the present invention may be configured such that the first web is more hydrophobic than the second web either via additive, fiber material selection, or combinations thereof. In other forms, the hydrophobic additive and/or hydrophilic additive may be sprayed on or otherwise topically applied. Additional additives are contemplated. For example, an additive for softness may be added to any of the crimped fiber spunbond nonwoven webs or crimped fiber spunbond nonwoven laminates. A suitable example of an additive for softness includes Erucamide which may be provided in amounts ranging from about 1 to about 20 percent by weight.

Hydrophobic Additive

In addition to selecting constituent precursor materials which exhibit the desired hydrophobic/hydrophilic qualities, other methods are contemplated for producing the hydrophobic/hydrophilic gradient as described above. For example, crimped fiber nonwoven webs and/or other nonwoven webs in the case of a laminate described herein may comprise an additive which blooms on a surface of at least a portion of a first plurality of fibers. In some forms, the additive may be added directly to the fibers or as master batch to the polymer melt during spinning of the filaments as a melt additive. Where the additive is melt blended into the filaments, the additive can bloom to the surface of the fibers and create a film covering a portion of the external surface of the fiber and/or can create fibrils, flakes, particles, and/or other surface features. For those fibers comprising fibrils, the fibrils may extend outwardly, or radially outwardly, from the surface.

While the fibrils extend outwardly from surfaces of individual fibers, the fibrils may also extend to or from (i.e., contact) other fibers within the same layer or a different layer of a nonwoven web and/or to fibrils extending from fibers within the same layer or a different layer of the nonwoven laminate. When the fibrils extend between fibers and/or other fibrils, the nonwoven web may achieve a greater liquid contact angle for polar and non-polar liquids. A similar effect may be obtained for additives which are applied to the first plurality of fibers post production. Without wishing to be bound by theory, it is believed that the additive, regardless of whether a melt additive or applied post fiber production, changes the surface energy of the constituent fibers. The change in surface energy increases the hydrophobic nature of the constituent fibers and therefore the nonwoven web. Additionally, it is believed that the additive, whether a melt additive or applied post fiber production, increases the surface roughness of the constituent fibers which can increase hydrophobicity. It is believed that an increase in hydrophobicity due to surface roughness is achieved by metastable Wenzel and stable Cassie-Baxter non-wetting states.

The additive suitable for the present invention may be any suitable hydrophobic additive. Thus, the additives may increase the hydrophobicity of the fibers upon whose surface they bloom. This can lead to increased low surface tension fluid strikethrough times and higher hydrophobicity for the nonwoven web.

Some examples of suitable additives include fatty alcohols and fatty acid esters. Non-limiting examples of suitable fatty alcohols having from about 12 to about 24 carbon atoms include saturated, un-substituted, monohydric alcohols or combinations thereof, which have a melting point less than about 110° C., preferably from about 45° C. to about 110° C. Specific examples of fatty alcohol carriers for use in the skin care compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol are Stenol 1822 and behenyl alcohol is Lanette 22, both of which are available from the Cognis Corporation located in Cincinnati, Ohio.

Non-limiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

The additives of the present disclosure, may have a melting point in the range of about 40 degrees C. to about 80 degrees C., about 55 degrees C. to about 75 degrees C., about 60 degrees C. to about 73 degrees C., specifically reciting all one degree C. increments within the specified ranges and all ranges formed therein or thereby. The additives of the present disclosure may have a melting temperature above 30° C., above 40° C., or above 50° C., but less than 80 degrees C., including all ranges within the values expressed and all numbers within the ranges created by the values expressed.

The additive may have a hydrophilic/lipophilic balance ("HLB") value of less than about 4. In some forms, the HLB value may be greater than about 0 and less than about 4, between about 1 and about 3.5, between about 2 and about 3.3, or any ranges within the values provided or any value within the ranges provided. It is believed that above an HLB value of about 4, the additive will start to take on more surfactant-like hydrophilic properties and would thereby reduce the benefit provided by the highly hydrophobic additive. Namely, as mentioned previously, the hydrophobic additive can provide a masking benefit which makes the disposable absorbent article utilizing the nonwoven webs/laminates of the present invention appear more "clean" after a liquid insult has occurred.

In some forms, the additive may have an IOB (inorganic value/organic value) value of greater than about 0 and less than about 0.4, between about 0.1 and about 0.35, between about 0.2 and 0.33, specifically including all values within these ranges and any ranges created thereby. The IOB value is discussed in additional detail in EP Patent Application Publication No. 2517689.

The additives used, may comprise fatty acid derivatives, such as a fatty acid ester; typically an ester formed from an alcohol with two or more hydroxyl groups and one or more fatty acids having between at least 12 carbon atoms to 22 carbon atoms, or at least 14 carbon atoms, whereby within one ester compound, different fatty acid-derived groups may be present (herein referred to as fatty acid ester).

The fatty acid ester compound may be an ester of an alcohol carrying two or more, or three or more, functional hydroxyl group per alcohol molecule, whereby all of the hydroxyl groups form an ester bond with fatty acids (either the fatty acid or mixtures thereof).

In some forms, the alcohol may have three functional hydroxyl groups. It is understood that in a fatty acid ester having more than one ester bond, such as in di- or tri-glycerides, the fatty acid-derived group may be the same, or they may be two or even three different fatty acids-derived groups. It is further understood that the additive component may comprise a mixture of mono- di- and/or tri-fatty acid ester (e.g. mono- di-, and/or triglyceride) esters with the same fatty-acid derived group per molecule, and/or with different fatty acid-derived groups without exceeding the scope of the invention. Preferred fatty acids in at least one embodiment may range from a C8 fatty acid to a C30 fatty acid; or, in another embodiment range from a C12 fatty acid to a C22 fatty acid. Suitable vegetable fatty acids typically include unsaturated fatty acids. The fatty acid may suitably be selected from the group comprising an arachidec acid, a stearic acid, a palmitic acid, a myristic acid, a myristoleic acid, an oleic acid, a limoleic acid, a linolenic acid, and an arachidonic acid. In another further embodiment, a substantially saturated fatty acid is preferred, particularly when saturation arises as a result of hydrogenation of fatty acid precursor. The fatty acids may range from a C12 fatty acid to a C22 fatty acid as illustrated in [1],

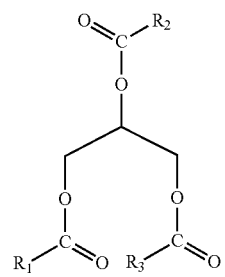

[1]

where R1' R2, and R3 each have a number of carbon atoms ranging from 11 to 21. In at least one other embodiment, the fatty acids may range from a C16 fatty acid to a C20 fatty acid.

In some forms, a substantially saturated fatty acid is preferred, particularly when saturation arises as a result of hydrogenation of fatty acid precursor. In at least one further form, a C18 fatty acid, stearic acid, is preferred. An example of the stearic acid-substituted fatty acid is [2-octadecanoyloxy-1-(octadecanoyloxymethyl)ethyl]octadecanoate having a CAS registry number of 555-43-1. It should be understood that the preferred triglyceride ester has an esterified glycerol backbone having no non-hydrogen sub-stituents on the glycerol backbone.

In some forms, the one or more additives may comprise a mono- and/or di-glyceride ester, and/or a triglyceride ester, (with one, two or three fatty acid-derived groups). It should be understood that while [1] illustrates a simple triglyceride in which all three pendent fatty acids may be the same, other embodiments may include a mixed triglyceride in which two or even three different pendent fatty acids are present without exceeding the scope of the invention. It should be further understood that while the triglyceride ester is illustrated in [1] is a single triglyceride ester formulation, the triglyceride ester used in the preparation of the master batch may include a plurality of triglyceride esters having different pendent fatty acid groups and/or one or more derivatives of the fatty acid, without exceeding the scope of the invention. It should be further understood that while the triglyceride ester illustrated in [1] is a monomer, the triglyceride ester used in the preparation of the master batch may include a polymerized triglyceride ester, such as a polymerized, saturated glyceride ester without exceeding the scope of the invention. It should be further understood that the polymerized triglyceride ester may comprise a mixture of polymers having different numbers of monomeric units included in the polymer. For example the polymerized triglyceride ester may include a mixture of monoesters, diesters, and the like.

The fatty acids used to form the ester compounds include fatty acid derivatives for the purpose of the present disclosure. A mono-fatty acid ester, or for example, a mono-glyceride, comprises a single fatty acid, e.g., connected a glycerol; a di-fatty acid ester, or e.g., di-glyceride, comprises two fatty acids, e.g., connected to the glycerol; a tri-fatty acid ester, or e.g. tri-glyceride, comprises three fatty acids, e.g., connected to a glycerol. In an embodiment, the additive may comprise at least a triglyceride ester of fatty acids (i.e., the same or different fatty acids).

It should be understood that the triglyceride ester may have an esterified glycerol backbone having no nonhydrogen substituents on the glycerol backbone; however, the glycerol backbone may also comprise other substituents. In some forms, the glycerol backbone of the glycerol ester may only comprise hydrogen. The glyceride esters may also comprise polymerized (e.g., tri) glyceride esters, such as a polymerized, saturated glyceride esters.

In a fatty acid ester having more than one ester bond, such as in di- or tri-glycerides, the fatty acid-derived group may be the same, or they may be two or even three different fatty acids-derived groups.

The additive may comprise a mixture of mono-, di-, and/or tri-fatty acid ester (e.g., mono-di- and/or triglyceride) esters with the same fatty-acid derived group per molecule, and/or with different fatty acid-derived groups.

The fatty acids may originate from vegetable, animal, and/or synthetic sources. Some fatty acids may range from a C8 fatty acid to a C30 fatty acid, or from a C12 fatty acid to a C22 fatty acid. Suitable vegetable fatty acids typically include unsaturated fatty acids such as oleic acid, palmitic acid, linoleic acid, and linolenic acid. The fatty acid may be arachidec, stearic, palmitic, myristic, myristoleic, oleic, limoleic, linolenic, and/or arachidonic acid.

In some forms, a substantially saturated fatty acid may be used, particularly when saturation arises as a result of hydrogenation of fatty acid precursor. In an embodiment, a C18 fatty acid, or octadecanoic acid, or more commonly called stearic acid may be used to form an ester bond of the fatty acid ester herein; stearic acid may be derived from animal fat and oils as well as some vegetable oils. The stearic acid may also be prepared by hydrogenation of vegetable oils, such as cottonseed oil. The fatty acid ester herein may comprise fatty acids of mixed hydrogenated vegetable oil, such as one having CAS registration number 68334-28-1.

At least one stearic acid, at least two, or three stearic acids are connected to a glycerol, to form a glycerol tristearate, for the additive herein. In an embodiment, the additive may comprise a glycerol tristearate (CAS No. 555-43-1), also known by such names as tristearin or 1,2,3-Trioctadecanoyl-glycerol. (In the following, the name glycerol tristearate will be used, and in case of doubt the CAS No., shall be seen as the primary identifier).

In some forms, additives with chemical structures similar to glycerol tristearate or tristearin such as triacylglycerols (triglycerides) including but not limited to trimyristin, tripalmitin, trilaurin, trimargarine, and waxes such as distearin, and mixtures of saturated and unsaturated glycerides, such as 1,3-distearoyl-2-oleoylglycerol (SOS) may be utilized. Non-limiting examples additives having molecular and crystallite structures as similar to tristearin include Alkylketene dimers (AKD), inorganic and organic salts of fatty acids (also known as alkyl carboxylic acids) that comprise of alkyl chains that are mostly saturated, and contain between 12 and 22 carbon atoms. Non-limiting examples of salts of fatty acids include zinc stearate, calcium stearate, magnesium stearate, titanium stearate, silver stearate, aluminum di- and tri-stearates, aluminum tripalmitate, aluminum trimyristate, aluminum trilaurate, sorbitan tristearate, sorbitan tripalmitate, sorbitan trimyristate, sorbitan trilaurate, and combinations thereof, which are believed to form flaky and fibrillar lamellar structures on surfaces due to blooming.

In some forms, the fatty acid ester of the additive may have a number-averaged molecular weight ranging from 500 to 2000, from 650 to 1200, or from 750 to 1000, specifically reciting all whole integer increments within the above-specified ranges and any ranges formed therein or thereby.

The additive may comprise very little or no halogen atoms; for example, the additive may comprise less than 5 wt. % halogen atoms (by weight of the additive), or less than 1 wt. %, or less than 0.1 wt. % of the additive; the additive may be substantially halogen-free.

In some forms, the additive may be or may comprise a lipid ester or glycerol tristearate. In various forms, the fibrils may comprise, consist of, or consist essentially of (i.e., 51% to 100%, 51% to 99%, 60% to 99%, 70% to 95%, 75% to 95%, 80% to 95%, specifically including all 0.1% increments within the specified ranges and all ranges formed therein or thereby) of the additive.

Nonlimiting examples of suitable alkyl ethoxylates include $C_{12}$-$C_{22}$ fatty alcohol ethoxylates having an average degree of ethoxylation of from about 2 to about 30. Non-limiting examples of suitable lower alcohols having from about 1 to about 6 carbon atoms include ethanol, isopropanol, butanediol, 1,2,4-butanetriol, 1,2 hexanediol, ether propanol, and mixtures thereof. Non-limiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof.

The master batch added to the composition from which the fibers of the present disclosure are formed may be the master batch disclosed in U.S. Pat. No. 8,026,188 to Mor.

In some forms, the fibrils may grow out of the fibers post-nonwoven substrate formation under ambient conditions. The fibrils may be noticeable using an SEM after about 6 hours post-nonwoven substrate formation under ambient conditions. Fibril growth may reach a plateau after about 50 hours, 75 hours, 100 hours, 200 hours, or 300 hours post-nonwoven substrate formation under ambient conditions. In some embodiments, fibril growth may continue well beyond 300 hours. The time range of noticeable fibril growth post-nonwoven substrate formation may be in the range of 1 minute to 300 hours, 5 hours to 250 hours, 6 hours to 200 hours, 6 hours to 100 hours, 6 hours to 24 hours, 6 hours to 48 hours, or 6 hours to 72 hours, under ambient conditions, specifically reciting all 1 minute increments within the above specified ranges and all ranges formed therein or thereby. The time to allow full fibril growth post-nonwoven substrate formation may be 12 hours, 24 hours, 48 hours, 60 hours, 72 hours, 100 hours, or 200 hours, for example, under ambient conditions. In some embodiments, fibril growth may occur almost immediately post nonwoven production.

Typical size scale of fibril or flake or other surface structures protruding from surface due to blooming may be of the order of few nanometers to few tens of micrometers. For example, the average length of the bloomed surface structures can range from about 5 nanometers to about 50 micrometers, from about 100 nanometers to about 30 micrometers, or from about 500 nanometers to about 20 micrometers. Preferred average width of the bloomed surface structures can range from about 5 nanometers to about 50 micrometers, from about 100 nanometers to about 20 micrometers, or from about 500 nanometers to about 5 micrometers. Preferred average thickness of the bloomed surface structures would range from about 5 nanometers to about 10 micrometers, more preferably from about 50 nanometers to about 5 micrometers, and most preferably from about 100 nanometers to about 1 micrometers. Preferred average hydraulic diameter, calculated as 4*(Cross-sectional Area)/(Cross-sectional Perimeter) of the bloomed surface structure can range from about 5 nanometers to about 20 micrometers, from about 50 nanometers to about 10 micrometers, or from about 100 nanometers to about 1.5 micrometers. In a specific embodiment, the average hydraulic diameter of a fibril is in the range of from about 100 nanometers to about 800 nanometers. Average separation of the bloomed surface structures from one another can range from about 100 nanometers to about 20 micrometers, from about 500 nanometers to about 10 micrometers, or from about 500 nanometers to about 5 micrometers.

The crimped fiber spunbond nonwoven webs of the present disclosure or crimped fiber spunbond nonwoven laminates of the present disclosure that have at least one layer comprising fibers comprising fibrils may be configured to be softer or harder than, or have the same softness as, conventional nonwoven laminates and/or may have a rougher, smoother, or the same tactile property as compared to conventional nonwoven substrates. The softness, hardness, and/or tactile property of the nonwoven substrates may vary depending on the type and amount of lipid esters present in the composition used to form the fibers and the length of the fibrils, for example. The softness, hardness, and/or texture may also vary depending on where the one or more layers of fibers having fibrils are positioned within a nonwoven substrate.

The additive may be applied at a basis weight of from about 0.1 gsm to 10 gsm, preferably <1 gsm or alternatively 0.4 percent by weight. The additive may be blended with other melt additive or topical ingredients, for example in a lotion composition. For those forms where bi-component fibers are utilized, the additive may be present at the same level in each of the constituents of the bi-component fiber, may be at different levels with regard to the constituents of the bi-component fiber, or may be preset in one constituent but not the other of a bi-component fiber.

For those forms where the hydrophobic additive is provided as a melt additive, e.g. part of the master batch, preferably between 0.5 percent by weight to about 20 percent by weight, preferably less than 10 percent by weight or any range within these values or any value within these ranges.

The additive may be applied to the fibers of the nonwoven laminates of the present invention by any suitable process. Some examples include spraying, slot coating, or the like. Other suitable hydrophobic additives are available from Techmer PM, LLC.

EXAMPLES

Figure 17:
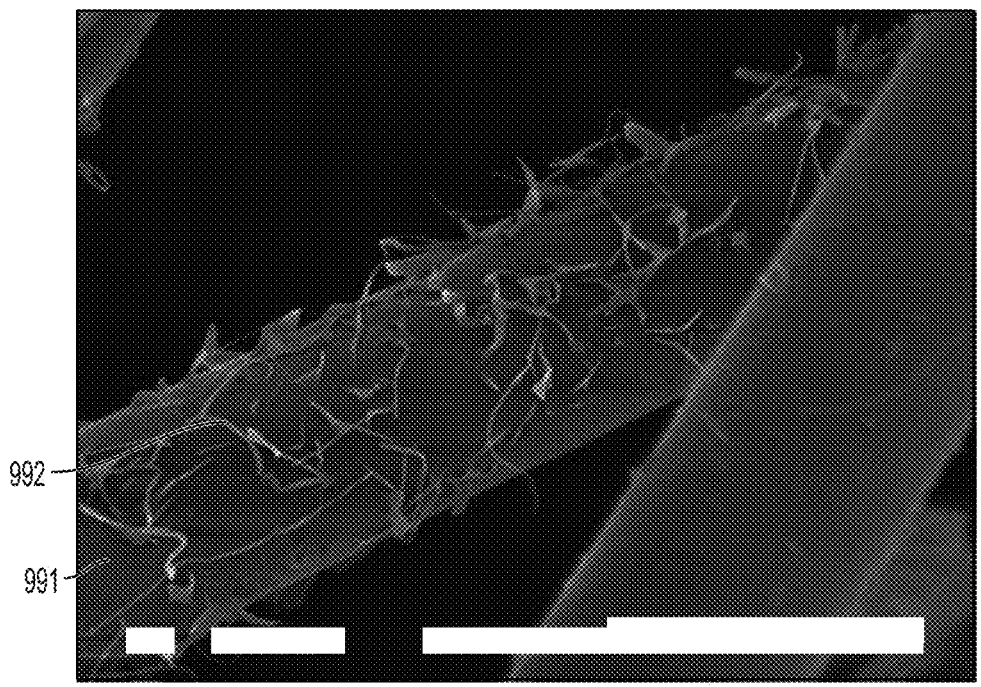
FIG. 17 is a scanning electron micrograph ("SEM") photo showing a nonwoven fiber with additive that has bloomed on the surface of the fiber.
Figure 18:
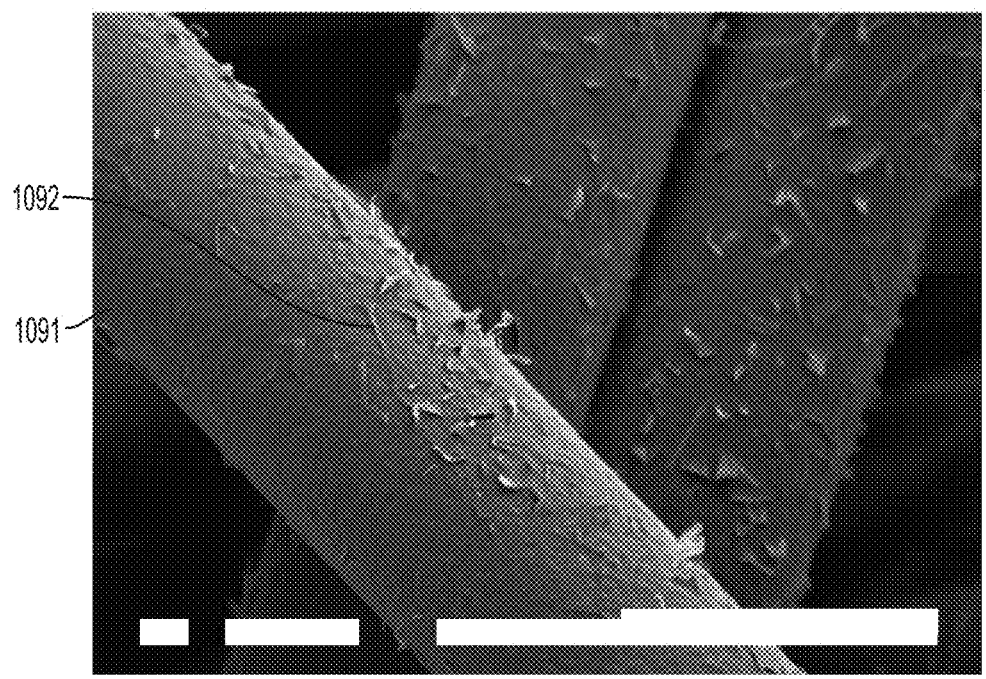
FIG. 18 is an SEM photo showing another nonwoven fiber with additive that has bloomed on the surface of the fiber.
Figure 19:
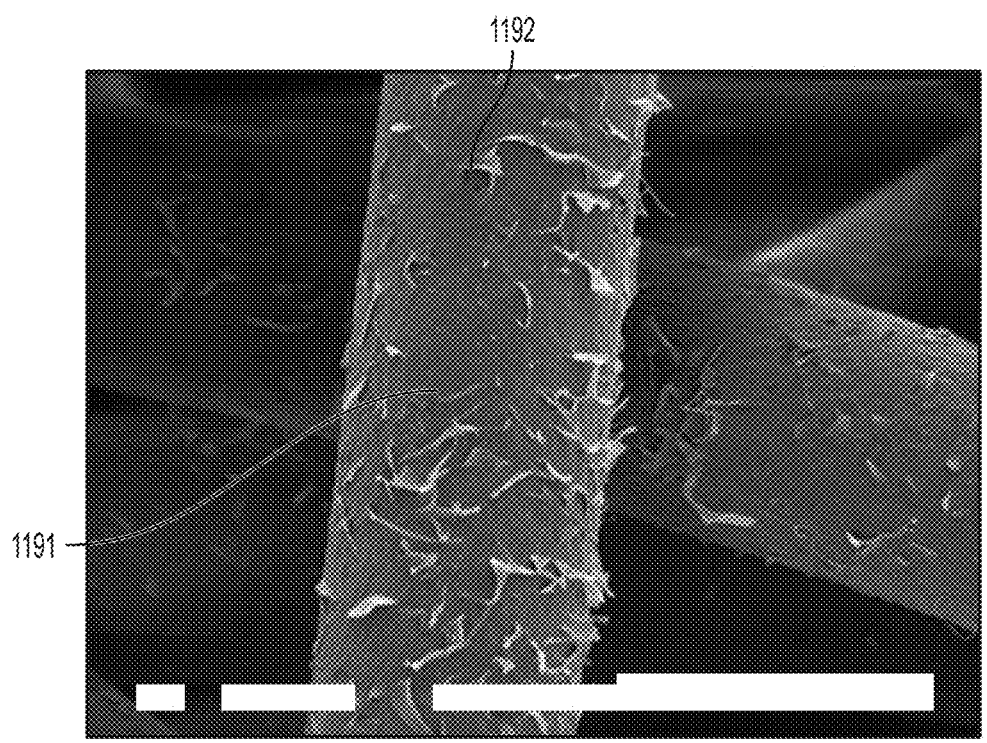
FIG. 19 is an SEM photo showing another nonwoven fiber with additive that has bloomed on the surface of the fiber.

FIG. 17 is an SEM photo of a polypropylene fiber with glycerol tristearate additive added to the fibers as a master batch (8 wt % Techmer PPM17000 High Load Hydrophobic). The masterbatch comprised about 60 percent by weight polypropylene and about 40 percent by weight glycerol tristearate. As shown the fiber 991 comprise a plurality of fibrils 992 extending from the surface thereof. FIG. 18 is an SEM photo of a bi-component fiber 1091 of polyethylene and polypropylene arranged in 30/70 sheath/core configuration—the polyethylene being the sheath. The additive (glycerol tristearate) was added to the fibers as a master batch. The master batch comprised about 60 percent by weight polyethylene and about 40 percent by weight glycerol tristearate. The sheath of the fiber comprised 17 percent by weight master batch and 83 percent by weight polyethylene. As shown, the fiber 1091 comprises a plurality of fibrils 1092 extending therefrom. FIG. 19 is an SEM photo of a bi-component fiber 1191 of polyethylene and polypropylene arranged in 30/70 sheath/core configuration—polyethylene being the sheath. The additive (glycerol tristearate) was added to the fibers as a master batch. The master batch comprised about 60 percent by weight polyethylene and about 40 percent by weight glycerol tristearate. The sheath of the fiber comprised 30 percent by weight master batch and 70 percent by weight polyethylene. As shown, the fiber 1191 comprises a plurality of fibrils 1192 extending therefrom.

Figure 20:
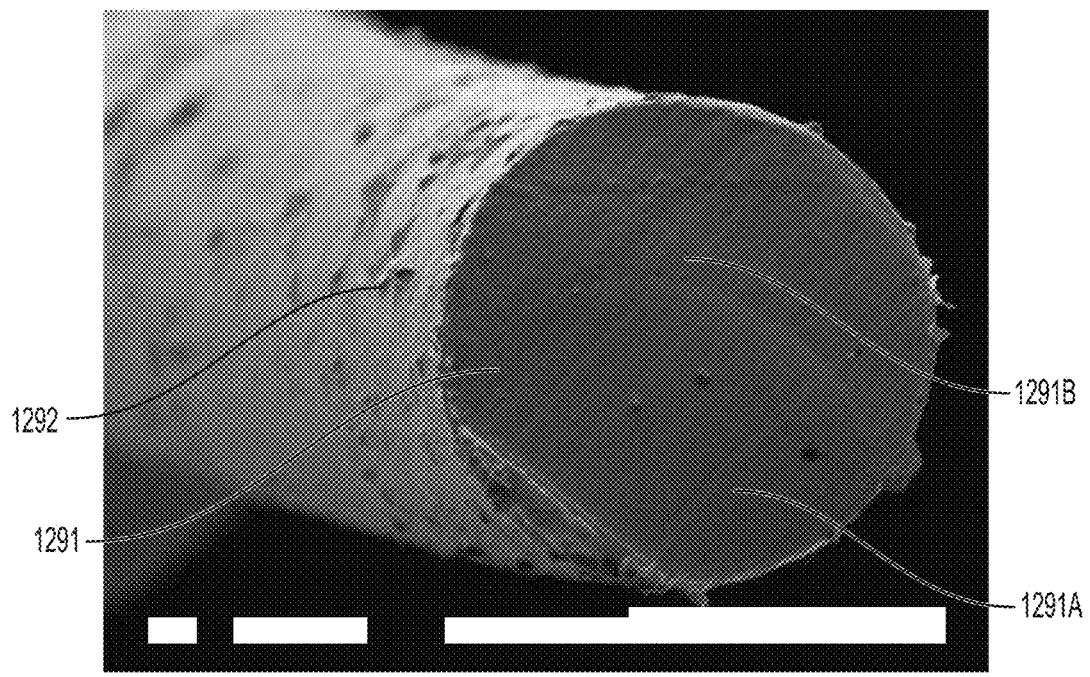
FIG. 20 is an SEM photo showing another nonwoven fiber with additive that has bloomed on the surface of the fiber.
Figure 21:
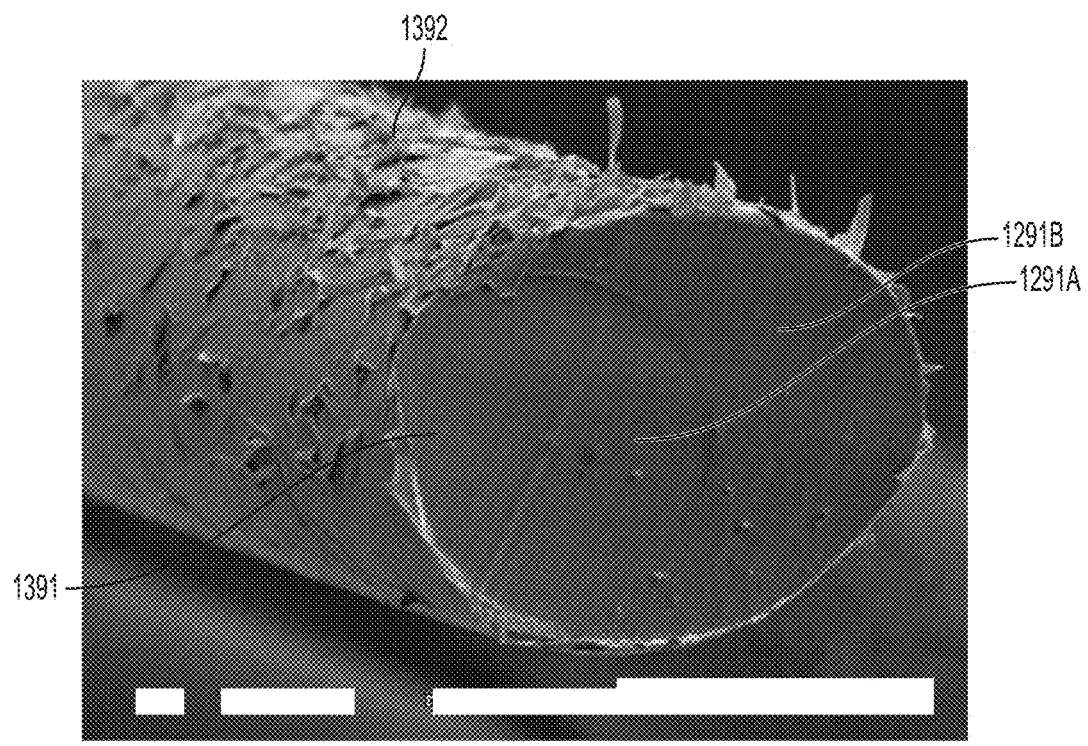
FIG. 21 is an SEM photo showing another nonwoven fiber with additive that has bloomed on the surface of the fiber.

FIGS. 20 and 21 demonstrate that the additive can be added variably with regard to differing components of a fiber. FIG. 20 is an SEM photo of a polypropylene/polyethylene bi-component fiber 1291 where the polypropylene and the polyethylene are configured side by side—polyethylene 1291A and polypropylene 1291B. The additive was added at varying levels as a master batch (Techmer PPM17000 High Load Hydrophobic)—10% master batch was added to the polypropylene component and 5% of the same master batch was added to the polyethylene component.

FIG. 21 is an SEM photo of a polypropylene/polyethylene bi-component fiber 1391 where the polypropylene and polyethylene are configured side by side—polypropylene 1391A and polyethylene 1391B comprising fibrils 1392. The additive was added at varying levels as a master batch (Techmer PPM17000 High Load Hydrophobic)—16% master batch was added to the polypropylene component and 8% master batch was added to the polyethylene component. In some instances, the additive may bloom more on one side of the bi-component fiber 1391 than the other.

Figure 22:
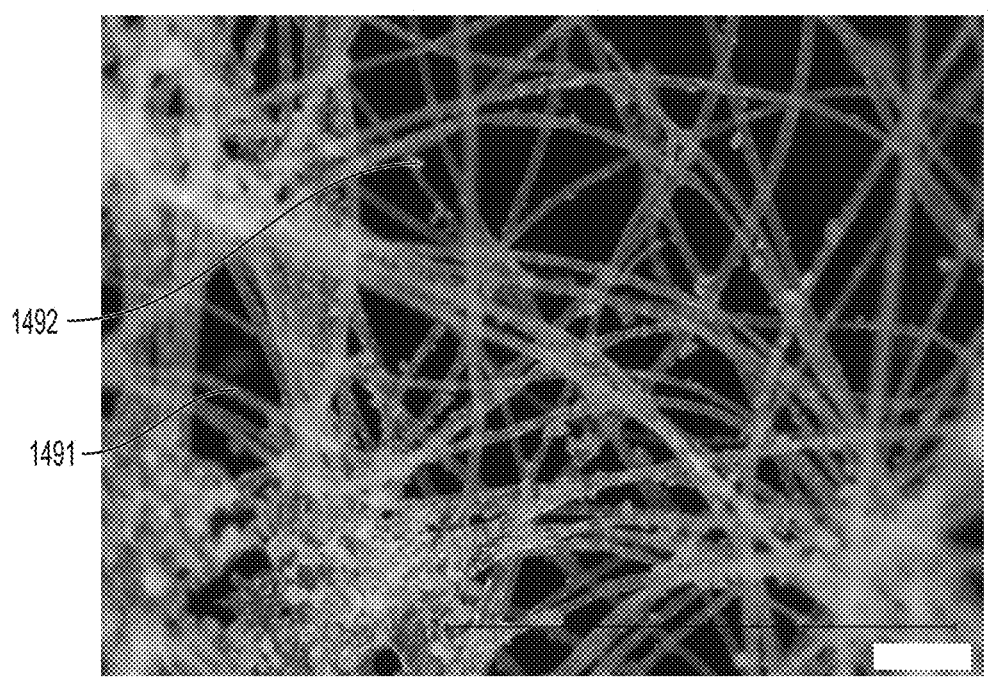
FIG. 22 is a photomicrograph showing other nonwoven fibers with additive that has been applied to the fibers.

FIG. 22 is a photomicrograph showing a plurality of fibers of a nonwoven where the additive has been applied post fiber production. As shown, the additive forms a plurality of droplets/particles 1492 on the surface of the fibers 1491.

Figure 23:
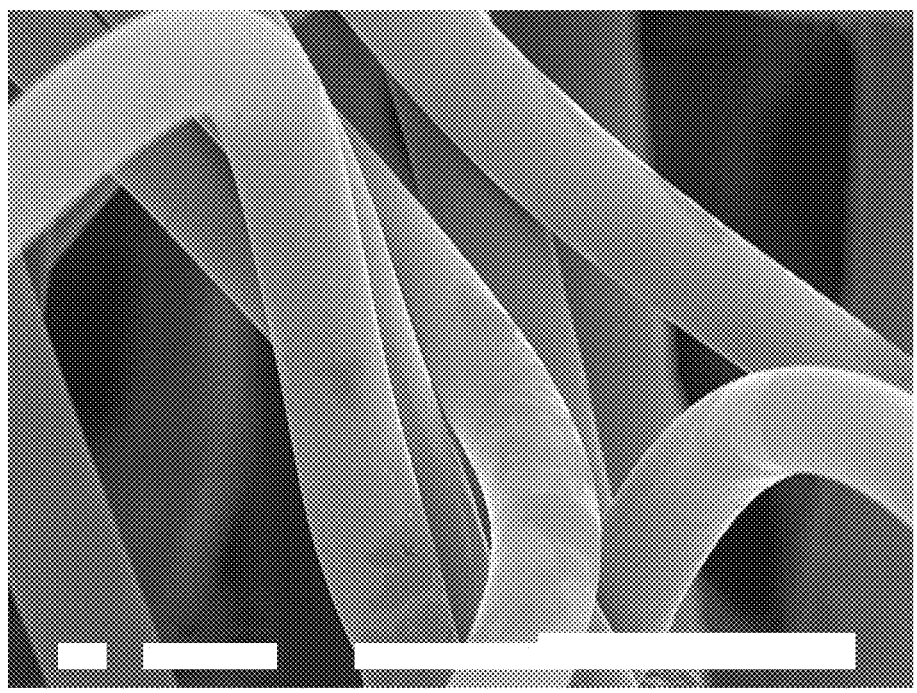
FIG. 23 is an SEM photo showing nonwoven fibers with additive that has formed a film on the surface of the fibers.
Figure 24:
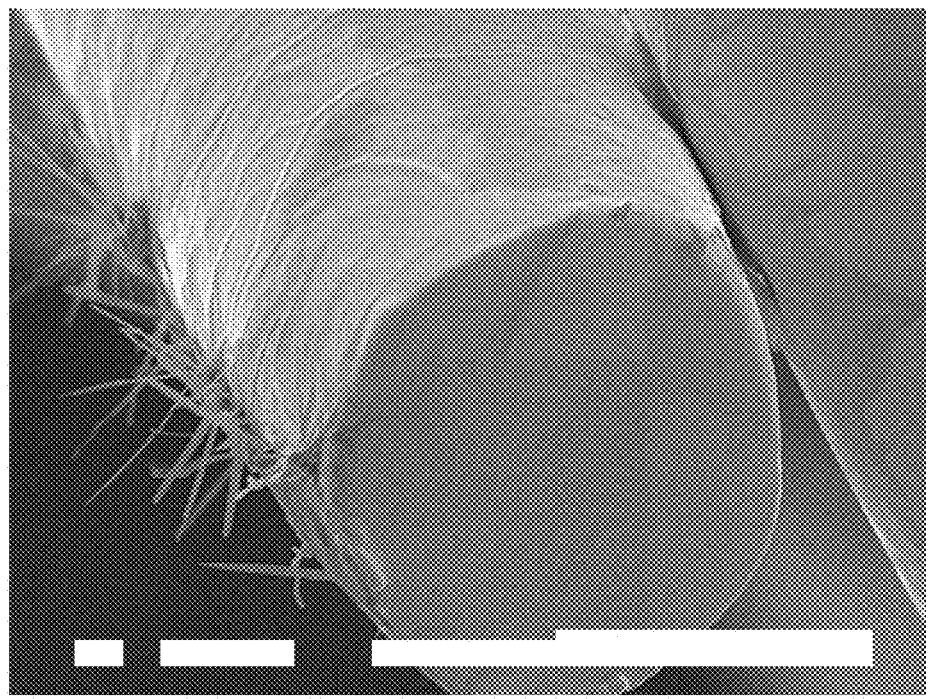
FIG. 24 is an SEM photo showing nonwoven fibers with additive that has formed a film and fibrils on the surface of the fibers.

FIGS. 23 and 24 are SEM photos showing fibers comprising a melt additive. In FIG. 23, the additive has bloomed to the surface of the fibers to form a film, and in FIG. 24, the additive has bloomed to the surface of the fiber to form a film/fibril combination. In FIG. 24, the fibers are bi-component polypropylene/polyethylene fibers in a side by side configuration. The polypropylene comprises 16 percent by weight master batch (Techmer PPM17000 High Load Hydrophobic), and the polyethylene component comprises 8 percent by weight of the same master batch.

Hydrophilic Additive

As mentioned previously, the first layers described herein, may comprise a hydrophobic additive which blooms on a surface of at least a portion of the first plurality of fibers and/or may comprise an after production spray on hydrophobic additive. Similarly, the second layer may comprise a hydrophilic additive which can be a portion of the second layer master blended into the fibers of the second layer or can be subsequently added on via kiss coating, spraying or any other suitable process.

Any suitable additive can be used. Some suitable examples include: Techmer PPM15560; Techmer TPM12713; Polyvel VW351 PP Wetting Agent; Goulston Hydrosorb 1001; as well as those hydrophilic additive disclosed in US Patent Application Publication No. 2012/

0077886. Some suitable examples of post formation additives include Silastol PH26, PHP90 or PST-N available from Schill & Seilacher, or Stantex S6327 available from Pulcra Chemicals GmbH.

Example

Figure 25:
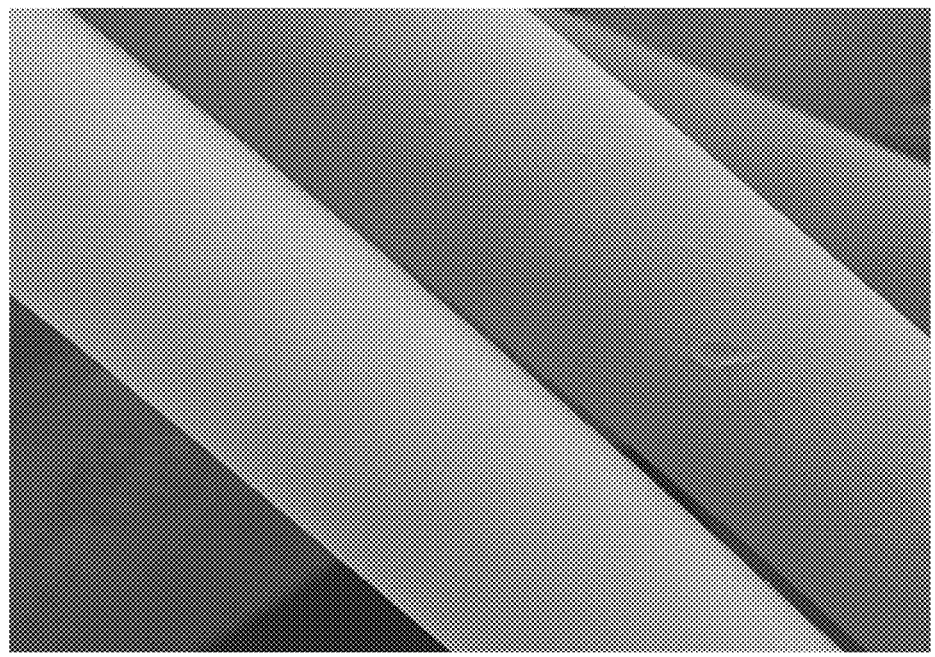
FIG. 25 is an SEM photo showing nonwoven fibers with a hydrophilic melt additive.

FIG. 25 is an SEM photo showing fibers comprising a hydrophilic melt additive. The fibers depicted are polypropylene/polypropylene side by side (70/30) configured bicomponent fibers. Both of the polypropylene components comprised 2.0% Techmer TPM12713 hydrophilic masterbatch, and the first component additionally comprised 1.0% of TiO2 masterbatch (MBWhite009). As shown, the hydrophilic additive appears to form no visible structure as opposed to forming fibrils as provided with regard to the hydrophobic melt additive disclosed above.

Additional forms are contemplated where the nonwoven webs include compositions in addition to the hydrophobic or hydrophilic additive. Some examples include lotions, skin care actives, odor absorbing or inhibiting or masking, fragrances, pigments, dyes, agents affecting the coefficient of friction, antimicrobial/antibacterial agents, the like or combinations thereof.

Opacity

The opacity of the crimped fiber spunbond nonwoven webs may differ from the opacity of adjacent layers of an absorbent article. In some instances, the crimped fiber spunbond nonwoven web may form a wearer-facing surface which is closest to an external observer. In such instances, the crimped fiber spunbond nonwoven web may have a lower opacity than an underlying layer in order to maximize observable contrast differences between the layers and/or to observe printing or colored adhesives. In some forms, the crimped fiber spunbond nonwoven webs may have a low opacity in the context of an absorbent article outer cover such that graphics on subjacent layers may be visible therethrough.

Alternatively, the crimped fiber spunbond nonwoven web as part of the wearer-facing surface may have a higher opacity than an underlying layer in order to more effectively mask bodily exudates (e.g., urine, menses, or BM) or to provide for greater color contrast with the layers below. When a crimped fiber spunbond nonwoven web is used as a fluid-permeable topsheet, the layer closest to an external observer would be the wearer-facing surface. In a form, where the crimped fiber spunbond nonwoven web is located on the external surface of an absorbent article (e.g., an outer cover, fastening system element, stretch ear, belt, or side panel), the layer closest to an external observer would be the garment-facing surface.

As noted, crimped fiber spunbond nonwoven web of the present invention may have a high opacity. This enables an aperture pattern to be more easily distinguished, provides contrast to any colors and materials underneath, and in the case of a diaper topsheet or a sanitary napkin topsheet, masks the presence of bodily fluids contained within the absorbent core, providing a cleaner appearance to the wearer. To achieve this benefit, opacities of greater than about 30, about 40, about 50, or about 60 may be desired. In some forms of the present invention, opacities may range from about 40-100 or from about 50-90, specifically reciting all values within these ranges and any ranges created thereby.

Increases in opacity can be achieved via any known suitable product/process. Some suitable examples include adding fillers (e.g. TiO2), fiber shape (e.g. Trilobal vs. round), smaller fiber diameters (including microfibers and/or nano fibers), etc. A specific example of nonwoven web having high opacity is an SMS (spunbond, meltblown, spunbond) or an SMNS (spunbond, meltblown, nano fiber, spunbond) construction. Another specific example is a nonwoven comprising nano fibers, such as those produced by melt film fibrillation as described in U.S. Pat. No. 8,487,156 and U.S. Patent Application Publication No. 2004/0266300. In one specific example, the web of the invention may comprise a layer having meltblown and nanofibers—SMNS construction.

Disposable Absorbent Articles

Disposable absorbent articles of the present invention may utilize the crimped fiber spunbond nonwoven webs/laminates described herein in any suitable location. And, the crimped fiber spunbond nonwoven webs/laminates described herein may be incorporated into any suitable disposable absorbent article. Some suitable examples of absorbent articles include diapers, including taped diapers—refastenable; diaper pants—pre-fastened refastenable or pre-fastened non-refastenable; feminine sanitary napkins; tampons; adult incontinence products, e.g. pants or pads; baby wipes, sanitary wipes, cleansing wipes, and/or the like. Some suitable uses for the crimped fiber spunbond nonwoven webs of the present invention in some absorbent articles include a topsheet, a backsheet, a secondary layer between the topsheet and backsheet, etc.

Figure 26:
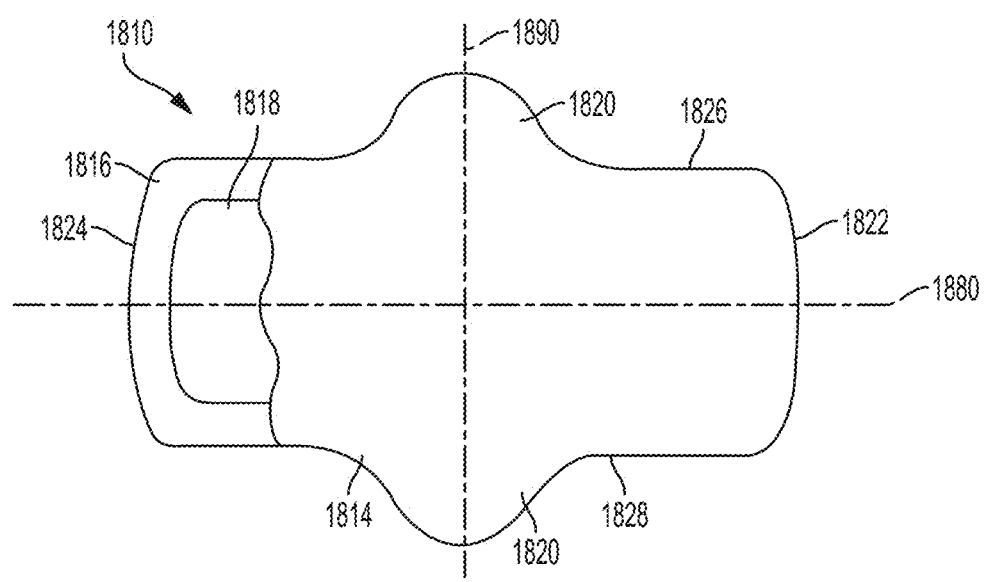
FIG. 26 is a top view of a feminine hygiene article, i.e. sanitary napkin, constructed in accordance with the present invention.

Referring to FIG. 26, an absorbent article 1810 which may utilize the crimped fiber spunbond nonwoven webs/laminates described herein may be a sanitary napkin/feminine hygiene pad. As shown, the sanitary napkin 1810 may comprise a liquid permeable topsheet 1814, a liquid impermeable, or substantially liquid impermeable, backsheet 1816, and an absorbent core 1818 positioned intermediate the topsheet 1814 and the backsheet 1816. The sanitary napkin 1810 may comprise wings 1820 extending outwardly with respect to a longitudinal axis 1880 of the sanitary napkin 1810. The sanitary napkin 1810 may also comprise a lateral axis 1890. The wings 1820 may be joined to the topsheet 1814, the backsheet 1816, and/or the absorbent core 1818. The sanitary napkin 1810 may also comprise a front edge 1822, a rear edge 1824 longitudinally opposing the front edge 1822, a first side edge 1826, and a second side edge 1828 laterally opposing the first side edge 1826. The longitudinal axis 1880 may extend from a midpoint of the front edge 1822 to a midpoint of the rear edge 1824. The lateral axis 1890 may extend from a midpoint of the first side edge 1828 to a midpoint of the second side edge 1828. The sanitary napkin 1810 may also be provided with additional features commonly found in sanitary napkins as is known in the art. In some forms of the present invention, the wings may be provided with zones of extensibility as described in U.S. Pat. No. 5,972,806.

Any suitable absorbent core known in the art may be utilized. The absorbent core 1818 may be any absorbent member which is generally compressible, conformable, non-irritating to the wearer's skin, and capable of absorbing and retaining liquids such as urine, menses, and/or other body exudates. The absorbent core 1818 may be manufactured from a wide variety of liquid-absorbent materials commonly used in disposable absorbent articles such as comminuted wood pulp which is generally referred to as airfelt. The absorbent core 1818 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 1818 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 1818 may comprise one or more channels, such as two, three, four, five, or six channels.

The absorbent core 1818 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

The absorbent article 1810 may comprise additional layers between the topsheet 1814 and the absorbent core 1818. For example, the absorbent article 1810 may comprise a secondary topsheet and/or an acquisition layer positioned between the topsheet 1814 and the absorbent core 1818.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m² to about 35 g/m². However, it should be noted that other flexible liquid impervious materials may be used as the backsheet. Herein, "flexible" refers to materials which are compliant and which will readily conform to the general shape and contours of the wearer's body.

The backsheet can be typically positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986 entitled "Disposable Waste-Containment Garment", which issued to Minetola et al. on Mar. 4, 1986. Another suitable attachment device including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment device may include heat bonds, thermal fusion bonds, pressure bonds, ultrasonic bonds, dynamic mechanical bonds, or any other suitable attachment device or combinations of these attachment devices. The backsheet may be additionally secured to the topsheet by any of the above-cited attachment devices/methods.

The topsheet may comprise the crimped fiber spunbond nonwonven web or crimped fiber spunbond nonwoven laminates described herein. Options for utilization of the crimped fiber spundonb nonwoven webs/laminates described herein as topsheets are discussed hereafter.

Still another example of a disposable absorbent article which may utilize the crimped fiber spunbond nonwoven webs/laminates of the present invention are diapers which include non-refastenable pants and/or re-fastenable diapers. Diapers have can have a similar construction to that of sanitary napkins. An exemplary diaper is described below.

Figure 27:
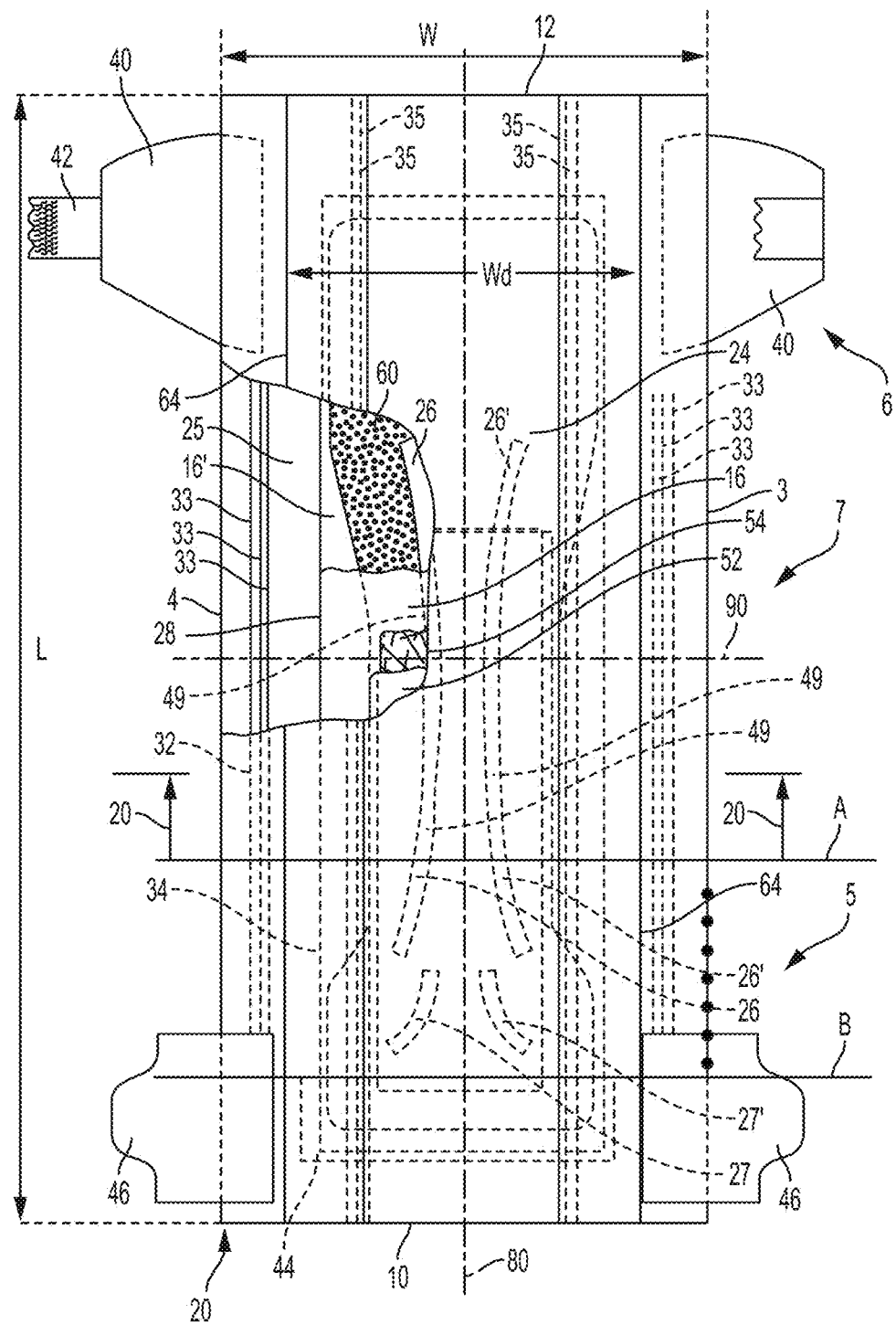
FIG. 27 is a top view of an absorbent article with some layers partially removed in accordance with the present disclosure.

Referring to FIG. 27, a plan view of an example absorbent article that is a diaper 20 in its flat-out, uncontracted state (i.e., with elastic induced contraction pulled out) with portions of the structure being cut-away to more clearly show the construction of the diaper 20 and with its wearer-facing surface toward the viewer. This diaper is shown for illustration purpose only as the present disclosure may be used for making a wide variety of diapers and other absorbent articles.

Figure 28:
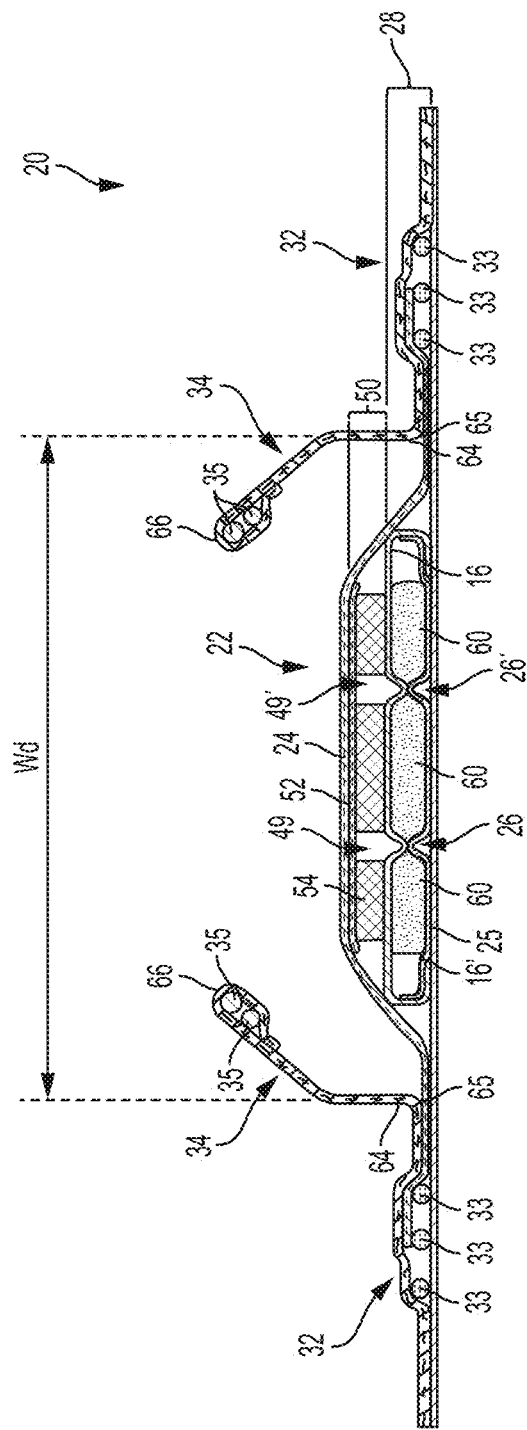
FIG. 28 is a cross-sectional view of the absorbent article taken about line 20-20 of FIG. 27 in accordance with the present disclosure.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise a liquid management system ("LMS") 50 (shown in FIG. 28), which, in the example represented, comprises a distribution layer 54 and an acquisition layer 52 that will both be further discussed below. In various forms, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature and a front elastic waist feature, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. Together the front waist edge 10 and the rear waist edge form waist opening when the absorbent article 20 is donned on a wearer. The absorbent article 20 may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from the wearer-facing surface as illustrated FIG. 27. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width of the absorbent article 20 may be measured along the lateral axis 90 from the first side edge 3 to the second side edge 4. The absorbent article 20 may comprise a front waist region 5, a rear waist region 6, and a crotch region 7. The front waist region, the rear waist region, and the crotch region each define ⅓ of the longitudinal length of the absorbent article. Front and back portions may also be defined on opposite sides of the lateral axis 90.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 28 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' for the top side and bottom side of the core.

Figure 29:
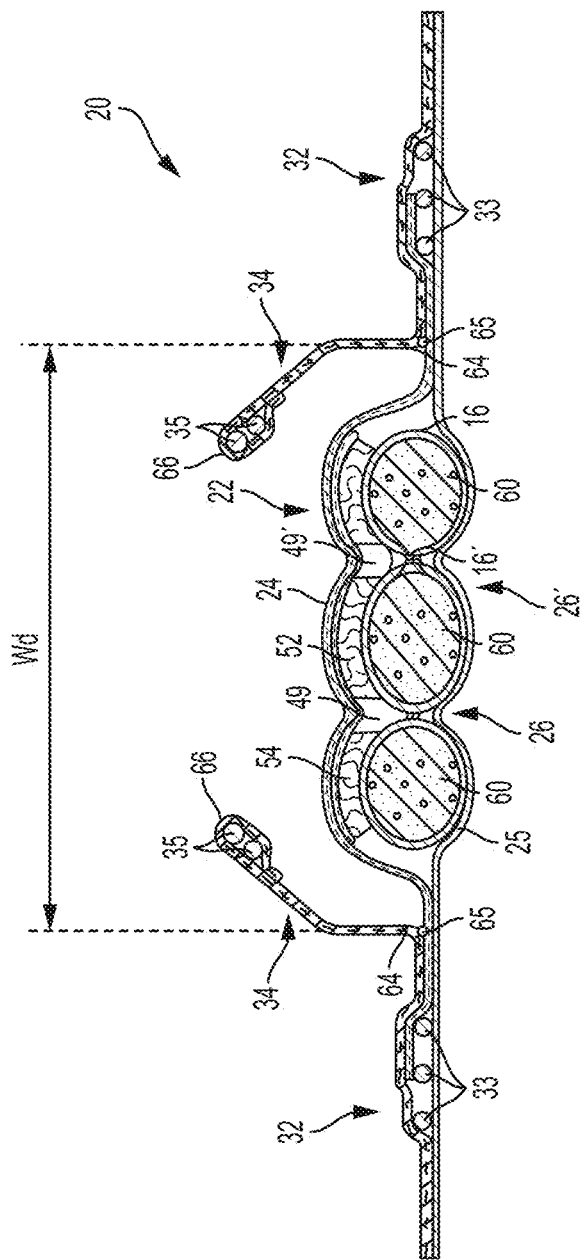
FIG. 29 is a view of the absorbent article of FIG. 28 where the absorbent article has been at least partially loaded with fluid in accordance with the present disclosure.
Figure 30:
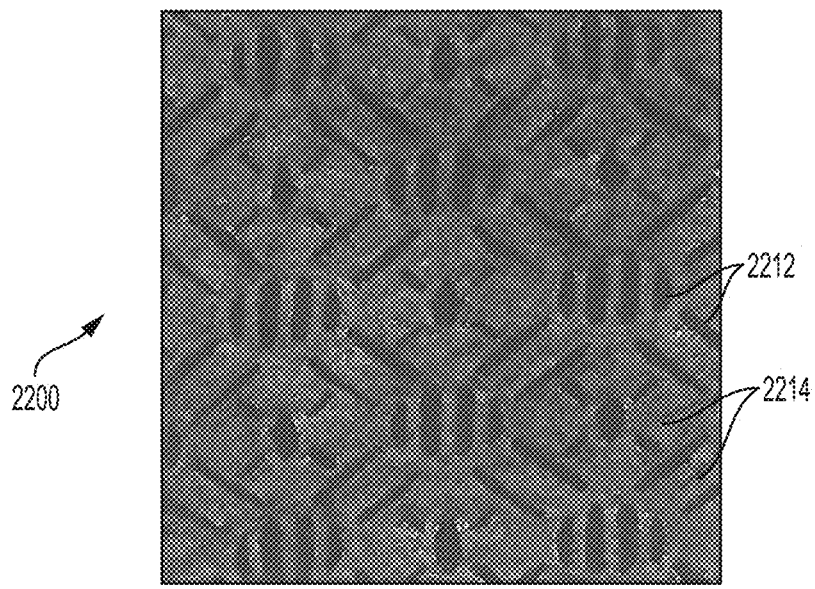
FIGS. 30-33 are photographs of portions of example nonwoven laminates in accordance with the present disclosure.
Figure 31:
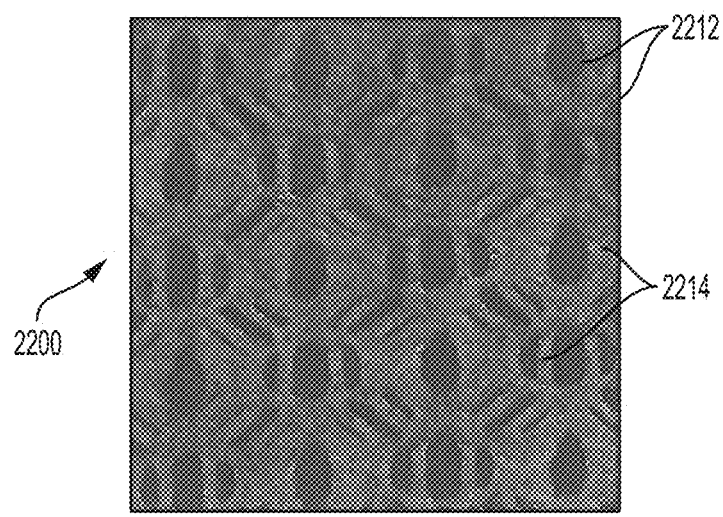
Figure 32:
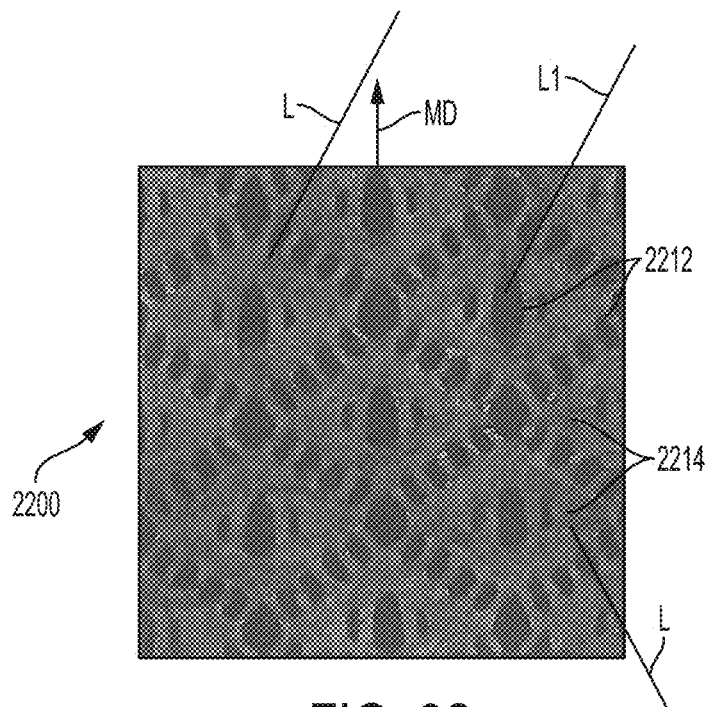
Figure 33:
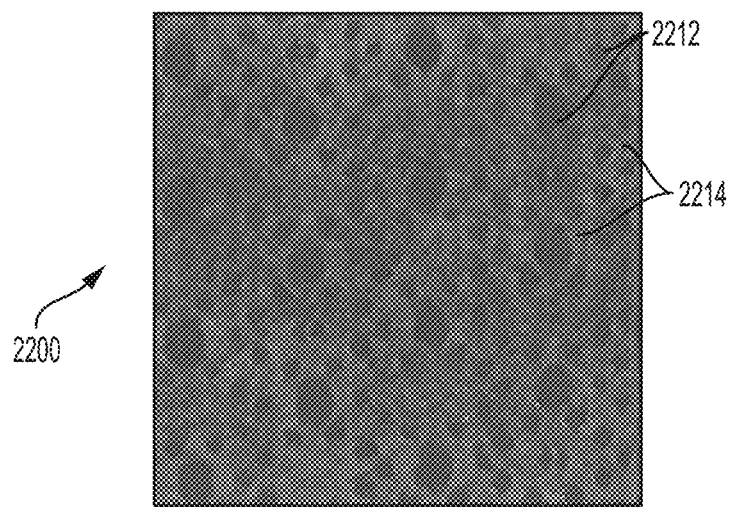

The absorbent core 28 may comprises one or more channels, represented in FIG. 27 as the four channels 26, 26' and 27, 27'. Additionally or alternative, the LMS 50 may comprises one or more channels, represented in FIGS. 27-29 as channels 49, 49'. In some forms, the channels of the LMS 50 may be positioned within the absorbent article 20 such they aligned with, substantially aligned with, overlap, or at least partially overlap, the channels of the absorbent core 28. These and other components of the absorbent articles will now be discussed in more details.

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The backsheet 25 is generally that portion of the absorbent article 20 positioned adjacent the garment-facing surface of the absorbent core 28 and which prevents, or at least inhibits, the bodily exudates absorbed and contained therein from soiling articles such as bedsheets and undergarments. The backsheet 25 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, bodily exudates from passing through the backsheet 25. Example breathable materials may include materials such as woven webs, nonwoven webs, and composite materials such as film-coated nonwoven webs, microporous films, and monolithic films.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20.

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 28 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

The absorbent core 28 may also comprise a generally planar top side and a generally planar bottom side. The core 28 may have a longitudinal axis 80' corresponding substantially to the longitudinal axis 80 of the absorbent article, as seen from the top in a planar view as in FIG. 19. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 16, 16' which may be at least partially sealed along the sides of the absorbent core. The core wrap may be at least partially sealed along its front side, rear side, and two longitudinal sides so that substantially no absorbent material leaks out of the absorbent core wrap. The first material, substrate, or nonwoven 16 may at least partially surround the second material, substrate, or nonwoven 16' to form the core wrap. The first material 16 may surround a portion of the second material 16' proximate to the first and second side edges 284 and 286.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present in the crotch region 7. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 or the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

In a form, the absorbent article may comprise front ears 46 and rear ears 40. The ears may be an integral part of the chassis, such as formed from the topsheet 24 and/or backsheet 25 as side panel. Alternatively, as represented on FIG. 27, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

One function of the LMS 50 is to quickly acquire the fluid and distribute it to the absorbent core 28 in an efficient manner. The LMS 50 may comprise one or more layers, which may form a unitary layer or may remain as discrete layers which may be attached to each other. The LMS 50 may comprise two layers: a distribution layer 54 and an acquisition layer 52 disposed between the absorbent core and the topsheet, but the present disclosure is not limited to such a configuration.

The LMS 50 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

The LMS 50 may comprise a distribution layer 54. The distribution layer 54 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

The LMS 50 may alternatively or additionally comprise an acquisition layer 52. The acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The acquisition layer 52 may comprise air or wet-laid cellulosic, cross-linked cellulosic, or synthetic fibers, or blends thereof. The acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded.

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, BM or other bodily exudates within the absorbent article, leading to reduced leakage and skin contact. Channels in the LMS 50 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

As stated previously, the crimped fiber spunbond nonwoven webs/laminates of the present invention may be utilized as a topsheet for a disposable absorbent article, examples of which include the sanitary napkin 1810 and diaper 20 discussed heretofore.

The crimped fiber spunbond nonwoven webs/laminates of the present disclosure may be used as components of absorbent articles. More than one crimped fiber spunbond nonwoven web/laminate may be used in a single absorbent article. In such a context, the crimped fiber spunbond nonwoven webs/laminates may form at least a portion of: a topsheet; a topsheet and an acquisition layer; a topsheet and a distribution layer; an acquisition layer and a distribution layer; a topsheet, an acquisition layer, and a distribution layer; an outer cover; a backsheet; an outer cover and a backsheet, wherein a film (non-apertured layer) forms the backsheet and a crimped fiber spunbond nonwoven web/laminate forms the outer cover; a leg cuff; an ear or side panel; a fastener; a waist band; belt or any other suitable portion of an absorbent article. The number of layers in a crimped fiber spunbond nonwoven laminate may also be determined by the nonwoven laminates' particular use.

In some forms, additional layers may be positioned between the topsheet and the absorbent core. For example, a secondary topsheet, acquisition layer, and/or distribution layer, each of which are known in the art, may be positioned between the topsheet and the absorbent core of the absorbent article.

Figure 82:
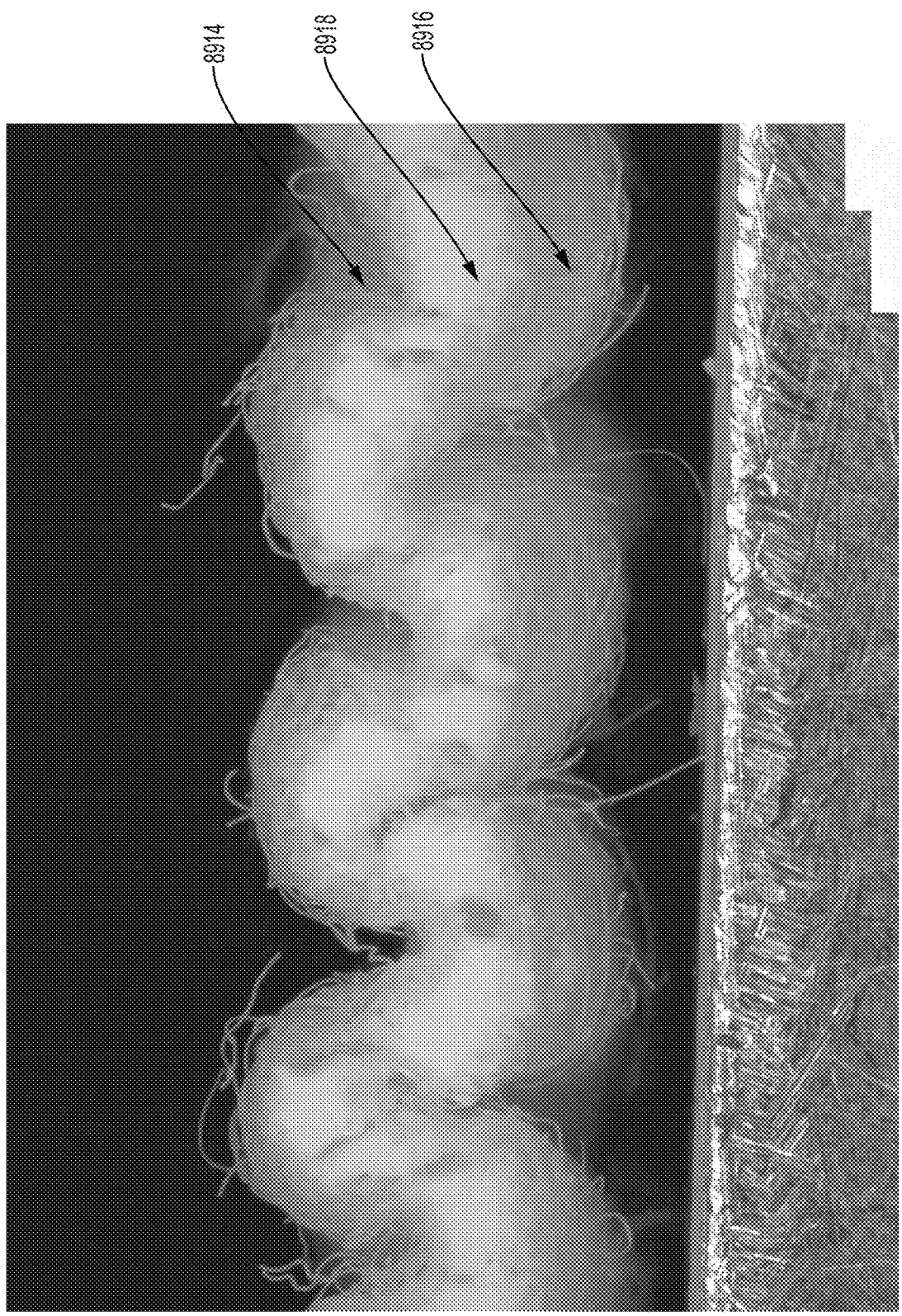
FIG. 82 is an exemplary cross section of a laminate structure constructed in accordance with the present invention.

Forms of the present invention are contemplated where webs of the present invention comprise structures as described herein in the negative Z-direction. In such forms, the urging of the material of the web in the negative Z-direction may fracture material of an absorbent core or a portion thereof. As shown in FIG. 82, a sanitary pad, or portion thereof, may comprise the web 8914, an absorbent material 8918, and a support layer 8916. As shown, the structures described herein may cause fracturing of the absorbent material 8918, particularly where the absorbent material comprises a high internal phase emulsion foam. However, other forms of the invention are contemplated where the absorbent material 8918 comprises SAP. Still in other forms, the web 8914 may comprise the topsheet, the absorbent material 8918 may comprise a first liquid retention layer, and the support layer 8916 may comprise a secondary topsheet or acquisition layer. In such forms, additional absorbent cores in addition to a backsheet may be provided.

Forms of the present invention are contemplated where the absorbent material 8918 and the support layer 8916 comprise a heterogeneous mass. The heterogeneous mass along with the absorbent material 8918 and support layer 8916 are further described in U.S. Provisional Patent Application Publication No. 62/118,232.

As shown, the web 8914 comprises a crimped fiber spunbond nonwoven web having 2.0 denier per filament polypropylene/polypropylene 70/30 bi-component fibers. Any suitable crimped fiber spunbond nonwoven web may be utilized. The support layer 8916 may comprise any suitable material. For example, in some forms, the support layer 8916 may comprise a spunlaced nonwoven web.

The depressions in the apertured web 8914 and absorbent material 8918 may extend through the thickness of the absorbent material 8918 such that a plurality of discrete pieces of absorbent material are produced. In other forms, the depressions in the apertured web 8914 and the absorbent material 8918 may only partially extend through the thickness of the absorbent material 8916 such that absorbent material remains a continuous element.

High internal phase emulsion foams are known in the art. Methods of making high internal phase emulsion foams are described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

Aperturing and Patterns Thereof

As previously disclosed, the first layer may comprise apertures while the second layer is sans apertures. In other forms both the first and second layers may comprise apertures. And, for those forms with more than two layers, a plurality of layers of the crimped fiber spunbond nonwoven laminate may comprise apertures. For those forms where apertures are present, the apertures may be arranged in patterns forming designs, shapes, etc.—apertured indicia. In other forms, the apertures may be arranged in rows/columns which may be staggered or may not be staggered from adjacent column/row to adjacent column/row. And recall, that in some forms, a crimped fiber spunbond web may comprise apertures and may be joined with additional layers in a disposable absorbent article.

The apertures in at least one or more layers of a crimped fiber spunbond nonwoven laminate or in a crimped fiber spunbond nonwoven web as described herein, may be grouped in spaced arrays of apertures (see e.g., FIGS. 30-33). An aperture array includes two or more apertures having much closer spacing between the apertures than the distance between the aperture arrays. The distance between the array and other apertures is at least about 1.5, at least about 2 times, or at least about 3 times the maximum distance between apertures in the array. Four examples of nonwoven laminates 2200 of the present invention comprising patterned apertures are illustrated in FIGS. 30-33. As illustrated, the nonwoven laminate 2200 may take on a number of configurations. The apertures are labeled 2212 and the land areas (non-apertured areas) are labeled 2214. A number of additional example aperture pattern configurations are illustrated in subsequent figures.

The aperture arrays may form a regular or recognizable shape, such as a heart shape, polygon, ellipse, arrow, chevron, and/or other shapes known in the pattern art. The apertures arrays may differ in one portion of the nonwoven laminate compared to another portion of the nonwoven laminate. In an absorbent article context, the aperture arrays may differ in one region of the absorbent article compared to another region of the absorbent article. Additionally, the aperture arrays may be coordinated in regions of the absorbent article where the aperture arrays are present. The aperture arrays may be concave, convex, or may include concavities and convexities. The aperture arrays may be organized into "macro-arrays" having a higher order structure. For example, referring to FIGS. 35-48, a nonwoven laminate 2600 of the present invention is illustrated with aperture arrays 2602 that may be separated by a continuous, inter-connected land area pattern 2604. In such an instance, the land area pattern 2604 may function as a fluid distribution pathway and the aperture arrays 2602 may function as fluid "drains" thereby promoting fluid access to the underlying absorbent material or absorbent core. The shape of the aperture arrays may enhance the ability of the arrays to manage fluid, such as bodily exudates (i.e., urine, runny BM, menses). For example, aperture arrays including a concavity facing a fluid insult location in an absorbent article may function as fluid collection "traps" as the fluid may travel along the "land area" in the concavity to a point where the concavity ends. At this location, the fluid may enter the apertures in the direction of the fluid path or those on either side of the concavity if the fluid turns in either lateral direction. Example aperture array shapes having a concavity include heart shapes, star shapes, some polygons, crescents, and chevrons, to name a few examples.

In some forms, apertures, or arrays thereof, in a nonwoven laminate 2600, may form one or more continuous or semi-continuous patterns 2606, resulting in discrete "macro" land areas 2608. In such an instance, the discrete macro land areas 2608 may function as fluid deposition regions. Fluid moving from the discrete macro land areas 2608 in any direction may be absorbed into the apertures of the continuous or semi-continuous pattern 2606.

In some forms, the apertures, or aperture arrays thereof, in a nonwoven laminate 2600 may form linear patterns alternating with continuous or semi-continuous land areas. The nonwoven laminate may include unidirectional or multi-directional (and intersecting) aperture or aperture array patterns. Linear aperture or array patterns may be oriented parallel to the longitudinal or lateral axis, or at an angle between 0 and 90 degrees, specifically reciting all 0.5 degree increments within the specified range and all ranges formed therein, from either the longitudinal or lateral axis. Linear apertures or aperture array patterns may function to restrict fluid movement along the nonwoven laminate to a greater degree in one direction compared to another direction. Apertures for nonwoven webs may be similarly configured.

Still referring to FIGS. 35-48, a nonwoven laminate 2600 may comprise an array of apertures comprising a plurality of patterns 2610A and 2610B with continuous or semi-continuous land areas. As shown, a first pattern 2610A may comprise apertures which are oriented in a direction which is generally parallel to a machine direction 1675 (shown in FIG. 34) as well as apertures which are oriented at multiple angles with respect to the machine direction. Similarly, a second pattern 2610B may comprise apertures which are oriented at multiple angles with respect to the machine direction 1675 as well as apertures which are generally parallel to the machine direction 1675. As shown, the apertures of the first pattern 2610A and/or the second pattern 2610B may be of different lengths, different angles with respect to the machine direction 1675, and/or different Effective Aperture AREAs.

Additionally, at least one or a plurality of apertures in the first pattern 2610A may be substantially enclosed by the second pattern 2610B. For example, the second pattern may form a quilt like pattern, e.g. diamond shaped boundaries or any other suitable shape, with the first pattern disposed within the second pattern thereby forming a unit. The combination of the first pattern and the second pattern may repeat so that there are a plurality of units. Additionally, the first pattern within the second pattern may be different from one unit to the next. Additional patterns may be utilized. The apertures angled with respect to the machine direction 1675 are believed to aid in fluid acquisition/distribution. For example, fluid moving along the nonwoven laminate 2600 in the machine direction 1675 may be diverted, in part, because of the angled apertures.

Figure 34:
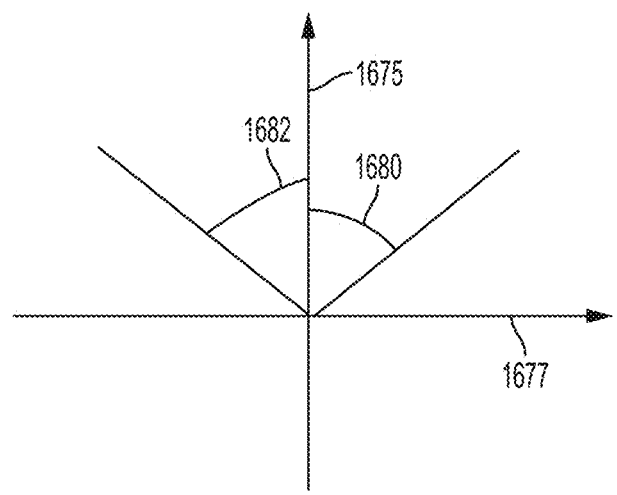
FIG. 34 is a depiction of a coordinate system for the nonwoven laminates of the present invention.
Figure 35:
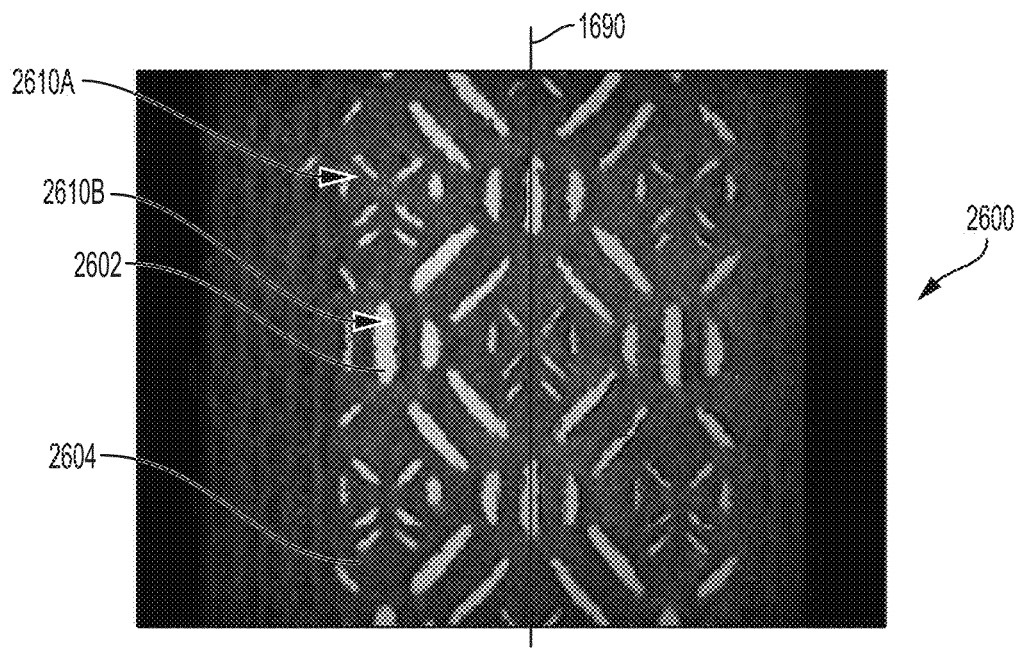
FIGS. 35-48 are photographs of nonwoven laminates constructed in accordance with the present invention.
Figure 36:
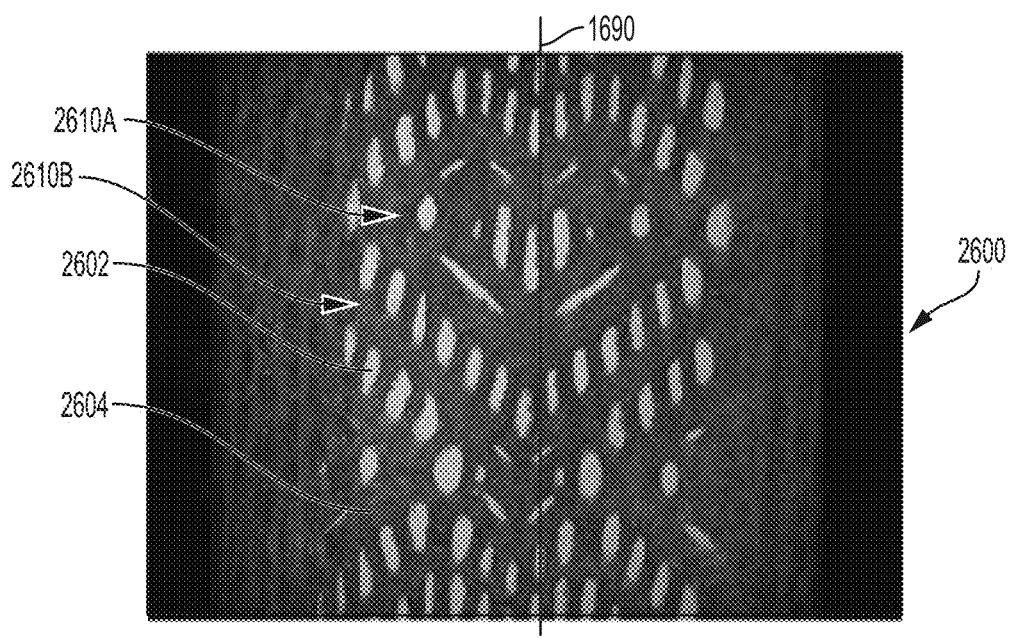
Figure 37:
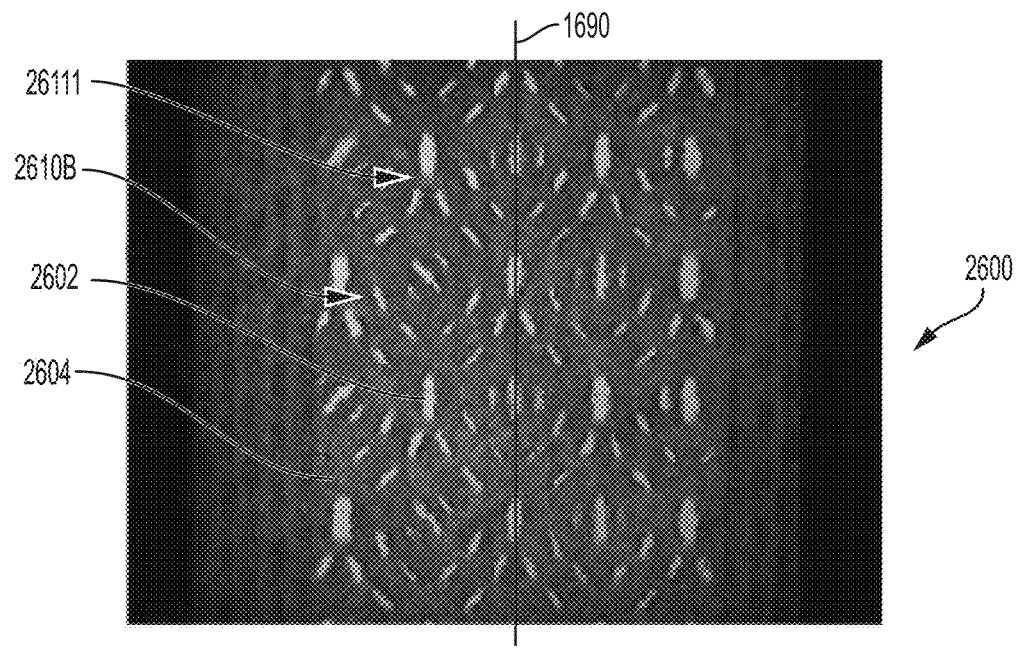
Figure 38:
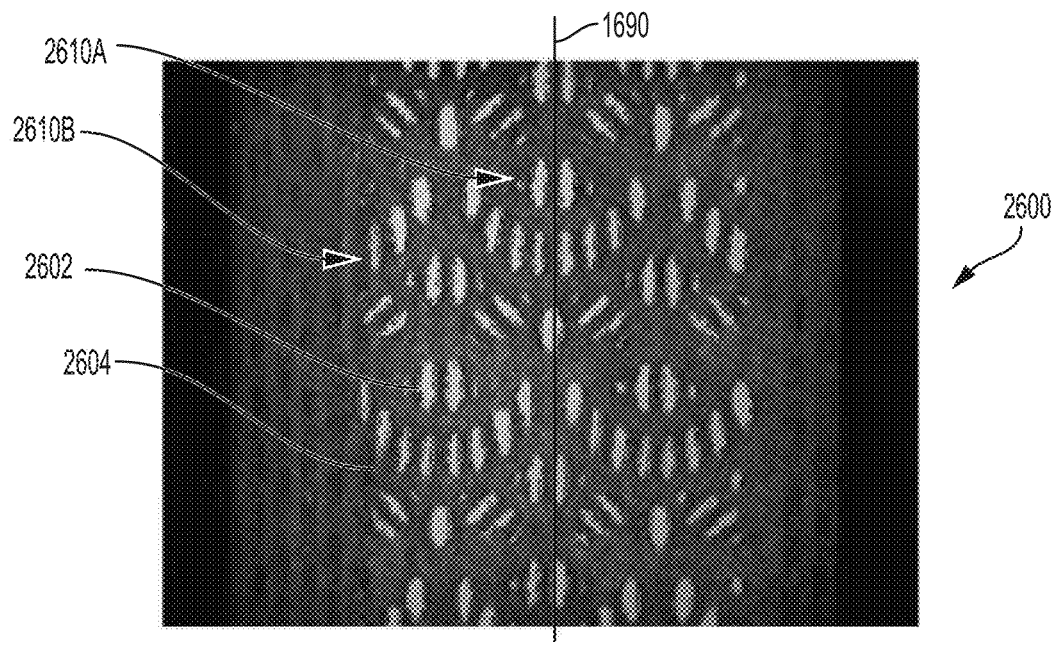
Figure 39:
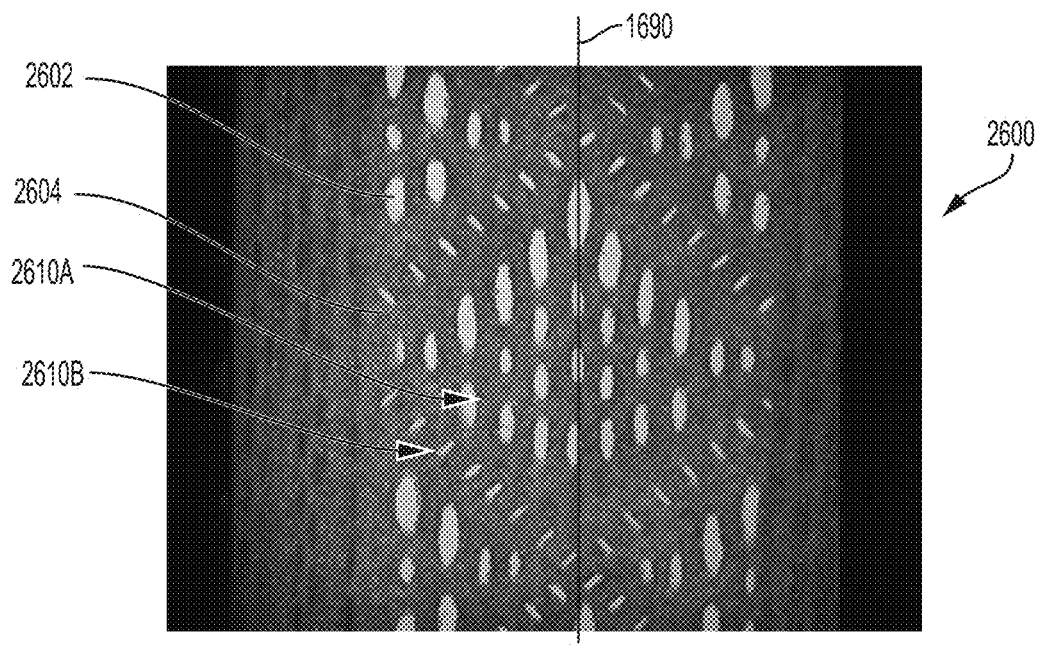
Figure 40:
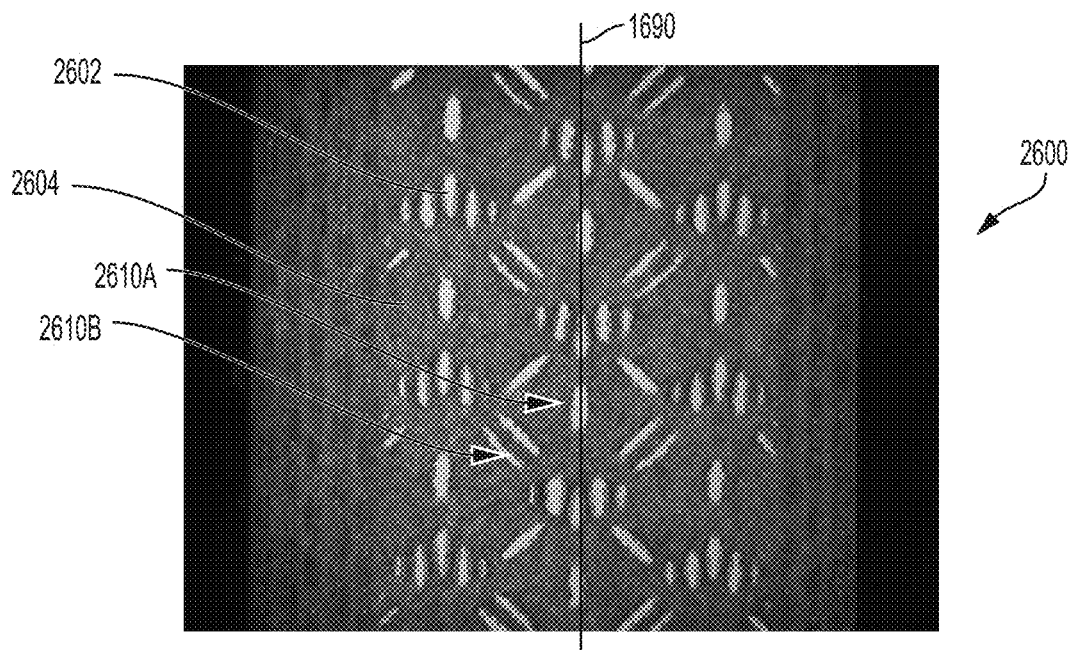
Figure 41:
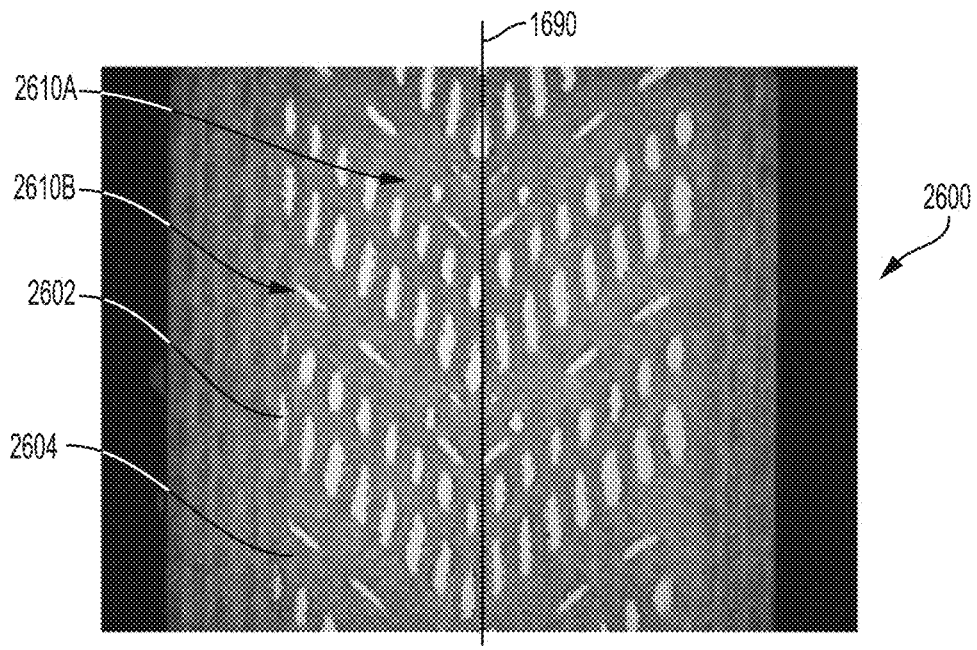
Figure 42:
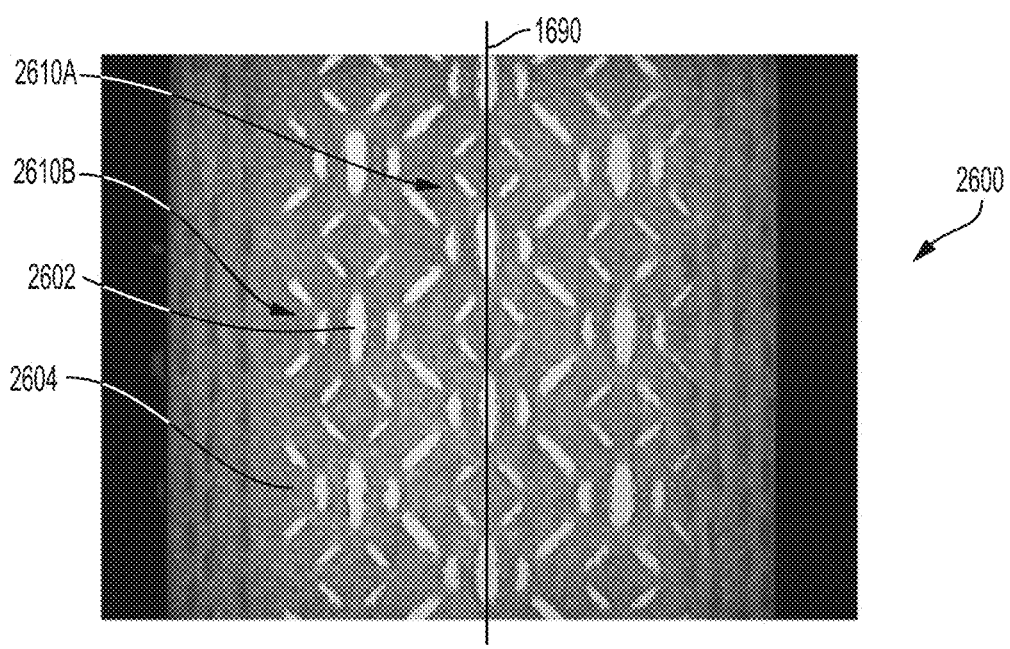
Figure 43:
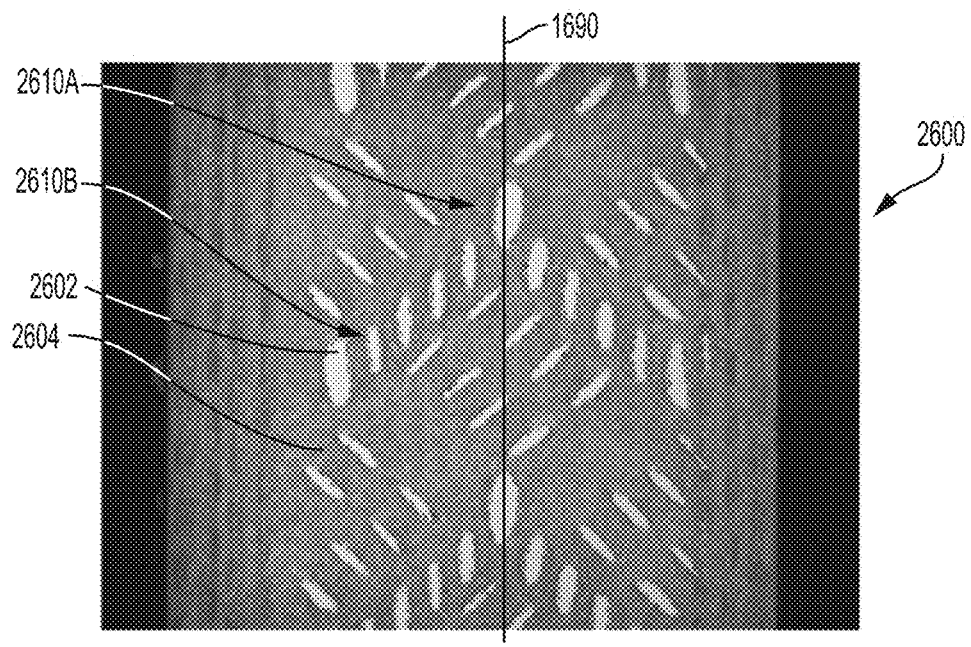
Figure 44:
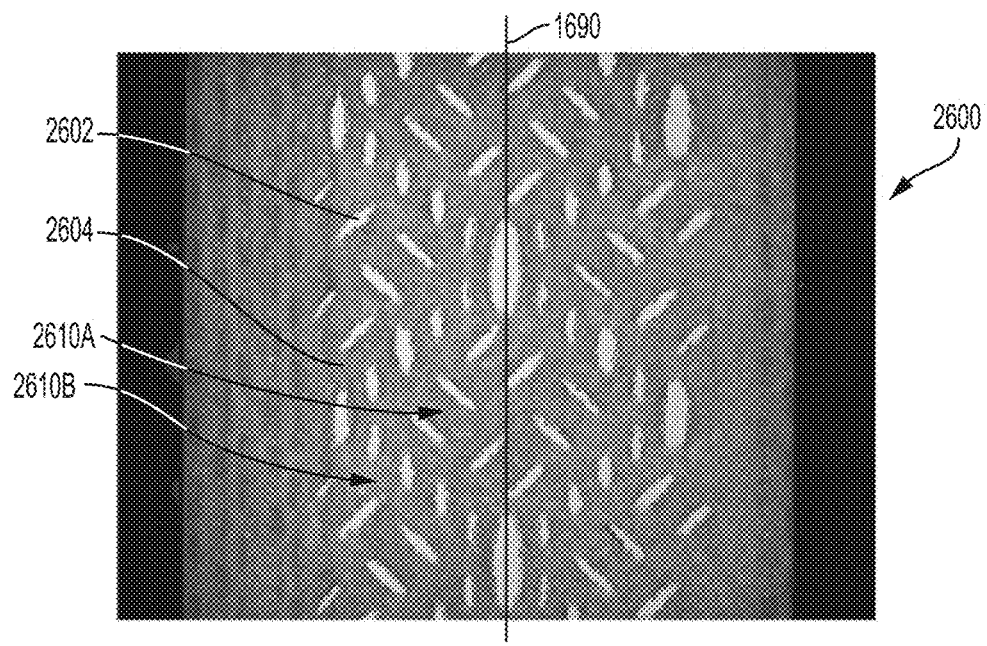
Figure 45:
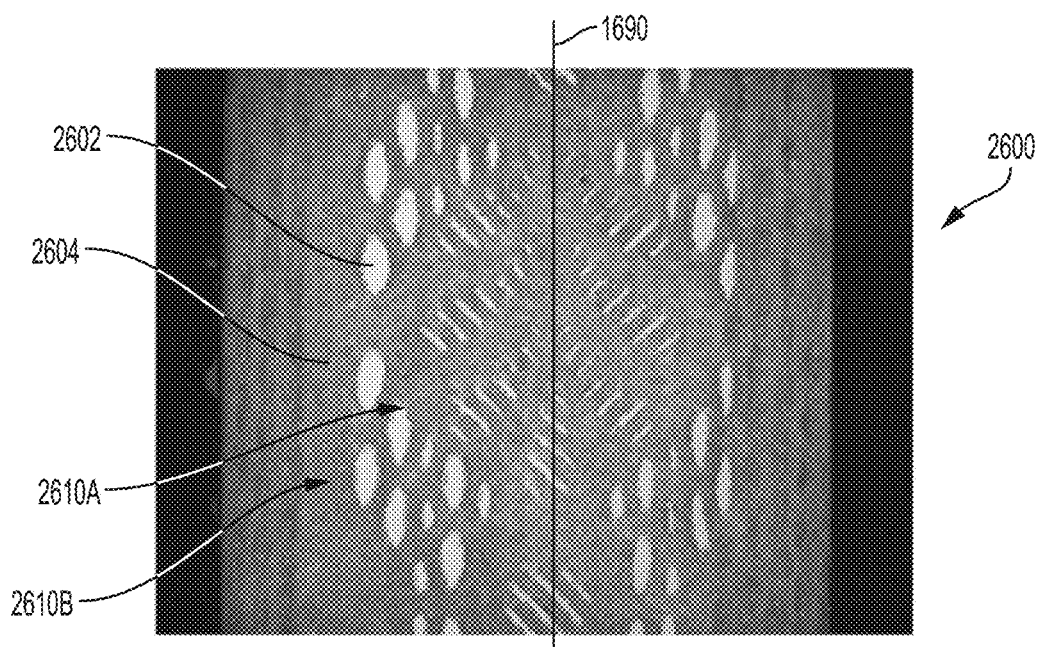
Figure 46:
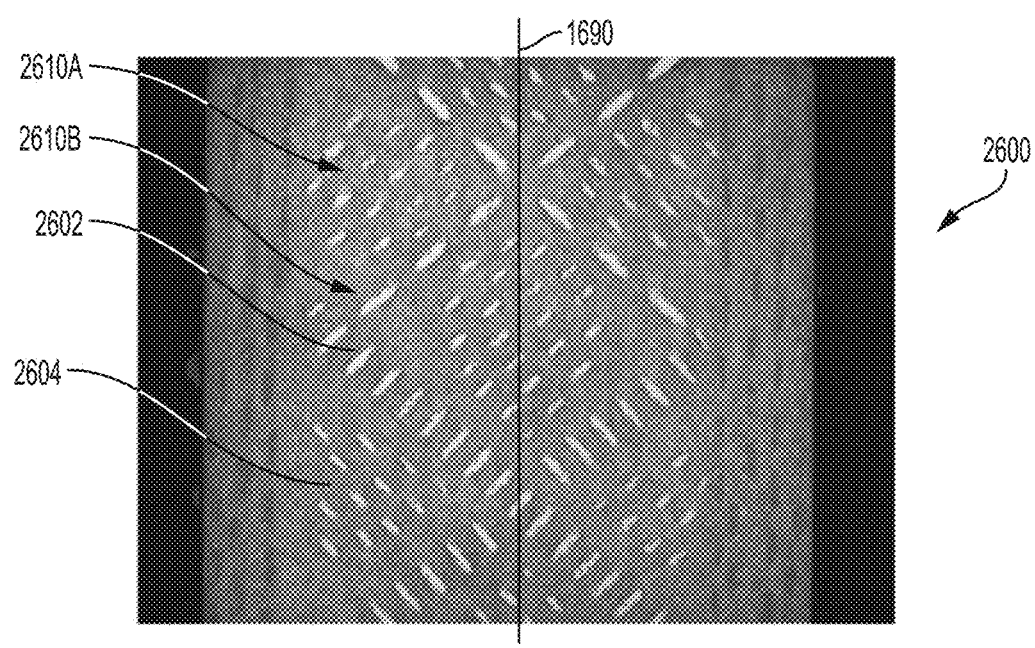
Figure 47:
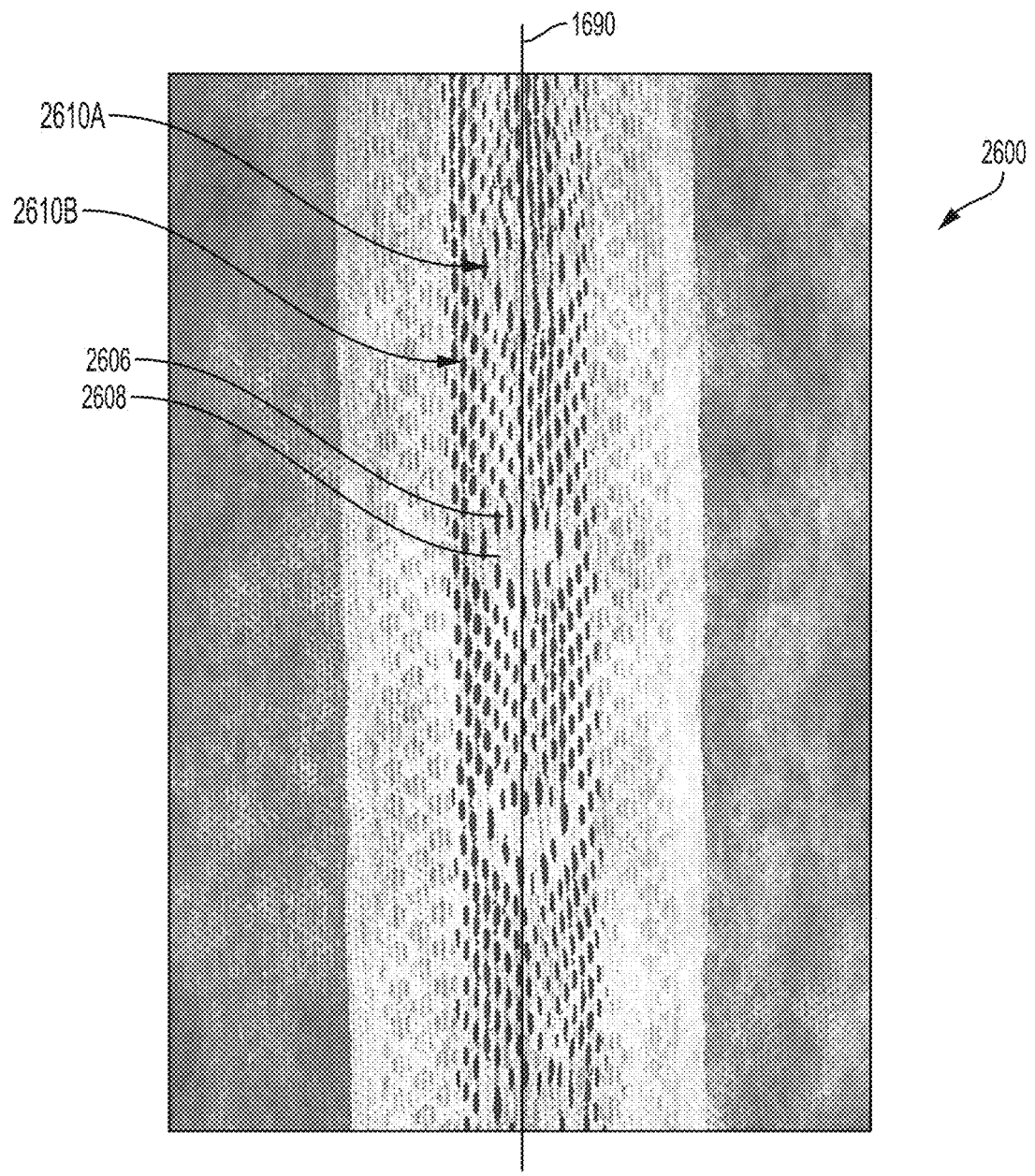
Figure 48:
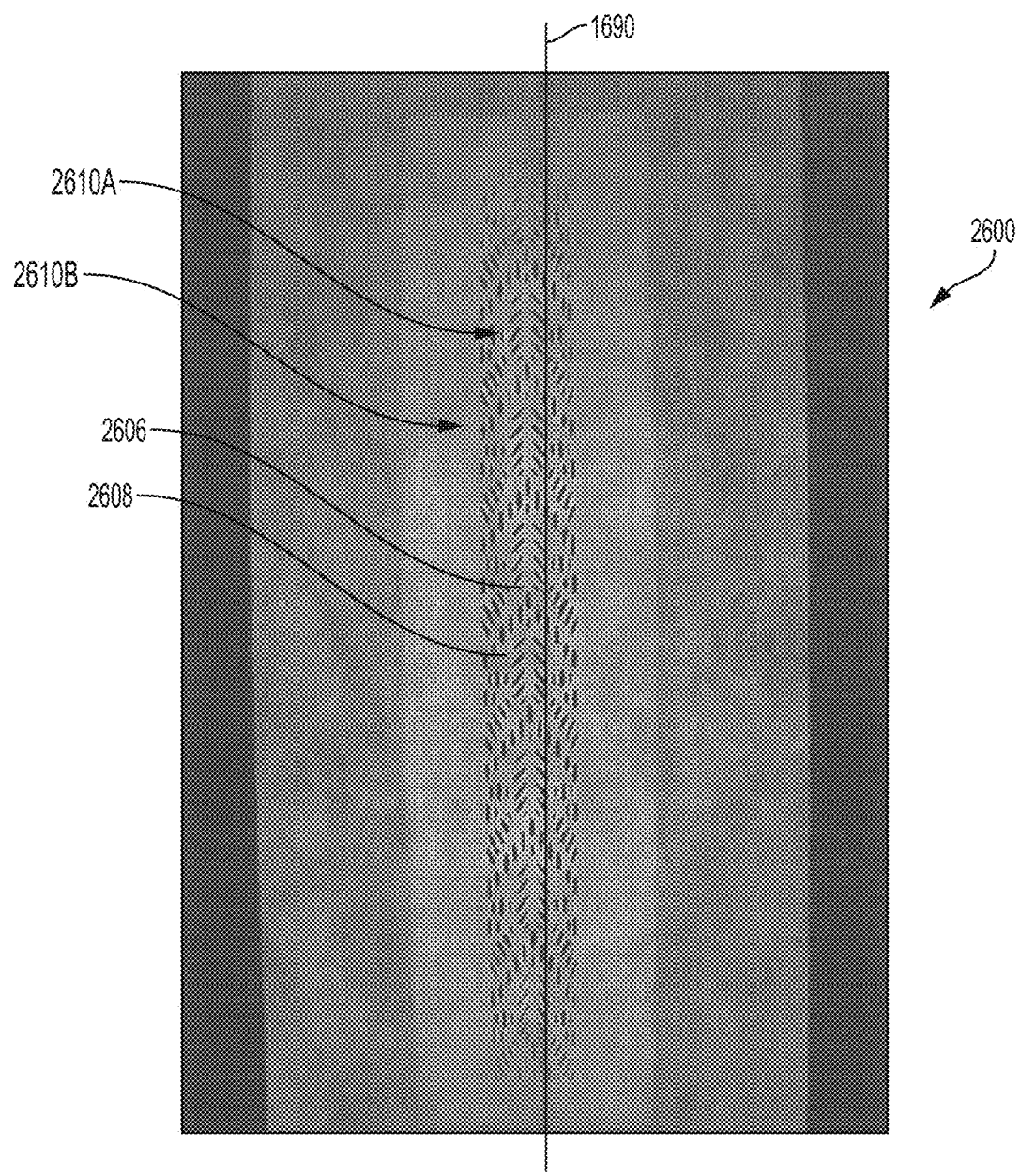

Referring to additionally to FIG. 34, as noted previously, the first pattern 2610A and/or the second pattern 2610B may comprise a plurality of apertures of which at least a portion are angled with respect to the machine direction 1675 at a first angle 1680 and another portion are angled with respect to the machine direction 1675 at a second angle 1682. The first angle 1680 and the second angle 1682 may be different from one another. In some forms, the second angle 1682 may be the mirror image of the first angle 1680. For example, the first angle may be about 30 degrees from an axis parallel to the machine direction 1675 while a second angle is −30 degrees from the axis parallel to the machine direction 1675. Similarly, the first pattern 2610A and/or the second pattern 2610B may comprise a plurality of apertures which are oriented generally parallel to the machine direction 1675. As mentioned previously, apertures which are oriented generally parallel to the machine direction 1675 generally have a lower aspect ratio and larger Effective Aperture AREA (described hereafter) as opposed to those apertures which are angled with respect to the machine direction 1675. It is believed that those apertures with increased Effective Aperture AREA allow for quicker fluid acquisitions time. While any suitable angle may be utilized, as discussed hereafter, once the first angle 1680 and the second angle 1682 are increased beyond 45 degrees from the machine direction 1675, the forces of the cross-direction 1677 stretching act more along the long axis of the aperture than perpendicular thereto. So, apertures which are angled more than 45 degrees with respect to the machine direction 1675 typically comprise less Effective Aperture AREA than those which are angled to a lesser extent with respect to the machine direction 1675.

As stated previously, the angled apertures are believed to provide additional fluid handling benefits for the nonwoven laminate 2600 for example a decrease in fluid run-off. In some forms, greater than about 10 percent of the apertures are angled with respect to the machine direction 1675. Additional forms are contemplated where greater than about 20 percent, greater than about 30 percent, greater than about 40 percent, greater than about 50 percent, greater than about 60 percent, greater than about 70 percent, greater than about 80 percent and/or less than 100 percent, less than about 95 percent, less than about 90 percent, less than about 85 percent of the apertures are angled with respect to the machine direction 1675 including any number or any ranges encompassed by the foregoing values.

Referring still to FIGS. 35-48, the population density of angled apertures may be greater nearer a centerline 1690 of the nonwoven laminate 2600. For example, spacing between adjacent apertures near the centerline 1690 may be a first distance while spacing between adjacent apertures further away from the centerline 1690 may be a second distance. The first distance may be less than the second distance. As an example, spacing between adjacent apertures can be about 1 mm. As such, the first distance may be about 1 mm while the second distance may be about 3 mm or greater.

Additional embodiments are contemplated where the distance between adjacent apertures increases with increasing distance from the centerline.

Additionally, in some instances, apertures nearer the centerline 1690 may be angled at the first angle 1680 while apertures further from the centerline 1690 are positioned at the second angle 1682. The first angle 1680 may be greater than the second angle 1682 with respect to the centerline 1690. For, example, the apertures further from the centerline 1690 may be oriented such that they are generally parallel to the centerline 1690 while the apertures positioned closer to the centerline 1690 are angled with respect to the centerline 1690. In some embodiments, the angle at which apertures are positioned relative to the centerline 1690 may decrease as the distance from the centerline 1690 increases. For example, a first aperture adjacent the centerline 1690 may be oriented at a first angle of 30 degrees with respect to the centerline 1690, while a second aperture 1 mm from the centerline 1690 may be oriented at 20 degrees from the centerline. The apertures positioned furthest away from the centerline 1690 may be generally parallel to the centerline 1690. Additional configurations are contemplated where apertures near the centerline 1690 are angled to a lesser extent than those further from the centerline 1690. In some forms, the apertures near the centerline 1690 may be generally parallel to the centerline 1690 while the apertures further from the centerline 1690 are angled with respect to the machine direction 1675.

As stated previously the lengths of the apertures may vary as well. In conjunction with being angled as disclosed above or independently therefrom, in some forms, the apertures adjacent the centerline 1690 may be longer than those which are further away from the centerline 1690. Similarly, the size of the apertures may vary. Variances in aperture size (Effective Aperture AREA) may be employed in conjunction with the variation of aperture angle and/or the variation in aperture length, or variances in aperture size may be employed independently of the variation of aperture angle and/or variation in aperture length. For those embodiments where aperture size may vary, larger apertures may be positioned adjacent the centerline 1690 while apertures having a smaller Effective Aperture AREA are positioned further away from the centerline 1690. For example, apertures adjacent the centerline 1690 may have an Effective Aperture AREA of 15 square millimeters while apertures further away from the centerline may have less Effective Aperture AREA, e.g. 1.0 square mm. Any of the values/ranges of Effective Aperture AREA provided herein may be utilized for configuring the Effective Aperture AREA variance described above.

As mentioned previously, the angle of orientation of the aperture can impact the fluid handling capabilities of a crimped fiber spunbond nonwoven web or nonwoven laminate 2600. Moreover, length of the aperture, width of the aperture, Effective Aperture AREA, spacing between apertures, as well as aperture density can similarly impact fluid handling. However, length of apertures, width of apertures, angle of orientation, spacing and density can have competing/negative impacts on the other variables. As stated previously, apertures which are at a greater angle to the machine direction 1675 tend to open less and therefore have less Effective Aperture AREA than apertures which are either parallel to the machine direction 1675 or which have a smaller angle with respect to the machine direction 1675. Similarly, angled apertures which are too closely spaced together tend to open less and therefore have less Effective Aperture AREA. As such, spacing between adjacent angled apertures may be increased over that which is between apertures which are generally oriented parallel to the machine direction 1675.

Additional aperture patterns are contemplated and are shown with regard to FIGS. 65-74.

Methods of Making Nonwoven Webs/Laminates Comprising Patterns of Apertures

The patterns of apertures of the present disclosure may be made generally by using the process generally described in U.S. Pat. No. 5,628,097 entitled "Method for Selectively Aperturing a Nonwoven Web" which issued May 13, 1997 and U.S. Patent Publication 2003/0021951 entitled "High Elongation Apertured Nonwoven Web and Method of Making" which published Jan. 20, 2003. Other methods of producing substrates comprising patterns of apertures known to those of skill in the art are also within the scope of the present disclosure and include for example rotary knife aperturing, hot pin aperturing, hydroentangling or needle punching. Other suitable processes are disclosed in U.S. Pat. Nos. 5,658,639; 5,628,097; 5,916,661; 7,917,985; and U.S. Patent Application Publication No. 2003/0021951. Other suitable processes for forming apertures may include those described in U.S. Pat. Nos. 8,679,391 and 8,158,043, and U.S. Patent Application Publication Nos. 2001/0024940 and 2012/0282436. Still other suitable methods for aperturing webs are provided in U.S. Pat. Nos. 3,566,726; 4,634,440; and 4,780,352.

Joining of Layers

The webs of a nonwoven laminate of the present invention or a nonwoven web and adjacent layers in a disposable absorbent article may be bonded together using any bonding methods known to those of skill in the art, such as adhesive bonding, patterned adhesive coating, ultrasonic bonding, thermal bonding, mechanical bonding, or any combination of these bonding methods. Alternatively, the various layers may be bonded together only at the perimeter of the apertures, through bonding the layers or overbonding the layers. The process of overbonding is disclosed in U.S. patent application Ser. No. 62/076,043, entitled "Patterned Apertured Webs and Methods For Making the Same," filed on Nov. 6, 2014. Additional references include U.S. Pat. Nos. 5,658,639; 5,628,097; 5,916,661; 6,498,284; 7,917,985; and U.S. Patent Application Publication Nos. 2003/0021951; 2005/154362. Additional references for bonding nonwoven webs/laminates together include U.S. Pat. No. 7,056,404 and U.S. application Ser. No. 14/135,687, filed on Dec. 20, 2013. And as noted previously, in some forms of the present invention, the formation of overbonds may subsequently be processed into apertures. Additional disclosure regarding overbonds is provided hereafter.

The bonding may be done in a pattern of bonds or in arrays of bonds. The pattern may be a regular, uniform pattern or an irregular, non-uniform pattern. The bonding patterns may comprise a substantially continuous bond pattern or may be formed of discrete bonding points. The discrete bonding points may form a pattern. The pattern of bonding points may be homogeneous or non-homogeneous. A bond pattern in one region of a nonwoven laminate of the present invention may differ from a bond pattern in another region of the nonwoven laminate. For example, the bond pattern may be different in the machine direction or the cross-machine direction of the nonwoven laminate. An absorbent article including the nonwoven laminate may have a different bond pattern in the front region vs. the back region, the center region vs. side regions, or the crotch region vs. waist regions of the absorbent article, for example. If adhesive is used in the bonding process, the adhesive may be tinted, pigmented, and/or patterned to create a pattern as discussed hereafter. Bonding in nonwoven laminates is typically accomplished by joining the land areas of various layers of the nonwoven laminates.

Substrates, layers, crimped fiber spunbond nonwoven webs and/or elements of a nonwoven laminate and/or disposable absorbent articles may be bonded together by any suitable method. Some specific examples of bonding can occur between multiple nonwoven layers of a topsheet. In another example, a topsheet (including one or more layers) may be bonded to a subjacent layer (layer between the topsheet and an absorbent core)—including secondary topsheets, acquisition layers or the like. In yet another example, the topsheet (including one or more layers) may be bonded to the absorbent core. In each of the above examples, the constituent layers of the topsheet may be bonded together in a separate step and then subsequently bonded to another component.

The bonding may comprise a pattern or a plurality of patterns which form graphics and/or other depictions, hereafter "bond indicia". Some examples of bond indicia are shown in FIGS. 49-52. In another example, substrates, layers, crimped fiber spunbonded webs and/or elements of a nonwoven laminate and/or disposable absorbent articles may be adhesively bonded together. Any suitable method may be utilized to form fusion bonds between layers/substrates described herein. Some suitable examples are ultrasonic, heated rolls, and the like.

Any suitable method may be utilized to form bonds between layers/substrates described herein. Some suitable examples are ultrasonic, heated rolls, and the like. In a specific example, substrates, layers and/or elements of a disposable absorbent articles may be bonded together via fusion bonding, ultrasonic bonding, or the like. The bonding may comprise a pattern or a plurality of patterns which form graphics and/or other depictions, hereafter "bond indicia". In another example, substrates, layers and/or elements of disposable absorbent articles may be adhesively bonded together.

The mechanical bonding methods, e.g. fusion bond, ultrasonic, etc. can cause localized areas of the web to thin and become film like—in the case of nonwovens. These thinner areas can have different opacity characteristics with respect to the constituent material around the bond. As such, visual/color effects can be achieved. For example, the thinner areas may appear as a different color than the constituent material around the bond.

Bonding of the layers of an absorbent article is critical to the performance of said article. Bonding is important for the integrity of the product and of the layers to ensure sustained performance and durability throughout wear. Bonding can ensure connectivity between desired layers of the product to aid in fluid transfer between the layers. This is especially critical in nonwoven topsheet laminates with a hydrophobic nonwoven upper layer to ensure fluid access to the hydrophilic nonwoven lower layer. Fusion bonding has additional advantages over adhesive in that it lowers raw material cost, eliminates line hygiene issues, and allows bonding of layers between which the use of adhesive would not be feasible.

In order to ensure the integrity of the product and of the crimped fiber spunbond nonwoven laminate topsheet, the total area of the bonding (calculated as a percent area of the outer perimeter of bonding region) may range from 5% to 25%, 10% to 20%, or 12% to 18%. The size of each individual fusion bond nub may range from 0.5 sqmm to 5 sqmm, 1 sqmm to 3 sqmm. The spacing between fusion bond nubs can range from 1 mm to 5 cm, 1.6 mm to 3 cm.

In some forms, the bonds, as stated previously, may be configured in patterns so as to create bond indicia. But apart from forming bond indicia, the bonds can help secure the layers of the nonwoven laminate together. Additionally, in some forms, the bonds may be utilized to secure the crimped fiber spunbond nonwoven web or nonwoven laminate to adjacent layers of a disposable absorbent article, e.g. a secondary topsheet, absorbent core, etc.

As shown in FIGS. 49-52, bond patterns 3000A, 3000B, 3000C, and 3000D of the present invention may comprise a plurality of bond sites 3002. The bond sites may be any suitable shape. As shown, the bond sites are approximately circular; however, elliptical, diamond, heart, star, clover (3 leaf, 4 leaf), bowtie, combinations thereof, and the like are contemplated. In some forms, the constituent bond sites 3002 of a fusion bond pattern may comprise combinations of shapes.

As shown, the fusion bond pattern 3000A may comprise a plurality of arrays of bond sites, e.g. 3010, 3020, 3030, and 3040. The first array 3010 may be a continuous series of bond sites 3002 which enclose the second array 3020, the third array 3030, and the fourth array 3040. As shown, the second array 3020 may be discontinuous and disposed between the first array 3010 and the third array 3030. The third array 3030, much like the first array 3010 may be continuous and may enclosed the fourth array 3040. The fourth array 3040 may be discontinuous and be disposed in a target area on the absorbent article. The target area signifies the location of the article which is likely to receive the fluid insult from the wearer assuming the absorbent product is donned properly.

With the discontinuous fourth array 3040, fluid insults can be provided with adequate access to the nonwoven laminate. Additionally, with the continuous third array 3030, fluid insults are encouraged to stay within the target area as opposed to meandering to outer edges of the article.

Figure 49:
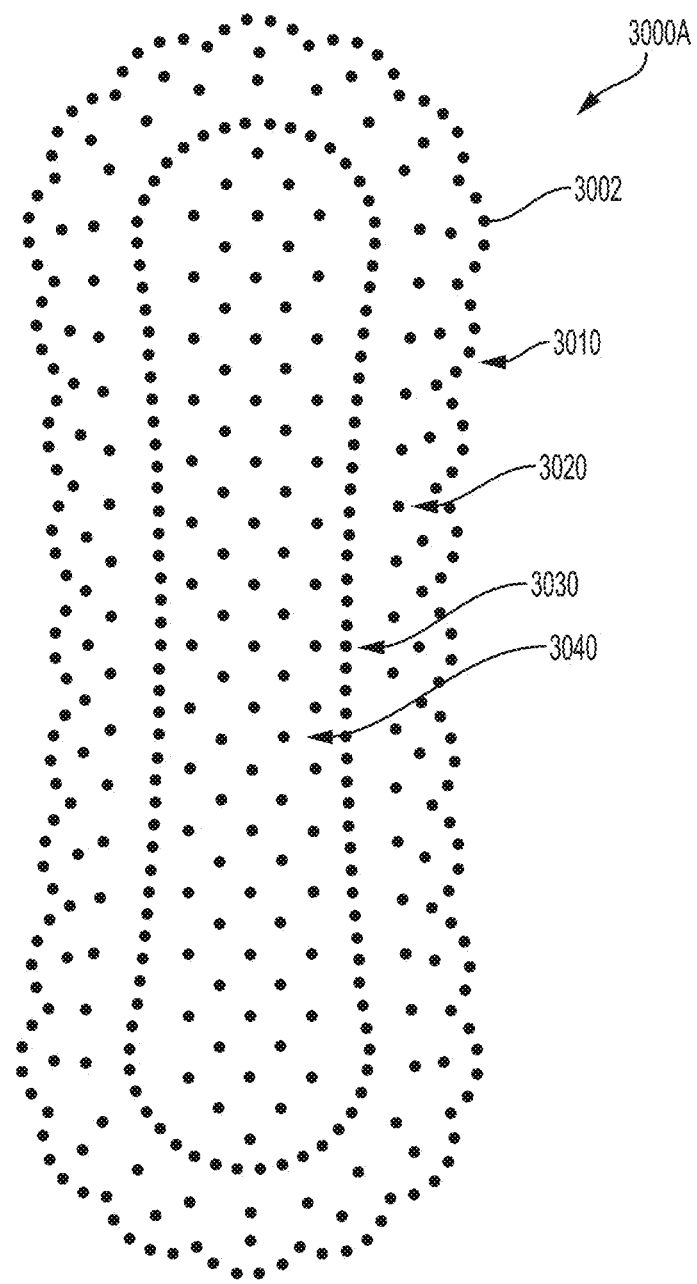
FIGS. 49-52 represent a schematic illustration of fusion bond patterns for nonwoven laminates of the present invention.

As shown in FIG. 49, the fusion bond pattern 3000B may comprise a plurality of arrays of bond sites. For example, a first array 3010B may be continuous and comprise bond sites which are arranged in the shape of hearts, clouds, etc. A second array 3020B is disposed within the first array 3010B and disposed about a third array 3030B. The third array 3030B is continuous and surrounds the fourth array 3040B. Much like the arrays of the fusion bond pattern 3000A, the arrays of the fusion bond pattern 3000B can provide fluid handling benefits.

Figure 50:
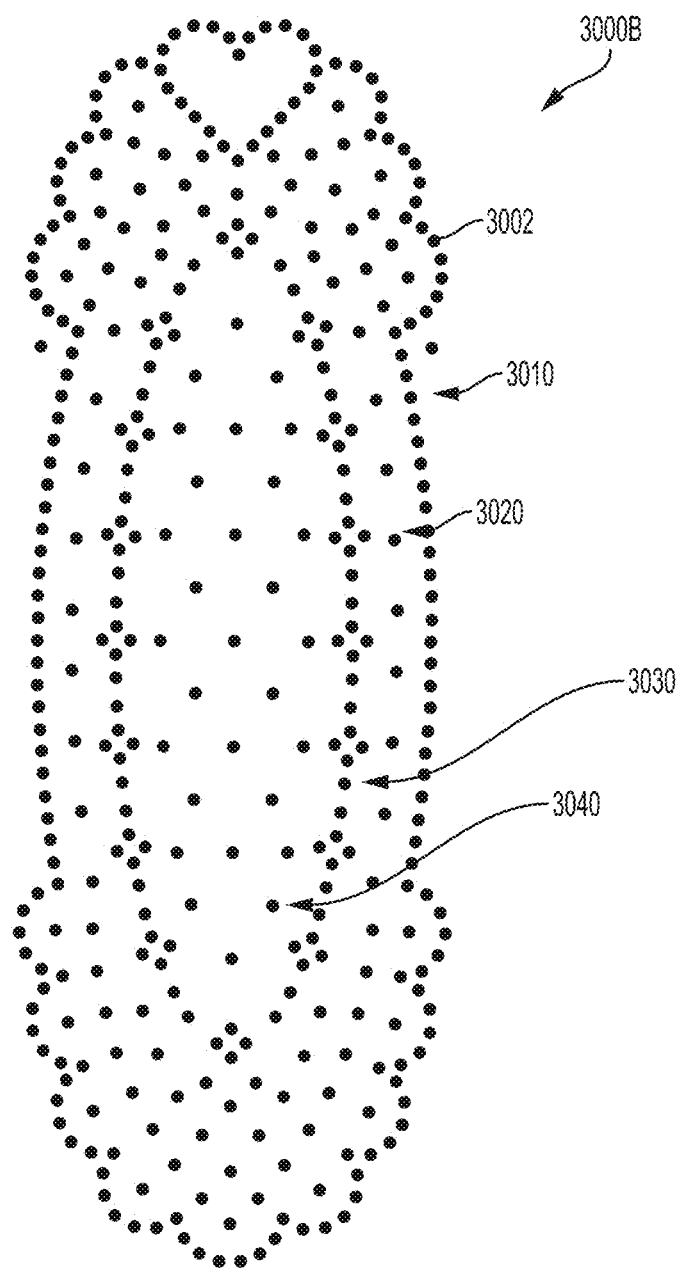

As shown in FIG. 50, a fusion bond pattern 3000C may comprise a plurality of arrays of bond sites. However, in contrast with the previous fusion bond patterns, a first array 3010C may be discontinuous about the entire periphery of a pad. As shown, the first array 3010C comprises a plurality of continuous segments of bond sites each of which is disconnected from one another. A second array 3020C may be disposed inboard of the first plurality 3010C and may also comprise a plurality of continuous segments which are discontinuous. A third array 3030C may comprise continuous bond sites and enclose a fourth array 3040C. The fourth array 3040C comprises a plurality of discontinuous bond sites. Much like the fusion bond patterns discussed previously, the fusion bond pattern 3000C may provide fluid handling benefits.

Figure 51:
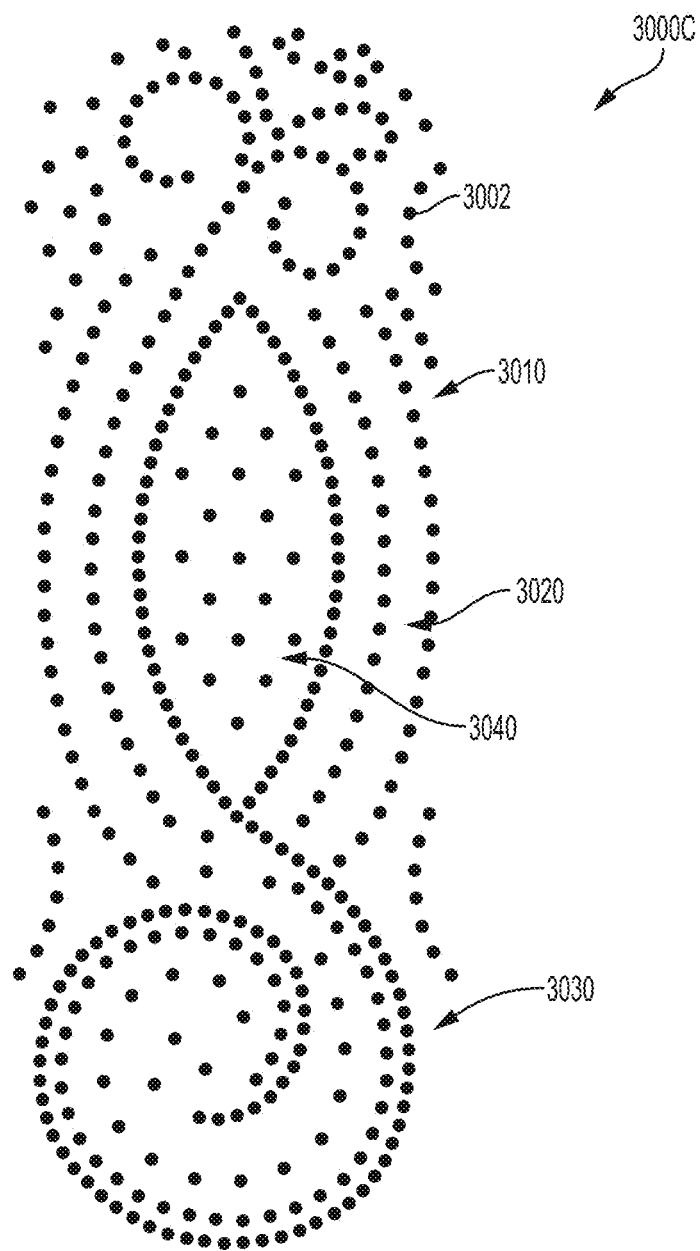
Figure 52:
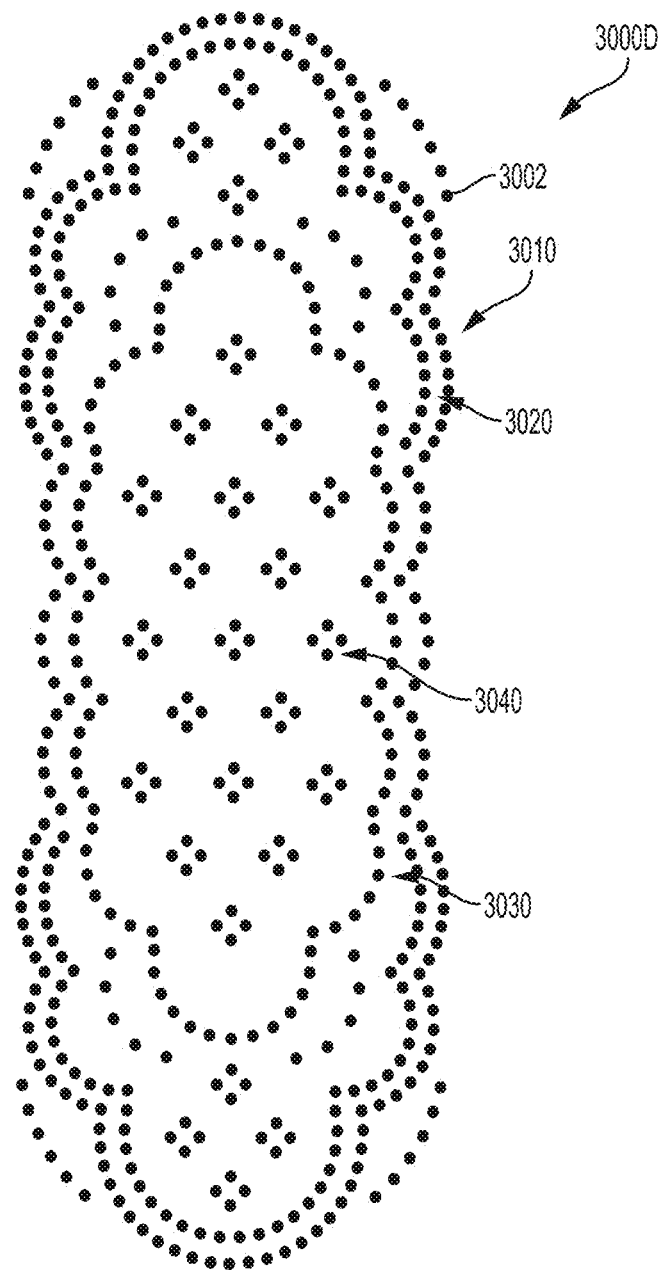

As shown in FIG. 51, a fusion bond pattern 3000D may comprise a plurality of arrays of bond sites. For example, a first array 3010D may comprise a plurality of bond sites which are arranged in a continuous fashion and may enclosed a second array 3020D, a third array 3030D and a fourth array 3040D of bond sites. The second array 3020D may comprise a plurality of bond sites which form continuous elements as well as a plurality of bond sites which form discontinuous elements. These continuous elements may be disposed at a first end and second end of the absorbent article. The third array 3030D of plurality of bond sites may be continuous and may enclosed the fourth array 3040D. The fourth array 3040D may comprise a plurality of bond sites which form a plurality of elements. Each of the elements may be continuous but discontinuous with respect to the other elements. For example, each element may comprise a plurality of bond sites, e.g. 4. The bond sites would be considered continuous for each respective element, but the bond sites from element to element would be discontinuous.

Patterned Adhesive

As noted previously, the nonwoven laminates of the present invention comprise at least two webs and may include additional webs—at least one of the webs being a crimped fiber spunbond nonwoven. In some forms, adhesive may be used to join the layers of the nonwoven laminate together and/or may be utilized to join the nonwoven laminate to a portion of an absorbent article. In some forms, adhesive may be used to join a crimped fiber spunbond nonwoven web to adjacent layers/elements of a disposable absorbent article. The adhesive may comprise a pigment, a tint, or a dye. The colored adhesive, in a form, may be positioned between the first layer and second layer of a nonwoven laminate. In some forms, more than one colored adhesive may be used in a nonwoven laminate. The colored adhesive may also be situated in any suitable location when joining two or more webs (e.g., on the surface of or intermediate any of the layers). The colored adhesive may also be deposited in zones and/or in patterns throughout the joined layers. The colored adhesive may be different or the same in different zones of the joined layers. The colored adhesive may be positioned intermediate the layers of the joined layers or positioned on any other surfaces of the joined layers. Additional layers may also be provided having one or more colored adhesives. As stated previously, adhesive and particularly colored adhesive may be applied such that the adhesive forms a pattern or a plurality of patterns which form graphics and/or other depictions, referred to as "adhesive indicia." Adhesive indicia, in some forms, may also be created via the use of clear adhesive. The application of clear adhesive, in some instances can change the opacity of materials which are being adhesively joined.

In an instance, a colored adhesive may be positioned between two low basis weight materials (e.g., 15 gsm or less, 10 gsm or less) forming a nonwoven laminate, so that the colored adhesive may be visible from either side of the nonwoven laminate. In a topsheet context, this can provide a high basis weight topsheet to achieve improved softness, while still retaining the benefit of seeing the colored adhesive from either side of the nonwoven laminate.

As stated previously, the adhesive utilized to bond/join layers and/or elements of disposable absorbent articles using the crimped fiber spunbond nonwoven webs/nonwoven laminates of the present invention may comprise adhesive indicia. Accordingly, the nonwoven laminates and/or absorbent articles of the present disclosure, or portions thereof, may comprise one or more patterned adhesives applied thereto or printed thereon. The patterned adhesives may be associated with the crimped fiber spunbond nonwoven webs/nonwoven laminates such that at least a portion of the patterned adhesives can be viewable through the crimped fiber spunbond nonwoven web/nonwoven laminates, e.g. through apertures and/or land areas. Patterned adhesives are adhesives that are applied to one or more layers, or between layers, in particular patterns to provide the absorbent articles, or portions thereof, with certain patterns, visible patterns, and/or certain textures. The patterned adhesives may be printed on or otherwise applied to any suitable layer of the absorbent articles. Methods for applying patterned adhesives to layers or substrates by adhesive printing are disclosed, for example, in U.S. Pat. No. 8,186,296, to Brown et al., issued on May 29, 2012, and in U.S. Pat. Appl. Publ. No., 2014/0148774, published on May 29, 2014, to Brown et al. Other methods of applying patterned adhesives to substrates known to those of skill in the art are also within the scope of the present disclosure.

A patterned adhesive may have the same color or a different color as at least one layer of a nonwoven laminate or different than a color of the crimped fiber spunbond nonwoven web. In some instances, the patterned adhesive may have the same or a different color as both or all layers of a nonwoven laminate. In some instances, aperture patterns in at least one layer of a crimped fiber spunbond nonwoven webs/nonwoven laminate may coordinate with patterned adhesive to visually create a three-dimensional appearance. The apertured patterns may be the same or different than patterns of the patterned adhesive.

In an instance, a nonwoven laminate may comprise a first layer comprising a plurality of apertures and a plurality of land areas and a second layer comprising a plurality of apertures and a plurality of land areas. A patterned pigmented substance, such as ink or a patterned adhesive, may be positioned at least partially intermediate the first layer and the second layer. The plurality of apertures of the first layer may be at least partially aligned with the plurality of apertures of the second layer. The patterned pigmented or colored substance may be at least partially viewable through the aligned portions of the apertures in the first and second layers. Examples of patterned adhesive are provided with regard to FIGS. 75-81.

Figure 75:
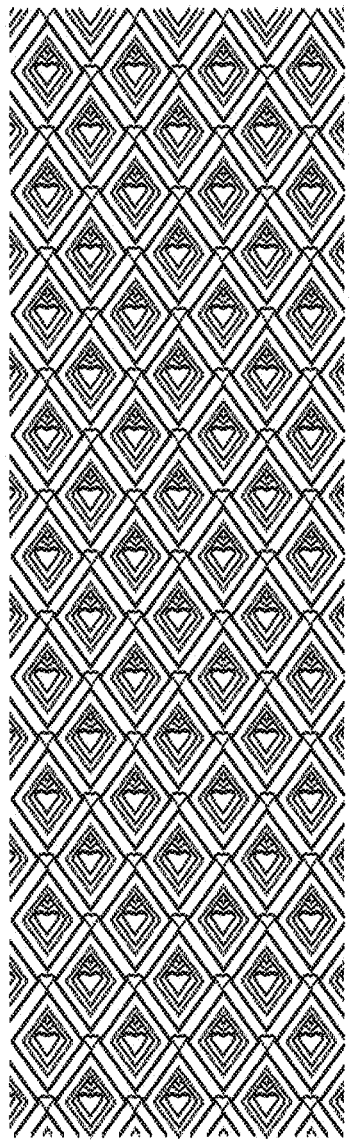
FIGS. 75-81 are illustrations showing overbonds, patterned adhesive and combination of overbonds and patterned adhesive, respectively.
Figure 76:
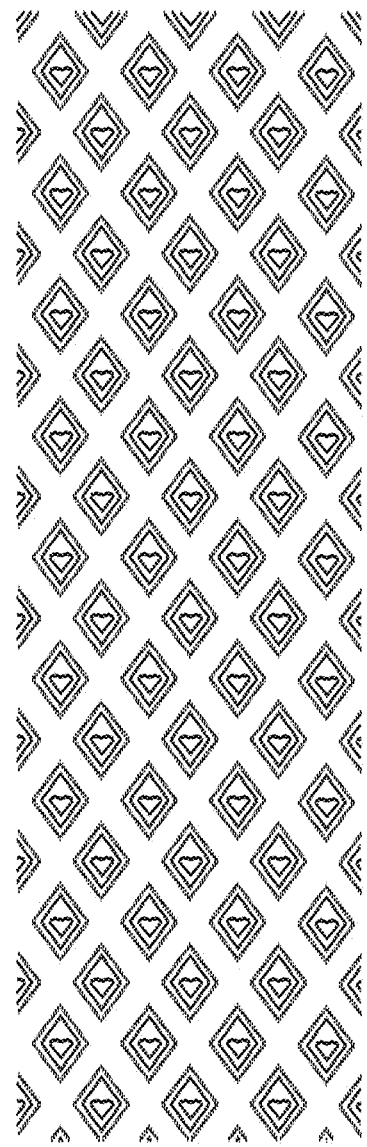
Figure 77:
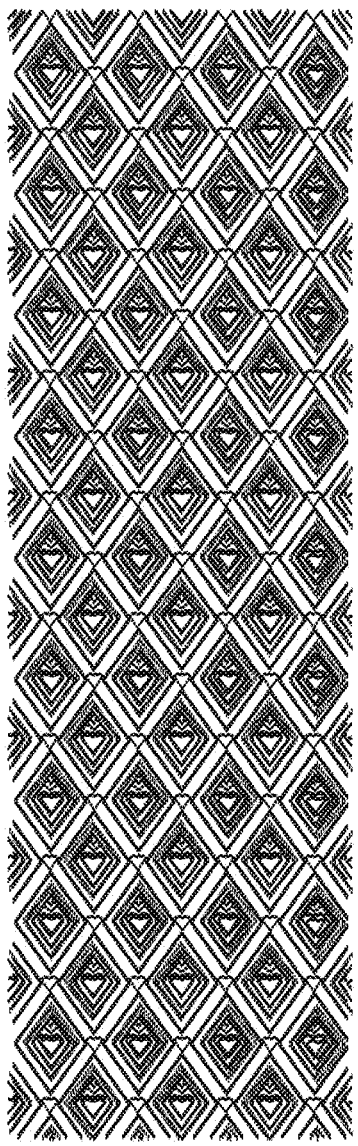
Figure 78:
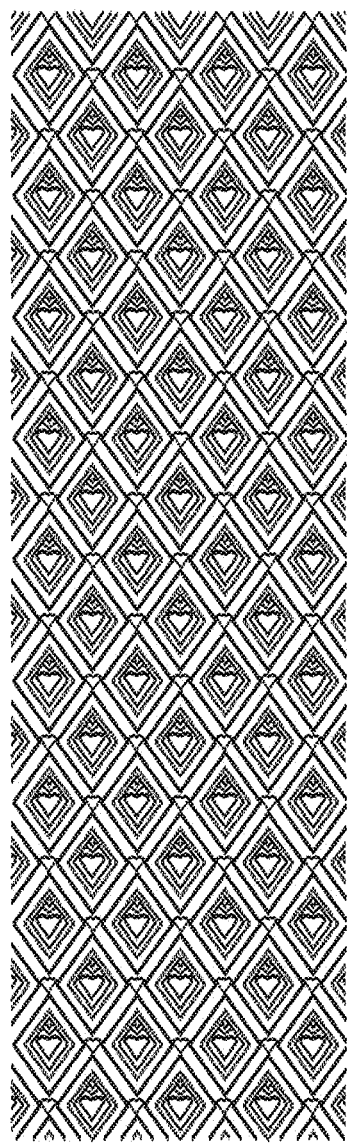
Figure 79:
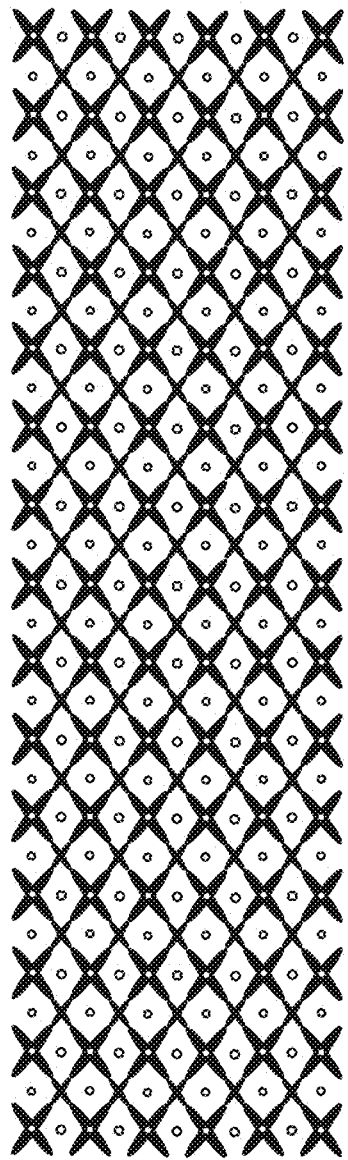
Figure 80:
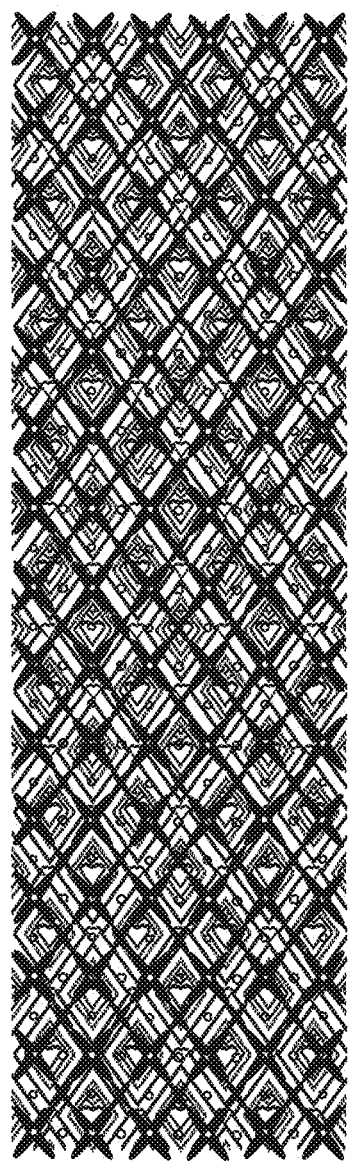

Regarding FIGS. 75-77, a plurality of overbonds are shown on a web arranged in a plurality of arrays which will eventually—when processed as described herein—produce apertured indicia. In FIG. 76 adhesive indicia on a web is depicted. As noted previously, the adhesive may comprise a color or may be clear in some forms. Regarding FIG. 77, a combination of the overbonds of FIG. 75 and the adhesive indicia of FIG. 76 are shown. Note that given the arrangement of the overbonds of FIG. 75, the resulting apertured indicia would appear similar (coordinated) with the adhesive indicia shown in FIG. 76. In such forms, it may be beneficial to register the apertured indicia with the adhesive indicia to produce the desired visual effect. Adhesive indicia and apertured indicia which may not require registration are depicted in FIGS. 78-80. A similar effect is depicted in FIG. 81.

Figure 81:
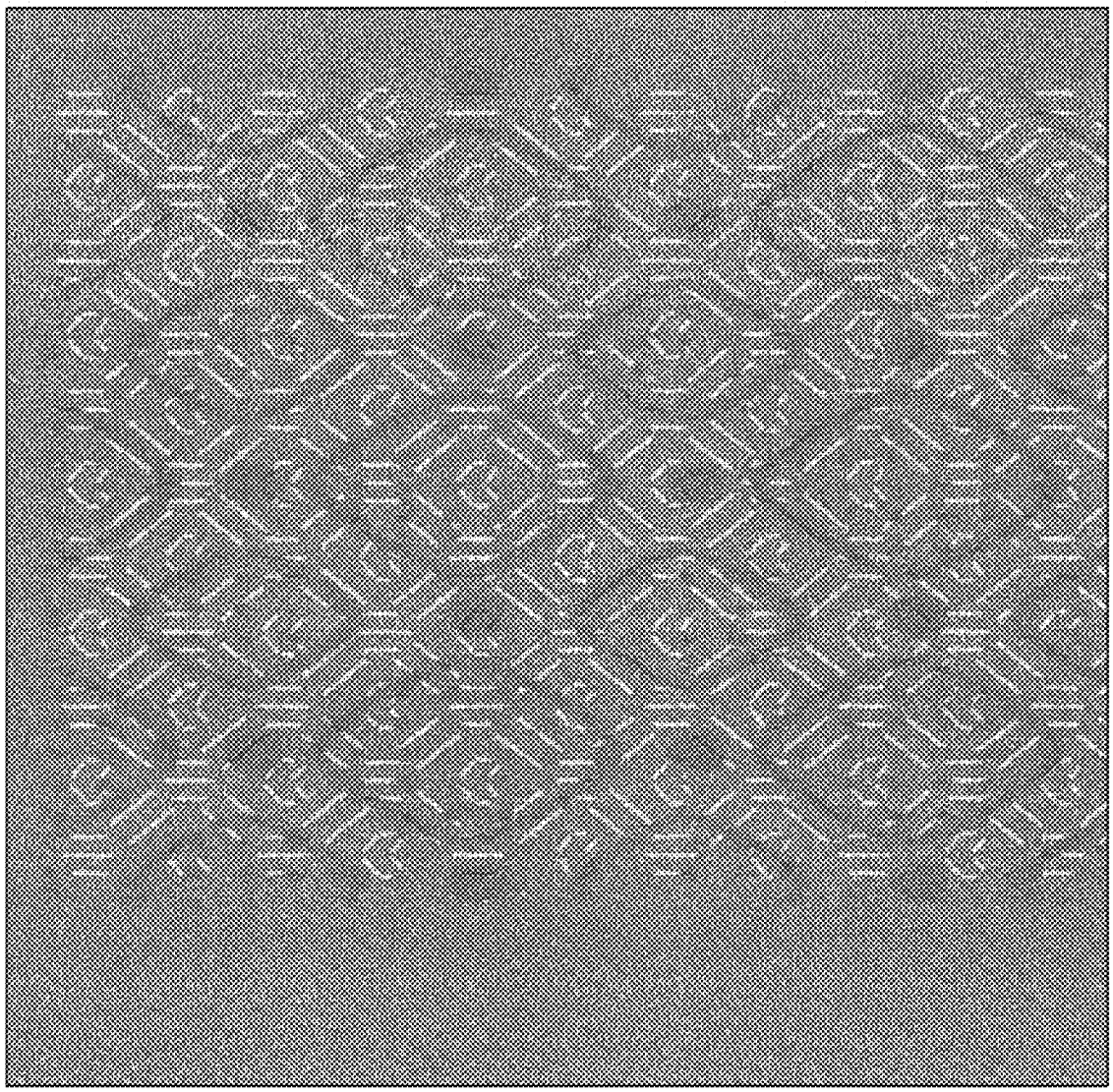

Regarding FIG. 81, a combination of apertured indicia and adhesive indicia is shown on a web. The apertured indicia and the adhesive indicia are not registered. As such, portions of the adhesive indicia are visible through only a portion of the apertures. The effect can highlight portions of the adhesive indicia which are visible through the apertures. The remainder of the adhesive indicia may still be visible through the web which comprises the apertured indicia.

Printing

Either in addition to or in lieu of the various layers/web being colored, one or more of the layers of the nonwoven laminates or the crimped fiber spunbond nonwoven webs of the present disclosure may include printing, e.g., with ink or a pigmented or colored pattern. The ink may be deposited via any printing process known in the art including, but not limited to, flexographic printing and digital inkjet printing. The printing may comprise a pattern or a plurality of patterns which form graphics and/or other depictions, hereafter, "printed indicia." The printing may be on an external surface of a first layer of the nonwoven laminate, between the first and second layers of the nonwoven laminate, or may be on a surface beneath the second layer of the nonwoven laminate. The printing may also be situated in any suitable location if the nonwoven laminate has more than two layers (e.g., on the surface of any of the layers). The printing may also be deposited in zones of the nonwoven laminate and/or in patterns throughout the nonwoven laminate. The printing may be different or the same in different zones of the nonwoven laminate. If the printing will be covered by one of the layers, e.g. the covering layer, it may have a relatively low opacity to enhance the visual appearance of the printing. The density of the printing (e.g., clarity and contrast) may be enhanced by including small-denier fibers in the printed layer including, but not limited to, melt-blown fibers, microfibers, and nanofibers. The printing may be on the first layer, the second layer, and/or may be on a separate layer positioned at least partially intermediate the first and second layers. In an instance, the printing may indicate the proper orientation of an absorbent article on a wearer (e.g., front/rear). It will be understood that printing may be used with any of the various forms and configurations of the nonwoven laminates disclosed herein. In some forms, more than one type or color, for example, of printing may be used in a single nonwoven web. Additional layers may also be provided in a nonwoven laminate having one or more printed patterns.

Coordinated Patterns

Heretofore, bond indicia, adhesive indicia, structural indicia, and printed indicia have been introduced. Additionally, for those forms where the crimped fiber spunbond nonwoven webs and/or nonwoven laminates of the present invention comprise patterned apertures, the array of apertures may comprise a pattern or a plurality of patterns which form graphics and/or other depictions, hereafter, "apertured indicia." The apertured indicia may coordinate with at least one of printed indicia, bond indicia, adhesive indicia, and/or structural indicia. For example, in the absorbent article context, located beneath the nonwoven laminate or within the nonwoven laminate adhesive indicia may be present which coordinate with the apertured indicia. In an instance, the nonwoven laminate may be used a topsheet, an outer cover, an ear, or other portion of an absorbent article.

The aperture pattern in a nonwoven web may coordinate with features under it, such as bond sites, material edges, channels, and/or discolored or colored materials. In some specific executions, the nonwoven web may be used to accentuate or block/hide these features. The aperture patterns of a nonwoven laminate may also be used to indicate the correct front vs. rear, left vs. right orientation of an absorbent article or other consumer product.

Apertured indicia may be coordinated with printed indicia elsewhere on the product and/or packaging. For example, a disposable absorbent article of the present invention may comprise apertured indicia which provides the appearance of a snowflake. The article may additionally comprise printed indicia elsewhere on the article itself and/or its packaging, wherein the printed indicia provides the appearance of a snowflake. In such embodiments, the feminine article may comprise a release liner which includes a printed snowflake pattern and/or be placed in a package comprising a printed snowflake pattern.

Forms of the present invention are contemplated where the apertured indicia is coordinated with adhesive indicia, bond indicia, and/or structural indicia. Embodiments are contemplated where at least two of the following are coordinated on an absorbent article: apertured indicia, adhesive indicia, printed indicia, bond indicia, structural indicia. Similar embodiments are contemplated with regard to the packaging for the disposable absorbent articles described herein (including release liners and/or secondary packaging). Additionally, the aforementioned indicia may be coordinated across the absorbent article, its packaging, and/or its secondary packaging (including release liners) or any combination thereof.

In some specific forms, while a portion of the topsheet may include apertured indicia, other portions of the topsheet may include printed indicia which is coordinated with the apertured indicia. In other forms, a sub-layer, e.g. acquisition layer, secondary topsheet, and/or absorbent core may comprise printed indicia which is coordinated with the apertured indicia of the topsheet. Still in other forms, the backsheet may comprise printed indicia which is coordinated with the apertured indicia of the topsheet. Additional forms are contemplated where a portion of the topsheet includes apertured indicia, the backsheet includes printed indicia coordinated with the apertured indicia, packaging of the feminine article includes printed indicia coordinated with the apertured indicia, a non-apertured portion of the topsheet includes printed indicia which is coordinated with the apertured indicia and/or a sub-layer, e.g. acquisition layer, secondary topsheet, and/or absorbent core comprise printed indicia which is coordinated with the apertured indicia. Similar embodiments are contemplated with adhesive indicia, structural indicia, bond indicia, and/or any combinations thereof.

In other specific forms, the topsheet may comprise apertured indicia and first printed indicia. The first printed indicia may coordinate with second printed indicia on secondary packaging while apertured indicia may coordinate with printed indicia on primary packaging for the absorbent article.

Indicia is visually coordinated when one or more elements of the indicia have two or more visual characteristics that are either matched or are caused to match. As used herein, the term "match" or "matched" is used to describe the way or degree to which apertured indicia, printed indicia, bond indicia, adhesive indicia, and/or structural indicia, or characteristics thereof visually fit together or are caused to fit together. For example, apertured indicia and printed indicia are considered matched if some aspects of the apertured indicia are identical to similar aspects of the printed indicia. In one form of match, for example, apertured indicia and printed indicia that resemble each other are said to match. The same can be true for any combination of the heretofore mentioned indicia. As used herein, the term "coordinate" or "coordination" is used to describe how indicia of the overall absorbent article and/or its packaging visually belong together. Components or elements are considered to be coordinated if they match, or are caused to match. As used herein, the term "caused to match" is used to describe how any combination of aforementioned indicia are made to appear matched to one another by using coordinating indicia (any combination of the above) which has a coordinating feature which ties the aforementioned indicia together. For example, if apertured indicia and printed indicia each have a visual characteristic different from one another and coordinating indicia has visual characteristics which match each of the apertured indicia and printed indicia, the coordinating feature causes the apertured indicia and printed indicia to be matched to one another.

Additionally, patterns comprising multiple features may be coordinated. As an example, a first array of apertures may be grouped with adjacent bond sites to form a pattern unit. This pattern unit may be repeating. For example, a first pattern unit may be disposed adjacent a first end of an absorbent article while a second pattern unit is disposed adjacent a second end of an absorbent article. As another example, the first pattern unit may be disposed adjacent a first end of an absorbent article while the second pattern unit is disposed adjacent a transverse axis of the absorbent article. Still another example may comprise additional pattern units which may be disposed in any suitable location on an absorbent article. Pattern units may comprise any combination of features. For example a pattern unit may comprise apertures, bonds, print, structures, or combinations thereof.

Some examples of coordinated indicia include theme related indicia. In some embodiments, indicia described herein may be coordinated where at least two of the indicia, e.g. apertured and printed include at least one of items generally thought of as lucky, e.g. balloons, rainbows, pots of gold, moons (printed indicia may include blue moon), clovers, horseshoes, stars, hearts, and the like or combinations thereof. Other examples of coordinated indicia include numbers, letters, combinations of numbers and letters; winter themes including snowflakes and/or the like; spring themes including flowers, bees, birds, trees, sun, geometric shapes, squares, rectangles, triangles, oval, circles; curves including uni-radial arcs, multi-radial arcs, spirals, truncated sinusoidal waves.

Crimped fiber spunbond nonwoven webs/nonwoven laminates of the present invention may be utilized in multiple areas of the disposable absorbent articles described herein. For example, in some embodiments, a nonwoven laminate of the present invention may be utilized as a leg cuff of an absorbent article, a backsheet and/or outer cover, and/or a topsheet. For such embodiments, the array of apertures utilized for the topsheet may be coordinated with the array of apertures utilized for the leg cuffs and/or backsheet. In some embodiments, the array of apertures in the leg cuff may coordinate with the array of apertures for the backsheet but not for the topsheet. In other embodiments, the array of apertures of the backsheet may coordinate with the array of apertures for the topsheet.

If a crimped fiber spunbond nonwoven web/nonwoven laminate is used as part, or all of, an outer cover (garment-facing layer) of an absorbent article, the aperture pattern or patterns may provide enhanced breathability in certain regions (e.g., waist, hips) or reduced breathability in areas over an absorbent core, for example. The aperture pattern or patterns in a nonwoven laminate used as an outer cover may also provide enhanced textures and/or signals in certain regions of the outer cover. Such texture and/or signals may provide intuitive instructions on how to property apply the absorbent article, where to grip the absorbent article, and/or where/how to fasten the absorbent article, among other functions, such as to enhance graphics or aesthetics.

If a crimped fiber spunbond nonwoven web/nonwoven laminate is used as a portion of a fastener (e.g., taped fastener) of an absorbent article, an apertured pattern of a crimped fiber spunbond nonwoven web/nonwoven laminate of the fastener may indicate how to grip and fasten the fastener and indicate when it is and is not fastened correctly. An apertured pattern of the crimped fiber spunbond nonwoven web/nonwoven laminate used as a fastener, or portion thereof, may coordinate with an aperture pattern of a crimped fiber spunbond nonwoven web/nonwoven laminate used as a topsheet and/or an outer cover of the same absorbent article to signal a holistic function.

In another form, crimped fiber spunbond nonwoven web/nonwoven laminates of the present invention may comprise a nonwoven layer (comprising spunbond crimped fiber) and a film. The laminate can be joined together via glue lamination or extrusion lamination—film extruded onto the crimped fiber spunbonded nonwoven web. Such laminates may be utilized as a topsheet and/or a backsheet of an absorbent article. Regarding such laminates—in the context of topsheets—the film may serve as an upper layer while the crimped fiber spunbond nonwoven layer may serve as the lower layer (more proximal to the absorbent core than the upper layer) of the laminate. In the context of backsheets, the film may form a lower layer of the laminate while the crimped fiber spunbond nonwoven web forms the upper layer (more outer facing than the lower layer) of the absorbent article.

The optimum balance of bodily exudate acquisition speed and rewet in an absorbent article comprising a nonwoven laminate as a topsheet and/or topsheet and acquisition system may be derived from a combination of aperture diameter, shape or area, depth or thickness of the nonwoven laminate, and the spacing between the various apertures or aperture arrays within the nonwoven laminate.

An absorbent article comprising a nonwoven laminate as a topsheet and/or a topsheet and an acquisition system may comprise a longitudinal axis, much like the longitudinal axis of 1880 of FIG. 26. Arrays of apertures in the nonwoven laminate may repeat themselves along a line that is angled about 20 degrees to about 160 degrees from a longitudinal axis, e.g. 1880 which is generally parallel to the MD direction 1675 (shown in FIG. 34), specifically reciting all 1 degree increments within the specified range and all ranges formed therein, relative to the longitudinal axis. Additionally, there may be a plurality of aperture sizes, shapes, or areas along the line or the spacing between the apertures may not the same between all of the apertures along the line for purposes of channeling liquid bodily exudates into preferred areas of the absorbent article or the absorbent core thereof to help avoid leakage.

An aperture pattern in a nonwoven laminate may form a recognizable visual element, such as a heart or a water droplet, for example. An aperture pattern that forms one or more water droplet shapes in a nonwoven laminate used as a topsheet or an outer cover of an absorbent article may be used to aid communication of absorbency and/or wetness. Such a feature may be combined with a wetness indicator of an absorbent article.

Various commonly understood shapes may be created in a crimped fiber spunbond nonwoven web/nonwoven laminate. These shapes may be shapes that have commonly understood proper orientations, such as hearts, for example. An example is the use of one or more hearts on an outer cover or topsheet of a front waist region and/or a back waist region of a diaper. The caregiver would understand to place the diaper on the wearer with the point of the heart facing toward the wearer's feet or toward the posterior portion of a wearer's body because of the common knowledge of the orientation of hearts.

In one instance, a nonwoven laminate of the present invention may comprise a first non-apertured layer comprising a pattern having a color and a second layer comprising a pattern of apertures. The pattern on the first non-apertured layer may be printed on the layer, for example, and may form graphics or other indicia. At least 50% to 100% of the pattern on the first non-apertured layer may be aligned with the pattern of apertures to draw attention to the apertures. The alignment, or partial alignment, of the pattern of apertures on the first layer with the pattern having a color of the second layer may make aid in aligning the product on a wearer if the nonwoven laminate is provided on an absorbent article. In other examples, a nonwoven laminate may comprise a first layer and a second layer which are co-apertured as described herein. In such configurations, the first layer may be fused to the second layer about a periphery of each of the apertures formed in the nonwoven laminate. In such configurations, the first layer may have a different color than the second layer. In yet another example, a first layer may be apertured and may be joined to a second layer which is not apertured. In such configurations, the first layer and the second layer may comprise different colors. In another example, a crimped fiber spunbond nonwoven web may comprise apertures while a subjacent layer in an absorbent article comprises printed indicia and/or adhesive indicia. The printed indicia and/or adhesive indicia may be at least partially aligned with the apertures of the crimped fiber spunbond nonwoven web.

Additional forms are contemplated where the first layer of a nonwoven laminate comprises a first color and the second layer of the nonwoven laminate comprises a second color. The first color and the second color may be different. In a specific form where the nonwoven laminate is utilized as a topsheet, subjacent layers to the topsheet, e.g. disposed between the topsheet and the absorbent core can have a third color. The third color may be different than the first and the second colors. For other forms, a nonwoven laminate comprises a first layer and a second layer comprising a first color and second color, respectively, which are different from one another. Additionally, where the nonwoven laminate is utilized as a topsheet, a secondary topsheet—disposed between the topsheet and an absorbent core—may comprise printing/printed indicia. Such printing may be of a different color than that of the first color and/or the second color. And, such printing is visible through the topsheet such that the wearer can view the printing prior to donning the absorbent article. Where a crimped fiber spunbond nonwoven web is utilized, subjacent layers of an absorbent article may be configured similarly.

The apertured indicia, printed indicia, adhesive indicia, bond indicia when used on a topsheet and/or backsheet of a disposable absorbent article, may be utilized to ensure proper alignment of the absorbent article. For example, any one of apertured indicia, printed indicia, adhesive indicia, bond indicia, and/or combinations thereof, may be utilized to highlight proper alignment. In one specific example, printed indicia may be utilized to communicate to a wearer the proper orientation of a feminine hygiene pad. Proper orientation of the feminine hygiene pad can reduce the likelihood of leakage.

Additionally, the apertured indicia, printed indicia, adhesive indicia, bond indicia when used on a topsheet and/or backsheet of a disposable absorbent article may be utilized to highlight features of the absorbent article which would otherwise not be noticeable by simple visual inspection of the article. For example, absorbent cores of disposable absorbent articles are generally disposed between the topsheet and the backsheet. In many instances, upon visual inspection, a wearer may not be able to discern the boundaries of the absorbent core which are typically inboard of the periphery of the absorbent article. In such instances, at least one of apertured indicia, printed indicia, adhesive indicia, bond indicia or any combination thereof, may be utilized to communicate the boundaries of the absorbent core. This may provide some reassurance to the wearer regarding the "zone" of absorbency. Still in other configurations, at least one of apertured indicia, printed indicia, adhesive indicia, bond indicia or any combination thereof, may be utilized to communicate a particular area of the absorbent core. For example, an absorbent article may comprise an absorbent core having variable absorbing capacity. In such instances, at least one of the apertured indicia, printed indicia, adhesive indicia, bond indicia or any combination thereof, may be utilized to highlight an area of the core having higher absorbing capacity than other areas. Conversely, apertured indicia, printed indicia, adhesive indicia, bond indicia or any combination thereof, may be utilized to highlight those portions of the absorbent core which have lower capacity than another portion of the absorbent core. Still other executions are contemplated where a first array of apertured indicia, printed indicia, adhesive indicia, bond indicia or any combination thereof is utilized to communicate to the wearer a portion of the absorbent core having higher absorbing capacity than other portions while a second array of apertured indicia, printed indicia, adhesive indicia, bond indicia or any combination thereof are used to communicate to the wearer regarding other portions of the absorbent core having lower absorbing capacity. In such executions, the first array and the second array may or may not be coordinated.

Zones

In any context of a crimped fiber spunbond nonwoven web/nonwoven laminate, but especially in an absorbent article context, the crimped fiber spunbond nonwoven web/nonwoven laminates may be employed in a zonal fashion. For instance, a first zone of a topsheet of an absorbent article may have a first aperture pattern, while a second zone of a topsheet of an absorbent article may have a second, different aperture pattern.

Aperture patterns in the different zones may be configured to receive certain bodily exudates or inhibit or encourage their flow in any desired direction. For example, the first pattern may be better configured to receive and/or direct the flow of urine, while the second pattern may be better configured to receive and/or direct the flow of runny BM. In other instances, a first zone having a first pattern may be configured to receive heavy gushes of bodily exudates while a second zone having a second different pattern may be configured to restrict lateral bodily exudate flow in any desired direction. The first pattern may be situated in, for instance, the middle of the absorbent article or in the crotch region, while the second pattern may be situated in the front and rear waist regions or outer perimeter topsheet regions of the absorbent article.

The zones in a crimped fiber spunbond nonwoven web/nonwoven laminate may be positioned in the machine direction, the cross direction, or may be concentric. If a product, such as an absorbent article, has two different zones in the machine direction, the zones may have the same or a similar cross-direction width (e.g., +/−2 mm) for ease in processing. One or more of the zones may have curved or straight boundaries or partial boundaries.

Any suitable zones, including more than two, of different or the same crimped fiber spunbond nonwoven web/nonwoven laminates are envisioned within the scope of the present disclosure. The various zones may be in the topsheet as mentioned above, but may also be present on an outer cover or a cuff for example. In some instances, the same or a different pattern of zones of crimped fiber spunbond non-woven web/nonwoven laminates may be used on the wearer-facing surface (e.g., topsheet) and the garment-facing surface (e.g., outer cover).

In an instance, a topsheet or other portion of an absorbent article may have two or more zones in a crimped fiber spunbond nonwoven web/nonwoven laminate. For example, a first zone of the nonwoven laminate may have a different aperture pattern than a second zone. The first zone and the second zone may have different functionalities owing to the different aperture patterns. A functionality of the first zone may be to provide liquid bodily exudate distribution (fluid moving on the nonwoven laminate), while the functionality of the second zone may be to provide liquid bodily exudate acquisition (fluid penetrating the nonwoven laminate). Benefits of such a zoned crimped fiber spunbond nonwoven web/nonwoven laminate can be better use of an absorbent core and more efficient liquid bodily exudate distribution within the absorbent core. This is especially important if an air-felt free core is used in that typical air-felt free cores somewhat struggle with liquid bodily exudate distribution once the liquid bodily exudate is received therein.

In an example, an absorbent article may comprise a nonwoven laminate that forms a first portion and a second, different portion thereof. Aperture patterns in each portion of the nonwoven laminate may be the same, substantially similar, or different. In another instance, an absorbent article may comprise a nonwoven laminate that comprises a first portion of an absorbent article, and wherein a second portion of the absorbent article has graphics, printing, patterned adhesives, or other indicia that forms a pattern that is similar to, substantially similar to, coordinates with, or is different than an aperture pattern in the nonwoven laminate. Crimped fiber spunbond nonwoven webs of the present invention may be similarly configured.

In some forms, a crimped fiber spunbond nonwoven web/nonwoven laminate may have a plurality of zones. A first zone may have at least some apertures having a first feret angle, first size, and/or first shape, while a second zone (or third or fourth zone etc.) may have apertures having a second, different feret angle, second, different size, and/or second, different shape.

Figure 53:
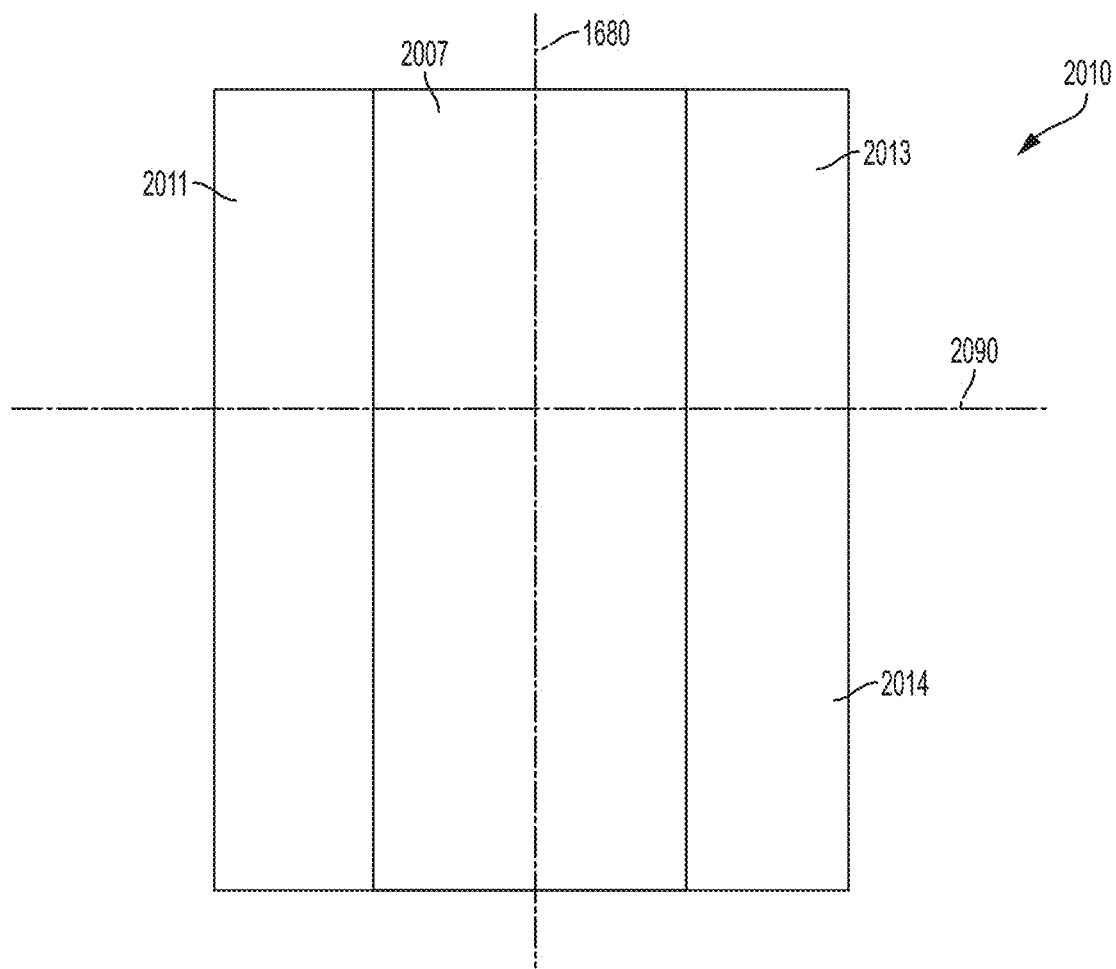
FIGS. 53-57 are schematic illustrations of disposable absorbent articles comprising a plurality of zones in accordance with the present invention.

As stated previously, the crimped fiber spunbond nonwoven web/nonwoven laminates of the present invention may be utilized in a number of different components of absorbent articles. Referring to FIG. 53, in one specific example, disposable absorbent articles utilizing the crimped fiber spunbond nonwoven web/nonwoven laminate of the present invention may comprise a plurality of zones. As shown, a topsheet 2014 of a disposable absorbent article 2010, may comprise a first zone 2007, a second zone 2011 and a third zone 2013. Absorbent articles may comprise more zones or less zones as described hereafter.

The first zone 2007 may comprise an array of apertures as described herein. As shown the first zone 2007 may have a width parallel to a lateral axis 2090 which does not extend the full width of the topsheet 2014. Instead, the second zone 2011 and the third zone 2013 may be placed on either side of the first zone 2007. In some embodiments, the second zone 2011 and the third zone 2013 may comprise a first array of structures and a second array of structures, respectively. For these forms, the array of apertures in the first zone 2007 may form apertured indicia which may be coordinated with the array of structures in the second zone 2011 and/or the array of structures in the third zone 2013. In a specific execution, the first zone 2007 comprises an array of apertures, the second and third zones 2011 and 2013, respectively, comprise an array of structures, wherein the array of structures in both the second zone 2011 and the third zone 2013 comprise tufts 1770 oriented in the Z-direction or negative Z-direction.

Still in other embodiments, the first zone 2007 may comprise an array of out-of-plane deformations while the second zone 2011 and the third zone 2013 comprise a first array of apertures and a second array of apertures, respectively. In such forms, the array of out-of-plane deformations may be coordinated with the array of apertures in the second zone 2011 and the third zone 2013.

In some embodiments, the first zone 2007 may comprise the array of apertures as well as an array of bonds. The bonds, as mentioned previously, may be configured to provide bond indicia. In some embodiments, bond indicia may be coordinated with the apertured indicia in the first zone 2007. In other embodiments, bond indicia may be present, in addition to the first zone 2007, in the second zone 2011 and/or third zone 2013. In such embodiments, the bond indicia may be coordinated with the apertured indicia in the first zone 2007 or may be un-coordinated with respect to the apertured indicia. Adhesive indicia, printed indicia may similarly be provided in the first zone 2007, the second zone 2011, and/or the third zone 2013. In such embodiments, the adhesive indicia, printed indicia may be coordinated with the apertured indicia or may be un-coordinated with the apertured indicia. In a specific execution, the first zone 2007 comprises an array of apertures forming apertured indicia and an array of fusion bonds forming bond indicia. The second zone 2011 and the third zone 2013 may each comprise an array of structures, wherein the array of structures comprise tufts 1770 oriented in the Z-direction. In such executions, the apertured indicia may be coordinated with bond indicia. In other executions, bond indicia may not be coordinated with apertured indicia.

In some forms, the first zone 2007, the second zone 2011 and/or the third zone 2013 may comprise a plurality of indicia selected from printed indicia, apertured indicia, adhesive indicia, structural indicia, and bond indicia. In such forms, any combination of the plurality of indicia may be coordinated with indicia within its respective zone and/or with regard to one of the other or both zones.

While heretofore, zones have been disclosed primarily in the context of nonwoven laminates, nonwoven laminates without apertures, nonwoven laminates without patterned apertures, and crimped fiber spunbond nonwoven webs of the present invention may similarly comprise variable zones. For example, the first zone 2007 may comprise printed indicia while the second zone 2011 and the third zone 2013 comprise structural indicia. The printed indicia and the structural indicia may be coordinated. In other examples, the first zone 2007 may comprise adhesive indicia while the second and the third zones 2011 and 2013, respectively, comprise structural indicia. The adhesive indicia may be coordinated with the structural indicia. In yet another example, the first zone 2007 may comprise bond indicia while the second zone 2011 and third zone 2013 comprise structural indicia. The bond indicia may be coordinated with the structural indicia. Still in other forms, the first zone 2007 may comprise apertured indicia and printed indicia while the second zone 2011 and the third zone 2013 comprise structural indicia. The structural indicia may be coordinate with the apertured indicia which in turn may be coordinated with the printed indicia.

Suitable configurations of zones are described with regard to FIGS. 54-57. FIGS. 54-57 may represent a portion of a wearer-facing surface of an absorbent article, such as a diaper, an adult incontinence product, and/or a sanitary napkin.

Figure 54:
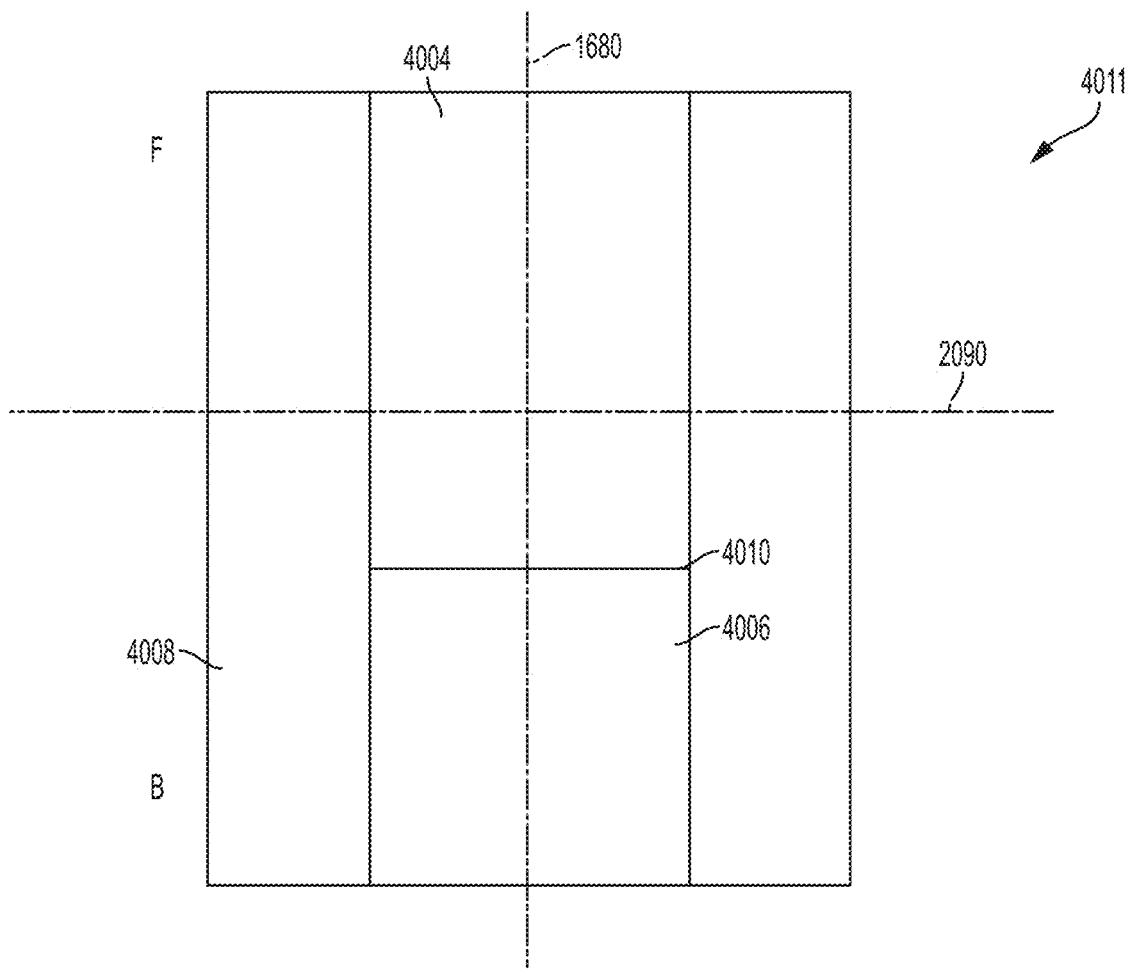

FIG. 54 illustrates an example of a substrate having three zones. The front portion, F, may be positioned in a front portion of an absorbent article or a back portion of an absorbent article. The back portion, B, may be positioned in a front portion of an absorbent article or a back portion of an absorbent article. A first zone 4004 and a second zone 4006 may be positioned intermediate two portions of the third zone 4008. The zones 4004, 4006, and 4008 may be provided as separate pieces of material that are partially overlapped and joined or bonded together or may be provided as one piece of material. In an instance, the first zone 4004 and the second zone 4006 may be provided as one piece of material or as two pieces of material that partially overlapped and joined or bonded together.

The first zone 4004 may comprise a plurality of out-of-plane deformations as described above with reference to FIGS. 2A-9B. The out-of-plane deformations may extend upwardly out of the page or downwardly into the page. The second zone 4006 may comprise a plurality of out-of-plane deformations as described above with reference to FIGS. 2A-9B. The out-of-plane deformations may extend upwardly out of the page or downwardly into the page. The second zone 4006 may have a different or the same pattern, shape, size, and/or orientation of the out-of-plane deformations compared to the pattern, shape, size, and/or orientation of the first zone 4004. The third zone 4008 may comprise a pattern of apertures, wherein at least two apertures of the pattern of apertures have different sizes, shapes, and/or orientations. The pattern of apertures may be any of the various patterns described herein or other suitable patterns. A substantially-laterally extending separation element, 4010, may extend between the intersection of the first zone 4004 and the second zone 4006.

In another instance, still referring to FIG. 54, the first zone 4004 may comprise a pattern of apertures, wherein at least two apertures of the pattern of apertures have different sizes, shapes, and/or orientations. The pattern of apertures may be any of the various patterns described herein or other suitable patterns. The second zone 4006 may comprise a pattern of apertures, wherein at least two apertures of the pattern of apertures have different sizes, shapes, and/or orientations. The pattern of apertures may be any of the various patterns described herein or other suitable patterns. The second zone 4006 may have a different or the same pattern of apertures as the first zone 4004. The third zone 4008 may comprise a plurality of out-of-plane deformations as described above with reference to FIGS. 2A-9B. The out-of-plane deformations may extend upwardly out of the page or downwardly into the page. A substantially-laterally extending separation element, 4010, may extend between the intersection of the first zone 4004 and the second zone 4006.

Figure 55:
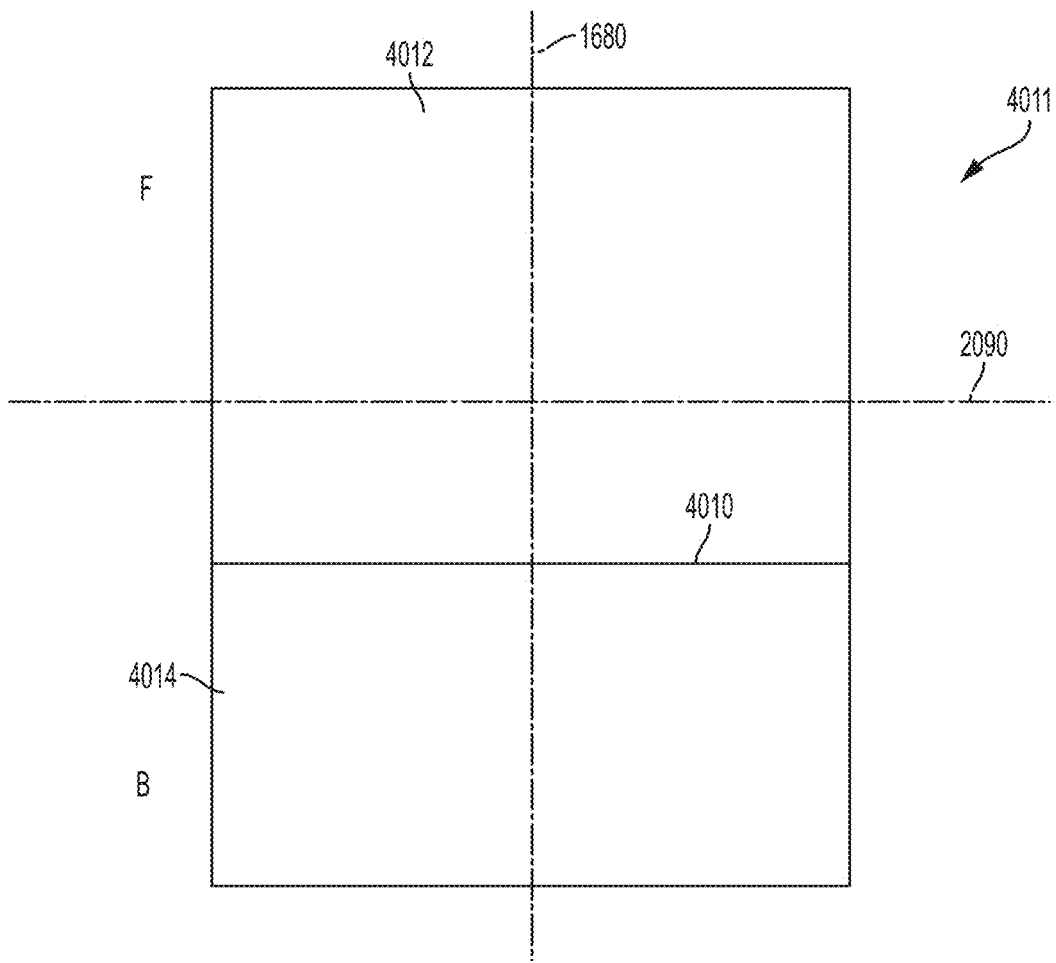

FIG. 55 illustrates an example of a substrate having a first zone 4012 and a second zone 4014. The front portion, F, may be positioned in a front portion of an absorbent article or a back portion of an absorbent article. The back portion, B, may be positioned in a front portion of an absorbent article or a back portion of an absorbent article. The zones 4012 and 4014 may be provided as two separate pieces of material that are partially overlapped and joined or bonded together or may be provided as one piece of material. The first zone 4012 may comprise a pattern of apertures, wherein at least two apertures of the pattern of apertures have different sizes, shapes, and/or orientations. The pattern of apertures may be any of the various patterns described herein or other suitable patterns. The second zone 4014 may comprise a plurality of out-of-plane deformations as described above with reference to FIGS. 2A-9B. The out-of-plane deformations may extend upwardly out of the page or downwardly into the page. A substantially-laterally extending separation element, 4010, may extend between the intersection of the first zone 4012 and the second zone 4014.

In another instance, still referring to FIG. 55, the second zone 4014 may comprise a pattern of apertures, wherein at least two apertures of the pattern of apertures have different sizes, shapes, and/or orientations. The pattern of apertures may be any of the various patterns described herein or other suitable patterns. The first zone 4012 may comprise a plurality of out-of-plane deformations as described above with reference to FIGS. 2A-9B. The out-of-plane deformations may extend upwardly out of the page or downwardly into the page. A substantially-laterally extending separation element, 4010, may extend between the intersection of the first zone 4012 and the second zone 4014.

Figure 56:
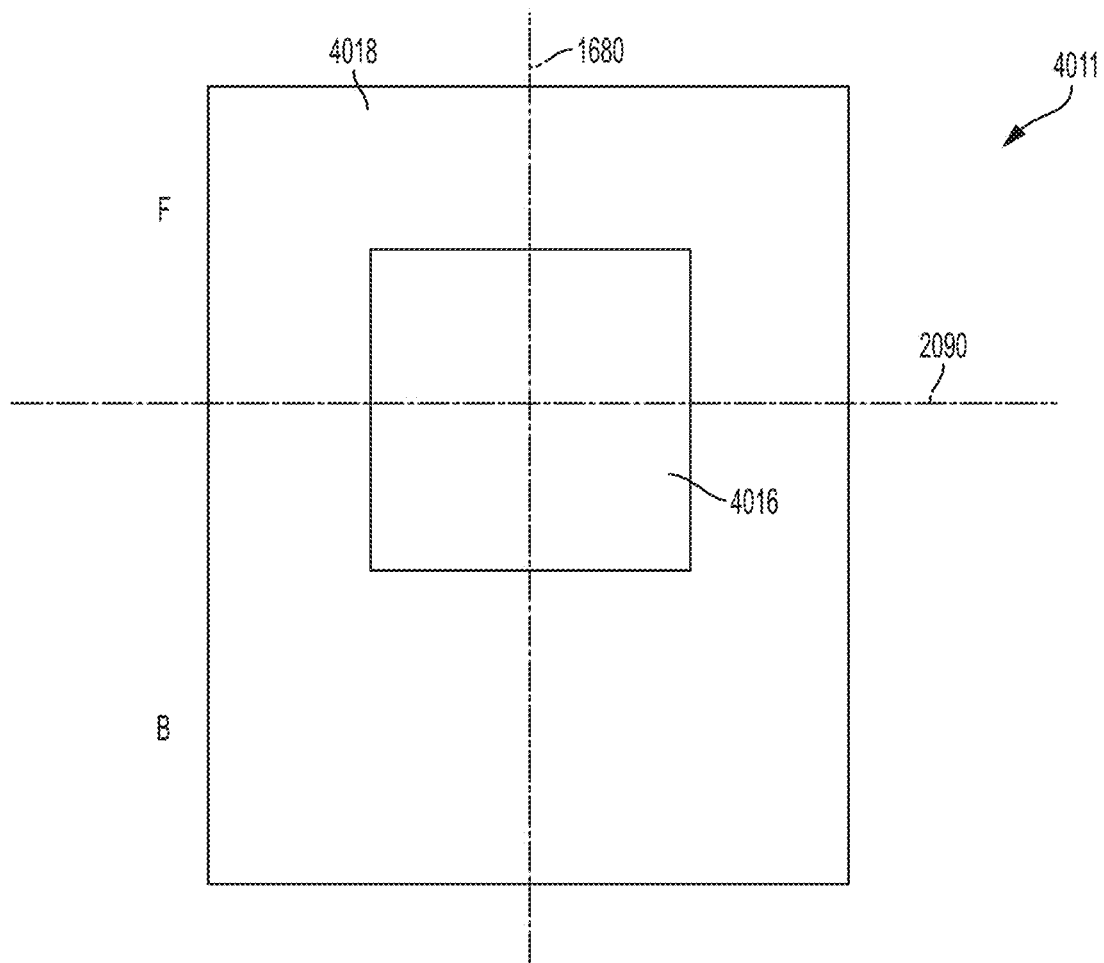

FIG. 56 illustrates an example of a substrate having a first zone 4016 and a second zone 4018. The front portion, F, may be positioned in a front portion of an absorbent article or a back portion of an absorbent article. The back portion, B, may be positioned in a front portion of an absorbent article or a back portion of an absorbent article. The zones 4016 and 4018 may be provided as two separate pieces of material that are partially overlapped and joined or bonded together or may be provided as one piece of material. The second zone 4018 may at least partially, or fully, surround the first zone 4016.

Still referring to FIG. 56, the first zone 4016 may comprise a plurality of out-of-plane deformations as described above with reference to FIGS. 2A-9B. The out-of-plane deformations may extend upwardly out of the page or downwardly into the page. The second zone 4018 may comprise a plurality of out-of-plane deformations as described above with reference to FIGS. 2A-9B. The out-of-plane deformations may extend upwardly out of the page or downwardly into the page. The second zone 4018 may have a different or the same pattern, shape, size, and/or orientation of the out-of-plane deformations compared to the pattern, shape, size, and/or orientation of the first zone 4016.

In another instance, still referring to FIG. 56, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a plurality of out-of-plane deformations as described above with reference to FIGS. 2A-9B. The out-of-plane deformations may extend upwardly out of the page or downwardly into the page.

In yet another instance, still referring to FIG. 56, the second zone 4018 may comprise a pattern of apertures, wherein at least two apertures of the pattern of apertures have different sizes, shapes, and/or orientations. The pattern of apertures may be any of the various patterns described herein or other suitable patterns. The first zone 4016 may comprise a plurality of out-of-plane deformations as described above with reference to FIGS. 2A-9B. The out-of-plane deformations may extend upwardly out of the page or downwardly into the page.

In another instance, still referring to FIG. 56, the first zone 4016 may comprise a pattern of apertures, wherein at least two apertures of the pattern of apertures have different sizes, shapes, and/or orientations. The pattern of apertures may be any of the various patterns described herein or other suitable patterns. The second zone 4018 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4016 and the second zone 4018 may be different or the same.

Figure 57:
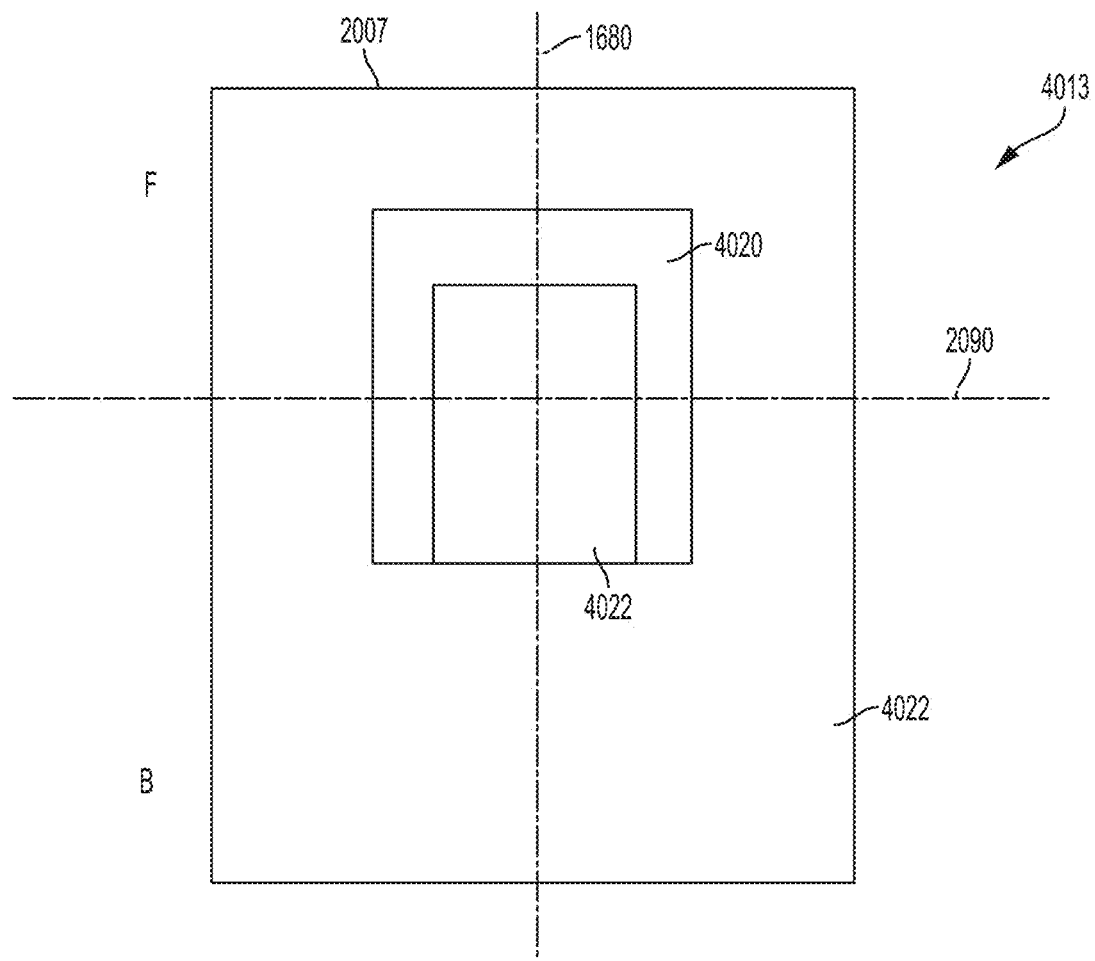

FIG. 57 illustrates an example of a substrate having a first zone 4020 and a second zone 4022. The front portion, F, may be positioned in a front portion of an absorbent article or a back portion of an absorbent article. The back portion, B, may be positioned in a front portion of an absorbent article or a back portion of an absorbent article. The zones 4020 and 4022 may be provided as two separate pieces of material that are partially overlapped and joined or bonded together or may be provided as one piece of material. The second zone 4022 may at least partially, or fully, surround the first zone 4020.

Still referring to FIG. 57, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a pattern of apertures, wherein at least two apertures of the pattern of apertures have different sizes, shapes, and/or orientations. The pattern of apertures may be any of the various patterns described herein or other suitable patterns. The patterns of apertures of the first zone 4020 and the second zone 4022 may be different or the same.

Still referring to FIG. 57, the first zone 4020 may comprise a pattern of apertures, wherein at least two apertures of the pattern of apertures have different sizes, shapes, and/or orientations. The pattern of apertures may be any of the various patterns described herein or other suitable patterns. The second zone 4022 may comprise a plurality of out-of-plane deformations as described above with reference to FIGS. 2A-9B. The out-of-plane deformations may extend upwardly out of the page or downwardly into the page Still referring to FIG. 57, the second zone 4022 may comprise a pattern of apertures, wherein at least two apertures of the pattern of apertures have different sizes, shapes, and/or orientations. The pattern of apertures may be any of the various patterns described herein or other suitable patterns. The first zone 4020 may comprise a plurality of out-of-plane deformations as described above with reference to FIGS. 2A-9B. The out-of-plane deformations may extend upwardly out of the page or downwardly into the page Still referring to FIG. 57, the first zone 4020 may comprise a plurality of out-of-plane deformations as described above with reference to FIGS. 2A-9B. The out-of-plane deformations may extend upwardly out of the page or downwardly into the page. The second zone 4022 may comprise a plurality of out-of-plane deformations as described above with reference to FIGS. 2A-9B. The out-of-plane deformations may extend upwardly out of the page or downwardly into the page. The second zone 4022 may have a different or the same pattern, shape, size, and/or orientation of the out-of-plane deformations compared to the pattern, shape, size, and/or orientation of the first zone 4020.

Visual Texture

Apertures, aperture arrays, three-dimensional elements, tufts, printing, patterned adhesives, or any combinations of these "texture elements" may impart a variable visually observed texture in a nonwoven laminate. Variations in observable textures have been extensively studied in the psychological and neurological sciences. Some small texture elements are much more readily ("instantly") detected by the human visual perception system than others. Most texture patterns having similar "second order" (iso-dipole) statistics cannot be discriminated in a brief "flash" observation. However, exceptions to this (i.e., iso-dipole texture elements that are easily discriminated) have been defined and are known in the literature as "textons". Nonwoven laminates including texture elements forming texton shapes provide a way to create easily recognizable "zones" on a laminate or in an absorbent article, signaling regions having different functions, and/or providing strong cues as to correct product orientation on a wearer (e.g., front/back). Forms of the nonwoven laminates of the present disclosure may include texture elements forming texton shapes, including quasi-collinearity, corner features, and closure of local features. A reference is Julesz, B., et al, Visual Discrimination of Textures with Identical Third-Order Statistics, Biological Cybernetics vol. 31, 1978, pp. 137-140).

Effective Open Area

A crimped fiber spunbond nonwoven web/nonwoven laminate of the present invention may have an Effective Open Area between about 1% to about 50%, about 5% to about 40%, about 8% to about 35%, about 10% to about 30%, about 10% to about 25%, or about 3% to about 15%, specifically including all 0.1% increments within the specified ranges and all ranges formed therein or thereby. All Effective Open Area percentages are determined using the Aperture Test described herein. Crimped fiber spunbond nonwoven webs/nonwoven laminates having a higher Effective Open Area may have utility as a topsheet or acquisition layer or system in an absorbent article (more functional to absorbent bodily exudates), while crimped fiber spunbond nonwoven webs/nonwoven laminates having a lower Effective Open Area may have utility as an outer cover of an absorbent article (more decorative or for breathability purposes). In some forms of the present invention, for hydrophilic webs—where a body contacting surface is hydrophilic—the percentage open area can generally be less. For hydrophobic webs—where a body contacting surface is hydrophobic—the percentage open area may be increased to ensure good acquisition rates. As an example, for a hydrophobic topsheet, the percentage open area can be from about 5% to about 50%. As another example, for a hydrophilic topsheet, the percentage can be from about 1% to about 50%.

Effective Aperture Area

A crimped fiber spunbond nonwoven web/or nonwoven laminate may have apertures having an Effective Aperture AREA in the range of about 0.1 $mm^2$ to about 15 $mm^2$, 0.3 $mm^2$ to about 14 $mm^2$, 0.4 $mm^2$ to about 12 $mm^2$, 0.3 $mm^2$ to about 10 $mm^2$, 0.5 $mm^2$ to about 8 $mm^2$, 1.0 $mm^2$ to about 8 $mm^2$, or about 1.0 $mm^2$ to about 5 $mm^2$, specifically including all 0.05 mm increments within the specified ranges and all ranges formed therein or thereby. All Effective Aperture Areas are determined using the Aperture Test described herein. A plurality of the apertures in a crimped fiber spunbond nonwoven web/nonwoven laminate may be different in Effective Aperture Areas. The Relative Standard Deviation ("RSD") of the Effective Aperture Areas may be at least about 20 percent, at least about 30 percent, at least about 50 percent or at least about 55 percent, or at least about 60 percent.

Interaperture Distance and Average Interaperture Distance

The crimped fiber spunbond nonwoven webs/nonwoven laminates may have apertures that have an Average Interaperture Distance of less than about 3.5 mm, less than about 3 mm, less than about 2.5 mm, less than about 2 mm, less than about 1.5 mm, less than about 1 mm, in the range of about 1 mm to about 6 mm, in the range of about 1 mm to about 5 mm, in the range from about 1 mm to about 4 mm, in the range from about 1 mm to about 3.5 mm, in the range of about 1 mm to about 3 mm, in the range of about 1 mm to about 2.5 mm, in the range of about 2 mm to about 4 mm, in the range of about 3.5 mm to about 10 mm, or in the range of about 0.08 mm to about 11 mm, specifically reciting all 0.1 mm increments within the above-specified ranges and all ranges formed therein or thereby, according to the Interaperture Distance Test herein.

A crimped fiber spunbond nonwoven web/nonwoven laminate may have Interaperture Distances, calculated according to the Interaperture Distance Test herein. The Interaperture Distances may have a distribution having a mean and a median. The mean may be greater than, different than, or less than the median. The difference between the mean and the median may be in the range of about 1% to about 25%, about 4% to about 25%, about 5% to about 20%, about 8% to about 20%, about 4% to about 15%, or about 1% to about 8%, for example, specifically reciting all 0.1% increments within the above specified ranges and all ranges formed therein or thereby. A first zone of an apertured web may have Interaperture Distances. The Interaperture Distances of a first zone may have a first distribution having a first mean and a first median. The first mean may be greater than, different than, or less than the first median by the ranges set forth above in this paragraph. A second zone of the apertured web may have Interaperture Distances. The Interaperture Distances of the second zone may have a second distribution having a second mean and a second median. The second mean may be greater than, less than, or different than the second median by the ranges set forth above in this paragraph. A third zone of the apertured web may have Interaperture Distances. The Interaperture Distances of the third zone may have a third distribution having a third mean and a third median. The third mean may be greater than, different than, or less than the third median by the ranges set forth above in this paragraph. The first, second, and third means may be the same or different. The first, second, and third medians may be the same or different. The first, second, and third zones may be in a topsheet, a topsheet layer, an acquisition layer, an outercover, an outercover layer, or any other component of an absorbent article or other consumer products.

In other instances, a first portion of an absorbent article or other consumer product may have a first apertured web that has Interaperture Distances, according to the Interaperture Distance Test herein. The Interaperture Distances of the first portion have a first distribution. A second portion of an absorbent article or other consumer product may have a second apertured web that has Interaperture Distances, according to the Interaperture Distance Test herein. The Interaperture Distances of the second portion have a second distribution. A third portion of an absorbent article or other consumer product may have a third apertured web that has Interaperture Distances, according to the Interaperture Distance Test herein. The Interaperture Distances of the third portion have a third distribution. The first, second, and third distributions may be the same or different. The first distribution may have a first mean and a first median. The first mean may be greater than, less than, or different than the first median in the range of about 1% to about 25%, about 4% to about 25%, about 5% to about 20%, about 8% to about 20%, about 4% to about 15%, or about 1% to about 8%, for example, specifically reciting all 0.1% increments within the above-specified ranges and all ranges formed therein or thereby. The second distribution may have a second mean and a second median. The second mean may be greater than, different than, or less than the second median by the ranges set forth above in this paragraph. The third distribution may have a second mean and a second median. The second mean may be greater than, different than, or less than the second median by the ranges set forth above in this paragraph. The first, second, and third means may be the same or different. The first, second, and third medians may be the same or different. The Relative Standard Deviation (RSD) of the Interaperture Distances may be at least 25%, at least about 35%, at least about 40%, at least about about 50%, or at least about 55%. The Maximum Interaperture Distance in a given web or pattern may be at least about 5 mm, at least about 8 mm, at least about 10 mm, or at least about 11 mm.

Average Absolute Feret Angle and Absolute Feret Angle

A crimped fiber spunbond nonwoven web/nonwoven laminate may have one or more apertures having an Absolute Ferret Angle, according to the Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby.

A crimped fiber spunbond nonwoven web/nonwoven laminate may have a plurality of apertures having an Average Absolute Ferret Angle, according to the Average Absolute Feret Angle Test, of at least about 2 degrees, 5 degrees, 15 degrees, at least about 18 degrees, at least about 20 degrees, at least about 22 degrees, at least about 25 degrees, at least about 30 degrees, at least about 35 degrees, at least about 40 degrees, at least about 45 degrees, at least about 50 degrees, at least about 55 degrees, at least about 60 degrees, or in the range of about 2 degrees to about 80 degrees, in the range of about 5 degrees to about 75 degrees, in the range of about 10 degrees to about 70 degrees, or in the range of about 15 degrees to about 65 degrees, specifically reciting all 0.1 degrees increments within the above-specified ranges and all ranges formed therein or thereby. These apertures may all be within a single repeat unit of the apertured web.

At least two, at least 3, at least 4, at least 5, at least 6, at least 7, at least 8, at least 9, or at least 10 of the apertures in an apertured web, or a repeat unit of an apertured web, may each have a different Absolute Feret Angle, according to the Absolute Feret Angle Test herein. In other instances, some of the apertures may have Absolute Feret Angles that are the same, while other of the apertures may have Absolute Feret Angles that are different. In addition to having different Absolute Feret Angles, the at least two, at least 3, at least 4, at least 5, at least 6, at least 7, at least 8, at least 9, or at least 10 apertures may have different sizes and/or shapes. At least some of the at least two, at least 3, at least 4, at least 5, at least 6, at least 7, at least 8, at least 9, or at least 10 apertures may also have the same size and/or shape, while having different Absolute Feret Angles.

Apertures oriented at ferret angles greater than zero relative to the machine direction may have a higher aspect ratio than apertures that are aligned in the machine direction or vice versa. Apertured webs having elongated apertures oriented at different ferret angles may provide liquid bodily exudate handling benefits when the apertured web is used as a topsheet in an absorbent article. For example, fluid run-off may be reduced in the front or back of the absorbent article when the apertures are not all aligned in the machine direction, but instead are oriented at an angle relative to the machine direction (e.g., about 30 degrees, about 45 degrees, or even about 90 degrees) as the apertures can more readily acquire the liquid bodily exudates. Therefore, it may be desirable to have the central longitudinal axes of the elongated apertures oriented at multiple different ferret angles in order to most effectively acquire liquid bodily exudates running along the surface of the apertured web and prevent, or at least inhibit, run-off and soiling of garments.

In some forms of the present invention, a crimped fiber spunbond nonwoven web/nonwoven laminate may comprise a plurality of apertures wherein a first portion of the apertures have an Absolute Feret angle of less than about 20 degrees and wherein a second portion of the apertures have an Absolute Feret angle of greater than about 20 degrees. In some forms, the first portion may comprise about 50% of the plurality of apertures. In some forms, the first portion may comprise about 40% of the plurality of apertures. In some forms, a first plurality of apertures may comprise more apertures than a second plurality of apertures by a ratio of about 3 to 1 or about 5 to 1. In some forms, the first plurality of apertures may be disposed about the second plurality of apertures.

Crimped fiber spunbond nonwoven webs/nonwoven laminates having apertures having different feret angles may provide liquid bodily exudate handling benefits when used as a topsheet in an absorbent article. For example, fluid run-off may be reduced in the front or back of the absorbent article when all of the apertures are not all aligned in the machine direction, but instead are oriented at an angle relative to the machine direction (e.g., about 30 degrees, about 45 degrees, or even about 90 degrees) as the apertures can more readily acquire the liquid bodily exudates. Therefore, it may be desirable to have apertures oriented at multiple different feret angles in order to most effectively acquire liquid bodily exudates running along the surface of the crimped fiber spunbond nonwoven web/nonwoven laminate of the present invention and prevent, or at least inhibit, run-off and soiling of garments.

In some examples, a pattern of overbonds, each of which is oriented solely in the machine direction, or substantially in the machine direction (i.e., +/−5 degrees or less from the machine direction), may be used to create a crimped fiber spunbond nonwoven web/nonwoven laminate with apertures having central longitudinal axes that are not all oriented in the machine direction or, stated another way, that are angled more than 5 degrees with respect to the machine direction. The nonwoven laminate 2200 of FIGS. 31-32 may have some apertures 2212 having a central longitudinal axis, L, having an angle with respect to the machine direction. The angle may be from about 5 degrees to about 70 degrees with respect to the machine direction, specifically reciting all 0.5 degree increments within the specified range and all ranges formed therein. Some of the apertures 2212 in the nonwoven laminate 2200 may also have a central longitudinal axis, L1, that extends parallel to, or substantially parallel to (e.g., +/− less than 5 degrees), the machine direction. The cross directional stretching step or steps described herein may be used to create the apertures and to orient the central longitudinal axes, L, of at least some of the apertures in a direction not parallel to, or substantially parallel to, the machine direction. At least some of the apertures in a crimped fiber spunbond nonwoven web/nonwoven laminate having their central longitudinal axes not parallel to, or substantially parallel to, the machine direction may have a first plurality of apertures having central longitudinal axes extending in a first direction with respect to the machine direction and a second plurality of apertures having central longitudinal axes extending at a second, different direction relative to the machine direction. The first and second directions may be 30 degrees and −30 degrees, respectively, 10 degrees and 20 degrees respectively, or −20 degrees and 30 degrees respectively, to provide a few examples. Those of skill in the art will recognize that angles relative to the machined are also within the scope of the present disclosure.

The apertures in a crimped fiber spunbond nonwoven web or nonwoven laminate having apertures generally parallel to the machine direction and produced by machine direction overbonds may be more open (i.e., have a lower aspect ratio) than they would have been if the overbonds had been oriented at an angle (5 degrees or more) with respect to the machine direction. Overbonds oriented at an angle with respect to the machine direction typically produce apertures having higher aspect ratios post cross directional stretching that are less open.

Additional suitable overbond patterns are disclosed in U.S. application Ser. No. 62/177,405 filed on Mar. 13, 2015, with regard to FIGS. 55-116 which show schematic representations of a variety of overbond patterns. Those of skill in the art will recognize that other suitable overbond patterns are also within the scope of the present disclosure, along with variations of the illustrated patterns. Additional overbond patterns are disclosed with regard to FIGS. 58 and 59.

Figure 58:
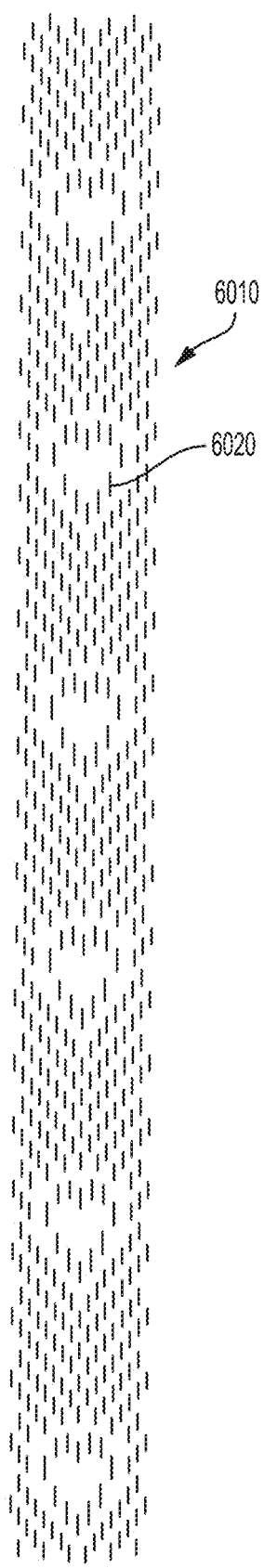
FIGS. 58-59 represent a schematic illustrations exemplary overbond patterns having at least some overbonds with central longitudinal axes that are substantially parallel to a machine direction in accordance with the present disclosure.

As shown in FIG. 58, a suitable overbond pattern for use with the crimped fiber spunbond nonwoven webs/nonwoven laminates of the present invention may comprise an array of overbonds disposed in several groups. For example, a first plurality of overbond sites 6010 may surround a second plurality of overbond sites 6020. Generally, the second plurality of overbond sites 6020 may be arranged to form (subsequent to processing) apertured indicia. As shown, hearts.

Figure 59:
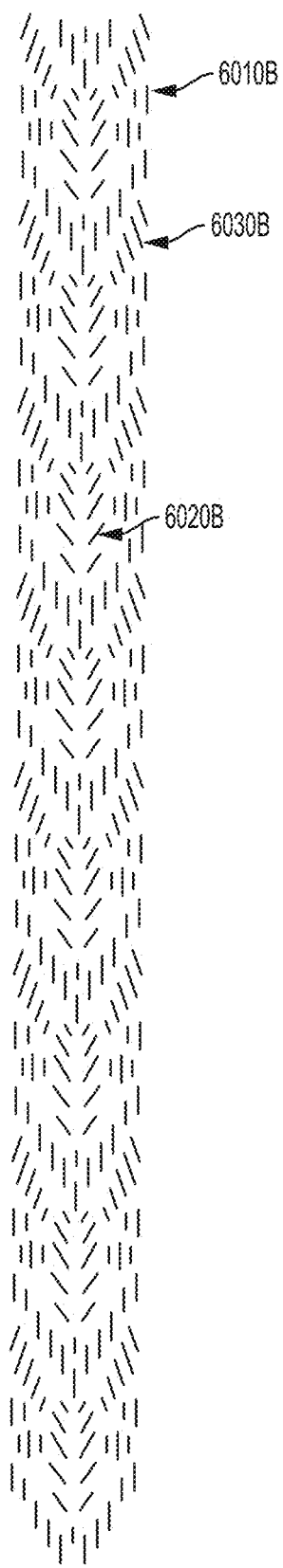

As shown in FIG. 59, another suitable overbond pattern for use with the nonwoven webs of the present invention may comprise a first plurality of overbond sites 6010B, a second plurality of overbond sites 6020B, and a third plurality of overbond sites 6030B. As shown, the first plurality of overbond sites 6010B may, at least in part, surround the second plurality of overbond sites 6020B. Much like the overbond pattern of FIG. 58, the overbond sites 6010B are shown generally parallel to a longitudinal axis (not shown). The resulting apertures will generally be aligned with respect to the longitudinal axis. Additionally, the third plurality of overbond sites 6030B is angled with respect to the longitudinal axis at a first angle. The second plurality of overbond sites 6020B is angled with respect to the longitudinal axis at a second angle. In the form shown, the first angle and the second angle are different. The first and the second angle may be any of the ranges described heretofore with regard to the angles of the apertures.

Similarly, additional suitable aperture patterns for crimped fiber spunbond nonwoven webs/nonwoven laminates of the present invention are disclosed in U.S. application Ser. No. 62/177,405 filed on Mar. 13, 2015, with regard to FIGS. 117-162 which show schematic representations of a variety of overbond patterns. In these Figures, the white areas represent non-apertured areas (land areas) and the black areas represent apertured areas. Those of skill in the art will recognize that other suitable patterns of nonwoven laminates are also within the scope of the present disclosure, along with variations of the illustrated patterns.

Additionally, in some forms of the present invention, the nonwoven web of the present invention may be produced and subsequently provided to a disposable absorbent article converting line. However, in some forms, a manufacturer may obtain a crimped fiber spunbond nonwoven web which comprises apertures as described herein. In some forms, a manufacturer may obtain a nonwoven web which comprises out-of-plane deformations as described herein. In some forms, a manufacturer may obtain a nonwoven web which comprises overbonds as described herein. Similarly, a manufacturer may obtain a supply roll which comprises a laminate comprising a crimped fiber spunbond nonwoven web and another web as described herein.

Overbonds are typically a melt-stabilized area in a material, e.g. nonwoven, which has a stabilized film-like form.

Aperture Aspect Ratio and Area

The apertures of the crimped fiber spunbond nonwoven webs/nonwoven laminates of the present invention may have an aspect ratio of greater than one, for example, greater than two, greater than 3, greater than 5, or greater than 10, but typically less than 15. The aperture patterns in the crimped fiber spunbond nonwoven web/nonwoven laminate may comprise apertures having more than one aspect ratio, such as two or more distinct populations or having a substantially continuous distribution of aspect ratios having a slope greater than zero. Additionally, the aperture patterns may comprise apertures with more than two effective aperture area, either as two or more distinct populations or as a distribution of aperture areas having a slope greater than zero. The Relative Standard Deviation (RSD) of the aperture aspect ratios may be at least about 15%, at least about 25%, at least about 30%, or at least about 40%, or at least about 45%.

Fused Portions

Figure 60:
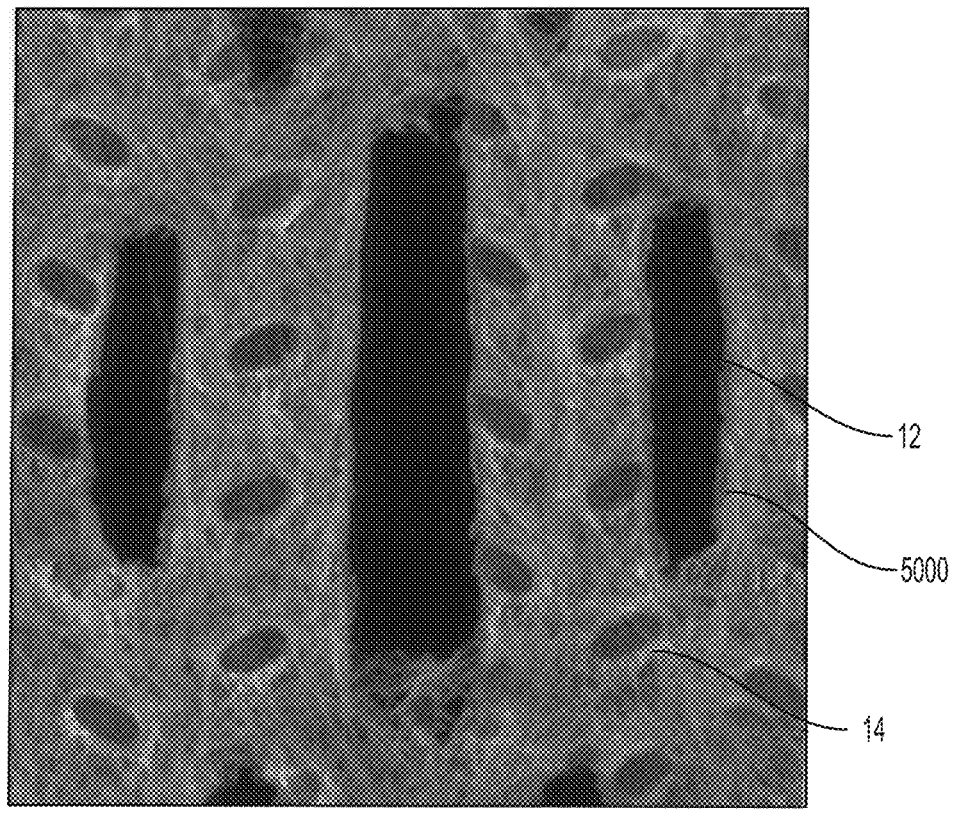
FIG. 60 is a photograph of a portion of a nonwoven laminate comprising fused portions surrounding the apertures in accordance with the present disclosure.

Referring to FIG. 60, areas surrounding at least a portion of an aperture 2212 in a nonwoven laminate of the present disclosure may comprise one or more fused portions 5000. The fused portions 5000 may at least partially surround the apertures 2212, or fully surround the apertures 2212. The fused portions 5000 may surround at least 25% of a perimeter of the apertures 2212 up to about 100% of the perimeter of the apertures 2212. In some instances, the fused portions 5000 may be formed on the lateral sides of the apertures 2212 and not on the leading and trailing edges of the apertures 12. The fused portions 5000 are believed to be formed during the overbonding step and are believed to add strength to the nonwoven laminates and/or bond layers together.

Packages

Absorbent articles comprising the crimped fiber spunbond nonwoven web/nonwoven laminate of the present invention may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles according to the present disclosure may have an in-bag stack height of less than about 80 mm, less than about 78 mm, or less than about 76 mm, according to the In-Bag Stack Height Test described herein. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test described herein. Further details regarding in-back stack height are disclosed in U.S. Pat. No. 8,585,666, to Weisman et al., issued on Nov. 19, 2013.

TEST METHODS

Opacity Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2 C.° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Aperture/Feret Angle Test

Aperture dimensions, Effective Open Area and Inter-Aperture Distance measurements are obtained from specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif. or equivalent). The scanner is interfaced with a computer running an image analysis program (a suitable program is ImageJ v. 1.47 or equivalent, National Institute of Health, USA). The specimen images are distance calibrated against an acquired image of a ruler certified by NIST. A steel frame is used to mount the specimen, which is then backed with a black glass tile (P/N 11-0050-30, available from HunterLab, Reston, Va.) prior to acquiring the specimen image. The resulting image is then threshold, separating open aperture regions from specimen material regions, and analyzed using the image analysis program. All testing is performed in a conditioned room maintained at about 23±2° C. and about 50±2% relative humidity.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. An apertured substrate raw material is prepared for testing by extending or activating it under the same process conditions, and to the same extent, as it would be for use on the absorbent article, and then in its extended state adhering it to the steel frame as described above for testing. Condition the samples at about 23° C.±2 C.° and about 50%±2% relative humidity for 2 hours prior to testing.

Image Acquisition:

Place the ruler on the scanner bed, oriented parallel to the sides of the scanner glass, and close the lid. Acquire a calibration image of the ruler in reflectance mode at a resolution of 6400 dpi (approximately 252 pixels per mm) and 8 bit grayscale, with the field of view corresponding to the dimensions of the interior of the steel frame. Save the calibration image as an uncompressed TIFF format file. Lift the lid and remove the ruler. After obtaining the calibration image, all specimens are scanned under the same conditions and measured based on the same calibration file. Next, place the framed specimen onto the center of the scanner bed, lying flat, with the outward facing surface of the specimen facing the scanner's glass surface. Orient the specimen so that sides of the frame are aligned parallel with and perpendicular to the sides of the scanner's glass surface, so that the resulting specimen image will have the MD vertically running from top to bottom. Place the black glass tile on top of the frame covering the specimen, close the lid and acquire a scanned image. Scan the remaining four replicates in like fashion. If necessary, crop all images to a rectangular field of view circumscribing the apertured region, and resave the files.

Effective Open Area Calculation:

Open the calibration image file in the image analysis program and perform a linear distance calibration using the imaged ruler. This distance calibration scale will be applied to all subsequent specimen images prior to analysis. Open a specimen image in the image analysis program and set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0.

Using the image analysis program, analyze each of the discrete aperture regions. Measure and record all of the individual aperture areas to the nearest 0.01 mm$^2$, including partial apertures along the edges of the image. Discard any apertures with an area less than 0.3 mm$^2$. Apertures having a lower area than 0.3 mm$^2$ may prove difficult to measure particularly when stray fibers cross the boundary of the aperture. And such apertures with that small of an area are considered to contribute insignificantly to the Effective Open Area. Sum the remaining aperture areas (including whole and partial apertures), divide by the total area included in the image and multiply by 100. Record this value as the % Effective Open Area to the nearest 0.01%.

In like fashion, analyze the remaining four specimen images. Calculate and report the average % effective area values to the nearest 0.01% for the five replicates.

Effective Aperture Area and Absolute Feret Angle:

Open the calibration image (containing the ruler) file in the image analysis program. Resize the resolution of the original image from 6400 dpi to 640 dpi (approximately 25.2 pixels per mm) using a bicubic interpolation. Perform a linear distance calibration using the imaged ruler. This distance calibration scale will be applied to all subsequent specimen images prior to analysis. Open a specimen image in the image analysis program. Resize the resolution of the original image from 6400 dpi to 640 dpi (approximately 25.2 pixels per mm) using a bicubic interpolation. Set the distance scale. View the 8 bit histogram (0 to 255, with one bin per GL) and identify the gray level (GL) value for the minimum population located between the dark pixel peak of the aperture holes and the lighter pixel peak of the specimen material. Threshold the image at the minimum gray level value to generate a binary image. In the binary image the apertures appear as black, with a GL value of 255, and specimen as white, with a GL value of 0. Next, two morphological operations are performed on the binary image. First, a closing (a dilation operation followed by an erosion operation, iterations=1, pixel count=1), which removes stray fibers within an aperture hole. Second, an opening (an erosion operation followed by a dilation operation, iterations=1, pixel count=1), which removes isolated black pixels. Pad the edges of the image during the erosion step to ensure that black boundary pixels are maintained during the operation. Lastly, fill any remaining voids enclosed within the black aperture regions.

Using the image analysis program, analyze each of the discrete aperture regions. During the analysis exclude measurements of partial apertures along the edges of the image, so that only whole apertures are measured. Measure and record all of the individual aperture areas, perimeters, feret diameters (length of the apertures) along with its corresponding angle of orientation in degrees from 0 to 180, and minimum feret diameters (width of the apertures). Record the measurements for each of the individual aperture areas to the nearest 0.01 mm$^2$, the perimeters and feret diameters (length and width), to the nearest 0.01 mm, and angles to the nearest 0.01 degree. Discard any apertures with an area less than 0.3 mm$^2$. Record the number of remaining apertures, divide by the area of the image and record as the Aperture Density value. The angle of orientation for an aperture aligned with the MD (vertical in the image) will have an angle of 90 degrees. Apertures with a positive slope, increasing from left to right, will have an angle between zero and 90 degrees. Apertures with a negative slope, decreasing from left to right, will have an angle between 90 and 180 degrees. Using the individual aperture angles calculate an Absolute Aperture Angle by subtracting 90 degrees from the original angle of orientation and taking its absolute value. In addition to these measurements, calculate an Aspect Ratio value for each individual aperture by dividing the aperture length by its width. Repeat this analysis for each of the remaining four replicate images. Calculate and report the statistical mean and standard deviation for each of the effective aperture dimension measurements using all of the aperture values recorded from the replicates. Calculate and report the % relative standard deviation (RSD) for each of the aperture dimension measurements by dividing the standard deviation by the mean and multiplying by 100.

Inter-Aperture Distance Measurements:

The average, standard deviation, median, and maximum distance between the apertures can be measured by further analyzing the binary image that was analyzed for the aperture dimension measurements. First, obtain a duplicate copy of the resized binary image following the morphological operations, and using the image analysis program, perform a Voronoi operation. This generates an image of cells bounded by lines of pixels having equal distance to the borders of the two nearest pattern apertures, where the pixel values are outputs from a Euclidian distance map (EDM) of the binary image. An EDM is generated when each inter-aperture pixel in the binary image is replaced with a value equal to that pixel's distance from the nearest pattern aperture. Next, remove the background zeros to enable statistical analysis of the distance values. This is accomplished by using the image calculator to divide the Voronoi cell image by itself to generate a 32-bit floating point image where all of the cell lines have a value of one, and the remaining parts of the image are identified as Not a Number (NaN). Lastly, using the image calculator, multiply this image by the original Voronoi cell image to generate a 32-bit floating point image where the distance values along the cell lines remain, and all of the zero values have been replaced with NaN. Next, convert the pixel distance values into actual inter-aperture distances by multiplying the values in the image by the pixel resolution of the image (approximately 0.04 mm per pixel), and then multiply the image again by 2 since the values represent the midpoint distance between apertures. Measure and record the mean, standard deviation, median and maximum inter-aperture distances for the image to the nearest 0.01 mm. Repeat this procedure for all replicate images. Calculate the % relative standard deviation (RSD) for the inter-aperture distance by dividing the standard deviation by the mean and multiplying by 100.

Land Area Light Transmission Method

The land area light transmission method measures the average amount of light transmitted through specific regions of a specimen. A calibrated light transmission image is obtained using a flatbed scanner. A binary mask is generated to separate discrete aperture regions from the surrounding land area. The binary mask is then registered to the light transmission image, and used to exclude the apertures from the land area in the light transmission image. This enables the average light transmission value for the land area to be calculated.

Sample Preparation:

To obtain a specimen, tape the absorbent article to a rigid flat surface in a planar configuration. Any leg elastics may be cut to facilitate laying the article flat. A rectilinear steel frame (100 mm square, 1.5 mm thick with an opening 60 mm square) is used to mount the specimen. Take the steel frame and place double-sided adhesive tape on the bottom surface surrounding the interior opening. Remove the release paper of the tape, and adhere the steel frame to the apertured layer of the article. Align the frame so that it is parallel and perpendicular to the machine direction (MD) and cross direction (CD) of the apertured layer. Using a razor blade excise the apertured layer from the underlying layers of the article around the outer perimeter of the frame. Carefully remove the specimen such that its longitudinal and lateral extension is maintained to avoid distortion of the apertures. A cryogenic spray (such as Cyto-Freeze, Control Company, Houston Tex.) can be used to remove the specimen from the underlying layers if necessary. Five replicates obtained from five substantially similar articles are prepared for analysis. If the aperture layer of interest is too small to accommodate the steel frame, reduce the frame dimensions accordingly to accomplish the goals of removal of the specimen without distortion of the apertures while leaving an opening of sufficient size to allow for scanning a significant portion of the apertured layer. Condition the samples at about 23° C.±2 C.° and about 50%±2% relative humidity for 2 hours prior to testing.

Light Transmission Image

The light transmission measurement is based on the CIE L*a*b* color system (CIELAB). A flatbed scanner capable of scanning a minimum of 24 bit color at 800 dpi and has manual control of color management (a suitable scanner is an Epson Perfection V750 Pro from Epson America Inc., Long Beach Calif. or equivalent) is used to acquire images. The scanner is interfaced with a computer running color management software (suitable color management software is MonacoEZColor available from X-Rite Grand Rapids, Mich. or equivalent). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L*a*b* (a suitable program is Photoshop S4 available from Adobe Systems Inc., San Jose, Calif. or equivalent). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 200 dpi and 24 bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the outward facing surface facing the glass. Acquire and import a scan of the specimen region within the interior of the frame into the image analysis software at 24 bit color and at 800 dpi in transparency mode. If necessary, crop image to a rectangular field of view circumscribing the apertured region. Transparency mode illuminates the specimen from one side with the sensor capturing the image from the opposite side. Assign the calibrated color profile to the image and change the color space mode to L*a*b* Color corresponding to the CIE L*a*b* standard. This produces a color corrected image for analysis. Save this color corrected image in an uncompressed format, such as a TIFF file.

Land Area Mask

The boundaries of the apertured areas and land area are identified by thresholding the L* channel image to generate a binary image, separating apertured areas from the surrounding land area. This binary image will then be used as a mask on the corresponding light transmission image to measure the average Light Transmission Value of only the land area.

To do this, first open the color corrected light transmission image in the image analysis software. To generate the land area mask, first separate the L*, a* and b* channels, and select only the L* channel for analysis. The L* channel represents the "Lightness" of the image and has values that range from 0-100. Threshold the L* channel image at a value of 90 to generate a binary image. By thresholding at the level described above, a binary mask image is produced with the discrete aperture areas assigned one value, and the surrounding land area assigned a different value. For example, the discrete aperture areas could appear black, and the surrounding land area could appear white. Save this binary mask image in an uncompressed format, such as a TIFF file.

Analysis of Light Transmission Image

Open both the color corrected light transmission image and the corresponding binary mask image in the image analysis software. To analyze the specimen light transmission image, first separate the L*, a* and b* channels, and select only the L* channel for analysis. Register the light transmission image and the binary mask image to each other. Use the binary mask to exclude the apertures from the light transmission image, and calculate an average L* value (Light Transmission Value) for the remaining surrounding land area. Record this value as the Land Area Light Transmission Value to the nearest 0.1 units. In like fashion, repeat this procedure on all of the replicate specimens. Calculate and report the average of the five individual Land Area Light Transmission Values to the nearest 0.1 units.

Basis Weight Method

Basis weight of the crimped fiber spunbond nonwoven web/nonwoven laminate of the present invention may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the nonwoven laminate (e.g., topsheet, outer cover) from the approximate center of the absorbent article or other consumer product in a location which avoids to the greatest extent possible any adhesive which may be used to fasten the nonwoven laminate to any other layers which may be present and removing the nonwoven laminate from other layers (using cryogenic spray, such as Cyto-Freeze, Control Company, Houston, Tex., if needed). The sample is then weighed and dividing by the area of the punch die yields the basis weight of the nonwoven laminate. Results are reported as a mean of 5 samples to the nearest 0.1 cm$^2$.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Definitions

Figure 61:
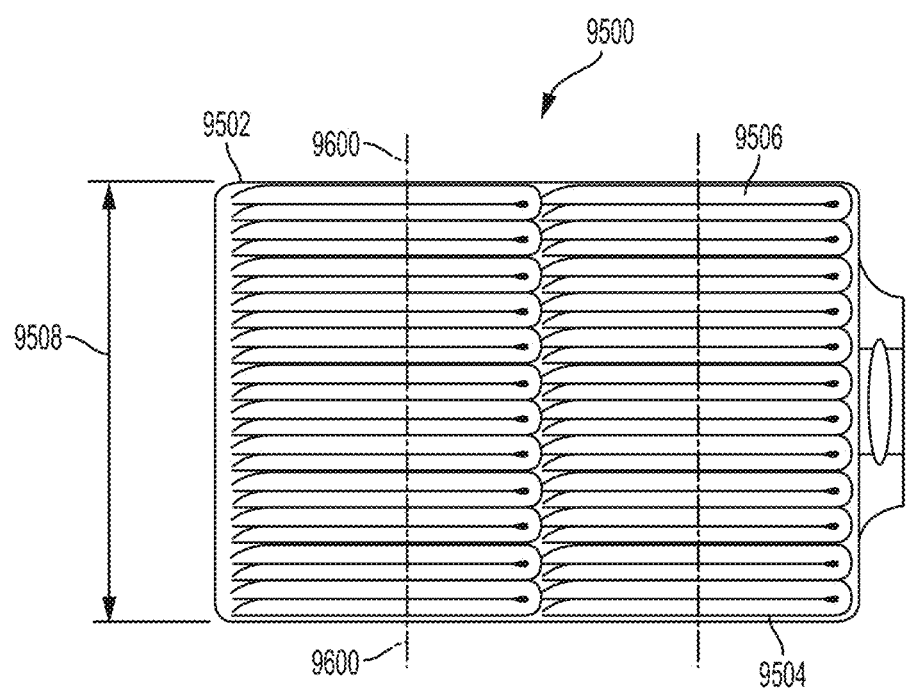
FIG. 61 is a schematic representation of a stack of absorbent articles within a package.

As illustrated in FIG. 61, a package 9500 defines an interior space 9502 and comprises a plurality of absorbent articles 9504. The absorbent articles are in a stack 9506. The package has a package width 9508. The package width is defined as the maximum distance between the two highest bulging points along the same compression stack axis of the absorbent article package 9500.

In-Bag Stack Height=(Package Width/Pad Count Per Stack)×10 absorbent articles.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

HLB (Hydrophilic/Lipophilic Balance)

The term "HLB" or "HLB value" of a surfactant refers to the Hydrophilic-Lipophilic Balance and is a measure of the degree to which it is hydrophilic or lipophilic, determined by calculating values for the different regions of the molecule. For nonionic surfactants the HLB=20*Mb/M, where M is the molecular mass of the whole molecule and Mb is the molecular mass of the hydrophilic portion of the Molecule. An HLB value of 0 corresponds to a completely lipidphilic/hydrophobic molecule, and a value of 20 corresponds to a completely hydrophilic/lipidphobic molecule. The above represents the Griffin method of calculation which is well known in the art.

Fiber Diameter and Denier Test

The diameter of fibers in a sample of a nonwoven substrate is determined by using a Scanning Electron Microscope (SEM) and image analysis software. A magnification of 500 to 10,000 times is chosen such that the fibers are suitably enlarged for measurement. The samples are sputtered with gold or a palladium compound to avoid electric charging and vibrations of the fibers in the electron beam. A manual procedure for determining the fiber diameters is used. Using a mouse and a cursor tool, the edge of a randomly selected fiber is sought and then measured across its width (i.e., perpendicular to fiber direction at that point) to the other edge of the fiber. For non-circular fibers, the area of the cross-section is measured using the image analysis software. The effective diameter is then calculated by calculating the diameter as if the found area was that of a circle. A scaled and calibrated image analysis tool provides the scaling to get actual reading in micrometers (µm). Several fibers are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

Fiber Diameter in denier=Cross-sectional area (in m2)*density (in kg/m3)*9000 m*1000 g/kg.

For round fibers, the cross-sectional area is defined by the equation:

$$A=\pi*(D/2)^2.$$

The density for polypropylene, for example, may be taken as 910 kg/m3.

Given the fiber diameter in denier, the physical circular fiber diameter in meters (or micrometers) is calculated from these relationships and vice versa. We denote the measured diameter (in microns) of an individual circular fiber as D.

In case the fibers have non-circular cross-sections, the measurement of the fiber diameter is determined as and set equal to the hydraulic diameter, as discussed above.

Specific Surface Area

The specific surface area of the nonwoven substrates of the present disclosure is determined by Krypton gas adsorption using a Micromeritic ASAP 2420 or equivalent instrument, using the continuous saturation vapor pressure (Po) method (according to ASTM D-6556-10), and following the principles and calculations of Brunauer, Emmett, and Teller, with a Kr-BET gas adsorption technique including automatic degas and thermal correction. Note that the specimens should not be degassed at 300 degrees Celsius as the method recommends, but instead should be degassed at room temperature. The specific surface area should be reported in $m^2/g$.

Obtaining Samples of Nonwoven Substrates

Each surface area measurement is taken from a specimen totaling 1 g of the nonwoven substrate of the present disclosure. In order to achieve 1 g of material, multiple specimens may be taken from one or more absorbent articles, one or more packages, or one or more wipes, depending on whether absorbent articles, packages, or wipes are being tested. Wet wipe specimens will be dried at 40 degrees C. for two hours or until liquid does not leak out of the specimen under light pressure. The specimens are cut from the absorbent articles, packages, or wipes (depending on whether absorbent articles, packages, or wipes are being tested) in areas free of, or substantially free of, adhesives using scissors. An ultraviolet fluorescence analysis cabinet is then used on the specimens to detect the presence of adhesives, as the adhesives will fluoresce under this light. Other methods of detecting the presence of adhesives may also be used. Areas of the specimens showing the presence of adhesives are cut away from the specimens, such that the specimens are free of the adhesives. The specimens may now be tested using the specific surface area method above.

Mass-Average Diameter

The mass-average diameter of fibers is calculated as follows:

$$\text{mass average diameter, } d_{mass} = \frac{\sum_{i=1}^{n}(m_i \cdot d_i)}{\sum_{i=1}^{n} m_i} = \frac{\sum_{i=1}^{n}(\rho \cdot V_i \cdot d_i)}{\sum_{i=1}^{n}(\rho \cdot V_i)} = \frac{\sum_{i=1}^{n}\left(\rho \cdot \frac{\pi d_i^2 \cdot \partial x}{4} \cdot d_i\right)}{\sum_{i=1}^{n}\left(\rho \cdot \frac{\pi d_i^2 \cdot \partial x}{4}\right)} = \frac{\sum_{i=1}^{n} d_i^3}{\sum_{i=1}^{n} d_i^2}$$

where fibers in the sample are assumed to be circular/cylindrical, $d_i$=measured diameter of the $i^{th}$ fiber in the sample, $\partial x$=infinitesimal longitudinal section of fiber where its diameter is measured, same for all the fibers in the sample, $m_i$=mass of the $i^{th}$ fiber in the sample, n=number of fibers whose diameter is measured in the sample $\rho$=density of fibers in the sample, same for all the fibers in the sample $V_i$=volume of the $i^{th}$ fiber in the sample.

The mass-average fiber diameter should be reported in μm.

Gravimetric Weight Loss Test

The Gravimetric Weight Loss Test is used to determine the amount of lipid ester (e.g., GTS) in a nonwoven substrate of the present disclosure. One or more samples of the nonwoven substrate are placed, with the narrowest sample dimension no greater than 1 mm, into acetone at a ratio of 1 g nonwoven substrate sample per 100 g of acetone using a refluxing flask system. First, the sample is weighed before being placed into the reflux flask, and then the mixture of the sample and the acetone is heated to 60° C. for 20 hours. The sample is then removed and air dried for 60 minutes and a final weight of the sample is determined. The equation for calculating the weight percent lipid ester in the sample is:

weight % lipid ester=([initial mass of the sample–final mass of the sample]/[initial mass of the sample])×100%.

Absorption Capillary Potential and Desorption Capillary Potential

Absorption Capillary Potential, also referred to as absorption energy, and Desorption Capillary Potential, also referred to as desorption energy, can be determined by evaluating capillary work potential for each tested material. The ability of absorbent materials to absorb or desorb fluid via capillary potential is measure by the Capillary Work Potential.

Equipment: A TRI Autoporosimeter from TRI, Princeton, N.J., is used to measure percentage of fluid saturation as a function of pressure of the samples in Table 2 or any other sample for which data is desired. Test fluid is n-hexadecane.

There are three testing cycles to generate three capillary pressure vs. percent saturation curves: (1) 1st Absorption with dry material (imbibition); (2) Draining; and (3) 2nd Absorption with wet material. The Absorption Capillary Potential (absorption Capillary Work Potential (CWP)) is calculated by the integration of the 1st absorption curve of capillary potential as a function of uptake volume.

$$W = \int P_{cap(CV)} dCV \left(\frac{\text{mJ}}{\text{m}^2}\right)$$

Where CV is the measured cumulative uptake volume (convertible to saturation).

The Desorption Capillary Pressure (desorption Capillary Work Potential (CWP)) is calculated by the integration of the draining curve of capillary pressure as a function of uptake volume.

$$W = \int P_{cap(CV)} dCV \left(\frac{\text{mJ}}{\text{m}^2}\right)$$

Where CV is the measured cumulative uptake volume (convertible to saturation).

The extended capillary work potential (eCWP) is calculated as follows:

$$\text{Correction Function} \frac{CWP\left(\frac{\text{mJ}}{\text{m}^2}\right)}{BWT\left(\frac{g_{web}}{\text{m}^2}\right) * \text{Uptake}\left(\frac{g_{fluid}}{g_{web}}\right)}$$

Where CWP is the capillary work potential for the material/fluid system. BWT is the material basis weight and Uptake is the maximum fluid uptake at full saturation, per gram of material.

Permeability (Darcy's) and Flow Rate (g/sec)

Permeability is determined from the mass flow rate of any given fluid through a porous medium. The procedure for determining both is as follows:

Step 1: A through plane permeability device is used to automatically dispense and measure flow of liquid through a sample by monitoring the distance a column of water drops in relation to time and pressure measure.

Step 2: The pressure drop determines the mass flow rate of a fluid through a porous medium across the sample.

Step 3 (for flow rate of Table 2): The flow rate is determined at constant pressure using the constant hydro head mode using distilled/de-ionized water as the fluid for all of the samples.

Step 4: Darcy permeability and Flow Rate is calculated by the equations below:

$$F = k*(A/\mu)*(\Delta p/l)$$

$$K = 9.87 \times 10^{-13} * k$$

Where: F=flow Rate (g/s); k=permeability of the porous material (m$^2$); A=Cross sectional area available for flow (m$^2$); l=Thickness of the material (m); μ=Fluid viscosity (cP); Δp=Pressure Drop (cm H$_2$0); and K=permeability (Darcy's).

Free Gush Run-off (Grams)

Handle all products without smoothing out wrinkles, pulling on, or pressing on the pad. Remove test product from all packaging including Fold & Wrap pouches. Allow all samples to equilibrate to the controlled room temperature and humidity for at least two hours prior to testing.

1. For winged-products, remove the back sheet and pat a small amount of corn starch onto the adhesive areas. This prevents the pad from sticking to the incline. Use the adhesive on the wings to attach the pad to the side of an incline. The incline shall be made of plexiglass and angled at 15 degrees from a level horizontal plane. The incline shall measure 30 cm long by 23 cm wide. (See FIG. 62, item 7020).
2. For non-winged products, remove the back sheet and use the adhesive to attach to the incline.
3. If the pad has a distinct front and back designation, orient the pad on the incline so that the back of the pad is towards the bottom of the incline.
4. Place a small piece of double sided tape at the bottom of the incline. Use this tape to secure the bottom of the pad.
5. Place the pad on the incline so that the bottom of the pad lines up with the bottom edge of the incline.
6. The pad must be smooth and flat on the incline in the MD.
7. Determine the geometric center of the pad being tested when looking down on the topsheet of the pad. Mark the center with a black felt tip pen. This marked center will be the assault point.

Fluid Assault Steps:

1. Tare four 10-ml beakers. Using a disposable plastic pipette with the tip cut off; load 3.0 g of AMF-B into each one of them. Pour each of them back into the AMF-B reservoir. This primes the beakers so that any fluid left is accounted for.
2. Tare the four primed beakers from step 1. Load each beaker with 3.00±0.03 g of AMF-B.
3. Place 5 layers of 5 in×5 in filter papers on balance and tare. Place the stack at the bottom of the incline to capture any fluid that runs off the incline.
4. Set a timer for 1 minute, 10 seconds.
5. Start the timer while simultaneously pouring one beaker of fluid onto the assault point on the test pad. Ensure that this assault takes place over 10±2 seconds. If the assault is shorter than eight seconds or longer than 12 seconds, the test must be terminated. Do not shake the beaker to dislodge the last drop of the fluid.
6. When the timer sounds, three measurements must be made:
    a. Run-Off: If there is any fluid that ran off the incline, it is captured in the stack of tared filter papers at the bottom. Reweigh the stack of filter paper to obtain the amount of fluid run off. Record the weight to the nearest 0.01 g. If there is no run off, record the weight as 0 g. Use the tared filter papers to get the rewet weight below.
7. Record data.
8. Repeat steps 3-6 three more times immediately for a total of four assaults recording data for each assault.
9. Review/determine final data in accord with the below steps.

Run-Off: Amount of fluid that ran off and captured on the filter paper at each assault is called Run Off. The total fluid that ran off from all 4 assaults is also calculated. The average amount of fluid that ran off at each assault for the replicate pads is also calculated.

Trickle Test

Figure 62:
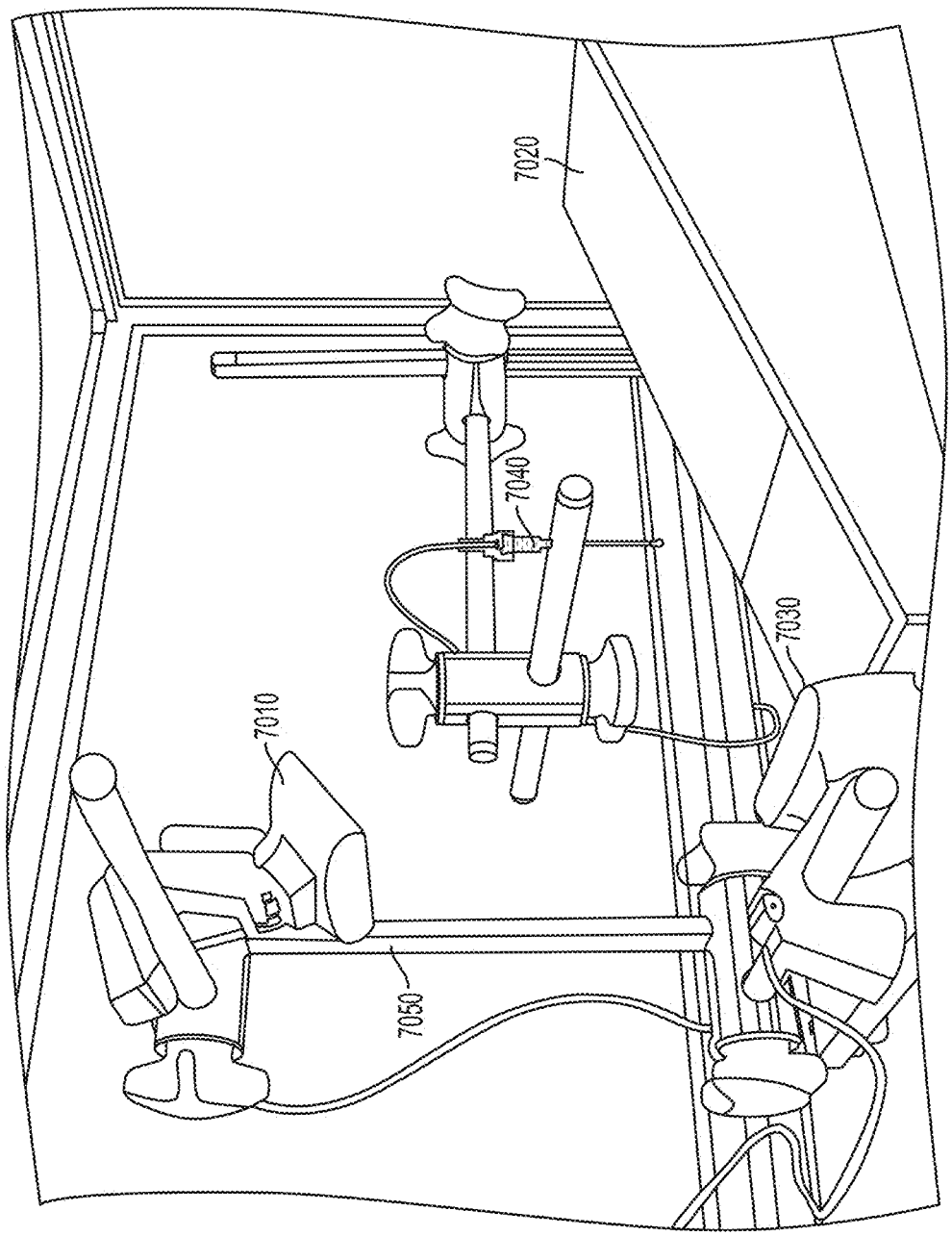
FIG. 62 is a schematic illustration of a test stand for performing the Trickle Test described herein.

1. Referring to FIG. 62, obtain a frame 7050 having multiple arms which can support a first camera 7010, a second camera 7030, and a delivery probe 7040. The first camera 7010 and second camera 7030 are Logitec C920 webcam or equivalent. The Delivery probe 7040 is an 18 gauge blunt end needle with luer fitting.
2. Program a syringe pump (KD Scientific Legato 100 infuse only syringe pump or equivalent) to deliver fluid to the delivery probe 7040 at the following rate 0.33 ml/min for 3 minutes.
3. Fill the syringe pump with AMF-A
4. Connect the delivery probe 7040 to the syringe on the syringe pump with PVC tubing having luer fitting ends.
5. Place a clean, standard chemistry beaker under the delivery probe.
6. Purge air from the pump, tubing, and delivery probe by indexing the pump.
7. Place a sample product on the incline 7020 such that the sample is fully supported by the incline 7020. The sample should be placed on the incline 7020 such that the length of the article is positioned generally parallel to the length of the incline 7020. The sample product is held by either adhesive backing on the pad sample or a rubber band at either end of the sample which wraps around the incline 7020.
8. Measure 90 mm from the leading edge (lower edge of the incline 7020) and mark the incline 7020 at this distance. Place a line across the incline 7020 at this distance.
9. Place the incline 7020 with the sample thereon, under the delivery probe 7040. The incline should be positioned under the delivery probe 7040 such that the fluid from the delivery probe strikes the incline 7020 at the line created in step 8.
10. Adjust the delivery probe 7040 to be 30 mm above the incline 7020 and centered along the width of the incline 7020.
11. Place a light box (box blocking out ambient light) over the frame 7050 once the sample is placed on the incline 7020.
12. Attach the first camera 7010 and second camera 7030 to a standard computer.
13. Initiate Logitech software or equivalent depending on webcam supplier.
14. Center and zoom the first camera 7010 so that the sample is in clear focus.
15. Focus the second camera 7030.
16. First camera 7010 and second camera 7030 should be focused such that each can visually capture—clearly—the liquid insult striking the sample and should be focused such that each camera clearly captures liquid breaching the topsheet of the sample.

Sample Prep:

1. Obtain the sample.
2. Trim off any wings from the sample.
3. Cut the sample into thirds, each cut extending laterally across the sample.
4. Identify the thirds of the sample that have formations which resemble tufts and/or caps. Test these samples.
5. Position one of the samples to be tested on the incline 7020 such that the probe is centered under the delivery probe 7040. If the tufts/caps are offset from the center of the sample, then center the delivery probe 7040 in the zone of tufts/caps nearest the center of the sample.

Fluid Insult:

1. Set the delivery of fluid insult to be 0.33 ml/min for 3 minutes.
2. Count the number of drops of fluid which strike the sample before the fluid breaches the topsheet.

Artificial Menstrual Fluid Preparation-A

For each of the tests using Artificial Menstrual Fluid-A (AMF-A), prepare as follows:

Step 1: Dilute 10 ml of reagent grade 85-95% w/w lactic acid to 100 ml with distilled water. Label as 10% v/v lactic acid.

Step 2: Add 11.76 g of reagent grade 85% w/w potassium hydroxide (KOH) to a flask and dilute to 100 ml with distilled water. Mix until completely dissolved. Label as 10% w/v KOH.

Step 3: Add 8.5 g sodium chloride and 1.38 g of hydrous monobasic sodium phosphate to a flask and dilute to 1000 ml with distilled water. Mix until completely dissolved. Label as monobasic sodium phosphate solution.

Step 4: Add 8.5 g sodium chloride and 1.42 g anhydrous dibasic sodium phosphate to a flask and dilute to 1000 ml with distilled water. Mix until completely dissolved. Label as dibasic sodium phosphate solution.

Step 5: Add 450 ml of dibasic phosphate solution to a 1000 ml beaker and add monobasic sodium phosphate solution until the PH is lowered to 7.2±0.1. Label as phosphate solution.

Step 6: Mix 460 ml of phosphate solution and 7.5 ml of 10% KOH in a 1000 ml beaker. Heat Solution to 45° C.±5° C. and then add 28 sterilized gastric mucin (ICN Biomedical Inc., Cleveland, Ohio). Continue heating for 2.5 hours to completely dissolve the gastric mucin. Allow the solution to cool to less than 40° C. and then add 1.8±0.2 ml of 10% v/v lactic acid solution. Autoclave the mixture at 121° C. for 15 minutes, then allow to cool to room temperature. Mucous mixture should be used within 7 days. Label as gastric mucin solution.

Step 7: Mix 500 ml of gastric mucin solution and 500 ml of fresh, sterile defibrinated sheep blood (Cleveland Scientific, American Biomedical, Bath, Ohio) in a beaker. Label as artificial menstrual fluid. Store refrigerated and use within 7 days.

Artificial Menstrual Fluid Preparation-B

Step 1: Preparation of Phosphate Buffer Saline Solution

Solution A:

Taring the balance with each weighing dish, weigh out 1.40+/−0.05 g of hydrous monobasic sodium phosphate and 8.50+/−0.05 g of sodium chloride. Record the weights in a lab notebook. Carefully, add the solids to a 1000 ml volumetric flask and fill the flask about half way with distilled water. Mix until completely dissolved. Bring the solution to volume.

Solution B:

Taring the balance with each weighing dish, weigh out 1.40+/−0.05 g of anhydrous dibasic sodium phosphate and 8.50+/−0.05 g of sodium chloride. Record the weights in a lab notebook. Add the solids to a 1000 mL volumetric flask and fill about half way with distilled water. Mix until the solids are completely dissolved. Continue filling the flask with distilled water until the bottom of the meniscus rests on the line in the neck of the flask. Transfer to a plastic storage bottle and label with "Solution B", the date, and your initials. Any unused solution should be discarded after 3 months.

PBS Solution: Combine 11 ml of solution A with 35 ml of solution B.

Step 2: Preparation of Gelatin

Measure about 100 g of distilled $H_2O$ and bring to boil. Without cooling, weigh 80.8+0.1 g of the hot water in a 100 mL Pyrex bottle with a screw cap. Weigh 4.20+0.05 g of unflavored gelatin in a weigh boat. Add it to the hot water slowly while mixing with a stir bar. Mix until dissolved. Dissolution can take up to 2 h. Place in refrigerator and refrigerate at least overnight. This concentration of gelatin allows the gelatin to be more rigid at room temperature. Expires in one week.

Step 3. Preparation of 1% Superfloc 150 in 1% NaCl solution

Boil about 130 ml of distilled water for 5 min to sterilize. No need to cool before proceeding to next step. Weigh 99 g of hot water and add 1.00±0.05 g of NaCl into a 250 mL beaker. Stir to dissolve completely. Transfer 99 g of above 1% NaCl solution to a 250-mL Pyrex bottle with a screw cap. Weigh 1.00±0.01 g of Superfloc 150 on a weigh boat and transfer to the 250 mL bottle. Invert the bottle several times to mix. The bottle must be inverted several times a day for up to a week to fully hydrate. The fluid must be a single phase, free from gel-like, hazy phase before it can be used. It takes up to a week to fully hydrate the Superfloc. Prepare this solution well before the previous stock is exhausted. Use until finished or within 3 months. Do not use if cloudiness exists which is an indication of bacterial growth.

Step 4: AMF-B Preparation

To Make 500 g:

Use a Pyrex bottle with a screw cap. Weigh out 35.00±0.05 g of the gelatin gel and add it to 107.5±0.05 g of PBS solution. Warm the mixture to 30-35 C to melt the gelatin. Once it is melted, let it cool down to 25 C and then add the 7.50±0.05 g of the 1% Superfloc 150 solution. Mix well by inverting several times. Add 350.0±0.1 g of sheep blood that is at 25 C. Mix well by inverting. Do not use a stirrer.

35.00 g gelatin
107.50 g PBS solution
7.50 g of 1% Superfloc 150 solution
350.0 g Sheep blood To Make 200 g:

Use the weights of ingredients listed below in the same way as described in making 500 g sample.

14.00 g gelatin
43.0 g PBS solution
3.0 g of 1% Superfloc 150 solution
140.0 g Sheep blood Measure and record the stringiness using a Ryometer as described below. The stringiness does not change with age of the fluid. It need not be measured again. Place the prepared AMF-B in refrigerator overnight. Its viscosity must be tested before each use as described below.

Fluid Testing (Viscosity/Stringiness)

Viscosity Measurement

Bring the temperature of the AMF-B to room temperature (25 degrees C.) by placing it in a warm water bath. The temperature of the water bath must be 35-40 degrees C. Do not stir or vigorously shake the bottle. Gently mix the solution before taking a sample to measure.

Measure the viscosity of each batch of artificial menses before use each day using an AR 2000 Rheometer or equivalent. These instructions are for the AR2000 Rheometer.

1. Turn on instrument, check cooling water level and make sure water is circulating into the reservoir.
2. Install the upper plate by holding the knob on top and screwing the plate on. Be careful that the top portion is steady since air bearings can be damaged easily.
3. Once plate is in place spin gently.
4. Move computer mouse to activate screen. Double click on instrument control icon.
5. Check temperature on sheet and instrument display, it should read 25 degrees C.

6. Run zero gap by hitting the zero gap icon. Follow instructions.
7. At least once per week, or if the plate has been removed, perform instrument rotational mapping.
8. Make folder for the data by dates tests are run. File/new file/daily.
9. Change name by highlighting the sample name and change the information then select browse to put the file in the proper folder.
10. Run Standard (S60) at least once a month—be sure to change the density.
11. With an Eppendorf pipette set at 1 ml with wide mouth pipette tip pull up AMF-B with no air bubbles by priming a couple times. Dispel sample on the platform without any bubbles and then lower the upper plate to the point where the plate touches the fluid. Turn the spindle a little without spinning.
12. Go to enter gap icon and decrease the distance until the fluid is parallel to the edge of plate. Manually turn the spindle so the fluid is evenly distributed under the plate.
13. If fluid comes out past the edge of the plate wipe off excess fluid—always hold top knob when wiping plate.
14. The gap should be within a range of 700-900 um range and then that gap needs to be entered under the 40 mm steel plate dimension under gap.
15. Place the cover over the plate.
16. The shear rate scan procedure is named Geoff's Procedure. This procedure makes a series of steady-state viscosity measurements from 0.01 to 30 $sec^{-1}$ and usually takes 20 minutes to complete. The oscillatory (structure measurement) and shear rate scan combined procedure is listed as Geoff's procedure.
17. Press the green triangle to start to run.
18. Once the procedure is done then the data needs to be analyzed using the Data Analysis Icon.
19. Pull up data and send to graph for analysis. You can pull up actual data by selecting the spreadsheet picture grid.
20. The AMF-B should be shear thinning and at 20 $sec^{-1}$ the viscosity should be 20.0±3.0 cP at 25 C. Viscosity at a shear rate of 20 $sec^{-1}$ was selected for its relevance to shear experienced by the fluid during gush acquisition events.
21. If AMF-B viscosity is too high (greater than 23.0 cP at 20 $sec^{-1}$), it can be brought down by adding some PBS buffer. The volume of the PBS buffer added should not exceed 10% of the total volume. For e.g., for a 500 ml AMF-B sample, do not add more than 50 ml of PBS buffer to get viscosity in the required range.
22. If the viscosity is too low (less than 17.0 cP at 20 $sec^{-1}$), discard the fluid or place the fluid back into the refrigerator for at least another 24 hours.

CLEAN UP— Wear latex/nitrile gloves, raise plate, wet with water a paper towel that is folded into quarters, wipe plate and platform making sure to hold knob while cleaning plate. Follow the water with alcohol wipe and drying.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article comprising:
a chassis having a topsheet, backsheet and an absorbent core disposed between the topsheet and backsheet; and
an elastic ear comprising:
a first layer comprising a nonwoven web, and a second layer comprising a film;
wherein the first layer and the second layer are joined together by ultrasonic bonding;
wherein the first layer comprises a first plurality of apertures, and a portion of the second layer is exposed through at least one of the first plurality of apertures; and
wherein the second layer comprises a second plurality of apertures, and a portion of the first layer is exposed through at least one of the second plurality of apertures.

2. The article of claim 1 wherein the nonwoven web comprises a crimped fiber spunbond nonwoven web.

3. The article of claim 2 wherein the crimped fiber spunbond nonwoven web comprises fibers having two different polypropylene polymers configured in a side-by-side configuration.

4. The article of claim 1 wherein the first plurality of apertures is disposed in a pattern.

5. The article of claim 1 comprising an additional layer comprising continuous spunbond crimped fibers.

6. The article of claim 1 wherein the first layer comprises a meltblown web.

7. The article of claim 1 wherein the first layer comprises a SMS construction.

8. The article of claim 1 wherein the elastic ear is disposed in the rear waist region.

9. The article of claim 1 further comprising a fastening system joined to the elastic ear.

10. The article of claim 1 wherein the elastic ear is integral with the chassis.

11. The article of claim 1 wherein the elastic ear is a separate component from the chassis.

12. The article of claim 2 wherein the crimped fiber spunbond nonwoven web is located on a garment-facing surface of the elastic ear.

* * * * *